United States Patent
Heiser et al.

(10) Patent No.: US 12,384,772 B2
(45) Date of Patent: Aug. 12, 2025

(54) INHIBITORS

(71) Applicant: VIVORYON THERAPEUTICS N.V., Halle (DE)

(72) Inventors: Ulrich Heiser, Halle (DE); Torsten Hoffmann, Halle (DE); Ingeborg Lues, Seeheim-Jugenheim (DE); Antje Meyer, Halle (DE)

(73) Assignee: VIVORYON THERAPEUTICS N.V., Halle (DE)

( * ) Notice: Subject to any disclaimer, the term of this patent is extended or adjusted under 35 U.S.C. 154(b) by 227 days.

(21) Appl. No.: 17/737,602

(22) Filed: May 5, 2022

(65) Prior Publication Data

US 2022/0274977 A1     Sep. 1, 2022

Related U.S. Application Data

(62) Division of application No. 16/497,040, filed as application No. PCT/EP2018/058391 on Apr. 3, 2018, now Pat. No. 11,339,152.

(30) Foreign Application Priority Data

Mar. 31, 2017 (GB) .................................. 1705263

(51) Int. Cl.
| | |
|---|---|
| *C07D 417/12* | (2006.01) |
| *A61K 45/06* | (2006.01) |
| *C07D 235/08* | (2006.01) |
| *C07D 249/14* | (2006.01) |
| *C07D 277/40* | (2006.01) |
| *C07D 285/135* | (2006.01) |
| *C07D 401/04* | (2006.01) |
| *C07D 401/12* | (2006.01) |
| *C07D 403/12* | (2006.01) |
| *C07D 417/04* | (2006.01) |

(52) U.S. Cl.
CPC ......... *C07D 417/12* (2013.01); *C07D 235/08* (2013.01); *C07D 249/14* (2013.01); *C07D 277/40* (2013.01); *C07D 285/135* (2013.01); *C07D 401/04* (2013.01); *C07D 401/12* (2013.01); *C07D 403/12* (2013.01); *C07D 417/04* (2013.01); *A61K 45/06* (2013.01); *C07B 2200/13* (2013.01)

(58) Field of Classification Search
CPC .. C07D 417/14; C07D 417/12; C07D 235/06; C07D 235/08; C07D 249/08; C07D 249/14; C07D 277/40; C07D 285/135; C07D 401/04; C07D 401/12; C07D 403/12; C07D 417/04; A61K 45/06; A61P 25/00; A61P 35/00; A61P 37/00; C07B 2200/13
USPC ................................................ 548/138, 198
See application file for complete search history.

(56) References Cited

U.S. PATENT DOCUMENTS

| | | |
|---|---|---|
| 5,525,604 A | 6/1996 | Lee et al. |
| 2001/0031760 A1 | 10/2001 | Pamukcu et al. |
| 2009/0048301 A1 | 2/2009 | Chen et al. |
| 2011/0262388 A1 | 10/2011 | Heiser et al. |
| 2013/0165458 A1 | 6/2013 | Huang et al. |

FOREIGN PATENT DOCUMENTS

| | | |
|---|---|---|
| DE | 69408750 T2 | 4/1998 |
| WO | 2008008375 A2 | 1/2008 |
| WO | 2011029920 A1 | 3/2011 |
| WO | 2011131748 A2 | 10/2011 |
| WO | 2017025868 A1 | 2/2017 |

OTHER PUBLICATIONS

Jimenez-Sanchez, Maria et al.: "siRNA screen identifies QPCT as a druggable target for Huntington's disease", Nature Chemical Biology, vol. 11, No. 5, 2, May 1, 2015 (May 1, 2015), pp. 347-354, XP055479437, Basingstoke, ISSN: 1552-4450, DOI: 10.1038jnchembio. 1790 figure 3a.
Saulnier, Mark G. et al: "Nucleophilic Capture of the Imino-Quinone Methide Type Intermediates Generated from 2-Aminothiazol-5-yl Carbinols", Organic Letters, vol. 11, No. 22, Nov. 19, 2009 (Nov. 19, 2009), pp. 5154-5157, XP055014692, ISSN: 1523-7060. DOI: 10.1021/ol902023g compounds 8, 9.
Ferrari, Stefania et al: "Virtual Screening Identification of Nonfolate Compounds, Including a CNS Drug, as Antiparasitic Agents Inhibiting Pteridine Reductase", Journal of Medicinal Chemistry, American Medical Society, vol. 1, 54, No. 1, Jan. 1, 2011 (Jan. 1, 2011). pp. 211-221, XP002643161, ISSN: 0022-2623, DOI: 10.1021/ JM1010572 [retrieved on Dec. 2, 2010] p. 214; compounds 24b. 25b.

(Continued)

*Primary Examiner* — Jeffrey H Murray
*Assistant Examiner* — Daniel John Burkett
(74) *Attorney, Agent, or Firm* — Olson & Cepuritis, Ltd.

(57) ABSTRACT

Compounds of formula (I):

A-B-D-E or a pharmaceutically acceptable salt, solvate or polymorph thereof, including all tautomers and stereoisomers thereof, wherein:

A is monocyclic and bicyclic heteroaryl;

B is alkyl, heteroalkyl, alkyl-amino, aryl, heteroaryl, cycloalkyl, heterocyclyl, or alkylene;

D is aryl-amino, heteroaryl-amino, cycloalkyl-amino, heterocyclyl, heterocyclyl-amino, urea, thioamide, thiourea, sulfonamide, sulfoximine, or sulfamoyl; and E is aryl, heteroaryl, cycloalkyl, or heterocyclyl.

These compounds of formula (I) are inhibitors of glutaminyl cyclase (QC, EC 2.3.2.5).

7 Claims, No Drawings

Specification includes a Sequence Listing.

(56) References Cited

OTHER PUBLICATIONS

STEC Markian M. et al: "Structure-Activity Relationships of Phosphoinositide 3-Kinase (PI3K)/Mammalian Target of Rapamycin (mTOR) Dual Inhibitors: Investigations of Various 6,5-Heterocycles to Improve Metabolic Stability", Journal of Chemistry, vol. 54, No. 14, Jul. 28, 2011 (Jul. 28, 2011), pp. 5174-5184, XP055258397, ISSN: 0022-2623, DOI: 10.1021jm2004442 compounds 15, 18.
Database Registry, 2014, RN 1609858-93-6, Retrieved from STN international [online]; retrieved on Feb. 3, 2022.
Database Registry, 2014, RN 1567371-28-1, Retrieved from STN international [online]; retrieved on Feb. 3, 2022.
Database Registry, 2010, RN 1211493-15-0, Retrieved from STN international [online]; retrieved on Feb. 3, 2022.
Database Registry, 2010, RN 1211492-61-3, Retrieved from STN international [online]; retrieved on Feb. 3, 2022.
Database Registry, 2010, RN 1211465-90-5, Retrieved from STN international [online]; retrieved on Feb. 3, 2022.
Database Registry, 2009, RN 1199216-00-6, Retrieved from STN international [online]; retrieved on Feb. 3, 2022.
Database Registry, 2004, RN 694497-92-2, Retrieved from STN international [online]; retrieved on Feb. 3, 2022.

SEQUENCE LISTING

<160> NUMBER OF SEQ ID NOS: 20

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 40
<212> TYPE: PRT
<213> ORGANISM: Homo sapiens

<400> SEQUENCE: 3

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 4
<211> LENGTH: 38
<212> TYPE: PRT
<213> ORGANISM: Homo sapiens

<400> SEQUENCE: 4

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 5
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

```
<400> SEQUENCE: 5

Gln Gly Pro Trp Leu Glu Glu Glu Glu Ala Tyr Gly Trp Met Asp
1               5                   10                  15

Phe

<210> SEQ ID NO 6
<211> LENGTH: 13
<212> TYPE: PRT
<213> ORGANISM: Homo sapiens

<400> SEQUENCE: 6

Gln Leu Tyr Glu Asn Lys Pro Arg Arg Pro Tyr Ile Leu
1               5                   10

<210> SEQ ID NO 7
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 7

Gln His Trp Ser Tyr Gly Leu Arg Pro Gly
1               5                   10

<210> SEQ ID NO 8
<211> LENGTH: 97
<212> TYPE: PRT
<213> ORGANISM: Homo sapiens

<400> SEQUENCE: 8

Gln Pro Lys Val Pro Glu Trp Val Asn Thr Pro Ser Thr Cys Cys Leu
1               5                   10                  15

Lys Tyr Tyr Glu Lys Val Leu Pro Arg Arg Leu Val Val Gly Tyr Arg
                20                  25                  30

Lys Ala Leu Asn Cys His Leu Pro Ala Ile Ile Phe Val Thr Lys Arg
            35                  40                  45

Asn Arg Glu Val Cys Thr Asn Pro Asn Asp Asp Trp Val Gln Glu Tyr
        50                  55                  60

Ile Lys Asp Pro Asn Leu Pro Leu Leu Pro Thr Arg Asn Leu Ser Thr
65                  70                  75                  80

Val Lys Ile Ile Thr Ala Lys Asn Gly Gln Pro Gln Leu Leu Asn Ser
                85                  90                  95

Gln

<210> SEQ ID NO 9
<211> LENGTH: 76
<212> TYPE: PRT
<213> ORGANISM: Homo sapiens

<400> SEQUENCE: 9

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
            35                  40                  45
```

```
Lys Glu Val Cys Ala Asp Pro Lys Glu Arg Trp Val Arg Asp Ser Met
 50                  55                  60

Lys His Leu Asp Gln Ile Phe Gln Asn Leu Lys Pro
 65                  70                  75
```

<210> SEQ ID NO 10
<211> LENGTH: 76
<212> TYPE: PRT
<213> ORGANISM: Homo sapiens

<400> SEQUENCE: 10

```
Gln Pro Asp Ala Ile Asn Ala Pro Val Thr Cys Cys Tyr Asn Phe Thr
 1               5                  10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
                35                  40                  45

Lys Glu Ile Cys Ala Asp Pro Lys Gln Lys Trp Val Gln Asp Ser Met
 50                  55                  60

Asp His Leu Asp Lys Gln Thr Gln Thr Pro Lys Thr
 65                  70                  75
```

<210> SEQ ID NO 11
<211> LENGTH: 68
<212> TYPE: PRT
<213> ORGANISM: Homo sapiens

<400> SEQUENCE: 11

```
Gln Val Gly Thr Asn Lys Glu Leu Cys Cys Leu Val Tyr Thr Ser Trp
 1               5                  10                  15

Gln Ile Pro Gln Lys Phe Ile Val Asp Tyr Ser Glu Thr Ser Pro Gln
                20                  25                  30

Cys Pro Lys Pro Gly Val Ile Leu Leu Thr Lys Arg Gly Arg Gln Ile
                35                  40                  45

Cys Ala Asp Pro Asn Lys Lys Trp Val Gln Lys Tyr Ile Ser Asp Leu
 50                  55                  60

Lys Leu Asn Ala
 65
```

<210> SEQ ID NO 12
<211> LENGTH: 373
<212> TYPE: PRT
<213> ORGANISM: Homo sapiens

<400> SEQUENCE: 12

```
Gln His His Gly Val Thr Lys Cys Asn Ile Thr Cys Ser Lys Met Thr
 1               5                  10                  15

Ser Lys Ile Pro Val Ala Leu Leu Ile His Tyr Gln Gln Asn Gln Ala
                20                  25                  30

Ser Cys Gly Lys Arg Ala Ile Ile Leu Glu Thr Arg Gln His Arg Leu
                35                  40                  45

Phe Cys Ala Asp Pro Lys Glu Gln Trp Val Lys Asp Ala Met Gln His
 50                  55                  60

Leu Asp Arg Gln Ala Ala Leu Thr Arg Asn Gly Gly Thr Phe Glu
 65                  70                  75                  80

Lys Gln Ile Gly Glu Val Lys Pro Arg Thr Thr Pro Ala Ala Gly Gly
                85                  90                  95

Met Asp Glu Ser Val Val Leu Glu Pro Glu Ala Thr Gly Glu Ser Ser
```

```
                  100                 105                 110
        Ser Leu Glu Pro Thr Pro Ser Ser Gln Glu Ala Gln Arg Ala Leu Gly
                    115                 120                 125
        Thr Ser Pro Glu Leu Pro Thr Gly Val Thr Gly Ser Ser Gly Thr Arg
            130                 135                 140
        Leu Pro Pro Thr Pro Lys Ala Gln Asp Gly Pro Val Gly Thr Glu
        145                 150                 155                 160
        Leu Phe Arg Val Pro Pro Val Ser Thr Ala Ala Thr Trp Gln Ser Ser
                        165                 170                 175
        Ala Pro His Gln Pro Gly Pro Ser Leu Trp Ala Glu Ala Lys Thr Ser
                    180                 185                 190
        Glu Ala Pro Ser Thr Gln Asp Pro Ser Thr Gln Ala Ser Thr Ala Ser
                    195                 200                 205
        Ser Pro Ala Pro Glu Glu Asn Ala Pro Ser Glu Gly Gln Arg Val Trp
                    210                 215                 220
        Gly Gln Gly Gln Ser Pro Arg Pro Glu Asn Ser Leu Glu Arg Glu Glu
        225                 230                 235                 240
        Met Gly Pro Val Pro Ala His Thr Asp Ala Phe Gln Asp Trp Gly Pro
                        245                 250                 255
        Gly Ser Met Ala His Val Ser Val Val Pro Val Ser Ser Glu Gly Thr
                    260                 265                 270
        Pro Ser Arg Glu Pro Val Ala Ser Gly Ser Trp Thr Pro Lys Ala Glu
                    275                 280                 285
        Glu Pro Ile His Ala Thr Met Asp Pro Gln Arg Leu Gly Val Leu Ile
                    290                 295                 300
        Thr Pro Val Pro Asp Ala Gln Ala Ala Thr Arg Arg Gln Ala Val Gly
        305                 310                 315                 320
        Leu Leu Ala Phe Leu Gly Leu Leu Phe Cys Leu Gly Val Ala Met Phe
                        325                 330                 335
        Thr Tyr Gln Ser Leu Gln Gly Cys Pro Arg Lys Met Ala Gly Glu Met
                    340                 345                 350
        Ala Glu Gly Leu Arg Tyr Ile Pro Arg Ser Cys Gly Ser Asn Ser Tyr
                    355                 360                 365
        Val Leu Val Pro Val
            370

<210> SEQ ID NO 13
<211> LENGTH: 76
<212> TYPE: PRT
<213> ORGANISM: Homo sapiens

<400> SEQUENCE: 13

Gln Pro Val Gly Ile Asn Thr Ser Thr Thr Cys Cys Tyr Arg Phe Ile
        1               5                   10                  15
        Asn Lys Lys Ile Pro Lys Gln Arg Leu Glu Ser Tyr Arg Arg Thr Thr
                    20                  25                  30
        Ser Ser His Cys Pro Arg Glu Ala Val Ile Phe Lys Thr Lys Leu Asp
                    35                  40                  45
        Lys Glu Ile Cys Ala Asp Pro Thr Gln Lys Trp Val Gln Asp Phe Met
            50                  55                  60
        Lys His Leu Asp Lys Lys Thr Gln Thr Pro Lys Leu
        65                  70                  75

<210> SEQ ID NO 14
<211> LENGTH: 33
```

```
<212> TYPE: PRT
<213> ORGANISM: Homo sapiens

<400> SEQUENCE: 14

Gln Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu

<210> SEQ ID NO 15
<211> LENGTH: 11
<212> TYPE: PRT
<213> ORGANISM: Homo sapiens

<400> SEQUENCE: 15

Arg Pro Lys Pro Gln Gln Phe Phe Gly Leu Met
1               5                   10

<210> SEQ ID NO 16
<211> LENGTH: 32
<212> TYPE: PRT
<213> ORGANISM: Artificial sequence
<220> FEATURE:
<223> OTHER INFORMATION: Synthetic peptide

<400> SEQUENCE: 16

Glu Val His His Gln Lys Leu Val Phe Phe Ala Glu Asp Val Gly Ser
1               5                   10                  15

Asn Lys Gly Ala Ile Ile Gly Leu Met Val Gly Val Val Ile Ala
            20                  25                  30

<210> SEQ ID NO 17
<211> LENGTH: 30
<212> TYPE: PRT
<213> ORGANISM: Artificial sequence
<220> FEATURE:
<223> OTHER INFORMATION: Synthetic peptide

<400> SEQUENCE: 17

Glu Val His His Gln Lys Leu Val Phe Phe Ala Glu Asp Val Gly Ser
1               5                   10                  15

Asn Lys Gly Ala Ile Ile Gly Leu Met Val Gly Val Val
            20                  25                  30

<210> SEQ ID NO 18
<211> LENGTH: 34
<212> TYPE: PRT
<213> ORGANISM: Artificial sequence
<220> FEATURE:
<223> OTHER INFORMATION: Synthetic peptide

<400> SEQUENCE: 18

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Asn

<210> SEQ ID NO 19
<211> LENGTH: 34
<212> TYPE: PRT
<213> ORGANISM: Artificial sequence
```

```
<220> FEATURE:
<223> OTHER INFORMATION: Synthetic peptide

<400> SEQUENCE: 19

Glu Ala Ser Asn Cys Phe Ala Ile Arg His Phe Glu Asn Lys Phe Ala
1               5                   10                  15

Val Glu Thr Leu Ile Cys Phe Asn Leu Phe Leu Asn Ser Gln Glu Lys
            20                  25                  30

His Tyr

<210> SEQ ID NO 20
<211> LENGTH: 5
<212> TYPE: PRT
<213> ORGANISM: Artificial sequence
<220> FEATURE:
<223> OTHER INFORMATION: Synthetic peptide

<400> SEQUENCE: 20

Gln Tyr Asn Ala Asp
1               5
```

INHIBITORS

CROSS-REFERENCE TO RELATED APPLICATIONS

This application is a divisional of U.S. patent application Ser. No. 16/497,040, filed on Sep. 24, 2019, which is a continuation to PCT/EP2018/058391, filed on Apr. 3, 2018, which claims priority of British Patent Application No. 1705263.0, filed on Mar. 31, 2017, each of which is incorporated herein by reference.

SEQUENCE LISTING INCORPORATION

Biological sequence information for this application is included in an ASCII text file, having the file name "eolfseq1.txt" and a having file size of 12 KB, which is part of said PCT/EP2018/058391 and is incorporated herein by reference.

FIELD OF THE INVENTION

The invention relates to novel heterocyclic derivatives as inhibitors of glutaminyl cyclase (QC, EC 2.3.2.5). QC catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer. W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In the case of the enzyme from *C. papaya*, a role in the plant defense against pathogenic microorganisms was suggested (El Moussaoui, A. et al. 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from *C. papaya* and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed $Glu_1$-conversion is favored around pH 6.0 while $Gln_1$-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of Alzheimer's disease.

Inhibitors of QC are e.g. described in WO 2004/098625, WO 2004/098591, WO 2005/039548, WO 2005/075436, WO 2008/055945, WO 2008/055947, WO 2008/055950, WO2008/065141, WO 2008/110523, WO 2008/128981, WO 2008/128982, WO 2008/128983, WO 2008/128984, WO 2008/128985, WO 2008/128986, WO 2008/128987, WO 2010/026212, WO 2011/029920, WO 2011/107530, WO 2011/110613, WO 2011/131748 and WO 2012/123563.

EP 02 011 349.4 discloses polynucleotides encoding insect glutaminyl cyclase, as well as polypeptides encoded thereby and their use in methods of screening for agents that reduce glutaminyl cyclase activity. Such agents are useful as pesticides.

Definitions

The terms "$k_i$" or "$K_i$" and "$K_D$" are binding constants, which describe the binding of an inhibitor to and the subsequent release from an enzyme. Another measure is the "$IC_{50}$" value, which reflects the inhibitor concentration, which at a given substrate concentration results in 50% enzyme activity.

The term "DP IV-inhibitor" or "dipeptidyl peptidase IV inhibitor" is generally known to a person skilled in the art and means enzyme inhibitors, which inhibit the catalytic activity of DP IV or DP IV-like enzymes.

"DP IV-activity" is defined as the catalytic activity of dipeptidyl peptidase IV (DP IV) and DP IV-like enzymes. These enzymes are post-proline (to a lesser extent post-alanine, post-serine or post-glycine) cleaving serine proteases found in various tissues of the body of a mammal including kidney, liver, and intestine, where they remove dipeptides from the N-terminus of biologically active peptides with a high specificity when proline or alanine form the residues that are adjacent to the N-terminal amino acid in their sequence.

The term "PEP-inhibitor" or "prolyl endopeptidase inhibitor" is generally known to a person skilled in the art and means enzyme inhibitors, which inhibit the catalytic activity of prolyl endopeptidase (PEP, prolyl oligopeptidase, POP).

"PEP-activity" is defined as the catalytic activity of an endoprotease that is capable to hydrolyze post proline bonds in peptides or proteins where the proline is in amino acid position 3 or higher counted from the N-terminus of a peptide or protein substrate.

The term 'QC' as used herein comprises glutaminyl cyclase (QC) and QC-like enzymes. QC and QC-like enzymes have identical or similar enzymatic activity, further defined as QC activity. In this regard, QC-like enzymes can fundamentally differ in their molecular structure from QC. Examples of QC-like enzymes are the glutaminyl-peptide cyclotransferase-like proteins (QPCTLs) from human (GenBank NM_017659), mouse (GenBank BC058181), *Macaca*

*fascicularis* (GenBank AB168255), *Macaca* mulatta (GenBank XM_001110995), *Canis familiaris* (GenBank XM_541552), *Rattus norvegicus* (GenBank XM_001066591). *Mus musculus* (GenBank BC058181) and *Bos taurus* (GenBank BT026254).

The term "QC activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See therefore schemes 1 and 2.

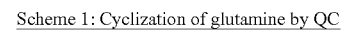

Scheme 1: Cyclization of glutamine by QC

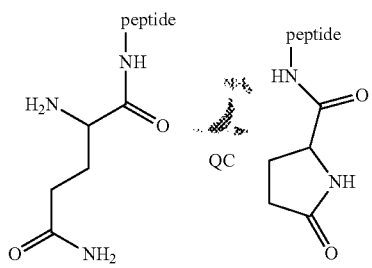

Scheme 2: Cyclization of L-homoglutamine by QC

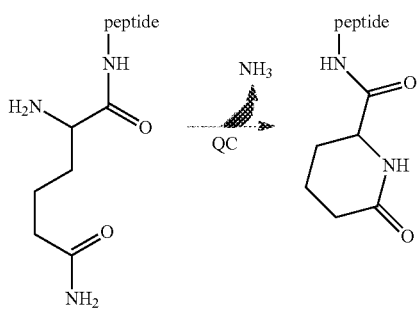

The term "EC" as used herein comprises the activity of QC and QC-like enzymes as glutamate cyclase (EC), further defined as EC activity.

The term "EC activity" as used herein is defined as intramolecular cyclization of N-terminal glutamate residues into pyroglutamic acid (pGlu*) by QC. See therefore scheme 3.

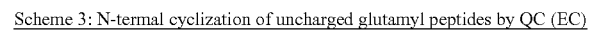

Scheme 3: N-termal cyclization of uncharged glutamyl peptides by QC (EC)

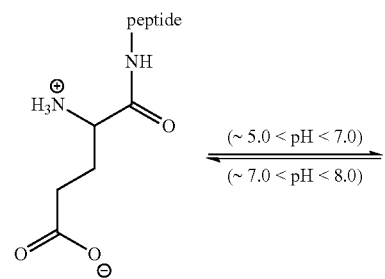

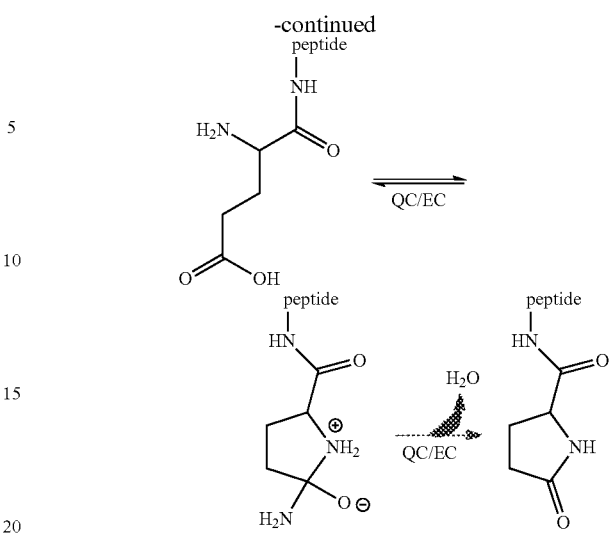

The term "QC-inhibitor" "glutaminyl cyclase inhibitor" is generally known to a person skilled in the art and means enzyme inhibitors, which inhibit the catalytic activity of glutaminyl cyclase (QC) or its glutamyl cyclase (EC) activity.

Potency of QC Inhibition

In light of the correlation with QC inhibition, in preferred embodiments, the subject method and medical use utilize an agent with an IC$_{50}$ for QC inhibition of 10 μM or less, more preferably of 1 μM or less, even more preferably of 0.1 μM or less or 0.01 μM or less, or most preferably 0.001 μM or less. Indeed, inhibitors with K$_i$ values in the lower micromolar, preferably the nanomolar and even more preferably the picomolar range are contemplated. Thus, while the active agents are described herein, for convenience, as "QC inhibitors", it will be understood that such nomenclature is not intending to limit the subject of the invention to a particular mechanism of action.

Molecular Weight of QC Inhibitors

In general, the QC inhibitors of the subject method or medical use will be small molecules, e.g., with molecular weights of 500 g/mole or less, 400 g/mole or less, preferably of 350 g/mole or less, and even more preferably of 300 g/mole or less and even of 250 g/mole or less.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: For example the term "pharmaceutically acceptable" embraces a veterinarily acceptable compound or a compound acceptable in human medicine and health care.

Throughout the description and the claims the expression "alkyl", unless specifically limited, denotes a C$_{1-12}$alkyl group, suitably a C$_{1-6}$ alkyl group, e.g. C$_{1-6}$ alkyl group, e.g. C$_{1-4}$ alkyl group. Alkyl groups may be straight chain or branched. Suitable alkyl groups include, for example, methyl, ethyl, propyl (e.g. n-propyl and isopropyl), butyl (e.g. n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary thioalkyl groups include methylthio-. Exemplary haloalkyl groups include fluoroalkyl e.g. $CF_3$.

The expression "alkylene" denotes a chain of formula —$(CH_2)_n$— wherein n is an integer e.g. 1-5, unless specifically limited.

The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-8}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six.

The expression "heterocyclyl", unless specifically limited, refers to a carbocyclyl group wherein one or more (e.g. 1, 2 or 3) ring atoms are replaced by heteroatoms selected from N, S and O. A specific example of a heterocyclyl group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O. Exemplary heterocyclyl groups containing one hetero atom include pyrrolidine, tetrahydrofuran and piperidine, and exemplary heterocyclyl groups containing two hetero atoms include morpholine, piperazine, dioxolane and dioxane. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-).

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings). An example of a typical aryl group with one aromatic ring is phenyl. An example of a typical aryl group with two aromatic rings is naphthyl.

The expression "heteroaryl", unless specifically limited, denotes an aryl residue, wherein one or more (e.g. 1, 2, 3, or 4, suitably 1, 2 or 3) ring atoms are replaced by heteroatoms selected from N, S and O, or else a 5-membered aromatic ring containing one or more (e.g. 1, 2, 3, or 4, suitably 1, 2 or 3) ring atoms selected from N, S and O. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole, oxazole, isoxazole, thiazole, isothiazole, imidazole, such as imidazol-1-yl, imidazol-2-yl imidazol-4-yl); six membered rings (e.g. pyridazine, pyrimidine, pyrazine). Exemplary monocyclic heteroaryl groups having three heteroatoms include: 1,2,3-triazole and 1,2,4-triazole. Exemplary monocyclic heteroaryl groups having four heteroatoms include tetrazole. Exemplary bicyclic heteroaryl groups include: indole (e.g. indol-6-yl), benzofuran, benzthiophene, quinoline, isoquinoline, indazole, benzimidazole, benzthiazole, quinazoline and purine.

The expression "-alkylaryl", unless specifically limited, denotes an aryl residue which is connected via an alkylene moiety e.g. a $C_{1-4}$alkylene moiety.

The expression "-alkylheteroaryl", unless specifically limited, denotes a heteroaryl residue which is connected via an alkylene moiety e.g. a $C_{1-4}$alkylene moiety.

The term "halogen" or "halo" comprises fluorine (F), chlorine (Cl) and bromine (Br).

The term "amino" refers to the group —$NH_2$.

When benzimidazolyl is shown as benzimidazol-5-yl, which is represented as:

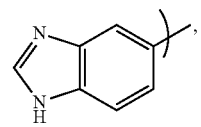

the person skilled in the art will appreciate that benzimidazol-6-yl, which is represented as:

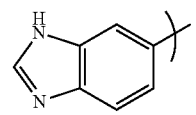

is an equivalent structure. As employed herein, the two forms of benzimidazolyl are covered by the term "benzimidazol-5-yl".

Stereoisomers:

All possible stereoisomers of the claimed compounds are included in the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts or solvates, whenever a compound is referred to in this context, a corresponding salt, solvate or polymorph is also intended, provided such is possible or appropriate under the circumstances.

Salts and solvates of the compounds of formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

Polymorph Crystal Forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis. John Wiley & Sons, 1991, fully incorporated herein by reference. The protecting groups may be removed at a convenient subsequent stage using methods known from the art.

As used herein, the term "composition" is intended to encompass a product comprising the claimed compounds in the therapeutically effective amounts, as well as any product which results, directly or indirectly, from combinations of the claimed compounds.

Carriers and Additives for Galenic Formulations:

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

DESCRIPTION OF THE INVENTION

According to the invention there is provided a compound of formula (I):

$$A\text{-}B\text{-}D\text{-}E \qquad (I)$$

or a pharmaceutically acceptable salt, solvate or polymorph thereof, including all tautomers and stereoisomers thereof, wherein:
  A is selected from monocyclic and bicyclic heteroaryl, which may independently substituted by alkyl or amino;
  B is selected from alkyl, heteroalkyl, alkyl-amino, aryl, heteroaryl, cycloalkyl, heterocyclyl and alkylene, wherein said groups may independently be substituted by alkyl;
  D is selected from aryl-amino, heteroaryl-amino, cycloalkyl-amino, heterocyclyl, heterocyclyl-amino, urea, thioamide, thiourea, sulfonamide and sulfoximine, wherein said aryl, heteroaryl, cycloalkyl and heterocyclyl groups may independently be substituted with one or more substituents;

In another embodiment, D is sulfamoyl;

E is selected from aryl, heteroaryl, cycloalkyl, heterocyclyl, wherein said aryl, heteroaryl, cycloalkyl and heterocyclyl groups may independently be substituted with one or more substituents.

In a preferred embodiment, there is provided a compound of formula (I) with the provisos that
i) when B is alkyl or heteroalkyl, then D may not be sulfonamide; and
ii) the compound of formula (I) is not a compound selected from:

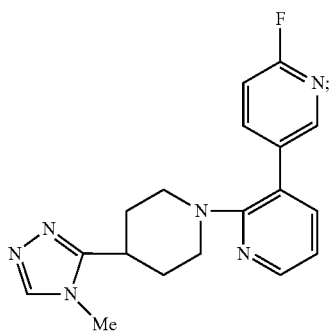

(compound V);

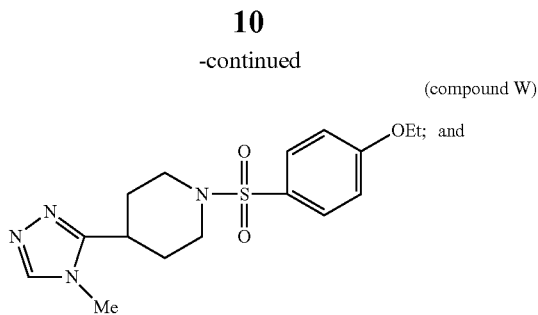

(compound W)

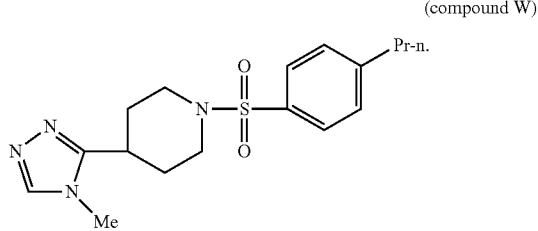

(compound W)

Compounds of proviso i) are known from the CAS Registry Database without any functional definition and are selected from

| Compound | Chemical Name | CAS No. |
|---|---|---|
| A | Benzenesulfonamide, N-[3-(5-amino-1,3,4-thiadiazol-2-yl)propyl]-4-chloro- | 1211493-15-0 |
| B | Benzenesulfonamide, N-[3-(5-amino-1,3,4-thiadiazol-2-yl)propyl]-4-bromo- | 1211465-90-5 |
| C | Benzenesulfonamide, N-[3-(5-amino-1,3,4-thiadiazol-2-yl)propyl]-4-methyl- | 1199216-00-6 |
| D | Benzenesulfonamide, 4-(1,1-dimethylethyl)-N-[3-(4-methyl-4H-1,2,4-triazol-3-yl)propyl]- | 2128710-23-4 |
| E | Benzenesulfonamide, N-[3-(5-amino-1,3,4-thiadiazol-2-yl)propyl]-4-fluoro- | 1211492-68-0 |
| F | Benzenesulfonamide, N-[3-(5-amino-1,3,4-thiadiazol-2-yl)propyl]-4-methoxy- | 1211492-61-3 |
| G | Benzenesulfonamide, N-[2-[(5-amino-1,3,4-thiadiazol-2-yl)thio]ethyl]-4-methyl- | 694497-92-2 |
| H | Benzenesulfonamide, 4-methyl-N-[2-[(4-methyl-4H-1,2,4-triazol-3-yl)thio]ethyl]- (CA INDEX NAME) | 329266-08-2 |
| I | Benzenesulfonamide, N-(1H-benzimidazol-6-ylmethyl)-4-(1-methylethoxy)- | 1798221-00-7 |
| J | Benzenesulfonamide, N-(1H-benzimidazol-6-ylmethyl)-4-chloro- | 1798220-92-4 |
| K | Benzenesulfonamide, N-(1H-benzimidazol-6-ylmethyl)-4-ethoxy- | 1798183-20-6 |
| L | Benzenesulfonamide, N-(1H-benzimidazol-6-ylmethyl)-4-fluoro-3-methyl- | 1798182-87-2 |
| M | Benzenesulfonamide, N-(1H-benzimidazol-6-ylmethyl)-4-(1,1-dimethylethyl)- | 1795649-47-6 |
| N | Benzenesulfonamide, N-(1H-benzimidazol-6-ylmethyl)-4-(1-methylethyl)- | 1795648-73-5 |
| O | Benzenesulfonamide, N-(1H-benzimidazol-6-ylmethyl)-4-ethyl- | 1795648-65-5 |
| P | Benzenesulfonamide, N-(1H-benzimidazol-6-ylmethyl)-3,4-dimethyl- | 1795648-57-5 |
| Q | Benzenesulfonamide, N-(1H-benzimidazol-6-ylmethyl)-4-methyl- | 1795648-51-9 |
| R | Benzenesulfonamide, N-(1H-benzimidazol-6-ylmethyl)-4-fluoro- | 1795588-58-7 |
| S | Benzenesulfonamide, N-(1H-benzimidazol-6-ylmethyl)-3,4-dimethoxy- | 1790918-17-0 |
| T | Benzenesulfonamide, N-(1H-benzimidazol-6-ylmethyl)-4-methoxy-3-methyl- | 1790918-11-4 |

| Compound | Chemical Name | CAS No. |
|---|---|---|
| U | Benzenesulfonamide, N-(1H-benzimidazol-6-ylmethyl)-4-methoxy- | 1787494-28-3 |

In a preferred embodiment according tp proviso i), the compound of formula (I) is not a compound selected from compounds A to U.

Compound V of proviso ii) is known from CAS Registry with CAS No. 2117405-13-5 without functional definition. Compound W of proviso ii) is known from CAS Registry with CAS No. 1090606-68-0 without functional definition. Compound W of proviso ii) is known from CAS Registry with CAS No. 2093539-54-7 without functional definition.

When A is a monocyclic heteroaryl, A is preferably selected from thiadiazolyl, such as 1,3,4-thiadiazolyl, thiazolyl and triazolyl, such as 1,2,4-triazolyl. In one embodiment of the invention, said monocyclic heteroaryl is substituted by amino or methyl. In another embodiment, said monocyclic heteroaryl is unsubstituted.

When cycloalkyl and heterocyclyl are substituted, they are typically substituted by 1 or 2 substituents (e.g. 1 substituent). Typically the substituent is $C_{1-6}$ alkyl (i.e. methyl) or halogen (i.e. chlorine or fluorine). More typically cycloalkyl and heterocyclyl groups are unsubstituted.

When aryl and heteroaryl are substituted, they are typically substituted by 1, 2 or 3 (e.g. 1 or 2) substituents. Substituents for aryl and heteroaryl are selected from $C_{1-6}$alkyl (e.g. methyl), $C_{2-6}$alkenyl (e.g. buten-3-yl), $C_{2-6}$alkynyl (e.g. butyn-3-yl), $C_{1-4}$ haloalkyl (e.g. fluoromethyl, trifluoromethyl), —$C_{1-6}$thioalkyl (e.g. —S-methyl), —$SOC_{1-4}$alkyl (e.g. —SOmethyl), —$SO_2C_{1-4}$alkyl (e.g. —$SO_2$methyl), $C_{1-6}$alkoxy- (e.g. methoxy, ethoxy), —O—$C_{3-8}$cycloalkyl (e.g. —O-cyclopentyl or —O-cyclohexyl), $C_{3-8}$cycloalkyl (e.g. cyclopropyl, cyclohexyl), —$SO_2C_{3-8}$cycloalkyl (e.g. —$SO_2$cyclohexyl), —$SOC_{3-8}$cycloalkyl (e.g. —SOcyclopropyl), —O-aryl (e.g. —O-phenyl) $C_{3-8}$alkenyloxy- (e.g. —O-buten-2-yl), $C_{3-8}$alkynyloxy- (e.g. —O-buten-2-yl), —$C(O)C_{1-6}$alkyl (e.g. —C(O)ethyl), —$C(O)OC_{1-6}$alkyl (e.g. —C(O)O-methyl), $C_{1-6}$alkoxy-$C_{1-6}$alkyl- (e.g. methoxy-ethyl-), nitro, halogen (e.g. fluoro, chloro, bromo), cyano, hydroxyl, —C(O)OH, —$NH_2$, —$NHC_{1-4}$alkyl (e.g. —NHmethyl), —$N(C_{1-4}$alkyl)($C_{1-4}$alkyl) (e.g. —N(methyl)$_2$), —$C(O)N(C_{1-4}$alkyl)($C_{1-4}$alkyl) (e.g. —C(O)N(methyl)$_2$), —$C(O)NH_2$, —$C(O)NH(C_{1-4}$alkyl) (e.g. —C(O)NHmethyl), —$C(O)NH(C_{3-10}$cycloalkyl) (e.g. —C(O)NHcyclopropyl). More typically, substituents will be selected from $C_{1-6}$alkyl (e.g. methyl), $C_{1-6}$haloalkyl (e.g. $C_{1-6}$fluoroalkyl, e.g. $CF_3$), $C_{1-6}$alkoxy (e.g. OMe), halogen and hydroxy.

When E represents aryl, said aryl suitably represents optionally substituted phenyl. Exemplary substituted phenyl groups for E include 2-bromophenyl, 2-bromo-4-fluorophenyl-, 2-bromo-5-fluorophenyl-, 2-fluoro-5-bromophenyl, 2-chlorophenyl-, 2-fluorophenyl-, 3-chlorophenyl-, 3-bromophenyl-, 3-fluorophenyl-, 4-chlorophenyl-, 4-fluorophenyl-, 4-bromophenyl-, 4-bromo-2-fluorophenyl-, 2-chloro-3,6-difluorophenyl-), 2,3-dichlorophenyl-, 2,3-difluorophenyl-, 2,3,4-trifluorophenyl-, 2,3,5-trifluorophenyl-, 2,4-dichlorophenyl-, 2,4-difluorophenyl-, 2,4,6-trifluorophenyl-, 2,5-dichlorophenyl-, 2,6-dichlorophenyl-, 2,6-difluorophenyl-, 3,4-dichlorophenyl-, 3,4-difluorophenyl-, 3,5-difluorophenyl-, 2,4,5-trifluorophenyl-, 3,4,5-trifluorophenyl-, 2,4-dimethylphenyl-, 3-methylphenyl-, 3,4-dimethylphenyl-, 4-methylphenyl-, 4-isopropylphenyl-, 4-tert-butylphenyl-, 2,4,6-trimethylphenyl-, 2-isopropyl-6-methylphenyl-, 2-(trifluoromethyl)phenyl-, 4-(trifluoromethyl)phenyl-. 2,4-bis(trifluoromethyl)phenyl-, 3,5-bis(trifluoromethyl)phenyl-, 2-methoxyphenyl-, 2,4-dimethoxyphenyl-, 2,6-dimethoxyphenyl-, 3-methoxyphenyl-, 4-methoxyphenyl-, 4-ethoxyphenyl-, 4-propoxyphenyl-, 4-butoxyphenyl-, 4-pentoxyphenyl-, 4-isopropyloxyphenyl-, 3-(cyclopentyloxy)-4-methoxyphenyl-, 3,4,5-trimethoxyphenyl-, 3,4-dimethoxyphenyl-, 3,5-dimethoxyphenyl-, 4-tetrafluoroethyloxyphenyl-, 4-cyanophenyl-, 4-thiomethylphenyl- and 4-dimethylaminophenyl. Alternatively, E may represent unsubstituted phenyl-. Further exemplary substituted phenyl groups include 2,3-difluoro-4-methylphenyl. 2-fluoro-5-(trifluoromethyl)phenyl-, 2-hydroxy-3-methoxyphenyl-, 2-hydroxy-5-methylphenyl-, 3-fluoro-4-(trifluoromethyl)phenyl-, 3-fluoro-5-(trifluoromethyl)phenyl-, 2-fluoro-4-(trifluoromethyl)phenyl-, 2-fluoro-3-(methyl)phenyl-, 3-fluoro-4-(methoxy)phenyl-, 3-hydroxy-4-methoxyphenyl-, 4-chloro-3-(trifluoromethyl)phenyl-, 4-chloro-3-methylphenyl-, 4-bromo-4-ethylphenyl-, 2,3,5,6-tetrafluoro-4-(methyl)phenyl-, 2,6-difluoro-4-(methoxy)phenyl- and 2-fluoro-4,5-(dimethoxy)phenyl-.

When E represents optionally substituted heteroaryl, examples include pyridinyl (e.g. pyridin-2-yl and pyridin-4-yl) and pyrimidinyl. Specific substituents that may be mentioned are one or more e.g. 1, 2 or 3 groups selected from halogen, hydroxyl, alkyl (e.g. methyl) and alkoxy- (e.g. methoxy-). An example substituted ring is 1-oxy-pyridin-4-yl-.

In a more preferred embodiment, when A is a monocyclic heteroaryl, A is selected from

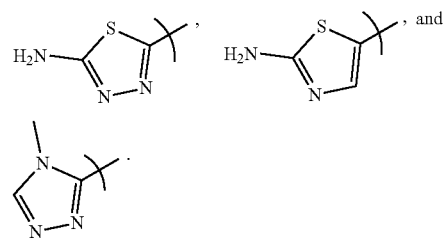

In a most preferred embodiment, when A is a monocyclic heteroaryl, A is

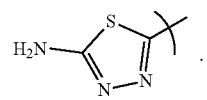

In a further a most preferred embodiment, when A is a monocyclic heteroaryl, A is

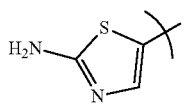

In yet a most preferred embodiment, when A is a monocyclic heteroaryl, A is

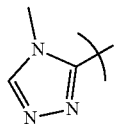

When A is a bicyclic heteroaryl, A is preferably selected from benzimidazole and imidazopyridine, such as imidazo[1,2-a]pyridine.

In a more preferred embodiment, when A is a bicyclic heteroaryl, A is selected from

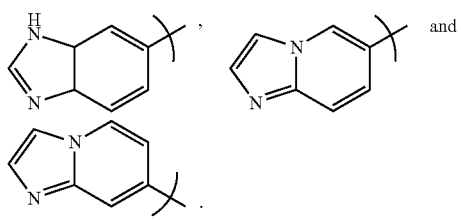

In a most preferred embodiment, when A is a bicyclic heteroaryl, A is

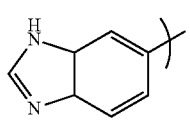

In a further a most preferred embodiment, when A is a bicyclic heteroaryl, A is

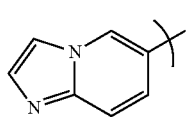

In yet a most preferred embodiment, when A is a bicyclic heteroaryl, A is

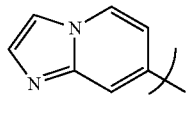

In a preferred embodiment, B is selected from $C_{3-5}$-heteroalkyl, phenyl, $C_5$-$C_6$-heterocyclyl and $C_{1-5}$ alkylene, wherein said $C_{1-5}$ alkylene group may independently be substituted by alkyl.

More preferably, B is selected from

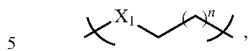

wherein $X_1$ is alkyl, N, O or S, preferably methyl or S; and n is an integer selected from 1 and 2;

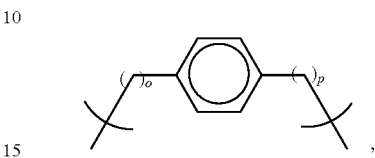

wherein o is 0 or 1; and p is 0 or 1; and

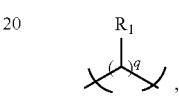

wherein $R_1$ is hydrogen or alkyl and q is 0, 1 or 2.

In a most preferred embodiment, B is

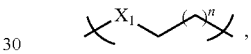

wherein $X_1$ and n are as defined above.

In a further most preferred embodiment, B is

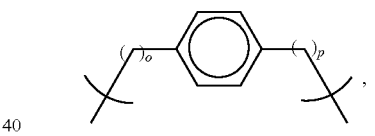

wherein o is as defined above.

In yet a most preferred embodiment, B is

wherein $R_1$ and p are as defined above.

In a preferred embodiment, D is a group selected from

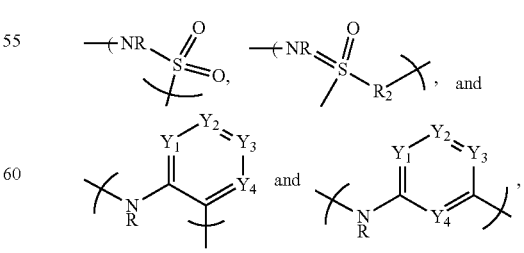

wherein

R is absent or is hydrogen; or R forms together with the nitrogen atom a heterocyclic ring of group B;

$R_2$ is hydrogen, alkyl or cycloalkyl;
$Y_1$, $Y_2$, $Y_3$ and $Y_4$ are independently selected from CH, N, S and O.

When D is

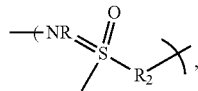

R is preferably absent and $R_2$ is preferably hydrogen or alkyl.

When D is

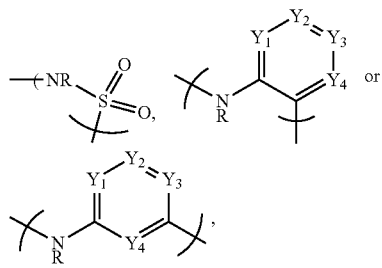

R is preferably hydrogen.

In a further embodiment, D is

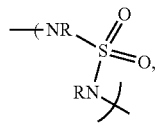

wherein R is hydrogen or alkyl.

In a further preferred embodiment, when D is one of the above groups, R forms together with the nitrogen, to which it is attached, a heterocyclic ring of group B. More preferably, said heterocyclic ring, which is formed by the NR group, is selected from piperidine, pyrrolidine, tetrahydrofuran, morpholine, piperazine, dioxolane and dioxane. Most preferably, when D is one of the above groups, R forms together with the nitrogen, to which it is attached, a piperidine ring having the structure

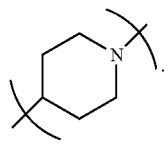

When D is

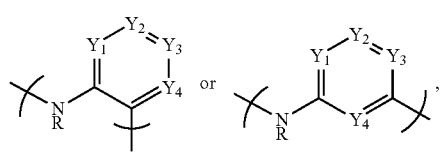

$Y_1$ to $Y_4$ are preferably CH or N.

In a more preferred embodiment, all of $Y_1$ to $Y_4$ are CH.

Even more preferably, one of $Y_1$ to $Y_4$ is N. and the other three are CH.

In a further more preferred embodiment, two of $Y_1$ to $Y_4$ are N and the other two are CH.

Yet more preferably, three of $Y_1$, to $Y_4$ are N and the other one is CH.

Still more preferably, all of $Y_1$ to $Y_4$ are N.

When $Y_4$ is CH, $Y_4$ may be substituted or unsubstituted.

In a preferred embodiment, $Y_4$ is CH and is unsubstituted.

In another preferred embodiment, $Y_4$ is CH and is substituted.

When $Y_4$ is CH and is substituted, $Y_4$ is preferably substituted with halogen or alkyl, most preferably with fluorine or methyl.

E is preferably

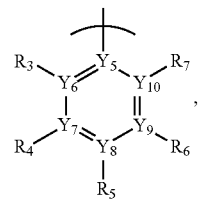

wherein $Y_5$ is C;

$Y_6$-$Y_{10}$ are independently selected from CH, N or O, and $R_3$, $R_4$, $R_5$, $R_6$, and $R_7$ are independently selected from hydrogen, halogen, alkyl, O-alkyl.

In a preferred embodiment, $Y_8$-$Y_{10}$ are independently selected from CH and N.

In a preferred embodiment, $R_3$, $R_4$, $R_5$, $R_6$, and $R_7$ are independently selected from hydrogen, halogen and O-alkyl.

In a further preferred embodiment, $R_3$, $R_4$, $R_5$, $R_6$, and $R_7$ are independently selected from O-phenyl and O-cycloalkyl.

When $R_3$, $R_4$, $R_5$, $R_6$, and $R_7$ independently are halogen, $R_3$, $R_4$, $R_5$, $R_6$, and $R_7$ are preferably fluorine or chlorine, most preferably fluorine.

When $R_3$, $R_4$, $R_5$, $R_6$, and $R_7$ independently are O-alkyl, $R_3$, $R_4$, $R_5$, $R_6$, and $R_7$ are O—$C_{1-4}$alkyl, preferably methoxy, ethoxy, propoxy or butoxy, more preferably methoxy or propoxy.

When $R_3$, $R_4$, $R_5$, $R_6$, and $R_7$ independently are O-alkyl, $R_3$, $R_4$, $R_5$, $R_6$, and $R_7$ are more most preferably methoxy.

$R_3$, $R_4$, $R_5$, $R_6$, and $R_7$ may independently be substituted or unsubstituted. Preferably, up to three of $R_3$-$R_7$ are substituted and the other ones are hydrogen.

In a most preferred embodiment, E represents a pyridine ring, wherein one of $Y_6$-$Y_{10}$ is N and the other ones are CH.

In another most preferred embodiment, E represents a pyridine ring, wherein two of $Y_6$-$Y_{10}$ are N and the other ones are CH.

Said pyrimidine ring may optionally be substituted with halo or alkyl, preferably fluorine and methoxy.

In a specifically preferred embodiment, there is provided a compound of formula (I), which is a compound of formula (IIa) or formula (IIb):

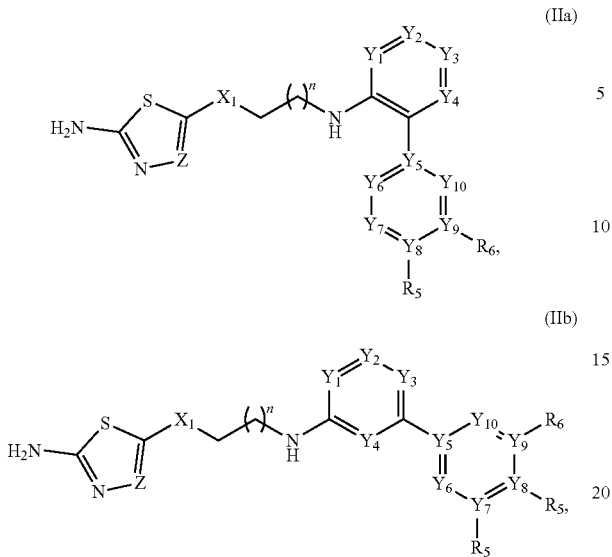

(IIa)

(IIb)

or a pharmaceutically acceptable salt, solvate or polymorph thereof, including all tautomers and stereoisomers thereof, wherein
Z is selected from CH and N;
$X_1$ is selected from alkyl, N, O, S, preferably from $CH_2$ and S;
n is 1 or 2;
$Y_1$ to $Y_4$ and $Y_6$ to $Y_{10}$ are independently selected from CH, N, S and O, preferably from CH and N,
$Y_5$ is C;
$R_5$ is selected from halogen, alkyl and O-alkyl, preferably from fluorine and methoxy; and
$R_6$ is selected from hydrogen, alkyl and O-alkyl, preferably from hydrogen and methoxy.
In a preferred embodiment, Z is CH.
In another preferred embodiment, Z is N.
Most preferably, $X_1$ is $CH_2$.
Further most preferably, $X_1$ is S.
Most preferably, n is 1.
Preferably, one, two, three or all four of $Y_1$, $Y_2$, $Y_3$ and $Y_4$ are N.
In more preferred embodiments,
$Y_1$, $Y_2$, $Y_3$ and $Y_4$ are CH; or
$Y_1$ is N and $Y_2$, $Y_3$ and $Y_4$ are CH; or
$Y_1$ and $Y_2$ are N and $Y_3$ and $Y_4$ are CH; or
$Y_1$ is CH, $Y_2$ is N and $Y_3$ and $Y_4$ are CH; or
$Y_1$ and $Y_3$ are N and $Y_2$ and $Y_4$ are CH; or
$Y_1$ and $Y_3$ are CH and $Y_2$ and $Y_4$ are N; or
$Y_1$ and $Y_2$ are CH and $Y_3$ and $Y_4$ are N; or
$Y_1$, $Y_2$ and $Y_3$ are CH and $Y_4$ is N.
Preferably one or two of $Y_6$ to $Y_{10}$ are N and the other of $Y_6$ to $Y_{10}$ are CH.
In more preferred embodiments,
$Y_6$, $Y_7$, $Y_8$, $Y_9$ and $Y_{10}$ are CH; or
$Y_6$ is N and $Y_7$, $Y_8$, $Y_9$ and $Y_{10}$ are CH; or
$Y_6$ is CH, $Y_7$ is N and $Y_8$, $Y_9$ and $Y_{10}$ are CH; or
$Y_6$ is N, $Y_7$, $Y_8$, $Y_9$ are CH and $Y_{10}$ is N; or
$Y_6$ and $Y_7$ are N and $Y_8$, $Y_9$ and $Y_{10}$ are CH; or
$Y_6$ is CH, $Y_7$ is N, $Y_8$ is CH, $Y_9$ is N and $Y_{10}$ is CH; or
$Y_6$ and $Y_7$ are CH, $Y_8$ is N, $Y_9$ is CH and $Y_{10}$ is N; or
$Y_6$ and $Y_7$ are CH, $Y_8$ is N, $Y_9$ and $Y_{10}$ are CH; or
$Y_6$ is N, $Y_7$ and $Y_8$ are CH, $Y_9$ is N and $Y_{10}$ is CH; or
$R_5$ is preferably hydrogen, fluorine or methoxy.

$R_6$ is preferably hydrogen or methoxy.
More preferably,
$R_5$ and $R_6$ are both hydrogen; or
$R_5$ is fluorine and $R_6$ is hydrogen; or
$R_5$ and $R_6$ are both methoxy.
In a further specifically preferred embodiment, there is provided a compound of formula (I), which is a compound of formula (IIIa) or formula (IIIb):

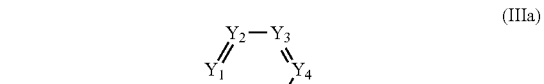

(IIIa)

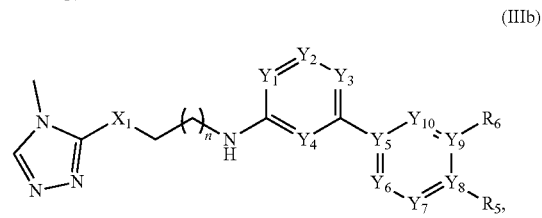

(IIIb)

or a pharmaceutically acceptable salt, solvate or polymorph thereof, including all tautomers and stereoisomers thereof, wherein
$X_1$ is selected from alkyl, N, O, S;
n is 1 or 2;
$Y_1$ to $Y_4$ and $Y_6$ to $Y_{10}$ are independently selected from CH, N, S and O, preferably from CH and N,
$Y_5$ is C;
$R_5$ is selected from halogen, alkyl and O-alkyl, preferably from fluorine and methoxy; and
$R_6$ is selected from hydrogen, alkyl and O-alkyl, preferably from hydrogen and methoxy.
Most preferably, $X_1$ is $CH_2$.
Further most preferably, $X_1$ is S.
Most preferably, n is 1.
Preferably, one, two, three or all four of $Y_1$, $Y_2$, $Y_3$ and $Y_4$ are N.
In more preferred embodiments,
$Y_1$, $Y_2$, $Y_3$ and $Y_4$ are CH; or
$Y_1$ is N and $Y_2$, $Y_3$ and $Y_4$ are CH; or
$Y_1$ and $Y_2$ are N and $Y_3$ and $Y_4$ are CH; or
$Y_1$ is CH, $Y_2$ is N and $Y_3$ and $Y_4$ are CH; or
$Y_1$ and $Y_3$ are N and $Y_2$ and $Y_4$ are CH; or
$Y_1$ and $Y_3$ are CH and $Y_2$ and $Y_4$ are N; or
$Y_1$ and $Y_2$ are CH and $Y_3$ and $Y_4$ are N; or
$Y_1$, $Y_2$ and $Y_3$ are CH and $Y_4$ is N.
Preferably one or two of $Y_6$ to $Y_{10}$ are N and the other of $Y_6$ to $Y_{10}$ are CH.
In more preferred embodiments.
$Y_6$, $Y_7$, $Y_8$, $Y_9$ and $Y_{10}$ are CH; or
$Y_6$ is N and $Y_7$, $Y_8$, $Y_9$ and $Y_{10}$ are CH; or
$Y_6$ is CH, $Y_7$ is N and $Y_8$, $Y_9$ and $Y_{10}$ are CH; or
$Y_6$ is N, $Y_7$, $Y_8$, $Y_9$ are CH and $Y_{10}$ is N; or
$Y_6$ and $Y_7$ are N and $Y_8$, $Y_9$ and $Y_{10}$ are CH; or
$Y_6$ is CH, $Y_7$ is N, $Y_8$ is CH, $Y_9$ is N and $Y_{10}$ is CH; or
$Y_6$ and $Y_7$ are CH, $Y_8$ is N, $Y_9$ is CH and $Y_{10}$ is N; or $Y_6$ and $Y_7$ are CH, $Y_8$ is N, $Y_9$ and $Y_{10}$ are CH; or
$Y_6$ is N, $Y_7$ and $Y_8$ are CH, $Y_9$ is N and $Y_{10}$ is CH; or
$R_5$ is preferably hydrogen, fluorine or methoxy.
R6 is preferably hydrogen or methoxy.
More preferably,
$R_5$ and $R_6$ are both hydrogen; or
$R_5$ is fluorine and $R_6$ is hydrogen; or
$R_5$ and $R_6$ are both methoxy.
In a further specifically preferred embodiment, there is provided a compound of formula (I), which is a compound of formula (IVa) or formula (IVb):

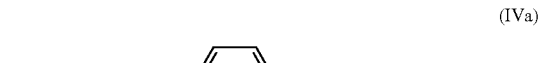
(IVa)

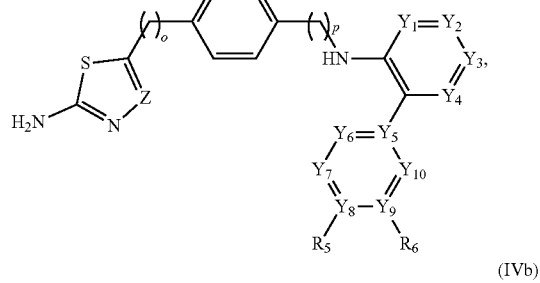
(IVb)

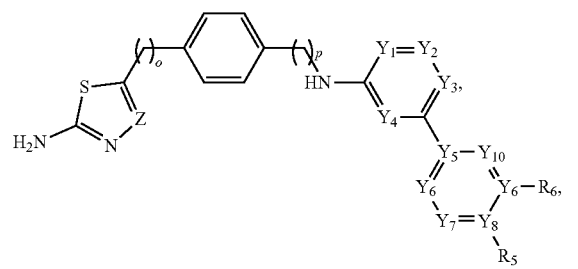

or a pharmaceutically acceptable salt, solvate or polymorph thereof, including all tautomers and stereoisomers thereof, wherein
Z is selected from CH and N;
is 0 or 1;
p is 0 or 1;
$Y_1$ to $Y_4$ and $Y_6$ to $Y_{10}$ are independently selected from CH, N, S and O, preferably from CH and N,
$Y_5$ is C;
$R_5$ is selected from halogen, alkyl and O-alkyl, preferably from fluorine and methoxy; and
$R_6$ is selected from hydrogen, alkyl and O-alkyl, preferably from hydrogen and methoxy.
In a further embodiment, $R_5$ is O-phenyl; and
$R_6$ is selected from hydrogen, alkyl and O-alkyl, preferably from hydrogen and methoxy.
In a preferred embodiment, Z is CH.
In another preferred embodiment, Z is N.
Most preferably, o is 0.
Most preferably, p is 0.
In a further most preferred embodiment, p is 1.
Preferably, one, two, three or all four of $Y_1$, $Y_2$, $Y_3$ and $Y_4$ are N.
In more preferred embodiments,
$Y_1$, $Y_2$, $Y_3$ and $Y_4$ are CH; or
$Y_1$ is N and $Y_2$, $Y_3$ and $Y_4$ are CH; or
$Y_1$ and $Y_2$ are N and $Y_3$ and $Y_4$ are CH; or
$Y_1$ is CH, $Y_2$ is N and $Y_3$ and $Y_4$ are CH; or
$Y_1$ and $Y_3$ are N and $Y_2$ and $Y_4$ are CH; or
$Y_1$ and $Y_3$ are CH and $Y_2$ and $Y_4$ are N; or
$Y_1$ and $Y_2$ are CH and $Y_3$ and $Y_4$ are N; or
$Y_1$, $Y_2$ and $Y_3$ are CH and $Y_4$ is N.
Preferably one or two of $Y_6$ to $Y_{10}$ are N and the other of $Y_6$ to $Y_{10}$ are CH.
In more preferred embodiments,
$Y_6$, $Y_7$, $Y_8$, $Y_9$ and $Y_{10}$ are CH; or
$Y_6$ is N and $Y_7$, $Y_8$, $Y_9$ and $Y_{10}$ are CH; or
$Y_6$ is CH, $Y_7$ is N and $Y_8$, $Y_9$ and $Y_{10}$ are CH; or
$Y_6$ is N, $Y_7$, $Y_8$, $Y_9$ are CH and $Y_{10}$ is N; or
$Y_6$ and $Y_7$ are N and $Y_8$, $Y_9$ and $Y_{10}$ are CH; or
$Y_6$ is CH, $Y_7$ is N, $Y_8$ is CH, $Y_9$ is N and $Y_{10}$ is CH; or
$Y_6$ and $Y_7$ are CH, $Y_8$ is N, $Y_9$ is CH and $Y_{10}$ is N; or
$Y_6$ and $Y_7$ are CH, $Y_8$ is N, $Y_9$ and $Y_{10}$ are CH; or
$Y_6$ is N, $Y_7$ and $Y_8$ are CH, $Y_9$ is N and $Y_{10}$ is CH; or
$R_5$ is preferably hydrogen, fluorine or methoxy.
Further preferably, $R_5$ is propoxy or O-phenyl.
$R_6$ is preferably hydrogen or methoxy.
More preferably,
$R_5$ and $R_6$ are both hydrogen; or
$R_5$ is fluorine and $R_6$ is hydrogen; or
$R_5$ is methoxy and $R_6$ is hydrogen; or
$R_5$ and $R_6$ are both methoxy; or
$R_5$ is propoxy and $R_6$ is hydrogen; or
$R_5$ is O-phenyl and $R_6$ is hydrogen; or.
In a further specifically preferred embodiment, there is provided a compound of formula (I), which is a compound of formula (Va) or formula (Vb):

(Va)

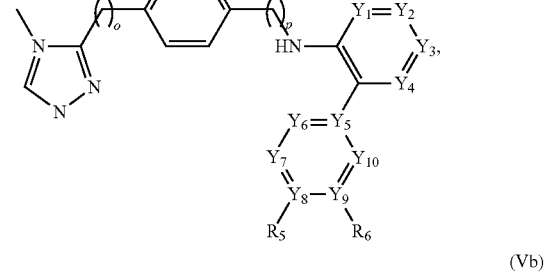
(Vb)

or a pharmaceutically acceptable salt, solvate or polymorph thereof, including all tautomers and stereoisomers thereof, wherein
o is 0 or 1;
p is 0 or 1;
$Y_1$ to $Y_4$ and $Y_6$ to $Y_{10}$ are independently selected from CH, N, S and O, preferably from CH and N,
$Y_5$ is C;
$R_5$ is selected from halogen, alkyl and O-alkyl, preferably from fluorine and methoxy; and
$R_6$ is selected from hydrogen, alkyl and O-alkyl, preferably from hydrogen and methoxy.

In a further embodiment, R₅ is O-phenyl; and
R₆ is selected from hydrogen, alkyl and O-alkyl, preferably from hydrogen and methoxy.
In a preferred embodiment, Z is CH.
In another preferred embodiment, Z is N.
Most preferably, o is 0.
Most preferably, p is 0.
In a further most preferred embodiment, p is 1.
Preferably, one, two, three or all four of Y₁, Y₂, Y₃ and Y₄ are N.
In more preferred embodiments,
Y₁, Y₂, Y₃ and Y₄ are CH; or
Y₁ is N and Y₂, Y₃ and Y₄ are CH; or
Y₁ and Y₂ are N and Y₃ and Y₄ are CH; or
Y₁ is CH, Y₂ is N and Y₃ and Y₄ are CH; or
Y₁ and Y₃ are N and Y₂ and Y₄ are CH; or
Y₁ and Y₃ are CH and Y₂ and Y₄ are N; or
Y₁ and Y₂ are CH and Y₃ and Y₄ are N; or
Y₁ and Y₂ are CH; Y₃ is N and Y₄ is CH, or
Y₁, Y₂ and Y₃ are CH and Y₄ is N.
Preferably one or two of Y₆ to Y₁₀ are N and the other of Y₆ to Y₁₀ are CH.
In more preferred embodiments.
Y₆, Y₇, Y₈, Y₉ and Y₁₀ are CH; or
Y₆ is N and Y₇, Y₈, Y₉ and Y₁₀ are CH; or
Y₆ is CH, Y₇ is N and Ye, Y₉ and Y₁₀ are CH; or
Y₆ is N, Y₇, Y₈, Y₉ are CH and Y₁₀ is N; or
Y₆ and Y₇ are N and Y₈, Y₉ and Y₁₀ are CH; or
Y₆ is CH, Y₇ is N, Y₈ is CH, Y₉ is N and Y₁₀ is CH; or
Y₆ and Y₇ are CH, Y₈ is N, Y₉ is CH and Y₁₀ is N; or
Y₆ and Y₇ are CH, Y₈ is N, Y₉ and Y₁₀ are CH; or
Y₆ is N, Y₇ and Y₈ are CH, Y₉ is N and Y₁₀ is CH; or
R₅ is preferably hydrogen, fluorine or methoxy.
R₆ is preferably hydrogen or methoxy.
More preferably,
R₅ and R₆ are both hydrogen; or
R₅ is fluorine and R₆ is hydrogen; or
R₅ and R₆ are both methoxy.
In a further specifically preferred embodiment, there is provided a compound of formula (I), which is a compound of formula (VI):

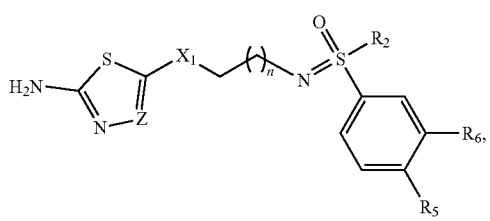

(VI)

or a pharmaceutically acceptable salt, solvate or polymorph thereof, including all tautomers and stereoisomers thereof, wherein
Z is selected from CH and N;
X₁ is selected from alkyl, N, O, S, preferably from CH₂ or S;
n is 1 or 2;
R₅ is selected from halogen, alkyl and O-alkyl, preferably from fluorine and methoxy; and
R₆ is selected from hydrogen, alkyl and O-alkyl, preferably from hydrogen and methoxy.
In a preferred embodiment, Z is CH.
In another preferred embodiment, Z is N.

Most preferably, X₁ is CH₂.
Further most preferably, X₁ is S.
Most preferably, n is 1.
R₅ is preferably hydrogen, fluorine or methoxy.
R₆ is preferably hydrogen or methoxy.
More preferably,
R₅ is fluorine and R₆ is hydrogen; or
R₅ and R₆ are both methoxy.
In a further specifically preferred embodiment, there is provided a compound of formula (I), which is a compound of formula (VII):

(VII)

or a pharmaceutically acceptable salt, solvate or polymorph thereof, including all tautomers and stereoisomers thereof, wherein
Z is selected from CH and N;
X₁ is selected from alkyl, N, O, S, preferably from CH₂ or S;
n is 1 or 2;
R₂ is selected from alkyl and cycloalkyl, preferably from methyl and cyclopropyl;
R₅ is selected from halogen, alkyl and O-alkyl, preferably from fluorine and methoxy; and
R₆ is selected from hydrogen, alkyl and O-alkyl, preferably from hydrogen and methoxy.
In a preferred embodiment, Z is CH.
In another preferred embodiment, Z is N.
Most preferably, X₁ is CH₂.
Further most preferably, X₁ is S.
Most preferably, n is 1.
In a preferred embodiment, R₂ is methyl.
In a further preferred embodiment, R₂ is cyclopropyl.
R₅ is preferably hydrogen, fluorine or methoxy.
R₆ is preferably hydrogen or methoxy.
More preferably,
R₅ is fluorine and R₆ is hydrogen; or
R₅ and R₆ are both methoxy.
In a further specifically preferred embodiment, there is provided a compound of formula (I), which is a compound of formula (VIII):

(VIII)

or a pharmaceutically acceptable salt, solvate or polymorph thereof, including all tautomers and stereoisomers thereof, wherein $X_1$ is selected from alkyl, N, O, S, preferably from $CH_2$ or S;

n is 1 or 2;

$R_5$ is selected from halogen, alkyl and O-alkyl, preferably from fluorine and methoxy; and $R_6$ is selected from hydrogen, alkyl and O-alkyl, preferably from hydrogen and methoxy.

Most preferably, $X_1$ is $CH_2$.

Further most preferably, $X_1$ is S.

Most preferably, n is 1.

$R_5$ is preferably hydrogen, fluorine or methoxy.

$R_6$ is preferably hydrogen or methoxy.

More preferably, $R_5$ is fluorine and $R_6$ is hydrogen; or $R_5$ and $R_6$ are both methoxy.

In a further specifically preferred embodiment, there is provided a compound of formula (I), which is a compound of formula (IX):

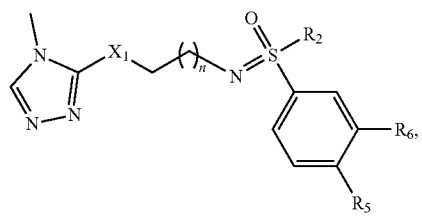

(IX)

or a pharmaceutically acceptable salt, solvate or polymorph thereof, including all tautomers and stereoisomers thereof, wherein $X_1$ is selected from alkyl, N, O, S, preferably from $CH_2$ or S;

n is 1 or 2;

$R_2$ is selected from alkyl and cycloalkyl, preferably from methyl and cyclopropyl;

$R_5$ is selected from halogen, alkyl and O-alkyl, preferably from fluorine and methoxy; and $R_6$ is selected from hydrogen, alkyl and O-alkyl, preferably from hydrogen and methoxy.

Most preferably, $X_1$ is $CH_2$.

Further most preferably, $X_1$ is S.

Most preferably, n is 1.

In a preferred embodiment, $R_2$ is methyl.

In a further preferred embodiment, $R_2$ is cyclopropyl.

$R_5$ is preferably hydrogen, fluorine or methoxy.

$R_6$ is preferably hydrogen or methoxy.

More preferably, $R_5$ is fluorine and $R_6$ is hydrogen; or $R_5$ and $R_6$ are both methoxy.

In a further specifically preferred embodiment, there is provided a compound of formula (I), which is a compound of formula (X):

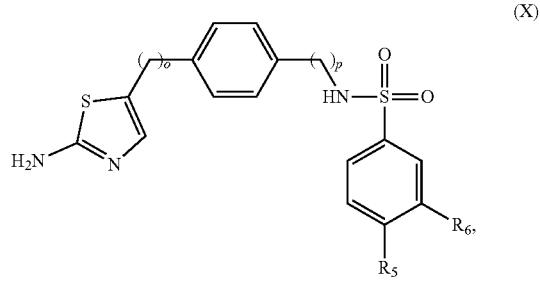

(X)

or a pharmaceutically acceptable salt, solvate or polymorph thereof, including all tautomers and stereoisomers thereof, wherein is 0 or 1;

$R_5$ is selected from halogen, alkyl and O-alkyl, preferably from fluorine and methoxy; and $R_6$ is selected from hydrogen, alkyl and O-alkyl, preferably from hydrogen and methoxy.

Most preferably, o is 0.

Most preferably, p is 0.

Even most preferably, p is 1.

$R_5$ is preferably hydrogen, fluorine or methoxy.

$R_6$ is preferably hydrogen or methoxy.

More preferably, $R_5$ is fluorine and $R_6$ is hydrogen; or $R_5$ and $R_6$ are both methoxy.

In a further specifically preferred embodiment, there is provided a compound of formula (I), which is a compound of formula (XI):

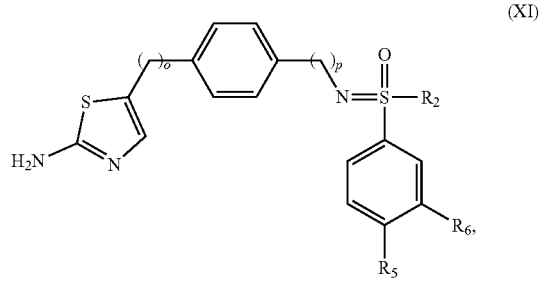

(XI)

or a pharmaceutically acceptable salt, solvate or polymorph thereof, including all tautomers and stereoisomers thereof, wherein o is 0 or 1;

$R_2$ is selected from alkyl and cycloalkyl, preferably from methyl and cyclopropyl;

$R_5$ is selected from halogen, alkyl and O-alkyl, preferably from fluorine and methoxy; and $R_6$ is selected from hydrogen, alkyl and O-alkyl, preferably from hydrogen and methoxy.

Most preferably, o is 0.

Most preferably, p is 0.

Even most preferably, p is 1.

In a preferred embodiment, $R_2$ is methyl.

In a further preferred embodiment, $R_2$ is cyclopropyl.

$R_5$ is preferably hydrogen, fluorine or methoxy.

R6 is preferably hydrogen or methoxy.

More preferably, $R_5$ is fluorine and $R_6$ is hydrogen; or $R_5$ and $R_6$ are both methoxy.

In a further specifically preferred embodiment, there is provided a compound of formula (I), which is a compound of formula (XIIa) or formula (XIIb):

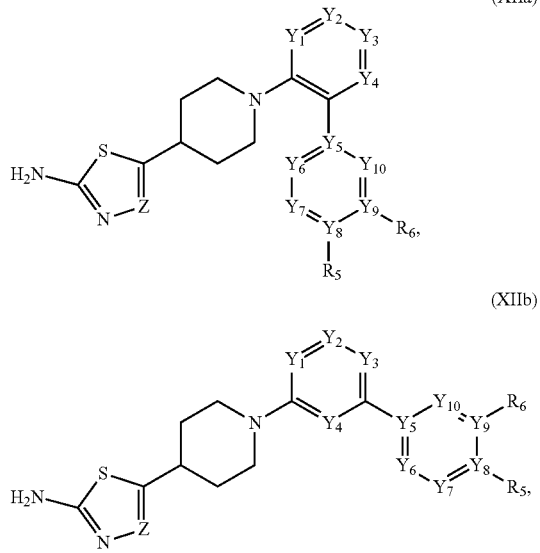

or a pharmaceutically acceptable salt, solvate or polymorph thereof, including all tautomers and stereoisomers thereof, wherein Z is selected from CH and N;
$Y_1$ to $Y_4$ and $Y_6$ to $Y_{10}$ are independently selected from CH, N, S and O, preferably from CH and N,
$Y_5$ is C;
$R_5$ is selected from halogen, alkyl and O-alkyl, preferably from fluorine and methoxy; and
$R_6$ is selected from hydrogen, alkyl and O-alkyl, preferably from hydrogen and methoxy.

In a preferred embodiment, Z is CH.
In another preferred embodiment, Z is N.
Preferably, one, two, three or all four of $Y_1$, $Y_2$, $Y_3$ and $Y_4$ are N.

In more preferred embodiments,
$Y_1$, $Y_2$, $Y_3$ and $Y_4$ are CH; or
$Y_1$ is N and $Y_2$, $Y_3$ and $Y_4$ are CH; or
$Y_1$ and $Y_2$ are N and $Y_3$ and $Y_4$ are CH; or
$Y_1$ is CH, $Y_2$ is N and $Y_3$ and $Y_4$ are CH; or
$Y_1$ and $Y_3$ are N and $Y_2$ and $Y_4$ are CH; or
$Y_1$ and $Y_3$ are CH and $Y_2$ and $Y_4$ are N; or
$Y_1$ and $Y_2$ are CH and $Y_3$ and $Y_4$ are N; or
$Y_1$, $Y_2$ and $Y_3$ are CH and $Y_4$ is N.
Preferably one or two of $Y_6$ to $Y_{10}$ are N and the other of $Y_6$ to $Y_{10}$ are CH.

In more preferred embodiments,
$Y_6$, $Y_7$, $Y_8$, $Y_9$ and $Y_{10}$ are CH; or
$Y_6$ is N and $Y_7$, $Y_8$, $Y_9$ and $Y_{10}$ are CH; or
$Y_6$ is CH, $Y_7$ is N and $Y_8$, $Y_9$ and $Y_{10}$ are CH; or
$Y_6$ is N, $Y_7$, $Y_8$, $Y_9$ are CH and $Y_{10}$ is N; or
$Y_6$ and $Y_7$ are N and $Y_8$, $Y_9$ and $Y_{10}$ are CH; or
$Y_6$ is CH, $Y_7$ is N, $Y_8$ is CH, $Y_9$ is N and $Y_{10}$ is CH; or
$Y_6$ and $Y_7$ are CH, $Y_8$ is N, $Y_9$ is CH and $Y_{10}$ is N; or
$Y_6$ and $Y_7$ are CH, $Y_8$ is N, $Y_9$ and $Y_{10}$ are CH; or
$Y_6$ is N, $Y_7$ and $Y_8$ are CH, $Y_9$ is N and $Y_{10}$ is CH; or
$R_5$ is preferably hydrogen, fluorine or methoxy.
$R_6$ is preferably hydrogen or methoxy.

More preferably,
$R_5$ and $R_6$ are both hydrogen; or
$R_5$ is fluorine and $R_6$ is hydrogen; or
$R_5$ and $R_6$ are both methoxy.

In a further specifically preferred embodiment, there is provided a compound of formula (I), which is a compound of formula (XIII):

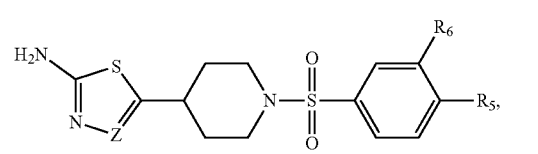

or a pharmaceutically acceptable salt, solvate or polymorph thereof, including all tautomers and stereoisomers thereof, wherein Z is selected from CH and N;
$R_5$ is selected from halogen, alkyl and O-alkyl, preferably from fluorine and methoxy; and
$R_6$ is selected from hydrogen, alkyl and O-alkyl, preferably from hydrogen and methoxy.

In a preferred embodiment, Z is CH.
In another preferred embodiment, Z is N.
$R_5$ is preferably hydrogen, fluorine or methoxy.
$R_6$ is preferably hydrogen or methoxy.

More preferably,
$R_5$ is fluorine and $R_6$ is hydrogen; or
$R_5$ and $R_6$ are both methoxy.

In a further specifically preferred embodiment, there is provided a compound of formula (I), which is a compound of formula (XIV):

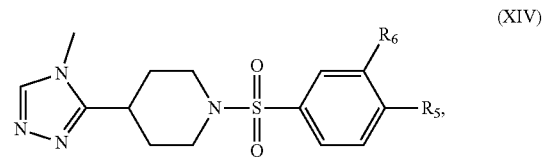

or a pharmaceutically acceptable salt, solvate or polymorph thereof, including all tautomers and stereoisomers thereof, wherein $R_5$ is selected from halogen, alkyl and O-alkyl, preferably from fluorine and methoxy; and
$R_6$ is selected from hydrogen, alkyl and O-alkyl, preferably from hydrogen and methoxy.
$R_5$ is preferably hydrogen, fluorine or methoxy.
$R_6$ is preferably hydrogen or methoxy.

More preferably,
$R_5$ is fluorine and $R_6$ is hydrogen; or
$R_5$ and $R_6$ are both methoxy.

In a further specifically preferred embodiment, there is provided a compound of formula (I), which is a compound of formula (XVa) or formula (XVb):

(XVa)

(XVb)

or a pharmaceutically acceptable salt, solvate or polymorph thereof, including all tautomers and stereoisomers thereof, wherein
  $Y_1$ to $Y_4$ and $Y_6$ to $Y_{10}$ are independently selected from CH, N, S and O, preferably from CH and N,
  $Y_5$ is C;
  $R_5$ is selected from halogen, alkyl, O-alkyl, O-phenyl and O-cycloalkyl, preferably from halogen, O—$C_{1-4}$alkyl, O-phenyl and O-cycloalkyl.
  In a more preferred embodiment, $R_5$ is fluorine or chlorine, most preferably fluorine.
  In another more preferred embodiment, $R_5$ is O—$C_{1-4}$alkyl, such as methoxy, ethoxy, propoxy or butoxy, most preferably methoxy, propoxy or propan-2-yloxy.
  In another more preferred embodiment, $R_5$ is O-phenyl.
  In another more preferred embodiment, $R_5$ is O-cycloalkyl, most preferably O-cyclohexyl.
  $R_6$ is selected from hydrogen, alkyl and O-alkyl, preferably from hydrogen and methoxy.
  Preferably, one, two, three or all four of $Y_1$, $Y_2$, $Y_3$ and $Y_4$ are N.
  In more preferred embodiments,
  $Y_1$, $Y_2$, $Y_3$ and $Y_4$ are CH; or
  $Y_1$ is N and $Y_2$, $Y_3$ and $Y_4$ are CH; or
  $Y_1$ and $Y_2$ are N and $Y_3$ and $Y_4$ are CH; or
  $Y_1$ is CH, $Y_2$ is N and $Y_3$ and $Y_4$ are CH; or
  $Y_1$ and $Y_3$ are N and $Y_2$ and $Y_4$ are CH; or
  $Y_1$ and $Y_3$ are CH and $Y_2$ and $Y_4$ are N; or
  $Y_1$ and $Y_2$ are CH and $Y_3$ and $Y_4$ are N; or
  $Y_1$ is N, $Y_2$ and $Y_3$ are CH and $Y_4$ is N; or
  $Y_1$, $Y_2$ and $Y_3$ are CH and $Y_4$ is N.
  When $Y_4$ is CH, $Y_4$ may be substituted or unsubstituted.
  In a preferred embodiment, $Y_4$ is CH and is unsubstituted.
  In another preferred embodiment, $Y_4$ is CH and is substituted.
  When $Y_4$ is CH and is substituted. $Y_4$ is preferably substituted with halogen or alkyl, most preferably with fluorine or methyl.
  Preferably one or two of $Y_6$ to $Y_{10}$ are N and the other of $Y_6$ to $Y_{10}$ are CH.
  In more preferred embodiments,
  $Y_6$, $Y_7$, $Y_8$, $Y_9$ and $Y_{10}$ are CH; or
  $Y_6$ is N and $Y_7$, $Y_8$, $Y_9$ and $Y_{10}$ are CH; or
  $Y_6$ is CH, $Y_7$ is N and $Y_8$, $Y_9$ and $Y_{10}$ are CH; or
  $Y_6$ is N, $Y_7$, $Y_8$, $Y_9$ are CH and $Y_{10}$ is N; or
  $Y_6$ and $Y_7$ are N and $Y_8$, $Y_9$ and $Y_{10}$ are CH; or
  $Y_6$ is CH, $Y_7$ is N, $Y_8$ is CH, $Y_9$ is N and $Y_{10}$ is CH; or
  $Y_6$ and $Y_7$ are CH, $Y_8$ is N, $Y_9$ is CH and $Y_{10}$ is N; or
  $Y_6$ and $Y_7$ are CH, $Y_8$ is N, $Y_9$ and $Y_{10}$ are CH; or
  $Y_6$ is N, $Y_7$ and $Y_8$ are CH, $Y_9$ is N and $Y_{10}$ is CH; or
  $R_5$ is preferably hydrogen, fluorine or methoxy.
  $R_6$ is preferably hydrogen or methoxy.
  More preferably,
  $R_5$ and $R_6$ are both hydrogen; or
  $R_5$ is fluorine and $R_6$ is hydrogen; or
  $R_5$ and $R_6$ are both methoxy.
  In a further specifically preferred embodiment, there is provided a compound of formula (I), which is a compound of formula (XVI):

(XVI)

or a pharmaceutically acceptable salt, solvate or polymorph thereof, including all tautomers and stereoisomers thereof, wherein
  $R_5$ is selected from halogen, alkyl and O-alkyl, preferably from fluorine and methoxy; and
  $R_6$ is selected from hydrogen, alkyl and O-alkyl, preferably from hydrogen and methoxy.
  $R_5$ is preferably hydrogen, fluorine or methoxy.
  R6 is preferably hydrogen or methoxy.
  More preferably,
  $R_5$ is fluorine and $R_6$ is hydrogen; or
  $R_5$ and $R_6$ are both methoxy.
  In a further specifically preferred embodiment, there is provided a compound of formula (I), which is a compound of formula (XVII):

(XVII)

or a pharmaceutically acceptable salt, solvate or polymorph thereof, including all tautomers and stereoisomers thereof, wherein
  $R_2$ is selected from alkyl and cycloalkyl, preferably from methyl and cyclopropyl;
  $R_5$ is selected from halogen, alkyl and O-alkyl, preferably from fluorine and methoxy; and
  $R_6$ is selected from hydrogen, alkyl and O-alkyl, preferably from hydrogen and methoxy.
  In a preferred embodiment, $R_2$ is methyl.
  In a further preferred embodiment, $R_2$ is cyclopropyl.
  $R_5$ is preferably hydrogen, fluorine or methoxy.
  R6 is preferably hydrogen or methoxy.

More preferably,
$R_5$ is fluorine and $R_6$ is hydrogen; or
$R_5$ and $R_6$ are both methoxy.

In a further specifically preferred embodiment, there is provided a compound of formula (I), which is a compound of formula (XVIII):

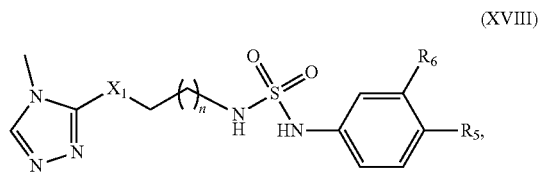

(XVIII)

or a pharmaceutically acceptable salt, solvate or polymorph thereof, including all tautomers and stereoisomers thereof, wherein
$X_1$ is selected from alkyl, N, O, S, preferably from $CH_2$ or S;
n is 1 or 2;
$R_5$ is selected from halogen, alkyl and O-alkyl, preferably from fluorine and methoxy; and
$R_6$ is selected from hydrogen, alkyl and O-alkyl, preferably from hydrogen and methoxy.
Most preferably, $X_1$ is $CH_2$.
Further most preferably, $X_1$ is S.
Most preferably, n is 1.
$R_5$ is preferably hydrogen, fluorine or methoxy.
$R_6$ is preferably hydrogen or methoxy.
More preferably,
$R_5$ is fluorine and $R_6$ is hydrogen; or
$R_5$ and $R_6$ are both methoxy.

In one embodiment, the compound of formula (I) is a compound according to any one of examples 1 to 1323 or a pharmaceutically acceptable salt, solvate or polymorph thereof, including all tautomers and stereoisomers.

In a preferred embodiment, the compound of formula (I) is a compound selected from:
5-[3-({4'-fluoro-[1,1'-biphenyl]-2-yl}amino)propyl]-1,3,4-thiadiazol-2-amine;
5-{[2-({4'-fluoro-[1,1'-biphenyl]-2-yl}amino)ethyl]sulfanyl}-1,3,4-thiadiazol-2-amine;
5-{[2-({3',4'-dimethoxy-[1,1'-biphenyl]-2-yl)amino)ethyl]sulfanyl}-1,3,4-thiadiazol-2-amine;
4'-fluoro-N-[3-(4-methyl-4H-1,2,4-triazol-3-yl)propyl]-[1,1'-biphenyl]-2-amine;
3',4'-dimethoxy-N-[3-(4-methyl-4H-1,2,4-triazol-3-yl)propyl]-[1,1'-biphenyl]-2-amine;
5-[4-({4'-fluoro-[1,1'-biphenyl]-2-yl}amino)phenyl]-1,3,4-thiadiazol-2-amine;
5-(4-{[2-(3,4-dimethoxyphenyl)phenyl]amino}phenyl)-1,3,4-thiadiazol-2-amine;
5-(4-{[2-(4-methoxyphenyl)phenyl]amino}phenyl)-1,3,4-thiadiazol-2-amine;
N-[4-(5-amino-1,3,4-thiadiazol-2-yl)phenyl]-3-(4-methoxyphenyl)pyridin-2-amine;
N-[4-(5-amino-1,3,4-thiadiazol-2-yl)phenyl]-3-(4-methoxyphenyl)pyridin-4-amine;
N-[4-(5-amino-1,3,4-thiadiazol-2-yl)phenyl]-3-(3,4-dimethoxyphenyl)pyridin-4-amine;
N-[4-(5-amino-1,3,4-thiadiazol-2-yl)phenyl]-3-(4-fluorophenyl)pyridin-2-amine;
N-[4-(5-amino-1,3,4-thiadiazol-2-yl)phenyl]-3-(4-fluorophenyl)pyrazin-2-amine;
5-(4-{[2-(4-phenoxyphenyl)phenyl]amino}phenyl)-1,3,4-thiadiazol-2-amine;
5-(4-{[2-(4-propoxyphenyl)phenyl]amino)phenyl)-1,3,4-thiadiazol-2-amine;
5-[4-({2-[4-(propan-2-yloxy)phenyl]phenyl}amino)phenyl]-1,3,4-thiadiazol-2-amine;
4'-fluoro-N-[4-(4-methyl-4H-1,2,4-triazol-3-yl)phenyl]-[1,1'-biphenyl]-2-amine;
3',4'-dimethoxy-N-[4-(4-methyl-4H-1,2,4-triazol-3-yl)phenyl]-[1,1'-biphenyl]-2-amine;
N-[2-(4-methoxyphenyl)phenyl]-4-(4-methyl-4H-1,2,4-triazol-3-yl)aniline:
2-(4-methoxyphenyl)-N-[4-(4-methyl-4H-1,2,4-triazol-3-yl)phenyl]pyridin-3-amine;
2-(4-fluorophenyl)-N-[4-(4-methyl-4H-1,2,4-triazol-3-yl)phenyl]pyridin-3-amine;
4-(4-methyl-4H-1,2,4-triazol-3-yl)-N-[2-(4-phenoxyphenyl)phenyl]aniline;
3-(3,4-dimethoxyphenyl)-N-[4-(4-methyl-4H-1,2,4-triazol-3-yl)phenyl]pyridin-4-amine;
N-[3-(5-amino-1,3,4-thiadiazol-2-yl)propyl]-4-fluorobenzene-1-sulfonamide;
N-{2-[(5-amino-1,3,4-thiadiazol-2-yl)sulfanyl]ethyl}-4-fluorobenzene-1-sulfonamide;
5-(3-{[(4-fluorophenyl)(methyl)oxo-λω-sulfanylidene]amino}propyl)-1,3,4-thiadiazol-2-amine;
4-fluoro-N-[3-(4-methyl-4H-1,2,4-triazol-3-yl)propyl]benzene-1-sulfonamide;
4-fluoro-N-{2-[(4-methyl-4H-1,2,4-triazol-3-yl)sulfanyl]ethyl}benzene-1-sulfonamide;
[(3,4-dimethoxyphenyl)sulfamoyl]({2-[(4-methyl-4H-1,2,4-triazol-3-yl)sulfanyl]ethyl})amine;
N-[4-(2-amino-1,3-thiazol-5-yl)phenyl]-4-fluorobenzene-1-sulfonamide;
N-[4-(2-amino-1,3-thiazol-5-yl)phenyl]-3,4-dimethoxybenzene-1-sulfonamide;
5-(1-{4'-fluoro-[1,1'-biphenyl]-2-yl}piperidin-4-yl)-1,3,4-thiadiazol-2-amine;
5-[1-(4-fluorobenzenesulfonyl)piperidin-4-yl]-1,3-thiazol-2-amine;
5-[1-(4-fluorobenzenesulfonyl)piperidin-4-yl]-1,3,4-thiadiazol-2-amine;
1-(4-fluorobenzenesulfonyl)-4-(4-methyl-4H-1,2,4-triazol-3-yl)piperidine;
N-[(1H-1,3-benzodiazol-5-yl)methyl]-4'-fluoro-[1,1'-biphenyl]-2-amine;
N-[(1H-1,3-benzodiazol-5-yl)methyl]-3',4'-dimethoxy-[1,1'-biphenyl]-2-amine:
N-(1H-1,3-benzodiazol-5-ylmethyl)-2-(4-methoxyphenyl)aniline;
N-(1H-1,3-benzodiazol-5-ylmethyl)-2-(4-methoxyphenyl)pyridin-3-amine;
N-(1H-1,3-benzodiazol-5-ylmethyl)-3-(4-methoxyphenyl)pyridin-2-amine;
N-(1H-1,3-benzodiazol-5-ylmethyl)-3-(4-methoxyphenyl)pyridin-4-amine;
N-(1H-1,3-benzodiazol-5-ylmethyl)-4-(4-methoxyphenyl)pyridin-3-amine;
N-(1H-1,3-benzodiazol-5-ylmethyl)-5-(4-methoxyphenyl)pyrimidin-4-amine;
N-(1H-1,3-benzodiazol-5-ylmethyl)-3-(4-methoxyphenyl)pyrazin-2-amine;
N-(1H-1,3-benzodiazol-5-ylmethyl)-3-(3,4-dimethoxyphenyl)pyridin-4-amine;
N-(1H-1,3-benzodiazol-5-ylmethyl)-3-(3,4-dimethoxyphenyl)pyridin-2-amine;

N-(1H-1,3-benzodiazol-5-ylmethyl)-3-(3,4-dimethoxyphenyl)pyrazin-2-amine;
N-(1H-1,3-benzodiazol-5-ylmethyl)-2-(4-fluorophenyl)pyridin-3-amine;
N-(1H-1,3-benzodiazol-5-ylmethyl)-3-(4-fluorophenyl)pyridin-2-amine;
N-(1H-1,3-benzodiazol-5-ylmethyl)-3-(4-fluorophenyl)pyrazin-2-amine;
N-(1H-1,3-benzodiazol-5-ylmethyl)-2-(4-phenoxyphenyl)aniline;
N-(1H-1,3-benzodiazol-5-ylmethyl)-2-[4-(cyclohexyloxy)phenyl]aniline;
N-(1H-1,3-benzodiazol-5-ylmethyl)-2-(4-propoxyphenyl)aniline;
N-(1H-1,3-benzodiazol-5-ylmethyl)-2-[4-(propan-2-yloxy)phenyl]aniline;
N-(1H-1,3-benzodiazol-5-ylmethyl)-2-(4-methoxyphenyl)-3-methylaniline;
N-(1H-1,3-benzodiazol-5-ylmethyl)-2-(3,4-dimethoxyphenyl)-3-methylaniline;
N-(1H-1,3-benzodiazol-5-ylmethyl)-2-(4-chlorophenyl)-3-fluoroaniline;
N-(1H-1,3-benzodiazol-5-ylmethyl)-2-(3,4-dimethoxyphenyl)-3-fluoroaniline;
N-(1H-1,3-benzodiazol-5-ylmethyl)-3-fluoro-2-(4-fluorophenyl)aniline;
N-[(1H-1,3-benzodiazol-5-yl)methyl]-4-fluorobenzene-1-sulfonamide; and
[(1H-1,3-benzodiazol-5-yl)methyl][(4-fluorophenyl)(methyl)oxo-λω-sulfanylidene]amine;
or a pharmaceutically acceptable salt, solvate or polymorph thereof, including all tautomers and stereoisomers.

In a more preferred embodiment, the compound of formula (I) is a compound selected from:
5-(1-{4'-fluoro-[1,1'-biphenyl]-2-yl}piperidin-4-yl)-1,3,4-thiadiazol-2-amine;
N-[(1H-1,3-benzodiazol-5-yl)methyl]-4'-fluoro-[1,1'-biphenyl]-2-amine;
N-[(1H-1,3-benzodiazol-5-yl)methyl]-3',4'-dimethoxy-[1,1'-biphenyl]-2-amine;
N-(1H-1,3-benzodiazol-5-ylmethyl)-2-(4-methoxyphenyl)aniline;
N-(1H-1,3-benzodiazol-5-ylmethyl)-2-(4-methoxyphenyl)pyridin-3-amine;
N-(1H-1,3-benzodiazol-5-ylmethyl)-3-(4-methoxyphenyl)pyridin-2-amine;
N-(1H-1,3-benzodiazol-5-ylmethyl)-3-(4-methoxyphenyl)pyridin-4-amine;
N-(1H-1,3-benzodiazol-5-ylmethyl)-4-(4-methoxyphenyl)pyridin-3-amine;
N-(1H-1,3-benzodiazol-5-ylmethyl)-5-(4-methoxyphenyl)pyrimidin-4-amine;
N-(1H-1,3-benzodiazol-5-ylmethyl)-3-(4-methoxyphenyl)pyrazin-2-amine;
N-(1H-1,3-benzodiazol-5-ylmethyl)-3-(3,4-dimethoxyphenyl)pyridin-4-amine;
N-(1H-1,3-benzodiazol-5-ylmethyl)-3-(3,4-dimethoxyphenyl)pyridin-2-amine;
N-(1H-1,3-benzodiazol-5-ylmethyl)-3-(3,4-dimethoxyphenyl)pyrazin-2-amine:
N-(1H-1,3-benzodiazol-5-ylmethyl)-2-(4-fluorophenyl)pyridin-3-amine;
N-(1H-1,3-benzodiazol-5-ylmethyl)-3-(4-fluorophenyl)pyridin-2-amine;
N-(1H-1,3-benzodiazol-5-ylmethyl)-3-(4-fluorophenyl)pyrazin-2-amine;
N-(1H-1,3-benzodiazol-5-ylmethyl)-2-(4-phenoxyphenyl)aniline;
N-(1H-1,3-benzodiazol-5-ylmethyl)-2-[4-(cyclohexyloxy)phenyl]aniline;
N-(1H-1,3-benzodiazol-5-ylmethyl)-2-(4-propoxyphenyl)aniline;
N-(1H-1,3-benzodiazol-5-ylmethyl)-2-[4-(propan-2-yloxy)phenyl]aniline;
N-(1H-1,3-benzodiazol-5-ylmethyl)-2-(4-methoxyphenyl)-3-methylaniline;
N-(1H-1,3-benzodiazol-5-ylmethyl)-2-(3,4-dimethoxyphenyl)-3-methylaniline;
N-(1H-1,3-benzodiazol-5-ylmethyl)-2-(4-chlorophenyl)-3-fluoroaniline;
N-(1H-1,3-benzodiazol-5-ylmethyl)-2-(3,4-dimethoxyphenyl)-3-fluoroaniline:
N-(1H-1,3-benzodiazol-5-ylmethyl)-3-fluoro-2-(4-fluorophenyl)aniline;
N-(1H-1,3-benzodiazol-5-ylmethyl)-2-(4-methoxyphenyl)-3-methylaniline:
N-(1H-1,3-benzodiazol-5-ylmethyl)-2-(3,4-dimethoxyphenyl)-3-methylaniline; and
N-(1H-1,3-benzodiazol-5-ylmethyl)-2-(3,4-dimethoxyphenyl)-3-fluoroaniline;
or a pharmaceutically acceptable salt, solvate or polymorph thereof, including all tautomers and stereoisomers.

In an evenly preferred embodiment, the compound of formula (I) is a compound selected from:
5-(1-{4'-fluoro-[1,1'-biphenyl]-2-yl}piperidin-4-yl)-1,3,4-thiadiazol-2-amine;
N-[(1H-1,3-benzodiazol-5-yl)methyl]-4'-fluoro-[1,1'-biphenyl]-2-amine:
N-(1H-1,3-benzodiazol-5-ylmethyl)-2-(4-methoxyphenyl)aniline;
N-(1H-1,3-benzodiazol-5-ylmethyl)-3-(4-methoxyphenyl)pyrazin-2-amine;
N-(1H-1,3-benzodiazol-5-ylmethyl)-3-(3,4-dimethoxyphenyl)pyridin-4-amine;
N-(1H-1,3-benzodiazol-5-ylmethyl)-3-(3,4-dimethoxyphenyl)pyridin-2-amine;
N-(1H-1,3-benzodiazol-5-ylmethyl)-3-(3,4-dimethoxyphenyl)pyrazin-2-amine;
N-(1H-1,3-benzodiazol-5-ylmethyl)-2-(4-phenoxyphenyl)aniline;
N-(1H-1,3-benzodiazol-5-ylmethyl)-2-[4-(cyclohexyloxy)phenyl]aniline:
N-(1H-1,3-benzodiazol-5-ylmethyl)-2-[4-(propan-2-yloxy)phenyl]aniline;
N-(1H-1,3-benzodiazol-5-ylmethyl)-2-(4-methoxyphenyl)-3-methylaniline:
N-(1H-1,3-benzodiazol-5-ylmethyl)-2-(3,4-dimethoxyphenyl)-3-methylaniline; and
N-(1H-1,3-benzodiazol-5-ylmethyl)-2-(3,4-dimethoxyphenyl)-3-fluoroaniline;
or a pharmaceutically acceptable salt, solvate or polymorph thereof, including all tautomers and stereoisomers.

In a most preferred embodiment, the compound of formula (I) is a compound selected from:
N-[(1H-1,3-benzodiazol-5-yl)methyl]-4'-fluoro-[1,1'-biphenyl]-2-amine;
N-(1H-1,3-benzodiazol-5-ylmethyl)-3-(3,4-dimethoxyphenyl)pyridin-2-amine;
N-(1H-1,3-benzodiazol-5-ylmethyl)-3-(3,4-dimethoxyphenyl)pyrazin-2-amine;
N-(1H-1,3-benzodiazol-5-ylmethyl)-2-(4-methoxyphenyl)-3-methylaniline;

N-(1H-1,3-benzodiazol-5-ylmethyl)-2-(3,4-dimethoxyphenyl)-3-methylaniline; and
N-(1H-1,3-benzodiazol-5-ylmethyl)-2-(3,4-dimethoxyphenyl)-3-fluoroaniline;
or a pharmaceutically acceptable salt, solvate or polymorph thereof, including all tautomers and stereoisomers.

In a further most preferred embodiment, the compound of formula (I) is:
5-(1-{4'-fluoro-[1,1'-biphenyl]-2-yl}piperidin-4-yl)-1,3,4-thiadiazol-2-amine;
or a pharmaceutically acceptable salt, solvate or polymorph thereof, including all tautomers and stereoisomers.

In a further most preferred embodiment, the compound of formula (I) is:
N-(1H-1,3-benzodiazol-5-ylmethyl)-2-(3,4-dimethoxyphenyl)-3-fluoroaniline;
or a pharmaceutically acceptable salt, solvate or polymorph thereof, including all tautomers and stereoisomers.

Synthesis Methods

The compounds of formula (I) of the present invention can be prepared by a method selected from synthesis methods A to R as described in the example section below. The invention thus further relates to synthesis methods A, B, C, D, E, F, G, H, I, K, L, M, N, O, P. Q and R.

In a preferred embodiment, the compounds of formula (I) of the present invention are prepared according to synthesis method A.

In a further preferred embodiment, the compounds of formula (I) of the present invention are prepared according to synthesis method B.

In a further preferred embodiment, the compounds of formula (I) of the present invention are prepared according to synthesis method C.

In a further preferred embodiment, the compounds of formula (I) of the present invention are prepared according to synthesis method D.

In a further preferred embodiment, the compounds of formula (I) of the present invention are prepared according to synthesis method E.

In a further preferred embodiment, the compounds of formula (I) of the present invention are prepared according to synthesis method F.

In a further preferred embodiment, the compounds of formula (I) of the present invention are prepared according to synthesis method G.

In a further preferred embodiment, the compounds of formula (I) of the present invention are prepared according to synthesis method H.

In a further preferred embodiment, the compounds of formula (I) of the present invention are prepared according to synthesis method I.

In a further preferred embodiment, the compounds of formula (I) of the present invention are prepared according to synthesis method K.

In a further preferred embodiment, the compounds of formula (I) of the present invention are prepared according to synthesis method L.

In a further preferred embodiment, the compounds of formula (I) of the present invention are prepared according to synthesis method M.

In a further preferred embodiment, the compounds of formula (I) of the present invention are prepared according to synthesis method N.

In a further preferred embodiment, the compounds of formula (I) of the present invention are prepared according to synthesis method O.

In a further preferred embodiment, the compounds of formula (I) of the present invention are prepared according to synthesis method P.

In a further preferred embodiment, the compounds of formula (I) of the present invention are prepared according to synthesis method Q.

In a further preferred embodiment, the compounds of formula (I) of the present invention are prepared according to synthesis method R.

Therapeutic Uses

Physiological substrates of QC (EC) in mammals are, e.g. amyloid beta-peptides (3-40), (3-42), (11-40 and (11-42), ABri, ADan, Gastrin, Neurotensin, FPP, CCL 2, CCL 7, CCL 8, CCL 16. CCL 18, Fractalkine, Orexin A, [Gln$^3$]-glucagon(3-29), [Gln$^5$]-substance P(5-11) and the peptide QYNAD. For further details see table 1. The compounds and/or combinations according to the present invention and pharmaceutical compositions comprising at least one inhibitor of QC (EC) are useful for the treatment of conditions that can be treated by modulation of QC activity.

TABLE 1

Amino acid sequences of physiological active peptides with an N-terminal glutamine residue, which are prone to be cyclized to final pGlu

| Peptide | Amino acid sequence | Function |
| --- | --- | --- |
| Abeta(1-42) | Asp-Ala-Glu-Phe-<br>Arg-His-Asp-Ser-<br>Gly-Tyr-Glu-Val-<br>His-His-Gln-Lys-<br>Leu-Val-Phe-Phe-<br>Ala-Glu-Asp-Val-<br>Gly-Ser-Asn-Lys-<br>Gly-Ala-Ile-Ile-<br>Gly-Leu-Met-Val-<br>Gly-Gly-Val-Val-<br>Ile-Ala | Plays a role in<br>neurodegeneration, e.g. in<br>Alzheimer's Disease, Familial<br>British Dementia, Familial<br>Danish Dementia, Down<br>Syndrome |
| Abeta(1-40) | Asp-Ala-Glu-Phe-<br>Arg-His-Asp-Ser-<br>Gly-Tyr-Glu-Val-<br>His-His-Gln-Lys-<br>Leu-Val-Phe-Phe-<br>Ala-Glu-Asp-Val-<br>Gly-Ser-Asn-Lys-<br>Gly-Ala-Ile-Ile- | Plays a role in<br>neurodegeneration, e.g. in<br>Alzheimer's Disease, Familial<br>British Dementia, Familial<br>Danish Dementia, Down<br>Syndrome |

TABLE 1-continued

Amino acid sequences of physiological active peptides with an N-terminal glutamine residue, which are prone to be cyclized to final pGlu

| Peptide | Amino acid sequence | Function |
|---|---|---|
|  | Gly-Leu-Met-Val-Gly-Gly-Val-Val |  |
| Abeta(3-42) | Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta(3-40) | Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| Abeta(11-42) | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta(11-40) | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| ABri | EASNCFA IRHFENKFAV ETLIC SRTVKKNIIEEN | Pyroglutamated form plays a role in Familial British Dementia |
| ADan | EASNCFA IRHFENKFAV ETLIC FNLFLNSQEKHY | Pyroglutamated form plays a role in Familial Danish Dementia |
| Gastrin 17 Swiss-Prot: P01350 | QGPWL EEEEEAYGWM DF (amide) | Gastrin stimulates the stomach mucosa to produce and secrete hydrochloric acid and the pancreas to secrete its digestive enzymes it siso stimulates smooth muscle contraction and increases blood circulation and water secretion in the stomach and intestine. |
| Neurotensin Swiss-Prot: P30990 | QLYENKPRRP YIL | Neurotensin plays an endocrine or paracrine role in the regulation of fat metabolism, it causes contraction of smooth muscle. |
| FPP | QEP amide | A tripeptide related to thyrotrophin releasing hormone (TRH), is found in seminal plasma. Recent evidence obtained in vitro and in vivo showed that FPP plays an important role in regulating sperm fertility. |

TABLE 1-continued

Amino acid sequences of physiological active peptides with an N-terminal glutamine residue, which are prone to be cyclized to final pGlu

| Peptide | Amino acid sequence | Function |
| --- | --- | --- |
| TRH<br>Swiss-Prot:<br>P20396 | QHP amide | TRH functions as a regulator of the biosynthesis of TSH in the anterior pituitary gland and as a neurotransmitter/neuromodulator in the central and peripheral nervous systems. |
| GnRH<br>Swiss-Prot:<br>P01148 | QHWSYGL RP(G) amide | Stimulates the secretion of gonadotropins; it stimulates the secretion of both luteinizing and follicle-stimulating hormones. |
| CCL16 (small inducible Cytokine A16)<br>Swiss-Prot:<br>O15467 | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ | Shows chemotactic activity for lymphocytes and monocytes but not neutrophils. Also shows potent myelosuppressive activity, suppresses proliferation of myeloid progenitor cells. Recombinant SCYA16 shows chemotactic activity for monocytes and THP-1 monocytes, but not for resting lymphocytes and neutrophils, induces a calcium flux in THP-1 cells that were desensitized by prior expression to RANTES. |
| CCL8 (small inducible Cytokine A8)<br>Swiss-Prot:<br>P80075 | QPDSVSI PITCCFNVIN RKIPIQRLES YTRITNIQCP KEAViFKTKR GKEVCADPKE RWVRDSMKHL DQIFQNLKP | Chemotactic factor that attracts monocytes, lymphocytes, basophils and eosinophils. May play a role in neoplasia and inflammatory host responses. This protein can bind heparin. |
| CCL2 (MCP-1, small inducible cytokine A2)<br>Swiss-Prot:<br>P13500 | QPDAINA PVTCCYNFTN RKISVQRLAS YRRITSSKCP KEAVIFKTIV AKEICADPKQ KWVQDSMDHL DKQTQTPKT | Chemotactic factor that attracts monocytes and basophils but not neutrophils or eosinophils. Augments monocyte anti-tumor activity Has been implicated in the pathogenesis of diseases characterized by monocytic infiltrates, like psoriasis, rheumatoid arthritis or atherosclerosis. May be involved in the recruitment of monocytes into the arterial wall during the disease process of atherosclerosis. Binds to CCR2 and CCR4. |
| CCL18 (small inducible Cytokine A18)<br>Swiss-Prot:<br>P55774 | QVGTNKELC CLVYTSWQIP QKFIVDYSET SPQCPKPGVI LLTKRGRQIC ADPNKKWVQK YISDLKLNA | Chemotactic factor that attracts lymphocytes but not monocytes or granulocytes. May be involved in B cell migration into B cell follicles in lymph nodes. Attracts naive T lymphocytes toward dendritic cells and activated macrophages in lymph nodes, has chemotactic activity for naive T cells, CD4+ and CD8+ T cells and thus may play a role in both humoral and cell-mediated immunity responses. |
| Fractalkine (neurotactin)<br>Swiss-Prot:<br>P78423 | QHHGVT KCNITCSKMT SKIPVALLIH YQQNQASCGK RAIILETRQH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP | The soluble form is chemotactic for T cells and monocytes, but not for neutrophils. The membrane-bound form promotes adhesion of those leukocytes to endothelial cells. May play a role in regulating leukocyte adhesion and |

TABLE 1-continued

Amino acid sequences of physiological active peptides with an N-terminal glutamine residue, which are prone to be cyclized to final pGlu

| Peptide | Amino acid sequence | Function |
|---|---|---|
| | VGTELFRVPP VSTAATWQSS<br>APHQPGPSLW AEAKTSEAPS<br>TQDPSTQAST ASSPAPEENA<br>PSEGQRVWGQ GQSPRPENSL<br>EREEMGPVPA HTDAFQDWGP<br>GSMAHVSVVP VSSEGTPSRE<br>PVASGSWTPK AEEPIHATMD<br>PGRLGVLITP VPDAGAATRR<br>QAVGLLAFLG LLFCLGVAMF<br>TYQSLQGCPR KMAGEMAEGL<br>RYIPRSCGSN SYVLVPV | migration processes at the endothelium binds to CX3CR1. |
| CCL7 (small inducible cytokine A7) Swiss-Prot: P80098 | QPVGINT STTCCYRFIN<br>KKIPKQRLES YRRTTSSHCP<br>REAVIFKTKL DKEICADPTQ<br>KWVQDFMKHL DKKTQTPKL | Chemotactic factor that attracts monocytes and eosinophils, but not neutrophils. Augments monocyte anti-tumor activity. Also induces the release of gelatinase B. This protein can bind heparin. Binds to CCR1, CCR2 and CCR3. |
| Orexin A (Hypocretin-1) Swiss-Prot 043612 | QPLPDCCRQK TCSCRLYELL<br>HGAGNHAAGI LTL | Neuropeptide that plays a significant role in the regulation of food intake and sleep-wakefulness, possibly by coordinating the complex behavioral and physiologic responses of these complementary homeostatic functions. It plays also a broader role in the homeostatic regulation of energy metabolism, autonomic function, hormonal balance and the regulation of body fluids. Orexin-A binds to both OX1R and OX2R with a high affinity. |
| Substance P | RPK PQQFFGLM | Belongs to the tachykinins. Tachykinins are active peptides which excite neurons, evoke behavioral responses, are potent vasodilators and secretagogues. and contract (directly or indirectly) many smooth muscles. |
| QYNAD | Gln-Tyr-Asn-Ala-Asp | Acts on voltage-gated sodium channels. |

Glutamate is found in positions 3, 11 and 22 of the amyloid fi-peptide. Among them the mutation from glutamic acid (E) to glutamine (0) in position 22 (corresponding to amyloid precursor protein APP 693, Swissprot P05067) has been described as the so called Dutch type cerebroarterial amyloidosis mutation.

The β-amyloid peptides with a pyroglutamic acid residue in position 3, 11 and/or 22 have been described to be more cytotoxic and hydrophobic than the amyloid β-peptides 1-40(42/43) (Saido T. C. 2000 Medical Hypotheses 54(3): 427-429).

The multiple N-terminal variations, e.g. Abeta(3-40), Abeta(3-42), Abeta(11-40) and Abeta (11-42) can be generated by the β-secretase enzyme β-site amyloid precursor protein-cleaving enzyme (BACE) at different sites (Huse J. T. et al. 2002 J. Biol. Chem. 277 (18): 16278-16284), and/or by aminopeptidase or dipeptidylaminopeptidase processing from the full length peptides Abeta(1-40) and Abeta(1-42). In all cases, cyclization of the then N-terminal occurring glutamic acid residue is catalyzed by QC.

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with *Helicobacter pylori*, who are known to have increased risk of duodenal ulcer disease and gastric cancer (Dockray, G. J. 1999 J Physiol 15 315-324).

The peptide hormone gastrin, released from antral G cells, is known to stimulate the synthesis and release of histamine from ECL cells in the oxyntic mucosa via CCK-2 receptors. The mobilized histamine induces acid secretion by binding to the H(2) receptors located on parietal cells. Recent studies suggest that gastrin, in both its fully amidated and less processed forms (progastrin and glycine-extended gastrin), is also a growth factor for the gastrointestinal tract. It has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g. glycine-extended gastrin) appears to be the colonic mucosa (Koh, T. J. and Chen, D. 2000 Regul Pept 9337-44).

Neurotensin (NT) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 Biol Psychiatry 50 856-872).

Fertilization promoting peptide (FPP), a tripeptide related to thyrotrophin releasing hormone (TRH), is found in seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on", others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser. L. R. and Adeoya-Osiguwa. S. A. 2001 Vitam Horm 63, 1-28).

CCL2 (MCP-1), CCL7, CCL8, CCL16, CCL18 and fractalkine play an important role in pathophysiological conditions, such as suppression of proliferation of myeloid progenitor cells, neoplasia, inflammatory host responses, cancer, psoriasis, rheumatoid arthritis, atherosclerosis, vasculitis, humoral and cell-mediated immunity responses, leukocyte adhesion and migration processes at the endothelium, inflammatory bowel disease, restenosis, pulmonary fibrosis, pulmonary hypertention, liver fibrosis, liver cirrhosis, nephrosclerosis, ventricular remodeling, heart failure, arteriopathy after organ transplantations and failure of vein grafts.

A number of studies have underlined in particular the crucial role of MCP-1 for the development of atherosclerosis (Gu, L., et al., (1998) Mol. Cell 2, 275-281; Gosling, J., et al., (1999) J Clin. Invest 103, 773-778); rheumatoid arthritis (Gong, J. H., et al., (1997) J Exp. Med 186, 131-137; Ogata, H., et al., (1997) J Pathol. 182, 106-114); pancreatitis (Bhatia. M., et al., (2005) Am. J Physiol Gastrointest. Liver Physiol 288, G1259-G1265); Alzheimer's disease (Yamamoto, M., et al., (2005) Am. J Pathol. 166, 1475-1485); lung fibrosis (Inoshima, I., et al., (2004) Am. J Physiol Lung Cell Mol. Physiol 286, L1038-L1044); renal fibrosis (Wada. T., et al., (2004) J Am. Soc. Nephrol. 15, 940-948), and graft rejection (Saiura, A., et al., (2004) Arterioscler. Thromb. Vasc. Biol. 24, 1886-1890). Furthermore, MCP-1 might also play a role in gestosis (Katabuchi, H., et al., (2003) Med Electron Microsc. 36, 253-262), as a paracrine factor in tumor development (Ohta, M., et al., (2003) Int. J Oncol. 22, 773-778; Li, S., et al., (2005) J Exp. Med 202, 617-624), neuropathic pain (White, F. A., et al., (2005) Proc. Natl. Acad. Sci. U.S.A) and AIDS (Park, I. W., Wang, J. F., and Groopman, J. E. (2001) Blood 97, 352-358; Coll, B., et al., (2006) Cytokine 34, 51-55).

MCP-1 levels are increased in CSF of AD patients and patients showing mild cognitive impairment (MCI) (Galimberti, D., et al., (2006) Arch. Neurol. 63, 538-543). Furthermore. MCP-1 shows an increased level in serum of patients with MCI and early AD (Clerici, F., et al., (2006) Neurobiol. Aging 27, 1763-1768).

Several cytotoxic T lymphocyte peptide-based vaccines against hepatitis B, human immunodeficiency virus and melanoma were recently studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class I major histocompatibility complex. Consequently, in order to conserve full activity of ELA, the formation of PyrELA must be avoided (Beck A. et al. 2001, J Pept Res 57(6):528-38.).

Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

Recently, increased levels of the pentapeptide QYNAD were identified in the cerebrospinal fluid (CSF) of patients suffering from multiple sclerosis or Guillain-Barré syndrome compared to healthy individuals (Brinkmeier H. et al. 2000, Nature Medicine 6, 808-811). There is a big controversy in the literature about the mechanism of action of the pentapeptide Gln-Tyr-Asn-Ala-Asp (QYNAD), especially its efficacy to interact with and block sodium channels resulting in the promotion of axonal dysfunction, which are involved in inflammatory autoimmune diseases of the central nervous system. But recently, it could be demonstrated that not QYNAD, but its cyclized, pyroglutamated form, pEYNAD, is the active form, which blocks sodium channels resulting in the promotion of axonal dysfunction. Sodium channels are expressed at high density in myelinated axons and play an obligatory role in conducting action potentials along axons within the mammalian brain and spinal cord. Therefore, it is speculated that they are involved in several aspects of the pathophysiology of inflammatory autoimmune diseases, especially multiple sclerosis, the Guillain-Barré syndrome and chronic inflammatory demyelinizing polyradiculoneuropathy.

Furthermore. QYNAD is a substrate of the enzyme glutaminyl cyclase (QC, EC 2.3.2.5), which is also present in the brain of mammals, especially in human brain. Glutaminyl cyclase catalyzes effectively the formation of pEYNAD from its precursor QYNAD.

Accordingly, the present invention provides the use of the compounds of formula (I) for the preparation of a medicament for the prevention or alleviation or treatment of a disease selected from the group consisting of mild cognitive impairment, Alzheimer's disease, Familial British Dementia, Familial Danish Dementia, neurodegeneration in Down Syndrome, Huntington's disease, Kennedy's disease, ulcer disease, duodenal cancer with or w/o *Helicobacter pylori* infections, colorectal cancer, Zolliger-Ellison syndrome, gastric cancer with or without *Helicobacter pylori* infections, pathogenic psychotic conditions, schizophrenia, infertility, neoplasia, inflammatory host responses, cancer, malign metastasis, melanoma, psoriasis, rheumatoid arthritis, atherosclerosis, pancreatitis, restenosis, impaired humoral and cell-mediated immune responses, leukocyte adhesion and migration processes in the endothelium, impaired food intake, impaired sleep-wakefulness, impaired homeostatic regulation of energy metabolism, impaired autonomic function, impaired hormonal balance or impaired regulation of body fluids, multiple sclerosis, the Guillain-Barré syndrome and chronic inflammatory demyelinizing polyradiculoneuropathy.

Furthermore, by administration of a compound according to the present invention to a mammal it can be possible to stimulate the proliferation of myeloid progenitor cells.

In addition, the administration of a QC inhibitor according to the present invention can lead to suppression of male fertility.

In a preferred embodiment, the present invention provides the use of inhibitors of QC (EC) activity in combination with other agents, especially for the treatment of neuronal diseases, artherosclerosis and multiple sclerosis.

The present invention also provides a method of treatment of the aforementioned diseases comprising the administration of a therapeutically active amount of at least one compound of formula (I) to a mammal, preferably a human.

Most preferably, said method and corresponding uses are for the treatment of a disease selected from the group consisting of mild cognitive impairment, Alzheimer's disease, Familial British Dementia, Familial Danish Dementia, neurodegeneration in Down Syndrome, Parkinson's disease and Chorea Huntington, comprising the administration of a therapeutically active amount of at least one compound of formula (I) to a mammal, preferably a human.

Even preferably, the present invention provides a method of treatment and corresponding uses for the treatment of rheumatoid arthritis, atherosclerosis, pancreatitis and restenosis.

Pharmaceutical Combinations

In a preferred embodiment, the present invention provides a composition, preferably a pharmaceutical composition, comprising at least one QC inhibitor optionally in combination with at least one other agent selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

Most preferably, said QC inhibitor is a compound of formula (I) of the present invention.

More specifically, the aforementioned other agent is selected from the group consisting of beta-amyloid antibodies, vaccines, cysteine protease inhibitors, PEP-inhibitors, LiCl, acetylcholinesterase (AChE) inhibitors, PIMT enhancers, inhibitors of beta secretases, inhibitors of gamma secretases, inhibitors of aminopeptidases, preferably inhibitors of dipeptidyl peptidases, most preferably DP IV inhibitors; inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents, MCP-1 antagonists or an agent selected from the group consisting of antegren (natalizumab), Neurelan (fampridine-SR), campath (alemtuzumab), IR 208. NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

Furthermore, the other agent may be, for example, an anti-anxiety drug or antidepressant selected from the group consisting of (a) Benzodiazepines, e.g. alprazolam, chlordiazepoxide, clobazam, clonazepam, clorazepate, diazepam, fludiazepam, loflazepate, lorazepam, methaqualone, oxazepam, prazepam, tranxene, (b) Selective serotonin re-uptake inhibitors (SSRI's), e.g. citalopram, fluoxetine, fluvoxamine, escitalopram, sertraline, paroxetine, (c) Tricyclic antidepressants, e.g. amitryptiline, clomipramine, desipramine, doxepin, imipramine (d) Monoamine oxidase (MAO) inhibitors, (e) Azapirones, e.g. buspirone, tandopsirone, (f) Serotonin-norepinephrine reuptake inhibitors (SNRI's), e.g. venlafaxine, duloxetine, (g) Mirtazapine, (h) Norepinephrine reuptake inhibitors (NRI's), e.g. reboxetine, (i) Bupropione, (j) Nefazodone, (k) beta-blockers.

(l) NPY-receptor ligands: NPY agonists or antagonists.

In a further embodiment, the other agent may be, for example, an anti-multiple sclerosis drug selected from the group consisting of a) dihydroorotate dehydrogenase inhibitors, e.g. SC-12267, teriflunomide, MNA-715, HMR-1279 (syn. to HMR-1715, MNA-279), b) autoimmune suppressant, e.g. laquinimod,
c) paclitaxel,
d) antibodies, e.g. AGT-1, anti-granulocyte-macrophage colony-stimulating factor (GM-CSF) monoclonal antibody, Nogo receptor modulators, ABT-874, alemtuzumab (CAMPATH), anti-OX40 antibody, CNTO-1275, DN-1921, natalizumab (syn. to AN-100226, Antegren, VLA-4 Mab), daclizumab (syn. to Zenepax, Ro-34-7375, SMART anti-Tac), J-695, priliximab (syn. to Centara, CEN-000029, cM-T412), MRA, Dantes, anti-IL-12-antibody,
e) peptide nucleic acid (PNA) preparations, e.g. reticulose,
f) interferon alpha, e.g. Alfaferone, human alpha interferon (syn. to Omniferon, Alpha Leukoferon),
g) interferon beta, e.g. Frone, interferon beta-1a like Avonex, Betron (Rebif), interferon beta analogs, interferon beta-transferrin fusion protein, recombinant interferon beta-1b like Betaseron,
h) interferon tau,
i) peptides, e.g. AT-008, AnergiX.MS, Immunokine (alpha-Immunokine-NNSO3), cyclic peptides like ZD-7349,
j) therapeutic enzymes, e.g. soluble CD8 (sCD8),
k) multiple sclerosis-specific autoantigen-encoding plasmid and cytokine-encoding plasmid, e.g. BHT-3009;
l) inhibitor of TNF-alpha, e.g. BLX-1002, thalidomide, SH-636,
m) TNF antagonists, e.g. solimastat, lenercept (syn. to RO-45-2081. Tenefuse), onercept (sTNFR1), CC-1069,
n) TNF alpha, e.g. etanercept (syn. to Enbrel, TNR-001)
o) CD28 antagonists, e.g. abatacept,
p) Lck tyrosine kinase inhibitors,
q) cathepsin K inhibitors,
r) analogs of the neuron-targeting membrane transporter protein taurine and the plant-derived calpain inhibitor leupeptin, e.g. Neurodur,
s) chemokine receptor-1 (CCR1) antagonist, e.g. BX-471,
t) CCR2 antagonists,
u) AMPA receptor antagonists, e.g. ER-167288-01 and ER-099487, E-2007, talampanel,
v) potassium channel blockers, e.g. fampridine,
w) tosyl-proline-phenylalanine small-molecule antagonists of the VLA-4NCAM interaction. e.g. TBC-3342,
x) cell adhesion molecule inhibitors, e.g. TBC-772,
y) antisense oligonucleotides, e.g. EN-101,
z) antagonists of free immunoglobulin light chain (IgLC) binding to mast cell receptors, e.g. F-991,
aa) apoptosis inducing antigens, e.g. Apogen MS,
bb) alpha-2 adrenoceptor agonist. e.g. tizanidine (syn. to Zanaflex, Temelin, Sirdalvo, Sirdalud, Mionidine),
cc) copolymer of L-tyrosine, L-lysine, L-glutamic acid and L-alanine, e.g. glatiramer acetate (syn. to Copaxone, COP-1, copolymer-1),
dd) topoisomerase II modulators, e.g. mitoxantrone hydrochloride,
ee) adenosine deaminase inhibitor, e.g. cladribine (syn. to Leustatin, Mylinax, RWJ-26251),
ff) interleukin-10, e.g. ilodecakin (syn. to Tenovil, Sch-52000, CSIF),
gg) interleukin-12 antagonists, e.g. lisofylline (syn. to CT-1501R, LSF, lysofylline),
hh) Ethanaminum, e.g. SRI-62-834 (syn. to CRC-8605, NSC-614383),
ii) immunomodulators, e.g. SAIK-MS, PNU-156804, alpha-fetoprotein peptide (AFP), IPDS.
jj) retinoid receptor agonists, e.g. adapalene (syn. to Differin, CD-271),
kk) TGF-beta, e.g. GDF-1 (growth and differentiation factor 1),
ii) TGF-beta-2, e.g. BetaKine,
mm) MMP inhibitors, e.g. glycomed,
nn) phosphodiesterase 4 (PDE4) inhibitors, e.g. RPR-122818,
oo) purine nucleoside phosphorylase inhibitors, e.g. 9-(3-pyridylmethyl)-9-deazaguanine, peldesine (syn. to BCX-34. TO-200),
mm) alpha-4/beta-1 integrin antagonists, e.g. ISIS-104278,
qq) antisense alpha4 integrin (CD49d), e.g. ISIS-17044, ISIS-27104,
rr) cytokine-inducing agents, e.g. nucleosides, ICN-17261,
ss) cytokine inhibitors,
tt) heat shock protein vaccines, e.g. HSPPC-96,
uu) neuregulin growth factors, e.g. GGF-2 (syn. to neuregulin, glial growth factor 2),
vv) cathepsin S—inhibitors,
ww) bropirimine analogs, e.g. PNU-56169. PNU-63693,
xx) Monocyte chemoattractant protein-1 inhibitors, e.g. benzimidazoles like MCP-1 inhibitors, LKS-1456, PD-064036, PD-064126, PD-084486, PD-172084, PD-172386.

Further, the present invention provides pharmaceutical compositions e.g. for parenteral, enteral or oral administration, comprising at least one QC inhibitor, optionally in combination with at least one of the other aforementioned agents.

These combinations provide a particularly beneficial effect. Such combinations are therefore shown to be effective and useful for the treatment of the aforementioned diseases. Accordingly, the invention provides a method for the treatment of these conditions.

The method comprises either co-administration of at least one QC inhibitor and at least one of the other agents or the sequential administration thereof.

Co-administration includes administration of a formulation, which comprises at least one QC inhibitor and at least one of the other agents or the essentially simultaneous administration of separate formulations of each agent.

Beta-amyloid antibodies and compositions containing the same are described, e.g. in WO/2009/065054, WO/2009/056490, WO/2009/053696, WO/2009/033743, WO/2007/113172, WO/2007/022416, WO 2006/137354, WO 2006/118959, WO 2006/103116, WO 2006/095041, WO 2006/081171, WO 2006/066233, WO 2006/066171, WO 2006/066089, WO 2006/066049, WO 2006/055178, WO 2006/046644, WO 2006/039470, WO 2006/036291, WO 2006/026408, WO 2006/016644, WO 2006/014638, WO 2006/014478, WO 2006/008661, WO 2005/123775, WO 2005/120571, WO 2005/105998, WO 2005/081872, WO 2005/080435, WO 2005/028511, WO 2005/025616, WO 2005/025516, WO 2005/023858, WO 2005/018424, WO 2005/011599, WO 2005/000193, WO 2004/108895, WO 2004/098631, WO 2004/080419, WO 2004/071408, WO 2004/069182, WO 2004/067561, WO 2004/044204, WO 2004/032868, WO 2004/031400, WO 2004/029630, WO 2004/029629, WO 2004/024770, WO 2004/024090, WO 2003/104437, WO 2003/089460, WO 2003/086310, WO 2003/077858, WO 2003/074081, WO 2003/070760, WO 2003/063760, WO 2003/055514, WO 2003/051374, WO 2003/048204, WO 2003/045128, WO 2003/040183, WO 2003/039467, WO 2003/016466, WO 2003/015691, WO 2003/

014162, WO 2003/012141, WO 2002/088307, WO 2002/088306, WO 2002/074240, WO 2002/046237, WO 2002/046222, WO 2002/041842, WO 2001/062801, WO 2001/012598, WO 2000/077178, WO 2000/072880, WO 2000/063250, WO 1999/060024, WO 1999/027944, WO 1998/044955, WO 1996/025435, WO 1994/017197, WO 1990/014840, WO 1990/012871, WO 1990/012870, WO 1989/006242.

The beta-amyloid antibodies may be selected from, for example, polyclonal, monoclonal, chimenic or humanized antibodies. Furthermore, said antibodies may be useful to develop active and passive immune therapies, i.e. vaccines and monoclonal antibodies.

Suitable examples of beta-amyloid antibodies are ACU-5A5, huC091 (Acumen/Merck); PF-4360365, RI-1014, RI-1219, RI-409, RN-1219 (Rinat Neuroscience Corp (Pfizer Inc)); the nanobody therapeutics of Ablynx/Boehringer Ingelheim; beta-amyloid-specific humanized monoclonal antibodies of Intellect Neurosciences/IBL; m266, m266.2 (Eli Lilly & Co.); AAB-02 (Elan); bapineuzumab (Elan); BAN-2401 (Bioarctic Neuroscience AB); ABP-102 (Abiogen Pharma SpA); BA-27, BC-05 (Takeda); R-1450 (Roche); ESBA-212 (ESBATech AG); AZD-3102 (AstraZeneca) and beta-amyloid antibodies of Mindset BioPharmaceuticals Inc.

Especially preferred are antibodies, which recognize the N-terminus of the Aβ peptide. A suitable antibody, which recognizes the Aβ-N-Terminus is, for example Acl-24 (AC Immune SA).

Monoclonal antibodies against beta-amyloid peptide are disclosed in WO 2007/068412, WO/2008/156621 and WO/2010/012004. Respective chimeric and humanized antibodies are disclosed in WO 2008/011348 and WO/2008/060364. Vaccine composition for treating an amyloid-associated disease is disclosed in WO/2002/096937, WO/2005/014041, WO 2007/068411. WO/2007/097251, WO/2009/029272, WO/2009/054537, WO/2009/090650 WO/2009/095857, WO/2010/016912, WO/2010/011947, WO/2010/011999, WO/2010/044464.

Suitable vaccines for treating an amyloid-associated disease are, e.g. Affitopes AD-01 and AD-02 (GlaxoSmithKline), ACC-01 and ACC-02 (Elan/Wyeth), CAD-106 (Novartis/Cytos Biotechnology), Suitable cysteine protease inhibitors are inhibitors of cathepsin B. Inhibitors of cathepsin B and compositions containing such inhibitors are described, e.g. in WO/2008/077109, WO/2007/038772, WO 2006/060473, WO 2006/042103, WO 2006/039807, WO 2006/021413, WO 2006/021409, WO 2005/097103, WO 2005/007199, WO2004/084830, WO 2004/078908, WO 2004/026851, WO 2002/094881, WO 2002/027418, WO 2002/021509, WO 1998/046559, WO 1996/021655.

Examples of suitable PIMT enhancers are 10-aminoaliphatyl-dibenz[b f] oxepines described in WO 98/15647 and WO 03/057204, respectively. Further useful according to the present invention are modulators of PIMT activity described in WO 2004/039773.

Inhibitors of beta secretase and compositions containing such inhibitors are described. e.g. in WO/2010/094242, WO/2010/058333, WO/2010/021680, WO12009/108550, WO/2009/042694, WO/2008/054698, WO/2007/051333, WO/2007/021793, WO/2007/019080, WO/2007/019078, WO/2007/011810, WO03/059346, WO2006/099352, WO2006/078576, WO2006/060109, WO2006/057983, WO2006/057945, WO2006/055434, WO2006/044497, WO2006/034296, WO2006/034277, WO2006/029850. WO2006/026204, WO2006/014944, WO2006/014762, WO2006/002004, U.S. Pat. No. 7,109,217, WO2005/113484, WO2005/103043, WO2005/103020, WO2005/065195, WO2005/051914, WO2005/044830, WO2005/032471, WO2005/018545, WO2005/004803, WO2005/004802, WO2004/062625, WO2004/043916, WO2004/013098, WO03/099202, WO03/043987, WO03/039454, U.S. Pat. No. 6,562,783, WO02/098849 and WO02/096897.

Suitable examples of beta secretase inhibitors for the purpose of the present invention are WY-25105 (Wyeth); Posiphen, (+)-phenserine (TorreyPines/NIH); LSN-2434074, LY-2070275, LY-2070273, LY-2070102 (Eli Lilly & Co.); PNU-159775A, PNU-178025A, PNU-17820A, PNU-33312. PNU-38773, PNU-90530 (Elan/Pfizer); KMI-370, KMI-358, kmi-008 (Kyoto University): OM-99-2, OM-003 (Athenagen Inc.); AZ-12304146 (AstraZeneca/Astex); GW-840736X (GlaxoSmithKline plc.), DNP-004089 (De Novo Pharmaceuticals Ltd.) and CT-21166 (CoMentis Inc.).

Inhibitors of gamma secretase and compositions containing such inhibitors are described, e.g. in WO/2010/090954, WO/2009/011851, WO/2009/008980, WO/2008/147800, WO/2007/084595, WO2005/008250, WO2006/004880, U.S. Pat. Nos. 7,122,675, 7,030,239, 6,992,081, 6,982,264, WO2005/097768, WO2005/028440, WO2004/101562, U.S. Pat. Nos. 6,756,511, 6,683,091, WO03/066592, WO03/014075, WO03/013527, WO02/36555, WO01/53255, U.S. Pat. Nos. 7,109,217, 7,101,895, 7,049,296, 7,034,182. U.S. Pat. No. 6,984,626. WO2005/040126, WO2005/030731, WO2005/014553, U.S. Pat. No. 6,890,956, EP 1334085, EP 1263774, WO2004/101538, WO2004/00958, WO2004/089911, WO2004/073630, WO2004/069826, WO2004/039370, WO2004/031139, WO2004/031137, U.S. Pat. Nos. 6,713,276, 6,686,449, WO03/091278, U.S. Pat. Nos. 6,649,196, 6,448,229, WO01/77144 and WO01/66564.

Suitable gamma secretase inhibitors for the purpose of the present invention are GSI-953, WAY-GSI-A, WAY-GSI-B (Wyeth); MK-0752, MRK-560, L-852505, L-685-458, L-852631, L-852646 (Merck & Co. Inc.); LY-450139, LY-411575, AN-37124 (Eli Lilly & Co.); BMS-299897. BMS-433796 (Bristol-Myers Squibb Co.); E-2012 (Eisai Co. Ltd.); EHT-0206, EHT-206 (ExonHit Therapeutics SA); NGX-555 (TorreyPines Therapeutics Inc.) and Semagacestat (Eli Lilly).

DP IV-inhibitors and compositions containing such inhibitors are described, e.g. in U.S. Pat. Nos. 6,011,155; 6,107,317; 6,110,949; 6,124,305; 6,172,081; WO99/61431, WO99/67278, WO99/67279, DE19834591, WO97/40832, WO95/15309, WO98/19998, WO00/07617, WO99/38501, WO99/46272, WO99/38501, WO01/68603. WO01/40180, WO01/81337, WO01/81304, WO01/55105, WO02/02560, WO01/34594, WO02/38541, WO02/083128, WO03/072556, WO03/002593, WO03/000250, WO03/000180, WO03/000181, EP1258476, WO03/002553, WO03/002531, WO03/002530, WO03/004496, WO03/004498, WO03/024942, WO03/024965, WO03/033524, WO03/035057, WO03/035067, WO03/037327, WO03/040174, WO03/045977. WO03/055881, WO03/057144, WO03/057666, WO03/068748, WO03/068757, WO03/082817, WO03/101449, WO03/101958, WO03/104229, WO03/74500, WO2004/007446, WO2004/007468, WO2004/018467, WO2004/018468, WO2004/018469, WO2004/026822, WO2004/032836, WO2004/033455, WO2004/037169, WO2004/041795, WO2004/043940, WO2004/048352. WO2004/050022, WO2004/052850, WO2004/058266. WO2004/064778, WO2004/069162, WO2004/071454, WO2004/076433, WO2004/076434, WO2004/087053, WO2004/089362, WO2004/099185, WO2004/

103276, WO2004/103993, WO2004/108730, WO2004/110436, WO2004/111041, WO2004/112701, WO2005/000846, WO2005/000848, WO2005/011581, WO2005/016911, WO2005/023762, WO2005/025554, WO2005/026148, WO2005/030751, WO2005/033106, WO2005/037828, WO2005/040095, WO2005/044195, WO2005/047297, WO2005/051950, WO2005/056003, WO2005/056013, WO2005/058849, WO2005/075426, WO2005/082348, WO2005/085246, WO2005/087235. WO2005/095339, WO2005/095343, WO2005/095381, WO2005/108382, WO2005/113510, WO2005/116014, WO2005/116029, WO2005/118555, WO2005/120494, WO2005/121089, WO2005/121131, WO2005/123685, WO2006/995613: WO20061009886; WO2006/013104; WO2006/017292; WO2006/019965; WO2006/020017; WO2006/023750; WO2006/039325; WO2006/041976; WO2006/047248; WO2006/058064; WO2006/058628; WO2006/066747; WO2006/066770 and WO2006/068978.

Suitable DP IV-inhibitors for the purpose of the present invention are for example Sitagliptin, des-fluoro-sitagliptin (Merck & Co. Inc.); vildagliptin, DPP-728, SDZ-272-070 (Novartis); ABT-279. ABT-341 (Abbott Laboratories); denagliptin, TA-6666 (GlaxoSmithKline plc.); SYR-322 (Takeda San Diego Inc.); talabostat (Point Therapeutics Inc.); Ro-0730699, R-1499, R-1438 (Roche Holding AG); FE-999011 (Ferring Pharmaceuticals); TS-021 (Taisho Pharmaceutical Co. Ltd.); GRC-8200 (Glenmark Pharmaceuticals Ltd.); ALS-2-0426 (Alantos Pharmaceuticals Holding Inc.); ARI-2243 (Arisaph Pharmaceuticals Inc.); SSR-162369 (Sanofi-Synthelabo); MP-513 (Mitsubishi Pharma Corp.); DP-893, CP-867534-01 (Pfizer Inc.); TSL-225, TMC-2A (Tanabe Seiyaku Co. Ltd.); PHX-1149 (Phenomenix Corp.); saxagliptin (Bristol-Myers Squibb Co.); PSN-9301 ((OSI) Prosidion), S-40755 (Servier); KRP-104 (ActivX Biosciences Inc.); sulphostin (Zaidan Hojin); KR-62436 (Korea Research Institute of Chemical Technology); P32/98 (Probiodrug AG); BI-A, BI-B (Boehringer Ingelheim Corp.); SK-0403 (Sanwa Kagaku Kenkyusho Co. Ltd.); and NNC-72-2138 (Novo Nordisk A/S).

Other preferred DP IV-inhibitors are
(i) dipeptide-like compounds, disclosed in WO 99/61431, e.g. N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof;
(ii) peptide structures, disclosed in WO 03/002593. e.g. tripeptides;
(iii) peptidylketones, disclosed in WO 03/033524;
(vi) substituted aminoketones, disclosed in WO 03/040174;
(v) topically active DP IV-inhibitors, disclosed in WO 01/14318;
(vi) prodrugs of DP IV-inhibitors, disclosed in WO 99/67278 and WO 99/67279; and
(v) glutaminyl based DP IV-inhibitors, disclosed in WO 03/072556 and WO 2004/099134.

Suitable beta amyloid synthesis inhibitors for the purpose of the present invention are for example Bisnorcymserine (Axonyx Inc.); (R)-flurbiprofen (MCP-7869; Flurizan) (Myriad Genetics); nitroflurbiprofen (NicOx); BGC-20-0406 (Sankyo Co. Ltd.) and BGC-20-0466 (BTG plc.), RQ-00000009 (RaQualia Pharma Inc).

Suitable amyloid protein deposition inhibitors for the purpose of the present invention are for example SP-233 (Samaritan Pharmaceuticals); AZD-103 (Ellipsis Neurotherapeutics Inc.); AAB-001 (Bapineuzumab), AAB-002, ACC-001 (Elan Corp plc.); Colostrinin (ReGen Therapeutics plc.); Tramiprosate (Neurochem); AdPEDI-(amyloid-beta1-6)11) (Vaxin Inc.); MPI-127585, MPI-423948 (Mayo Foundation); SP-08 (Georgetown University); ACU-5A5 (Acumen/Merck); Transthyretin (State University of New York); PTI-777, DP-74, DP 68, Exebryl (ProteoTech Inc.); m266 (Eli Lilly & Co.); EGb-761 (Dr. Willmar Schwabe GmbH); SPI-014 (Satori Pharmaceuticals Inc.); ALS-633, ALS-499 (Advanced Life Sciences Inc.); AGT-160 (ArmaGen Technologies Inc.); TAK-070 (Takeda Pharmaceutical Co. Ltd.); CHF-5022, CHF-5074. CHF-5096 and CHF-5105 (Chiesi Farmaceutici SpA.), SEN-1176 and SEN-1329 (Senexis Ltd.), AGT-160 (ArmaGen Technologies), Davunetide (Allon Therapeutics), ELND-005 (Elan Corp/Transition Therapeutics) and nilvadipine (Archer Pharmaceuticals).

Suitable PDE-4 inhibitors for the purpose of the present invention are for example Doxofylline (Instituto Biologico Chemioterapica ABC SpA.); idudilast eye drops, tipelukast, ibudilast (Kyorin Pharmaceutical Co. Ltd.); theophylline (Elan Corp.); cilomilast (GlaxoSmithKline plc.); Atopik (Barrier Therapeutics Inc.); tofimilast, CI-1044, PD-189659, CP-220629, PDE 4d inhibitor BHN (Pfizer Inc.); arofylline, LAS-37779 (Almirall Prodesfarma SA.); roflumilast, hydroxypumafentrine (Altana AG), tetomilast (Otska Pharmaceutical Co. Ltd.); tipelukast, ibudilast (Kyorin Pharmaceutical), CC-10004 (Celgene Corp.); HT-0712, IPL-4088 (Inflazyme Pharmaceuticals Ltd.); MEM-1414, MEM-1917 (Memory Pharmaceuticals Corp.); oglemilast, GRC-4039 (Glenmark Pharmaceuticals Ltd.); AWD-12-281, ELB-353, ELB-526 (Elbion AG); EHT-0202 (ExonHit Therapeutics SA.); ND-1251 (Neuro3d SA.); 4AZA-PDE4 (4 AZA Bioscience NV.); AVE-8112 (Sanofi-Aventis); CR-3465 (Rottapharm SpA.); GP-0203, NCS-613 (Centre National de la Recherche Scientifique); KF-19514 (Kyowa Hakko Kogyo Co. Ltd.); ONO-6126 (Ono Pharmaceutical Co. Ltd.); OS-0217 (Dainippon Pharmaceutical Co. Ltd.); IBFB-130011, IBFB-150007, IBFB-130020, IBFB-140301 (IBFB Pharma GmbH); IC-485 (ICOS Corp.); RBx-14016 and RBx-11082 (Ranbaxy Laboratories Ltd.). A preferred PDE-4-inhibitor is Rolipram.

MAO inhibitors and compositions containing such inhibitors are described, e.g. in WO2006/091988, WO2005/007614, WO2004/089351, WO01/26656, WO01/12176, WO99/57120, WO99/57119, WO99/13878, WO98/40102, WO98/01157. WO96/20946, WO94/07890 and WO92/21333.

Suitable MAO-inhibitors for the purpose of the present invention are for example Linezolid (Pharmacia Corp.); RWJ-416457 (RW Johnson Pharmaceutical Research Institute); budipine (Altana AG); GPX-325 (BioResearch Ireland); isocarboxazid; phenelzine; tranylcypromine; indantadol (Chiesi Farmaceutici SpA.); moclobemide (Roche Holding AG); SL-25.1131 (Sanofi-Synthelabo); CX-1370 (Burroughs Wellcome Co.); CX-157 (Krenitsky Pharmaceuticals Inc.); desoxypeganine (HF Arzneimittelforschung GmbH & Co. KG); bifemelane (Mitsubishi-Tokyo Pharmaceuticals Inc.); RS-1636 (Sankyo Co. Ltd.); esuprone (BASF AG); rasagiline (Teva Pharmaceutical Industries Ltd.); ladostigil (Hebrew University of Jerusalem); safinamide (Pfizer), NW-1048 (Newron Pharmaceuticals SpA.), EVT-302 (Evotec).

Suitable histamine H3 antagonists for the purpose of the present invention are, e.g. ABT-239, ABT-834 (Abbott Laboratories); 3874-Hi (Aventis Pharma); UCL-2173 (Berlin Free University). UCL-1470 (BioProjet, Societe Civile de Recherche); DWP-302 (Daewoong Pharmaceutical Co Ltd); GSK-189254A, GSK-207040A (GlaxoSmithKline Inc.); cipralisant, GT-2203 (Gliatech Inc.); Ciproxifan (INSERM), 1S,2S-2-(2-Aminoethyl)-1-(1H-imidazol-4-yl)cyclopropane (Hokkaido University); JNJ-17216498, JNJ-5207852 (Johnson & Johnson); NNC-0038-0000-1049 (Novo Nordisk A/S); and Sch-79687 (Schering-Plough).

PEP inhibitors and compositions containing such inhibitors are described, e.g. in JP 01042465, JP 03031298, JP 04208299, WO 00/71144, U.S. Pat. No. 5,847,155; JP 09040693, JP 10077300, JP 05331072, JP 05015314, WO 95/15310, WO 93/00361, EP 0556482, JP 06234693, JP 01068396. EP 0709373, U.S. Pat. Nos. 5,965,556, 5,756, 763, 6,121,311, JP 63264454, JP 64000069, JP 63162672, EP 0268190, EP 0277588, EP 0275482, U.S. Pat. Nos. 4,977,180, 5,091,406, 4,983,624, 5,112,847, 5,100,904, 5,254,550, 5,262,431, 5,340,832, 4,956,380, EP 0303434, JP 03056486, JP 01143897, JP 1226880, EP 0280956. U.S. Pat. No. 4,857,537, EP 0461677, EP 0345428, JP 02275858, U.S. Pat. No. 5,506,256, JP 06192298, EP 0618193, JP 03255080, EP 0468469, U.S. Pat. No. 5,118,811, JP 05025125, WO 9313065, JP 05201970, WO 9412474, EP 0670309, EP 0451547, JP 06339390, U.S. Pat. No. 5,073, 549. U.S. Pat. No. 4,999,349, EP 0268281, U.S. Pat. No. 4,743,616. EP 0232849. EP 0224272, JP 62114978, JP 62114957, U.S. Pat. Nos. 4,757,083, 4,810,721, 5,198,458, 4,826,870, EP 0201742, EP 0201741, U.S. Pat. No. 4,873, 342, EP 0172458, JP 61037764, EP 0201743, U.S. Pat. No. 4,772,587. EP 0372484, U.S. Pat. No. 5,028,604, WO 91/18877, JP 04009367, JP 04235162, U.S. Pat. No. 5,407, 950, WO 95/01352, JP 01250370, JP 02207070, U.S. Pat. No. 5,221,752, EP 0468339, JP 04211648, WO 99/46272, WO 2006/058720 and PCT/EP2006/061428.

Suitable prolyl endopeptidase inhibitors for the purpose of the present invention are, e.g. Fmoc-Ala-Pyrr-CN, Z-Phe-Pro-Benzothiazole (Probiodrug), Z-321 (Zeria Pharmaceutical Co Ltd); ONO-1603 (Ono Pharmaceutical Co Ltd); JTP-4819 (Japan Tobacco Inc.) and S-17092 (Servier).

Other suitable compounds that can be used according to the present invention in combination with QC-inhibitors are NPY, an NPY mimetic or an NPY agonist or antagonist or a ligand of the NPY receptors.

Preferred according to the present invention are antagonists of the NPY receptors.

Suitable ligands or antagonists of the NPY receptors are 3a,4,5,9b-tetrahydro-1h-benz[e]indol-2-yl amine-derived compounds as disclosed in WO 00/68197.

NPY receptor antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494 and WO 98/07420: WO 00/30674, U.S. Pat. Nos. 5,552,411, 5,663,192 and 5,567,714; 6,114,336, Japanese patent application JP 09157253; international patent applications WO 94/00486, WO 93/12139, WO 95/00161 and WO 99/15498; U.S. Pat. No. 5,328,899; German patent application DE 393 97 97; European patent applications EP 355 794 and EP 355 793; and Japanese patent applications JP 06116284 and JP 07267988. Preferred NPY antagonists include those compounds that are specifically disclosed in these patent documents. More preferred compounds include amino acid and non-peptide-based NPY antagonists. Amino acid and non-peptide-based NPY antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494, WO 98/07420 and WO 99/15498; U.S. Pat. Nos. 5,552,411, 5,663,192 and 5,567,714; and Japanese patent application JP 09157253. Preferred amino acid and non-peptide-based NPY antagonists include those compounds that are specifically disclosed in these patent documents.

Particularly preferred compounds include amino acid-based NPY antagonists. Amino acid-based compounds, which may be mentioned include those disclosed in international patent applications WO 94/17035, WO 97/19911, WO 97/19913, WO 97/19914 or, preferably, WO 99/15498. Preferred amino acid-based NPY antagonists include those that are specifically disclosed in these patent documents, for example BIBP3226 and, especially, (R)-N2-(diphenylacetyl)-(R)-N-[1-(4-hydroxy-phenyl) ethyl] arginine amide (Example 4 of international patent application WO 99/15498).

M1 receptor agonists and compositions containing such inhibitors are described, e.g. in WO2004/087158, WO91/10664.

Suitable M1 receptor antagonists for the purpose of the present invention are for example CDD-0102 (Cognitive Pharmaceuticals); Cevimeline (Evoxac) (Snow Brand Milk Products Co. Ltd.); NGX-267 (TorreyPines Therapeutics); sabcomeline (GlaxoSmithKline); alvameline (H Lundbeck A/S); LY-593093 (Eli Lilly & Co.); VRTX-3 (Vertex Pharmaceuticals Inc.); WAY-132983 (Wyeth), CI-101 7/(PD-151832) (Pfizer Inc.) and MCD-386 (Mitridion Inc.).

Acetylcholinesterase inhibitors and compositions containing such inhibitors are described, e.g. in WO2006/071274, WO2006/070394, WO2006/040688, WO2005/092009, WO2005/079789, WO2005/039580, WO2005/027975, WO2004/084884, WO2004/037234, WO2004/032929, WO03/101458, WO03/091220, WO03/082820, WO03/020289, WO02/32412, WO01/85145, WO01/78728, WO01/66096, WO00/02549, WO01/00215, WO00/15205, WO00/23057, WO00/33840, WO00/30446, WO00/23057. WO00/15205, WO00/09483, WO00/07600, WO00/02549, WO99/47131, WO99/07359, WO98/30243, WO97/38993, WO97/13754, WO94/29255, WO94/20476, WO94/19356, WO93/03034 and WO92/19238.

Suitable acetylcholinesterase inhibitors for the purpose of the present invention are for example Donepezil (Eisai Co. Ltd.); rivastigmine (Novartis AG); (−)-phenseine (TorreyPines Therapeutics); ladostigil (Hebrew University of Jerusalem); huperzine A (Mayo Foundation); galantamine (Johnson & Johnson); Memoquin (Universita di Bologna); SP-004 (Samaritan Pharmaceuticals Inc.); BGC-20-1259 (Sankyo Co. Ltd.); physostigmine (Forest Laboratories Inc.); NP-0361 (Neuropharma SA); ZT-1 (Debiopharm); tacrine (Wamer-Lambert Co.); metrifonate (Bayer Corp.). INM-176 (Whanin), huperzine A (Neuro-Hitech/Xel Pharmaceutical), mimopezil (Debiopharm) and Dimebon (Medivation/Pfizer).

NMDA receptor antagonists and compositions containing such inhibitors are described, e.g. in WO2006/094674, WO2006/058236, WO2006/058059, WO2006/010965, WO2005/000216, WO2005/102390, WO2005/079779, WO2005/079756, WO2005/072705, WO2005/070429, WO2005/055996, WO2005/035522, WO2005/009421, WO2005/000216. WO2004/092189, WO2004/039371, WO2004/028522, WO2004/009062, WO03/010159, WO02/072542, WO02/34718, WO01/98262, WO01/94321. WO01/92204, WO01/81295, WO01/32640, WO01/10833, WO01/10831, WO00/56711, WO00/29023, WO00/00197, WO99/53922, WO99/48891, WO99/45963, WO99/01416, WO99/07413, WO99/01416. WO98/50075, WO98/50044, WO98/10757, WO98/05337, WO97/32873, WO97/23216, WO97/23215, WO97/23214, WO96/14318. WO96/08485. WO95/31986, WO95/26352, WO95/26350, WO95/26349, WO95/26342, WO95/12594, WO95/02602, WO95/02601, WO94/20109, WO94/13641, WO94/09016 and WO93/25534.

Suitable NMDA receptor antagonists for the purpose of the present invention are for example Memantine (Merz & Co. GmbH); topiramate (Johnson & Johnson); AVP-923 (Neurodex) (Center for Neurologic Study); EN-3231 (Endo Pharmaceuticals Holdings Inc.); neramexane (MRZ-2/579) (Merz and Forest); CNS-5161 (CeNeS Pharmaceuticals Inc.); dexanabinol (HU-211; Sinnabidol; PA-50211) (Pharmos); EpiCept NP-1 (Dalhousie University); indantadol (V-3381; CNP-3381) (Vemalis); perzinfotel (EAA-090, WAY-126090, EAA-129) (Wyeth); RGH-896 (Gedeon Richter Ltd.); traxoprodil (CP-101606), besonprodil (PD-196860, CI-1041) (Pfizer Inc.); CGX-1007 (Cognetix Inc.); delucemine (NPS-1506) (NPS Pharmaceuticals Inc.); EVT-101 (Roche Holding AG); acamprosate (Synchroneuron LLC.); CR-3991, CR-2249, CR-3394 (Rottapharm SpA.); AV-101 (4-CI-kynurenine (4-CI-KYN)), 7-chloro-kynurenic acid (7-CI-KYNA) (VistaGen); NPS-1407 (NPS Pharmaceuticals Inc.); YT-1006 (Yaupon Therapeutics Inc.); ED-1812 (Sosei R&D Ltd.); himantane (hydrochloride N-2-(adamantly)-hexamethylen-imine) (RAMS); Lancicemine (AR-R-15896) (AstraZeneca); EVT-102, Ro-25-6981 and Ro-63-1908 (Hoffmann-La Roche AG/Evotec), neramexane (Merz).

Furthermore, the present invention relates to combination therapies useful for the treatment of atherosclerosis, restenosis or arthritis, administering a QC inhibitor in combination with another therapeutic agent selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors providing beneficial or synergistic therapeutic effects over each monotherapy component alone.

Angiotensin II receptor blockers are understood to be those active agents that bind to the AT1-receptor subtype of angiotensin II receptor but do not result in activation of the receptor. As a consequence of the blockade of the AT1 receptor, these antagonists can, e.g. be employed as antihypertensive agents.

Suitable angiotensin II receptor blockers which may be employed in the combination of the present invention include $AT_1$ receptor antagonists having differing structural features, preferred are those with non-peptidic structures. For example, mention may be made of the compounds that are selected from the group consisting of valsartan (EP 443983), losartan (EP 253310), candesartan (EP 459136), eprosartan (EP 403159), irbesartan (EP 454511), olmesartan (EP 503785), tasosartan (EP 539086), telmisartan (EP 522314), the compound with the designation E-41 77 of the formula

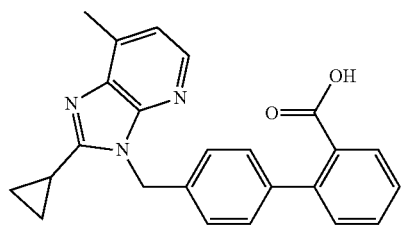 [SMILES: Cc1ccnc2c1nc(C1CC1)n2Cc1ccc(-c2ccccc2C(=O)O)cc1]

the compound with the designation SC-52458 of the following formula

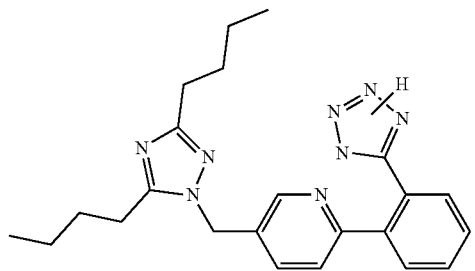

and the compound with the designation the compound ZD-8731 of the formula

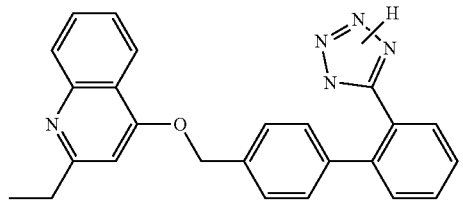

or, in each case, a pharmaceutically acceptable salt thereof.

Preferred AT1-receptor antagonists are those agents that have been approved and reached the market, most preferred is valsartan, or a pharmaceutically acceptable salt thereof.

The interruption of the enzymatic degradation of angiotensin to angiotensin II with ACE inhibitors is a successful variant for the regulation of blood pressure and thus also makes available a therapeutic method for the treatment of hypertension.

A suitable ACE inhibitor to be employed in the combination of the present invention is, e.g. a compound selected from the group consisting alacepril, benazepril, benazeprilat; captopril, ceronapril, cilazapril, delapril, enalapril, enaprilat, fosinopril, imidapril, lisinopril, moveltopril, perindopril, quinapril, ramipril, spirapril, temocapril and trandolapril, or in each case, a pharmaceutically acceptable salt thereof.

Preferred ACE inhibitors are those agents that have been marketed, most preferred are benazepril and enalapril.

A diuretic is, for example, a thiazide derivative selected from the group consisting of chlorothiazide, hydrochlorothiazide, methylclothiazide, and chlorothalidon. The most preferred diuretic is hydrochlorothiazide. A diuretic furthermore comprises a potassium sparing diuretic such as amiloride or triameterine, or a pharmaceutically acceptable saft thereof.

The class of CCBs essentially comprises dihydropyridines (DHPs) and non-DHPs, such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine and verapamil or, e.g. dependent on the specific CCB, a pharmaceutically acceptable salt thereof. Especially preferred as DHP is amlodipine or a pharmaceutically acceptable salt thereof, especially the besylate. An especially preferred representative of non-DHPs is verapamil or a pharmaceutically acceptable salt, especially the hydrochloride, thereof.

Beta-blockers suitable for use in the present invention include beta-adrenergic blocking agents (beta-blockers), which compete with epinephrine for beta-adrenergic receptors and interfere with the action of epinephrine. Preferably, the beta-blockers are selective for the beta-adrenergic receptor as compared to the alpha-adrenergic receptors, and so do not have a significant alpha-blocking effect. Suitable beta-blockers include compounds selected from acebutolol, atenolol, betaxolol, bisoprolol, carteolol, carvedilol, esmolol, labetalol, metoprolol, nadolol, oxprenolol, penbutolol, pindolol, propranolol, sotalol and timolol. Where the beta-blocker is an acid or base or otherwise capable of forming pharmaceutically acceptable salts or prodrugs, these forms are considered to be encompassed herein, and it is understood that the compounds may be administered in free form or in the form of a pharmaceutically acceptable salt or a prodrug, such as a physiologically hydrolyzable and acceptable ester. For example, metoprolol is suitably administered as its tartrate salt, propranolol is suitably administered as the hydrochloride salt, and so forth.

Platelet aggregation inhibitors include PLAVIX® (clopidogrel bisulfate), PLETAL® (cilostazol) and aspirin.

Cholesterol absorption modulators include ZETIA® (ezetimibe) and KT6-971 (Kotobuki Pharmaceutical Co. Japan).

HMG-Co-A reductase inhibitors (also called beta-hydroxy-beta-methylglutaryl-co-enzyme-A reductase inhibitors or statins) are understood to be those active agents which may be used to lower lipid levels including cholesterol in blood.

The class of HMG-Co-A reductase inhibitors comprises compounds having differing structural features. For example, mention may be made of the compounds, which are selected from the group consisting of atorvastatin, cerivastatin, fluvastatin, lovastatin, pitavastatin, pravastatin, rosuvastatin and simvastatin, or in each case, a pharmaceutically acceptable salt thereof.

Preferred HMG-Co-A reductase inhibitors are those agents, which have been marketed, most preferred is atorvastatin, pitavastatin or simvastatin, or a pharmaceutically acceptable salt thereof.

HDL-increasing compounds include, but are not limited to, cholesterol ester transfer protein (CETP) inhibitors. Examples of CETP inhibitors include JTT705 disclosed in Example 26 of U.S. Pat. No. 6,426,365 issued Jul. 30, 2002, and pharmaceutically acceptable salts thereof.

Inhibition of interleukin 6 mediated inflammation may be achieved indirectly through regulation of endogenous cholesterol synthesis and isoprenoid depletion or by direct inhibition of the signal transduction pathway utilizing interleukin-6 inhibitor/antibody, interleukin-6 receptor inhibitor/antibody, interleukin-6 antisense oligonucleotide (ASON), gp130 protein inhibitor/antibody, tyrosine kinase inhibitors/antibodies, serne/threonine kinase inhibitors/antibodies, mitogen-activated protein (MAP) kinase inhibitors/antibodies, phosphatidylinositol 3-kinase (PI3K) inhibitors/antibodies, Nuclear factor kappaB (NF-κB) inhibitors/antibodies, IκB kinase (IKK) inhibitors/antibodies, activator protein-1 (AP-1) inhibitors/antibodies, STAT transcription factors inhibitors/antibodies, altered IL-6, partial peptides of IL-6 or IL-6 receptor, or SOCS (suppressors of cytokine signaling) protein, PPAR gamma and/or PPAR beta/delta activators/ligands or a functional fragment thereof.

A suitable antiinflammatory corticosteroid is dexamethasone.

Suitable antiproliferative agents are cladribine, rapamycin, vincristine and taxol.

A suitable inhibitor of extracellular matrix synthesis is halofuginone.

A suitable growth factor or cytokine signal transduction inhibitor is, e.g. the ras inhibitor R115777.

A suitable tyrosine kinase inhibitor is tyrphostin.

Suitable renin inhibitors are described, e.g. in WO 2006/116435. A preferred renin inhibitor is aliskiren, preferably in the form of the hemi-fumarate salt thereof.

MCP-1 antagonists may, e.g. be selected from anti-MCP-1 antibodies, preferably monoclonal or humanized monoclonal antibodies, MCP-1 expression inhibitors, CCR2-antagonists, TNF-alpha inhibitors, VCAM-1 gene expression inhibitors and anti-C5a monoclonal antibodies.

MCP-1 antagonists and compositions containing such inhibitors are described, e.g. in WO02/070509, WO02/081463, WO02/060900, US2006/670364, US2006/677365, WO2006/097624, US2006/316449, WO2004/056727, WO03/053368, WO00/198289, WO00/157226, WO00/046195, WO00/046196, WO00/046199, WO00/046198, WO00/046197, WO99/046991, WO99/007351, WO98/006703, WO97/012615, WO2005/105133, WO03/037376, WO2006/125202, WO2006/085961, WO2004/024921, WO2006/074265.

Suitable MCP-1 antagonists are, for instance, C-243 (Telik Inc.); NOX-E36 (Noxxon Pharma AG); AP-761 (Actimis Pharmaceuticals Inc.); ABN-912, NIBR-177 (Novartis AG); CC-11006 (Celgene Corp.); SSR-150106 (Sanofi-Aventis); MLN-1202 (Millenium Pharmaceuticals Inc.); AGI-1067, AGIX-4207, AGI-1096 (AtherioGenics Inc.); PRS-211095, PRS-211092 (Pharmos Corp.); anti-C5a monoclonal antibodies, e.g. neutrazumab (G2 Therapies Ltd.); AZD-6942 (AstraZeneca plc.); 2-mercaptoimidazoles (Johnson & Johnson); TEI-E00526, TEI-6122 (Deltagen); RS-504393 (Roche Holding AG); SB-282241, SB-380732, ADR-7 (GlaxoSmithKline); anti-MCP-1 monoclonal antibodies (Johnson & Johnson).

Combinations of QC-inhibitors with MCP-1 antagonists may be useful for the treatment of inflammatory diseases in general, including neurodegenerative diseases.

Combinations of QC-inhibitors with MCP-1 antagonists are preferred for the treatment of Alzheimer's disease.

Most preferably the QC inhibitor is combined with one or more compounds selected from the following group:

PF-4360365, m266, bapineuzumab, R-1450, Posiphen, (+)-phenserine, MK-0752, LY-450139, E-2012, (R)-flurbiprofen, AZD-103, AAB-001 (Bapineuzumab), Tramiprosate, EGb-761, TAK-070, Doxofylline, theophylline, cilomilast, tofimilast, roflumilast, tetomilast, tipelukast, ibudilast, HT-0712, MEM-1414, oglemilast, Linezolid, budipine, isocarboxazid, phenelzine, tranylcypromine, indantadol, moclobemide, rasagiline, ladostigil, safinamide, ABT-239, ABT-834, GSK-189254A, Ciproxifan, JNJ-17216498, Fmoc-Ala-Pyrr-CN, Z-Phe-Pro-Benzothiazole, Z-321, ONO-1603, JTP-4819, S-17092, BIBP3226; (R)-N2-(diphenylacetyl)-(R)-N-[1-(4-hydroxyphenyl) ethyl] arginine amide, Cevimeline, sabcomeline, (PD-151832), Donepezil, rivastigmine, (−)-phenserine, ladostigil, galantamine, tacrine, metrifonate, Memantine, topiramate, AVP-923, EN-3231, neramexane, valsartan, benazepril, enalapril, hydrochlorothiazide, amlodipine, diltiazem, isradipine, nicardipine, nifedipine, nimodipine, nisoldipine, nitrendipine, verapamil, amlodipine, acebutolol, atenolol, betaxolol, bisoprolol, carteolol, carvedilol, esmolol, labetalol, metoprolol, nadolol, oxprenolol, penbutolol, pindolol, propranolol, sotalol, timolol, PLAVIX® (clopidogrel bisulfate), PLETAL® (cilostazol), aspirin, ZETIA® (ezetimibe) and KT6-971, statins, atorvastatin, pitavastatin or simvastatin; dexamethasone, ciadribine, rapamycin, vincristine, taxol, aliskiren, C-243, ABN-912, SSR-150106. MLN-1202 and betaferon.

In particular, the following combinations are considered:
- a QC inhibitor, preferably a QC inhibitor of formula (I), more preferably a QC inhibitor selected from any one of examples 1 to 1323, in combination with Atorvastatin for the treatment and/or prevention of artherosclerosis,
- a QC inhibitor, preferably a QC inhibitor of formula (I), more preferably a QC inhibitor selected from any one of examples 1 to 1323, in combination with immunosuppressive agents, preferably rapamycin for the prevention and/or treatment of restenosis,
- a QC inhibitor, preferably a QC inhibitor of formula (I), more preferably a QC inhibitor selected from any one of examples 1 to 1323, in combination with immunosuppressive agents, preferably paclitaxel for the prevention and/or treatment of restenosis,
- a QC inhibitor, preferably a QC inhibitor of formula (I), more preferably a QC inhibitor selected from any one of examples 1 to 1323, in combination with AChE inhibitors, preferably Donepezil, for the prevention and/or treatment of Alzheimer's disease,
- a QC inhibitor, preferably a QC inhibitor of formula (I), more preferably a QC inhibitor selected from any one of examples 1 to 1323, in combination with interferones, preferably Aronex, for the prevention and/or treatment of multiple sclerosis,
- a QC inhibitor, preferably a QC inhibitor of formula (I), more preferably a QC inhibitor selected from any one of examples 1 to 1323, in combination with interferones, preferably betaferon, for the prevention and/or treatment of multiple sclerosis,
- a QC inhibitor, preferably a QC inhibitor of formula (I), more preferably a QC inhibitor selected from any one of examples 1 to 1323, in combination with interferones, preferably Rebif, for the prevention and/or treatment of multiple sclerosis
- a QC inhibitor, preferably a QC inhibitor of formula (I), more preferably a QC inhibitor selected from any one of examples 1 to 1323, in combination with Copaxone, for the prevention and/or treatment of multiple sclerosis,
- a QC inhibitor, preferably a QC inhibitor of formula (I), more preferably a QC inhibitor selected from any one of examples 1 to 1323, in combination with dexamethasone, for the prevention and/or treatment of restenosis,
- a QC inhibitor, preferably a QC inhibitor of formula (I), more preferably a QC inhibitor selected from any one of examples 1 to 1323, in combination with dexamethasone, for the prevention and/or treatment of atherosclerosis,
- a QC inhibitor, preferably a QC inhibitor of formula (I), more preferably a QC inhibitor selected from any one of examples 1 to 1323, in combination with dexamethasone, for the prevention and/or treatment of rheumatid arthritis,
- a QC inhibitor, preferably a QC inhibitor of formula (I), more preferably a QC inhibitor selected from any one of examples 1 to 1323, in combination with HMG-Co-A-reductase inhibitors, for the prevention and/or treatment of restenosis, wherein the HMG-Co-A-reductase inhibitor is selected from atorvastatin, cerivastatin, fluvastatin, lovastatin, pitavastatin, pravastatin, rosuvastatin and simvastatin,
- a QC inhibitor, preferably a QC inhibitor of formula (I), more preferably a QC inhibitor selected from any one of examples 1 to 1323, in combination with HMG-Co-A reductase inhibitors, for the prevention and/or treatment of atherosclerosis wherein the HMG-Co-A-reductase inhibitor is selected from atorvastatin, cerivastatin, fluvastatin, lovastatin, pitavastatin, pravastatin, rosuvastatin and simvastatin,
- a QC inhibitor, preferably a QC inhibitor of formula (I), more preferably a QC inhibitor selected from any one of examples 1 to 1323, in combination with HMG-Co-A reductase inhibitors, for the prevention and/or treatment of rheumatoid arthritis wherein the HMG-Co-A-reductase inhibitor is selected from atorvastatin, cerivastatin, fluvastatin, lovastatin, pitavastatin, pravastatin, rosuvastatin and simvastatin,
- a QC inhibitor, preferably a QC inhibitor of formula (I), more preferably a QC inhibitor selected from any one of examples 1 to 1323, in combination with amyloid-beta antibodies for the prevention and/or treatment of mild cognitive impairment, wherein the amyloid-beta antibody is Acl-24,
- a QC inhibitor, preferably a QC inhibitor of formula (I), more preferably a QC inhibitor selected from any one of examples 1 to 1323, in combination with amyloid-beta antibodies for the prevention and/or treatment of Alzheimer's disease, wherein the amyloid-beta antibody is Acl-24,
- a QC inhibitor, preferably a QC inhibitor of formula (I), more preferably a QC inhibitor selected from any one of examples 1 to 1323, in combination with amyloid-beta antibodies for the prevention and/or treatment of neurodegeneration in Down Syndrome, wherein the amyloid-beta antibody is Acl-24,
- a QC inhibitor, preferably a QC inhibitor of formula (I), more preferably a QC inhibitor selected from any one of examples 1 to 1323, in combination with beta-secretase inhibitors for the prevention and/or treatment of mild cognitive impairment, wherein the beta-secretase inhibitor is selected from WY-25105, GW-840736X and CTS-21166, a QC inhibitor, preferably a QC inhibitor of formula (I), more preferably a QC inhibitor selected from any one of examples 1 to 1323, in combination with beta-secretase inhibitors for the prevention and/or treatment of Alzheimer's disease, wherein the beta-secretase inhibitor is selected from WY-25105, GW-840736X and CTS-21166, a QC inhibitor, preferably a QC inhibitor of formula (I), more preferably a QC inhibitor selected from any one of examples 1 to 1323, in combination with beta-secretase inhibitors for the prevention and/or treatment of neurodegeneration in Down Syndrome, wherein the beta-secretase inhibitor is selected from WY-25105, GW-840736X and CTS-21166, a QC inhibitor, preferably a QC inhibitor of formula (I), more preferably a QC inhibitor selected from any one of examples 1 to 1323, in combination with gamma-secretase inhibitors for the prevention and/or treatment of mild cognitive impairment, wherein the gamma-secretase inhibitor is selected from LY-450139, LY-411575 and AN-37124, a QC inhibitor, preferably a QC inhibitor of formula (I), more preferably a QC inhibitor selected from any one of examples 1 to 1323, in combination with gamma-secretase inhibitors for the prevention and/or treatment of Alzheimer's disease, wherein the gamma-secretase inhibitor is selected from LY-450139, LY-411575 and AN-37124, a QC inhibitor, preferably a QC inhibitor of formula (I), more preferably a QC inhibitor selected from any one of examples 1 to 1323, in combination with gamma-secretase inhibitors for the prevention and/or treatment of neurodegeneration in Down Syndrome, wherein the gamma-secretase inhibitor is selected from LY-450139, LY-411575 and AN-37124.

Such a combination therapy is in particular useful for AD, FAD, FDD and neurodegeneration in Down syndrome as well as atherosclerosis, rheumatoid arthritis, restenosis and pancreatitis.

Such combination therapies might result in a better therapeutic effect (less proliferation as well as less inflammation, a stimulus for proliferation) than would occur with either agent alone.

With regard to the specific combination of inhibitors of QC and further compounds it is referred in particular to WO 2004/098625 in this regard, which is incorporated herein by reference.

Pharmaceutical Compositions

To prepare the pharmaceutical compositions of this invention, at least one compound of formula (I) optionally in combination with at least one of the other aforementioned agents can be used as the active ingredient(s). The active ingredient(s) is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble saft of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

The pharmaceutical composition may contain between about 0.01 mg and 100 mg, preferably about 5 to 50 mg, of each compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamid-ephenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

In a further aspect, the invention also provides a process for preparing a pharmaceutical composition comprising at least one compound of formula (I), optionally in combination with at least one of the other aforementioned agents and a pharmaceutically acceptable carrier.

The compositions are preferably in a unit dosage form in an amount appropriate for the relevant daily dosage.

Suitable dosages, including especially unit dosages, of the compounds of the present invention include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

EXAMPLES

In a further embodiment, the present invention provides compounds of formula (IIa) and (IIb), wherein $X_1$, n, Z, $Y_1$, $Y_2$, $Y_3$, $Y_4$, $Y_5$, $Y_6$, $Y_7$, $Y_8$, $Y_9$, $Y_{10}$, $R_5$, and $R_6$ are as defined in examples 1 to 265:

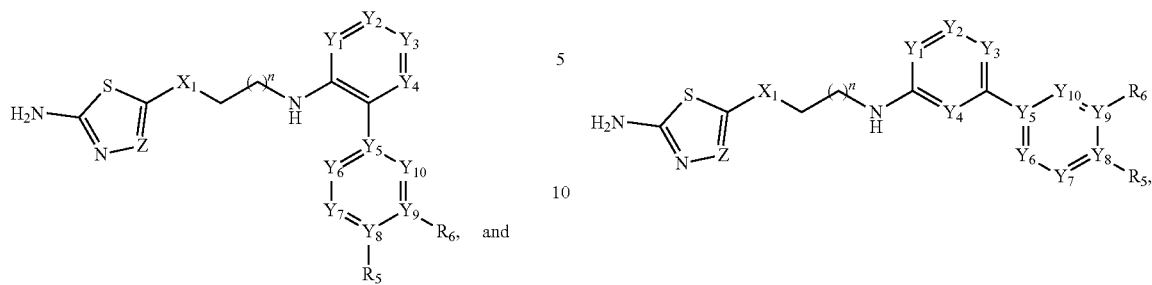

| Comp | X₁ | n | Z | Y₁ | Y₂ | Y₃ | Y₄ | Y₅ | Y₆ | Y₇ | Y₈ | Y₉ | Y₁₀ | R₅ | R₆ |
|---|---|---|---|---|---|---|---|---|---|---|---|---|---|---|---|
| 1 | CH₂ | 1 | CH | CH | CH | CH | CH | C | CH | CH | CH | CH | CH | H | H |
| 2 | CH₂ | 1 | N | CH | CH | CH | CH | C | CH | CH | CH | CH | CH | H | H |
| 3 | S | 1 | N | CH | CH | CH | CH | C | CH | CH | CH | CH | CH | H | H |
| 4 | CH₂ | 1 | CH | CH | CH | CH | CH | C | N | CH | CH | CH | CH | H | H |
| 5 | CH₂ | 1 | N | CH | CH | CH | CH | C | N | CH | CH | CH | CH | H | H |
| 6 | S | 1 | N | CH | CH | CH | CH | C | N | CH | CH | CH | CH | H | H |
| 7 | CH₂ | 1 | CH | CH | CH | CH | CH | C | CH | N | CH | CH | CH | H | H |
| 8 | CH₂ | 1 | N | CH | CH | CH | CH | C | CH | N | CH | CH | CH | H | H |
| 9 | S | 1 | N | CH | CH | CH | CH | C | CH | N | CH | CH | CH | H | H |
| 10 | CH₂ | 1 | CH | CH | CH | CH | CH | C | N | CH | CH | CH | N | H | H |
| 11 | CH₂ | 1 | N | CH | CH | CH | CH | C | N | CH | CH | CH | N | H | H |
| 12 | S | 1 | N | CH | CH | CH | CH | C | N | CH | CH | CH | N | H | H |
| 13 | CH₂ | 1 | CH | CH | CH | CH | CH | C | N | N | CH | CH | CH | H | H |
| 14 | CH₂ | 1 | N | CH | CH | CH | CH | C | N | N | CH | CH | CH | H | H |
| 15 | S | 1 | N | CH | CH | CH | CH | C | N | N | CH | CH | CH | H | H |
| 16 | CH₂ | 1 | CH | CH | CH | CH | CH | C | CH | N | CH | N | CH | H | absent |
| 17 | CH₂ | 1 | N | CH | CH | CH | CH | C | CH | N | CH | N | CH | H | H |
| 18 | S | 1 | N | CH | CH | CH | CH | C | CH | N | CH | N | CH | H | H |
| 19 | CH2 | 1 | CH | CH | CH | CH | CH | C | CH | CH | N | CH | N | absent | H |
| 20 | CH2 | 1 | N | CH | CH | CH | CH | C | CH | CH | N | CH | N |  | H |
| 21 | S | 1 | N | CH | CH | CH | CH | C | CH | CH | N | CH | N |  | H |
| 22 |  | 1 |  |  |  |  |  | C | CH | CH |  | CH | CH | H | H |
| 23 | CH₂ | 1 | CH | CH | CH | CH | CH | C | CH | CH | N | CH | CH | absent | H |
| 24 | CH₂ | 1 | N | CH | CH | CH | CH | C | CH | CH | N | CH | CH |  | H |
| 25 | S | 1 | N | CH | CH | CH | CH | C | CH | CH | N | CH | CH |  | H |
| 26 | CH₂ | 1 | CH | N | CH | CH | CH | C | CH | CH | CH | CH | CH | H | H |
| 27 | CH₂ | 1 | N | N | CH | CH | CH | C | CH | CH | CH | CH | CH | H | H |
| 28 | S | 1 | N | N | CH | CH | CH | C | CH | CH | CH | CH | CH | H | H |
| 29 | CH₂ | 1 | CH | N | CH | CH | CH | C | N | CH | CH | CH | CH | H | H |
| 30 | CH₂ | 1 | N | N | CH | CH | CH | C | N | CH | CH | CH | CH | H | H |
| 31 | S | 1 | N | N | CH | CH | CH | C | N | CH | CH | CH | CH | H | H |
| 32 | CH₂ | 1 | CH | N | CH | CH | CH | C | CH | N | CH | CH | CH | H | H |
| 33 | CH₂ | 1 | N | N | CH | CH | CH | C | CH | N | CH | CH | CH | H | H |
| 34 | S | 1 | N | N | CH | CH | CH | C | CH | N | CH | CH | CH | H | H |
| 35 | CH₂ | 1 | CH | N | CH | CH | CH | C | N | CH | CH | CH | N | H | H |
| 36 | CH₂ | 1 | N | N | CH | CH | CH | C | N | CH | CH | CH | N | H | H |
| 37 | S | 1 | N | N | CH | CH | CH | C | N | CH | CH | CH | N | H | H |
| 38 | CH₂ | 1 | CH | N | CH | CH | CH | C | CH | CH | N | CH | N | absent | H |
| 39 | CH₂ | 1 | N | N | CH | CH | CH | C | CH | CH | N | CH | N |  | H |
| 40 | S | 1 | N | N | CH | CH | CH | C | CH | CH | N | CH | N |  | H |
| 41 | CH₂ | 1 | CH | N | CH | CH | CH | C | N | CH | CH | CH | CH |  | H |
| 42 | CH₂ | 1 | N | N | CH | CH | CH | C | N | CH | CH | CH | CH | H | H |
| 43 | S | 1 | N | N | CH | CH | CH | C | N | CH | CH | CH | CH | H | H |
| 44 | CH₂ | 1 | CH | N | N | CH | CH | C | CH | CH | N | CH | N | absent | H |
| 45 | CH₂ | 1 | N | N | N | CH | CH | C | CH | CH | N | CH | N |  | H |
| 46 | S | 1 | N | N | N | CH | CH | C | CH | CH | N | CH | N |  | H |
| 47 | CH₂ | 1 | CH | N | N | CH | CH | C | CH | CH | CH | CH | CH | H | H |
| 48 | CH₂ | 1 | N | N | N | CH | CH | C | CH | CH | CH | CH | CH | H | H |
| 49 | S | 1 | N | N | N | CH | CH | C | CH | CH | CH | CH | CH | H | H |
| 50 | CH₂ | 1 | CH | CH | N | CH | CH | C | CH | CH | CH | CH | CH | H | H |
| 51 | CH₂ | 1 | N | CH | N | CH | CH | C | CH | CH | CH | CH | CH | H | H |
| 52 | S | 1 | N | CH | N | CH | CH | C | CH | CH | CH | CH | CH | H | H |
| 53 | CH₂ | 1 | CH | CH | N | CH | CH | C | N | CH | CH | CH | CH | H | H |
| 54 | CH₂ | 1 | N | CH | N | CH | CH | C | N | CH | CH | CH | CH | H | H |
| 55 | S | 1 | N | CH | N | CH | CH | C | N | CH | CH | CH | CH |  | H |
| 56 | CH₂ | 1 | CH | CH | N | CH | CH | C | CH | N | CH | CH | CH | H | H |
| 57 | CH₂ | 1 | N | CH | N | CH | CH | C | CH | N | CH | CH | CH | H | H |
| 58 | S | 1 | N | CH | N | CH | CH | C | CH | N | CH | CH | CH | H | H |
| 59 | CH₂ | 1 | CH | CH | N | CH | CH | C | CH | N | CH | N | CH | H | absent |
| 60 | CH₂ | 1 | N | CH | N | CH | CH | C | CH | N | CH | N | CH |  |  |

-continued

| Comp | $X_1$ | n | Z | $Y_1$ | $Y_2$ | $Y_3$ | $Y_4$ | $Y_5$ | $Y_6$ | $Y_7$ | $Y_8$ | $Y_9$ | $Y_{10}$ | $R_5$ | $R_6$ |
|---|---|---|---|---|---|---|---|---|---|---|---|---|---|---|---|
| 61 | S | 1 | N | CH | N | CH | CH | C | CH | N | CH | N | CH | H | H |
| 62 | $CH_2$ | 1 | CH | CH | N | CH | CH | C | N | CH | CH | N | CH | H | H |
| 63 | $CH_2$ | 1 | N | CH | N | CH | CH | C | N | CH | CH | N | CH | H | H |
| 64 | S | 1 | N | CH | N | CH | CH | C | N | CH | CH | N | CH | H | H |
| 65 | $CH_2$ | 1 | CH | CH | N | CH | CH | C | CH | CH | N | CH | N | absent | H |
| 66 | $CH_2$ | 1 | N | CH | N | CH | CH | C | CH | CH | N | CH | N | | H |
| 67 | S | 1 | N | CH | N | CH | CH | C | CH | CH | N | CH | N | | |
| 68 | $CH_2$ | 1 | CH | CH | N | CH | CH | C | CH | CH | N | CH | CH | absent | H |
| 69 | $CH_2$ | 1 | N | CH | N | CH | CH | C | CH | CH | N | CH | CH | | H |
| 70 | S | 1 | N | CH | N | CH | CH | C | CH | CH | N | CH | CH | | |
| 71 | $CH_2$ | 1 | CH | N | CH | N | CH | C | CH | CH | CH | CH | CH | H | H |
| 72 | $CH_2$ | 1 | N | N | CH | N | CH | C | CH | CH | CH | CH | CH | H | H |
| 73 | S | 1 | N | N | CH | N | CH | C | CH | CH | CH | CH | CH | H | H |
| 74 | $CH_2$ | 1 | CH | N | CH | N | CH | C | N | CH | CH | CH | CH | H | H |
| 75 | $CH_2$ | 1 | N | N | CH | N | CH | C | N | CH | CH | CH | CH | H | H |
| 76 | S | 1 | N | N | CH | N | CH | C | N | CH | CH | CH | CH | H | H |
| 77 | $CH_2$ | 1 | CH | N | CH | N | CH | C | CH | N | CH | CH | CH | H | H |
| 78 | $CH_2$ | 1 | N | N | CH | N | CH | C | CH | N | CH | CH | CH | H | H |
| 79 | S | 1 | N | N | CH | N | CH | C | CH | N | CH | CH | CH | H | H |
| 80 | $CH_2$ | 1 | CH | CH | N | CH | N | C | CH | CH | CH | CH | CH | H | H |
| 81 | $CH_2$ | 1 | N | CH | N | CH | N | C | CH | CH | CH | CH | CH | H | H |
| 82 | S | 1 | N | CH | N | CH | N | C | CH | CH | CH | CH | CH | H | H |
| 83 | $CH_2$ | 1 | CH | CH | CH | N | N | C | CH | CH | CH | CH | CH | H | H |
| 84 | $CH_2$ | 1 | N | CH | CH | N | N | C | CH | CH | CH | CH | CH | H | H |
| 85 | S | 1 | N | CH | CH | N | N | C | CH | CH | CH | CH | CH | H | H |
| 86 | $CH_2$ | 1 | CH | CH | CH | CH | N | C | CH | CH | CH | CH | CH | H | H |
| 87 | $CH_2$ | 1 | N | CH | CH | CH | N | C | CH | CH | CH | CH | CH | H | H |
| 88 | S | 1 | N | CH | CH | CH | N | C | CH | CH | CH | CH | CH | H | H |
| 89 | $CH_2$ | 1 | CH | CH | CH | CH | N | C | CH | CH | N | CH | CH | absent | H |
| 90 | $CH_2$ | 1 | N | CH | CH | CH | N | C | CH | CH | N | CH | CH | | H |
| 91 | S | 1 | N | CH | CH | CH | N | C | CH | CH | N | CH | CH | | H |
| 92 | $CH_2$ | 1 | CH | CH | CH | CH | CH | C | CH | CH | CH | CH | CH | F | H |
| 93 | $CH_2$ | 1 | N | CH | CH | CH | CH | C | CH | CH | CH | CH | CH | F | H |
| 94 | S | 1 | N | CH | CH | CH | CH | C | CH | CH | CH | CH | CH | F | H |
| 95 | $CH_2$ | 1 | CH | CH | CH | CH | CH | C | N | CH | CH | CH | CH | F | H |
| 96 | $CH_2$ | 1 | N | CH | CH | CH | CH | C | N | CH | CH | CH | CH | F | H |
| 97 | S | 1 | N | CH | CH | CH | CH | C | N | CH | CH | CH | CH | F | H |
| 98 | $CH_2$ | 1 | CH | CH | CH | CH | CH | C | CH | N | CH | CH | CH | F | H |
| 99 | $CH_2$ | 1 | N | CH | CH | CH | CH | C | CH | N | CH | CH | CH | F | H |
| 100 | S | 1 | N | CH | CH | CH | CH | C | CH | N | CH | CH | CH | F | H |
| 101 | $CH_2$ | 1 | CH | CH | CH | CH | CH | C | N | CH | CH | CH | N | F | H |
| 102 | $CH_2$ | 1 | N | CH | CH | CH | CH | C | N | CH | CH | CH | N | F | H |
| 103 | S | 1 | N | CH | CH | CH | CH | C | N | CH | CH | CH | N | F | H |
| 104 | $CH_2$ | 1 | CH | CH | CH | CH | CH | C | N | N | CH | CH | CH | F | H |
| 105 | $CH_2$ | 1 | N | CH | CH | CH | CH | C | N | N | CH | CH | CH | F | H |
| 106 | S | 1 | N | CH | CH | CH | CH | C | N | N | CH | CH | CH | F | H |
| 107 | $CH_2$ | 1 | CH | CH | CH | CH | CH | C | CH | N | CH | N | CH | F | absent |
| 108 | $CH_2$ | 1 | N | CH | CH | CH | CH | C | CH | N | CH | N | CH | F | |
| 109 | S | 1 | N | CH | CH | CH | CH | C | CH | N | CH | N | CH | F | |
| 110 | $CH_2$ | 1 | CH | CH | CH | CH | CH | C | CH | CH | N | CH | N | absent | |
| 111 | $CH_2$ | 1 | N | CH | CH | CH | CH | C | CH | CH | N | CH | N | | |
| 112 | S | 1 | N | CH | CH | CH | CH | C | CH | CH | N | CH | N | | |
| 113 | $CH_2$ | 1 | CH | CH | CH | CH | CH | C | CH | CH | N | CH | CH | absent | H |
| 114 | $CH_2$ | 1 | N | CH | CH | CH | CH | C | CH | CH | N | CH | CH | | H |
| 115 | S | 1 | N | CH | CH | CH | CH | C | CH | CH | N | CH | CH | | H |
| 116 | $CH_2$ | 1 | CH | N | CH | CH | CH | C | CH | CH | CH | CH | CH | F | H |
| 117 | $CH_2$ | 1 | N | N | CH | CH | CH | C | CH | CH | CH | CH | CH | F | H |
| 118 | S | 1 | N | N | CH | CH | CH | C | CH | CH | CH | CH | CH | F | H |
| 119 | $CH_2$ | 1 | CH | N | CH | CH | CH | C | N | CH | CH | CH | CH | F | H |
| 120 | $CH_2$ | 1 | N | N | CH | CH | CH | C | N | CH | CH | CH | CH | F | H |
| 121 | S | 1 | N | N | CH | CH | CH | C | N | CH | CH | CH | CH | F | H |
| 122 | $CH_2$ | 1 | CH | N | CH | CH | CH | C | CH | N | CH | CH | CH | F | H |
| 123 | $CH_2$ | 1 | N | N | CH | CH | CH | C | CH | N | CH | CH | CH | F | H |
| 124 | S | 1 | N | N | CH | CH | CH | C | CH | N | CH | CH | CH | F | H |
| 125 | $CH_2$ | 1 | CH | N | CH | CH | CH | C | N | CH | CH | CH | | F | H |
| 126 | $CH_2$ | 1 | N | N | CH | CH | CH | C | N | CH | CH | CH | | F | H |
| 127 | S | 1 | N | N | CH | CH | CH | C | N | CH | CH | CH | | F | H |
| 128 | $CH_2$ | 1 | CH | N | CH | CH | CH | C | CH | CH | N | CH | N | absent | H |
| 129 | $CH_2$ | 1 | N | N | CH | CH | CH | C | CH | CH | N | CH | N | | H |
| 130 | S | 1 | N | N | CH | CH | CH | C | CH | CH | N | CH | N | | H |
| 131 | $CH_2$ | 1 | CH | N | N | CH | CH | C | CH | CH | CH | CH | CH | F | H |
| 132 | $CH_2$ | 1 | N | N | N | CH | CH | C | CH | CH | CH | CH | CH | F | H |
| 133 | S | 1 | N | N | N | CH | CH | C | CH | CH | CH | CH | CH | F | H |
| 134 | $CH_2$ | 1 | CH | N | N | CH | CH | C | CH | CH | N | CH | N | absent | H |
| 135 | $CH_2$ | 1 | N | N | N | CH | CH | C | CH | CH | N | CH | N | | H |
| 136 | S | 1 | N | N | N | CH | CH | C | CH | CH | N | CH | N | | H |
| 137 | $CH_2$ | 1 | CH | CH | N | CH | CH | C | CH | CH | CH | CH | CH | F | H |

-continued

| Comp | $X_1$ | n | Z | $Y_1$ | $Y_2$ | $Y_3$ | $Y_4$ | $Y_5$ | $Y_6$ | $Y_7$ | $Y_8$ | $Y_9$ | $Y_{10}$ | $R_5$ | $R_6$ |
|---|---|---|---|---|---|---|---|---|---|---|---|---|---|---|---|
| 138 | $CH_2$ | 1 | N | CH | N | CH | CH | C | CH | CH | CH | CH | CH | F | H |
| 139 | S | 1 | N | CH | N | CH | CH | C | CH | CH | CH | CH | CH | F | H |
| 140 | $CH_2$ | 1 | CH | CH | N | CH | CH | C | N | CH | CH | CH | CH | F | H |
| 141 | $CH_2$ | 1 | N | CH | N | CH | CH | C | N | CH | CH | CH | CH | F | H |
| 142 | S | 1 | N | CH | N | CH | CH | C | N | CH | CH | CH | CH | F | H |
| 143 | $CH_2$ | 1 | CH | CH | N | CH | CH | C | CH | N | CH | CH | CH | F | H |
| 144 | $CH_2$ | 1 | N | CH | N | CH | CH | C | CH | N | CH | CH | CH | F | H |
| 145 | S | 1 | N | CH | N | CH | CH | C | CH | N | CH | CH | CH | F | H |
| 146 | $CH_2$ | 1 | CH | CH | N | CH | CH | C | CH | N | CH | N | CH | F | absent |
| 147 | $CH_2$ | 1 | N | CH | N | CH | CH | C | CH | N | CH | N | CH | F | |
| 148 | S | 1 | N | CH | N | CH | CH | C | CH | N | CH | N | CH | F | |
| 149 | $CH_2$ | 1 | CH | CH | N | CH | CH | C | N | CH | CH | N | CH | F | absent |
| 150 | $CH_2$ | 1 | N | CH | N | CH | CH | C | N | CH | CH | N | CH | F | |
| 151 | S | 1 | N | CH | N | CH | CH | C | N | CH | CH | N | CH | F | |
| 152 | $CH_2$ | 1 | CH | CH | N | CH | CH | C | CH | CH | N | CH | N | absent | H |
| 153 | $CH_2$ | 1 | N | CH | N | CH | CH | C | CH | CH | N | CH | N | | H |
| 154 | S | 1 | N | CH | N | CH | CH | C | CH | CH | N | CH | N | | H |
| 155 | $CH_2$ | 1 | CH | N | CH | N | CH | C | CH | CH | CH | CH | CH | F | H |
| 156 | $CH_2$ | 1 | N | N | CH | N | CH | C | CH | CH | CH | CH | CH | F | H |
| 157 | S | 1 | N | N | CH | N | CH | C | CH | CH | CH | CH | CH | F | H |
| 158 | $CH_2$ | 1 | CH | N | CH | N | CH | C | N | CH | CH | CH | CH | F | H |
| 159 | $CH_2$ | 1 | N | N | CH | N | CH | C | N | CH | CH | CH | CH | F | H |
| 160 | S | 1 | N | N | CH | N | CH | C | N | CH | CH | CH | CH | F | H |
| 161 | $CH_2$ | 1 | CH | N | CH | N | CH | C | CH | N | CH | CH | CH | F | H |
| 162 | $CH_2$ | 1 | N | N | CH | N | CH | C | CH | N | CH | CH | CH | F | H |
| 163 | S | 1 | N | N | CH | N | CH | C | CH | N | CH | CH | CH | F | H |
| 164 | $CH_2$ | 1 | CH | CH | N | CH | N | C | CH | CH | CH | CH | CH | F | H |
| 165 | $CH_2$ | 1 | N | CH | N | CH | N | C | CH | CH | CH | CH | CH | F | H |
| 166 | S | 1 | N | CH | N | CH | N | C | CH | CH | CH | CH | CH | F | H |
| 167 | $CH_2$ | 1 | CH | CH | CH | N | N | C | CH | CH | CH | CH | CH | F | H |
| 168 | $CH_2$ | 1 | N | CH | CH | N | N | C | CH | CH | CH | CH | CH | F | H |
| 169 | S | 1 | N | CH | CH | N | N | C | CH | CH | CH | CH | CH | F | H |
| 170 | $CH_2$ | 1 | CH | CH | CH | CH | N | C | CH | CH | CH | CH | CH | F | H |
| 171 | $CH_2$ | 1 | N | CH | CH | CH | N | C | CH | CH | CH | CH | CH | F | H |
| 172 | S | 1 | N | CH | CH | CH | N | C | CH | CH | CH | CH | CH | F | H |
| 173 | $CH_2$ | 1 | CH | CH | CH | CH | N | C | CH | N | CH | CH | CH | F | H |
| 174 | $CH_2$ | 1 | N | CH | CH | CH | N | C | CH | N | CH | CH | CH | F | H |
| 175 | S | 1 | N | CH | CH | CH | N | C | CH | N | CH | CH | CH | F | H |
| 176 | $CH_2$ | 1 | CH | CH | CH | CH | CH | C | CH | CH | CH | CH | CH | OMe | OMe |
| 177 | $CH_2$ | 1 | N | CH | CH | CH | CH | C | CH | CH | CH | CH | CH | OMe | OMe |
| 178 | S | 1 | N | CH | CH | CH | CH | C | CH | CH | CH | CH | CH | OMe | OMe |
| 179 | $CH_2$ | 1 | CH | CH | CH | CH | CH | C | N | CH | CH | CH | CH | OMe | OMe |
| 180 | $CH_2$ | 1 | N | CH | CH | CH | CH | C | N | CH | CH | CH | CH | OMe | OMe |
| 181 | S | 1 | N | CH | CH | CH | CH | C | N | CH | CH | CH | CH | OMe | OMe |
| 182 | $CH_2$ | 1 | CH | CH | CH | CH | CH | C | CH | N | CH | CH | CH | OMe | OMe |
| 183 | $CH_2$ | 1 | N | CH | CH | CH | CH | C | CH | N | CH | CH | CH | OMe | OMe |
| 184 | S | 1 | N | CH | CH | CH | CH | C | CH | N | CH | CH | CH | OMe | OMe |
| 185 | $CH_2$ | 1 | CH | CH | CH | CH | CH | C | N | CH | CH | CH | N | OMe | OMe |
| 186 | $CH_2$ | 1 | N | CH | CH | CH | CH | C | N | CH | CH | CH | N | OMe | OMe |
| 187 | S | 1 | N | CH | CH | CH | CH | C | N | CH | CH | CH | N | OMe | OMe |
| 188 | $CH_2$ | 1 | CH | CH | CH | CH | CH | C | N | N | CH | CH | CH | OMe | OMe |
| 189 | $CH_2$ | 1 | N | CH | CH | CH | CH | C | N | N | CH | CH | CH | OMe | OMe |
| 190 | S | 1 | N | CH | CH | CH | CH | C | N | N | CH | CH | CH | OMe | OMe |
| 191 | $CH_2$ | 1 | CH | CH | CH | CH | CH | C | CH | N | CH | N | CH | OMe | absent |
| 192 | $CH_2$ | 1 | N | CH | CH | CH | CH | C | CH | N | CH | N | CH | OMe | |
| 193 | S | 1 | N | CH | CH | CH | CH | C | CH | N | CH | N | CH | OMe | |
| 194 | $CH_2$ | 1 | CH | CH | CH | CH | CH | C | CH | CH | N | CH | N | absent | OMe |
| 195 | $CH_2$ | 1 | N | CH | CH | CH | CH | C | CH | CH | N | CH | N | | OMe |
| 196 | S | 1 | N | CH | CH | CH | CH | C | CH | CH | N | CH | N | | OMe |
| 197 | $CH_2$ | 1 | CH | CH | CH | CH | CH | C | CH | CH | N | CH | CH | absent | OMe |
| 198 | $CH_2$ | 1 | N | N | CH | CH | CH | C | CH | CH | N | CH | CH | | OMe |
| 199 | S | 1 | N | N | CH | CH | CH | C | CH | CH | N | CH | CH | | OMe |
| 200 | $CH_2$ | 1 | CH | N | CH | CH | CH | C | CH | CH | CH | CH | CH | OMe | OMe |
| 201 | $CH_2$ | 1 | N | N | CH | CH | CH | C | CH | CH | CH | CH | CH | OMe | OMe |
| 202 | S | 1 | N | N | CH | CH | CH | C | CH | CH | CH | CH | CH | OMe | OMe |
| 203 | $CH_2$ | 1 | CH | N | CH | CH | CH | C | N | CH | CH | CH | CH | OMe | OMe |
| 204 | CH2 | 1 | N | N | CH | CH | CH | C | N | CH | CH | CH | CH | OMe | OMe |
| 205 | S | 1 | N | N | CH | CH | CH | C | N | CH | CH | CH | CH | OMe | OMe |
| 206 | $CH_2$ | 1 | CH | N | CH | CH | CH | C | CH | N | CH | CH | CH | OMe | OMe |
| 207 | $CH_2$ | 1 | N | N | CH | CH | CH | C | CH | N | CH | CH | CH | OMe | OMe |
| 208 | S | 1 | N | N | CH | CH | CH | C | CH | N | CH | CH | CH | OMe | OMe |
| 209 | $CH_2$ | 1 | CH | N | CH | CH | CH | C | N | CH | CH | CH | N | OMe | OMe |
| 210 | $CH_2$ | 1 | N | N | CH | CH | CH | C | N | CH | CH | CH | N | OMe | OMe |
| 211 | S | 1 | N | N | CH | CH | CH | C | N | CH | CH | CH | N | OMe | OMe |
| 212 | $CH_2$ | 1 | CH | N | CH | CH | CH | C | CH | CH | N | CH | N | absent | OMe |
| 213 | $CH_2$ | 1 | N | N | CH | CH | CH | C | CH | CH | N | CH | N | | OMe |
| 214 | S | 1 | N | N | CH | CH | CH | C | CH | CH | N | CH | N | | OMe |

-continued

| Comp | $X_1$ | n | Z | $Y_1$ | $Y_2$ | $Y_3$ | $Y_4$ | $Y_5$ | $Y_6$ | $Y_7$ | $Y_8$ | $Y_9$ | $Y_{10}$ | $R_5$ | $R_6$ |
|---|---|---|---|---|---|---|---|---|---|---|---|---|---|---|---|
| 215 | $CH_2$ | 1 | CH | N | CH | CH | CH | C | N | CH | CH | CH | CH | OMe | OMe |
| 216 | $CH_2$ | 1 | N | N | CH | CH | CH | C | N | CH | CH | CH | CH | OMe | OMe |
| 217 | S | 1 | N | N | CH | CH | CH | C | N | CH | CH | CH | CH | OMe | OMe |
| 218 | $CH_2$ | 1 | CH | N | N | CH | CH | C | CH | CH | N | CH | N | absent | OMe |
| 219 | $CH_2$ | 1 | N | N | N | CH | CH | C | CH | CH | N | CH | N |  | OMe |
| 220 | S | 1 | N | N | N | CH | CH | C | CH | CH | N | CH | N |  | OMe |
| 221 | $CH_2$ | 1 | CH | N | N | CH | CH | C | CH | CH | CH | CH | CH | OMe | OMe |
| 222 | $CH_2$ | 1 | N | N | N | CH | CH | C | CH | CH | CH | CH | CH | OMe | OMe |
| 223 | S | 1 | N | N | N | CH | CH | C | CH | CH | CH | CH | CH | OMe | OMe |
| 224 | $CH_2$ | 1 | CH | CH | N | CH | CH | C | CH | CH | CH | CH | CH | OMe | OMe |
| 225 | $CH_2$ | 1 | N | CH | N | CH | CH | C | CH | CH | CH | CH | CH | OMe | OMe |
| 226 | S | 1 | N | CH | N | CH | CH | C | CH | CH | CH | CH | CH | OMe | OMe |
| 227 | $CH_2$ | 1 | CH | CH | N | CH | CH | C | N | CH | CH | CH | CH | OMe | OMe |
| 228 | $CH_2$ | 1 | N | CH | N | CH | CH | C | N | CH | CH | CH | CH | OMe | OMe |
| 229 | S | 1 | N | CH | N | CH | CH | C | N | CH | CH | CH | CH | OMe | OMe |
| 230 | $CH_2$ | 1 | CH | CH | N | CH | CH | C | CH | N | CH | CH | CH | OMe | OMe |
| 231 | $CH_2$ | 1 | N | CH | N | CH | CH | C | CH | N | CH | CH | CH | OMe | OMe |
| 232 | S | 1 | N | CH | N | CH | CH | C | CH | N | CH | CH | CH | OMe | OMe |
| 233 | $CH_2$ | 1 | CH | CH | N | CH | CH | C | CH | N | CH | N | CH | OMe | absent |
| 234 | $CH_2$ | 1 | N | CH | N | CH | CH | C | CH | N | CH | N | CH | OMe |  |
| 235 | S | 1 | N | CH | N | CH | CH | C | CH | N | CH | N | CH | OMe |  |
| 236 | $CH_2$ | 1 | CH | CH | N | CH | CH | C | N | CH | CH | N | CH | OMe | OMe |
| 237 | $CH_2$ | 1 | N | CH | N | CH | CH | C | N | CH | CH | N | CH | OMe | OMe |
| 238 | S | 1 | N | CH | N | CH | CH | C | N | CH | CH | N | CH | OMe | OMe |
| 239 | $CH_2$ | 1 | CH | CH | N | CH | CH | C | CH | CH | N | CH | N | absent | OMe |
| 240 | $CH_2$ | 1 | N | CH | N | CH | CH | C | CH | CH | N | CH | N |  | OMe |
| 241 | S | 1 | N | CH | N | CH | CH | C | CH | CH | N | CH | N |  | OMe |
| 242 | $CH_2$ | 1 | CH | CH | N | CH | CH | C | CH | CH | N | CH | CH | absent | OMe |
| 243 | $CH_2$ | 1 | N | CH | N | CH | CH | C | CH | CH | N | CH | CH |  | OMe |
| 244 | S | 1 | N | CH | N | CH | CH | C | CH | CH | N | CH | CH |  | OMe |
| 245 | $CH_2$ | 1 | CH | N | CH | N | CH | C | CH | CH | CH | CH | CH | OMe | OMe |
| 246 | $CH_2$ | 1 | N | N | CH | N | CH | C | CH | CH | CH | CH | CH | OMe | OMe |
| 247 | S | 1 | N | N | CH | N | CH | C | CH | CH | CH | CH | CH | OMe | OMe |
| 248 | $CH_2$ | 1 | CH | N | CH | N | CH | C | N | CH | CH | CH | CH | OMe | OMe |
| 249 | $CH_2$ | 1 | N | N | CH | N | CH | C | N | CH | CH | CH | CH | OMe | OMe |
| 250 | S | 1 | N | N | CH | N | CH | C | N | CH | CH | CH | CH | OMe | OMe |
| 251 | $CH_2$ | 1 | CH | N | CH | N | CH | C | CH | N | CH | CH | CH | OMe | OMe |
| 252 | $CH_2$ | 1 | N | N | CH | N | CH | C | CH | N | CH | CH | CH | OMe | OMe |
| 253 | S | 1 | N | N | CH | N | CH | C | CH | N | CH | CH | CH | OMe | OMe |
| 254 | $CH_2$ | 1 | CH | CH | N | CH | N | C | CH | CH | CH | CH | CH | OMe | OMe |
| 255 | $CH_2$ | 1 | N | CH | N | CH | N | C | CH | CH | CH | CH | CH | OMe | OMe |
| 256 | S | 1 | N | CH | N | CH | N | C | CH | CH | CH | CH | CH | OMe | OMe |
| 257 | $CH_2$ | 1 | CH | CH | CH | N | N | C | CH | CH | CH | CH | CH | OMe | OMe |
| 258 | $CH_2$ | 1 | N | CH | CH | N | N | C | CH | CH | CH | CH | CH | OMe | OMe |
| 259 | S | 1 | N | CH | CH | N | N | C | CH | CH | CH | CH | CH | OMe | OMe |
| 260 | $CH_2$ | 1 | CH | CH | CH | CH | N | C | CH | CH | CH | CH | CH | OMe | OMe |
| 261 | $CH_2$ | 1 | N | CH | CH | CH | N | C | CH | CH | CH | CH | CH | OMe | OMe |
| 262 | S | 1 | N | CH | CH | CH | N | C | CH | CH | CH | CH | CH | OMe | OMe |
| 263 | $CH_2$ | 1 | CH | CH | CH | CH | N | C | CH | CH | N | CH | CH | absent | OMe |
| 264 | $CH_2$ | 1 | N | CH | CH | CH | N | C | CH | CH | N | CH | CH |  | OMe |
| 265 | S | 1 | N | CH | CH | CH | N | C | CH | CH | N | CH | CH |  | OMe |

In a further embodiment, the present invention provides compounds of formula (IIIa) and (IIIb), wherein $X_1$, n, $Y_1$, $Y_2$, $Y_3$, $Y_4$, $Y_5$, $Y_6$, $Y_7$, $Y_8$, $Y_9$, $Y_{10}$, $R_5$, and $R_6$ are as defined in examples 266 to 443:

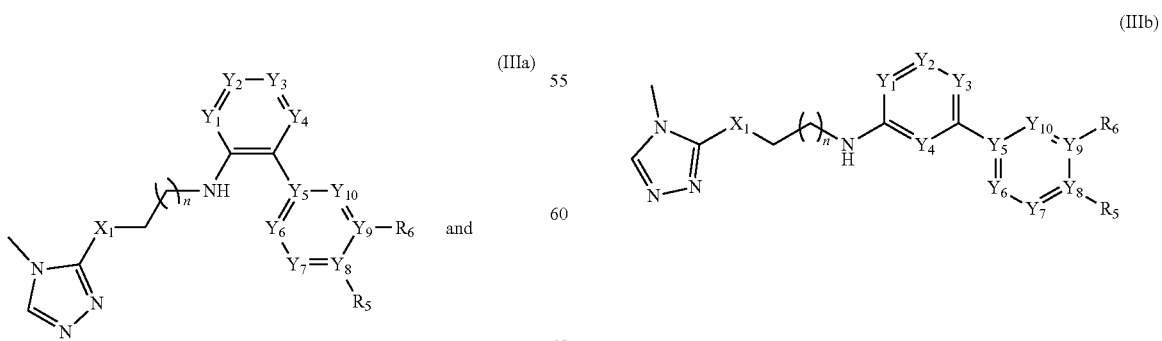

| Comp | $X_1$ | n | $Y_1$ | $Y_2$ | $Y_3$ | $Y_4$ | $Y_5$ | $Y_6$ | $Y_7$ | $Y_8$ | $Y_9$ | $Y_{10}$ | $R_5$ | $R_6$ |
|---|---|---|---|---|---|---|---|---|---|---|---|---|---|---|
| 266 | $CH_2$ | 1 | CH | CH | CH | CH | C | CH | CH | CH | CH | CH | H | H |
| 267 | S | 1 | CH | CH | CH | CH | C | CH | CH | CH | CH | CH | H | H |
| 268 | $CH_2$ | 1 | CH | CH | CH | CH | C | N | CH | CH | CH | CH | H | H |
| 269 | S | 1 | CH | CH | CH | CH | C | N | CH | CH | CH | CH | H | H |
| 270 | $CH_2$ | 1 | CH | CH | CH | CH | C | CH | N | CH | CH | CH | H | H |
| 271 | S | 1 | CH | CH | CH | CH | C | CH | N | CH | CH | CH | H | H |
| 272 | $CH_2$ | 1 | CH | CH | CH | CH | C | N | CH | CH | CH | N | H | H |
| 273 | S | 1 | CH | CH | CH | CH | C | N | CH | CH | CH | N | H | H |
| 274 | $CH_2$ | 1 | CH | CH | CH | CH | C | N | N | CH | CH | CH | H | H |
| 275 | S | 1 | CH | CH | CH | CH | C | N | N | CH | CH | CH | H | H |
| 276 | $CH_2$ | 1 | CH | CH | CH | CH | C | CH | N | CH | N | CH | H | absent |
| 277 | S | 1 | CH | CH | CH | CH | C | CH | N | CH | N | CH | H | |
| 278 | $CH_2$ | 1 | CH | CH | CH | CH | C | CH | CH | N | CH | N | absent | H |
| 279 | S | 1 | CH | CH | CH | CH | C | CH | CH | N | CH | N | | H |
| 280 | $CH_2$ | 1 | CH | CH | CH | CH | C | CH | CH | N | CH | CH | absent | H |
| 281 | S | 1 | CH | CH | CH | CH | C | CH | CH | N | CH | CH | | H |
| 282 | $CH_2$ | 1 | N | CH | CH | CH | C | CH | CH | CH | CH | CH | H | H |
| 283 | S | 1 | N | CH | CH | CH | C | CH | CH | CH | CH | CH | H | H |
| 284 | $CH_2$ | 1 | N | CH | CH | CH | C | N | CH | CH | CH | CH | H | H |
| 285 | S | 1 | N | CH | CH | CH | C | N | CH | CH | CH | CH | H | H |
| 286 | $CH_2$ | 1 | N | CH | CH | CH | C | CH | N | CH | CH | CH | H | H |
| 287 | $CH_2$ | 1 | N | CH | CH | CH | C | CH | N | CH | CH | CH | H | H |
| 288 | S | 1 | N | CH | CH | CH | C | CH | N | CH | CH | CH | H | H |
| 289 | $CH_2$ | 1 | N | CH | CH | CH | C | N | CH | CH | CH | N | H | H |
| 290 | S | 1 | N | CH | CH | CH | C | N | CH | CH | CH | N | H | H |
| 291 | $CH_2$ | 1 | N | CH | CH | CH | C | CH | CH | N | CH | N | absent | H |
| 292 | S | 1 | N | CH | CH | CH | C | CH | CH | N | CH | N | | H |
| 293 | $CH_2$ | 1 | N | CH | CH | CH | C | N | CH | CH | CH | CH | H | H |
| 294 | S | 1 | N | CH | CH | CH | C | N | CH | CH | CH | CH | H | H |
| 295 | $CH_2$ | 1 | N | N | CH | CH | C | CH | CH | N | CH | N | absent | H |
| 296 | $CH_2$ | 1 | N | N | CH | CH | C | CH | CH | N | CH | N | | H |
| 297 | S | 1 | N | N | CH | CH | C | CH | CH | N | CH | N | | H |
| 298 | $CH_2$ | 1 | N | N | CH | CH | C | CH | CH | CH | CH | CH | H | H |
| 299 | S | 1 | N | N | CH | CH | C | CH | CH | CH | CH | CH | H | H |
| 300 | $CH_2$ | 1 | CH | N | CH | CH | C | CH | CH | CH | CH | CH | H | H |
| 301 | S | 1 | CH | N | CH | CH | C | CH | CH | CH | CH | CH | H | H |
| 302 | $CH_2$ | 1 | CH | N | CH | CH | C | N | CH | CH | CH | CH | H | H |
| 303 | S | 1 | CH | N | CH | CH | C | N | CH | CH | CH | CH | H | H |
| 304 | $CH_2$ | 1 | CH | N | CH | CH | C | CH | N | CH | CH | CH | H | H |
| 305 | S | 1 | CH | N | CH | CH | C | CH | N | CH | CH | CH | H | H |
| 306 | $CH_2$ | 1 | CH | N | CH | CH | C | CH | N | CH | N | CH | H | absent |
| 307 | S | 1 | CH | N | CH | CH | C | CH | N | CH | N | CH | H | |
| 308 | $CH_2$ | 1 | CH | N | CH | CH | C | N | CH | CH | N | CH | H | H |
| 309 | S | 1 | CH | N | CH | CH | C | N | CH | CH | N | CH | H | H |
| 310 | $CH_2$ | 1 | CH | N | CH | CH | C | CH | CH | N | CH | N | absent | H |
| 311 | S | 1 | CH | N | CH | CH | C | CH | CH | N | CH | N | | H |
| 312 | $CH_2$ | 1 | CH | N | CH | CH | C | CH | CH | N | CH | CH | absent | H |
| 313 | S | 1 | CH | N | CH | CH | C | CH | CH | N | CH | CH | | H |
| 314 | $CH_2$ | 1 | N | CH | N | CH | C | CH | CH | CH | CH | CH | H | H |
| 315 | S | 1 | N | CH | N | CH | C | CH | CH | CH | CH | CH | H | H |
| 316 | $CH_2$ | 1 | N | CH | N | CH | C | N | CH | CH | CH | CH | H | H |
| 317 | S | 1 | N | CH | N | CH | C | N | CH | CH | CH | CH | H | H |
| 318 | $CH_2$ | 1 | N | CH | N | CH | C | CH | N | CH | CH | CH | H | H |
| 319 | S | 1 | N | CH | N | CH | C | CH | N | CH | CH | CH | H | H |
| 320 | $CH_2$ | 1 | CH | N | CH | N | C | CH | CH | CH | CH | CH | H | H |
| 321 | S | 1 | CH | N | CH | N | C | CH | CH | CH | CH | CH | H | H |
| 322 | $CH_2$ | 1 | CH | CH | N | N | C | CH | CH | CH | CH | CH | H | H |
| 323 | S | 1 | CH | CH | N | N | C | CH | CH | CH | CH | CH | H | H |
| 324 | $CH_2$ | 1 | CH | CH | CH | N | C | CH | CH | CH | CH | CH | H | H |
| 325 | S | 1 | CH | CH | CH | N | C | CH | CH | CH | CH | CH | H | H |
| 326 | $CH_2$ | 1 | CH | CH | CH | N | C | CH | CH | N | CH | CH | absent | H |
| 327 | S | 1 | CH | CH | CH | N | C | CH | CH | N | CH | CH | | H |
| 328 | $CH_2$ | 1 | CH | CH | CH | CH | C | CH | CH | CH | CH | CH | F | H |
| 329 | S | 1 | CH | CH | CH | CH | C | CH | CH | CH | CH | CH | F | H |
| 330 | $CH_2$ | 1 | CH | CH | CH | CH | C | N | CH | CH | CH | CH | F | H |
| 331 | S | 1 | CH | CH | CH | CH | C | N | CH | CH | CH | CH | F | H |
| 332 | $CH_2$ | 1 | CH | CH | CH | CH | C | CH | N | CH | CH | CH | F | H |
| 333 | S | 1 | CH | CH | CH | CH | C | CH | N | CH | CH | CH | F | H |
| 334 | $CH_2$ | 1 | CH | CH | CH | CH | C | N | CH | CH | CH | N | F | H |
| 335 | S | 1 | CH | CH | CH | CH | C | N | CH | CH | CH | N | F | H |
| 336 | $CH_2$ | 1 | CH | CH | CH | CH | C | N | N | CH | CH | CH | F | H |
| 337 | S | 1 | CH | CH | CH | CH | C | N | N | CH | CH | CH | F | H |
| 338 | $CH_2$ | 1 | CH | CH | CH | CH | C | CH | N | CH | N | CH | F | absent |
| 339 | S | 1 | CH | CH | CH | CH | C | CH | N | CH | N | CH | F | |
| 340 | $CH_2$ | 1 | CH | CH | CH | CH | C | CH | CH | N | CH | N | absent | |
| 341 | S | 1 | CH | CH | CH | CH | C | CH | CH | N | CH | N | | |
| 342 | $CH_2$ | 1 | CH | CH | CH | CH | C | CH | CH | N | CH | CH | absent | H |
| 343 | S | 1 | CH | CH | CH | CH | C | CH | CH | N | CH | CH | | H |
| 344 | $CH_2$ | 1 | N | CH | CH | CH | C | CH | CH | CH | CH | CH | F | H |

-continued

| Comp | $X_1$ | n | $Y_1$ | $Y_2$ | $Y_3$ | $Y_4$ | $Y_5$ | $Y_6$ | $Y_7$ | $Y_8$ | $Y_9$ | $Y_{10}$ | $R_5$ | $R_6$ |
|---|---|---|---|---|---|---|---|---|---|---|---|---|---|---|
| 345 | S | 1 | N | CH | CH | CH | C | CH | CH | CH | CH | CH | F | H |
| 346 | $CH_2$ | 1 | N | CH | CH | CH | C | N | CH | CH | CH | CH | F | H |
| 347 | S | 1 | N | CH | CH | CH | C | N | CH | CH | CH | CH | F | H |
| 348 | $CH_2$ | 1 | N | CH | CH | CH | C | CH | N | CH | CH | CH | F | H |
| 349 | S | 1 | N | CH | CH | CH | C | CH | N | CH | CH | CH | F | H |
| 350 | $CH_2$ | 1 | N | CH | CH | CH | C | N | CH | CH | CH | N | F | H |
| 351 | S | 1 | N | CH | CH | CH | C | N | CH | CH | CH | N | F | H |
| 352 | $CH_2$ | 1 | N | CH | CH | CH | C | CH | CH | N | CH | N | absent | H |
| 353 | S | 1 | N | CH | CH | CH | C | CH | CH | N | CH | N |  | H |
| 354 | $CH_2$ | 1 | N | N | CH | CH | C | CH | CH | CH | CH | CH | F | H |
| 355 | S | 1 | N | N | CH | CH | C | CH | CH | CH | CH | CH | F | H |
| 356 | $CH_2$ | 1 | N | N | CH | CH | C | CH | CH | N | CH | N | absent | H |
| 357 | S | 1 | N | N | CH | CH | C | CH | CH | N | CH | N |  | H |
| 358 | $CH_2$ | 1 | CH | N | CH | CH | C | CH | CH | CH | CH | CH | F | H |
| 359 | S | 1 | CH | N | CH | CH | C | CH | CH | CH | CH | CH | F | H |
| 360 | $CH_2$ | 1 | CH | N | CH | CH | C | N | CH | CH | CH | CH | F | H |
| 361 | S | 1 | CH | N | CH | CH | C | N | CH | CH | CH | CH | F | H |
| 362 | $CH_2$ | 1 | CH | N | CH | CH | C | CH | N | CH | CH | CH | F | H |
| 363 | S | 1 | CH | N | CH | CH | C | CH | N | CH | CH | CH | F | H |
| 364 | $CH_2$ | 1 | CH | N | CH | CH | C | CH | N | CH | N | CH | F | absent |
| 365 | S | 1 | CH | N | CH | CH | C | CH | N | CH | N | CH | F |  |
| 366 | $CH_2$ | 1 | CH | N | CH | CH | C | N | CH | CH | N | CH | F | absent |
| 367 | S | 1 | CH | N | CH | CH | C | N | CH | CH | N | CH | F |  |
| 368 | $CH_2$ | 1 | CH | N | CH | CH | C | CH | CH | N | CH | N | absent | H |
| 369 | S | 1 | CH | N | CH | CH | C | CH | CH | N | CH | N |  | H |
| 370 | $CH_2$ | 1 | N | CH | N | CH | C | CH | CH | CH | CH | CH | F | H |
| 371 | S | 1 | N | CH | N | CH | C | CH | CH | CH | CH | CH | F | H |
| 372 | $CH_2$ | 1 | N | CH | N | CH | C | N | CH | CH | CH | CH | F | H |
| 373 | S | 1 | N | CH | N | CH | C | N | CH | CH | CH | CH | F | H |
| 374 | $CH_2$ | 1 | N | CH | N | CH | C | CH | N | CH | CH | CH | F | H |
| 375 | S | 1 | N | CH | N | CH | C | CH | N | CH | CH | CH | F | H |
| 376 | $CH_2$ | 1 | CH | N | CH | N | C | CH | CH | CH | CH | CH | F | H |
| 377 | S | 1 | CH | N | CH | N | C | CH | CH | CH | CH | CH | F | H |
| 378 | $CH_2$ | 1 | CH | CH | N | N | C | CH | CH | CH | CH | CH | F | H |
| 379 | S | 1 | CH | CH | N | N | C | CH | CH | CH | CH | CH | F | H |
| 380 | $CH_2$ | 1 | CH | CH | CH | N | C | CH | CH | CH | CH | CH | F | H |
| 381 | S | 1 | CH | CH | CH | N | C | CH | CH | CH | CH | CH | F | H |
| 382 | $CH_2$ | 1 | CH | CH | CH | N | C | CH | N | CH | CH | CH | F | H |
| 383 | S | 1 | CH | CH | CH | N | C | CH | N | CH | CH | CH | F | H |
| 384 | $CH_2$ | 1 | CH | CH | CH | CH | C | CH | CH | CH | CH | CH | OMe | OMe |
| 385 | S | 1 | CH | CH | CH | CH | C | CH | CH | CH | CH | CH | OMe | OMe |
| 386 | $CH_2$ | 1 | CH | CH | CH | CH | C | N | CH | CH | CH | CH | OMe | OMe |
| 387 | S | 1 | CH | CH | CH | CH | C | N | CH | CH | CH | CH | OMe | OMe |
| 388 | $CH_2$ | 1 | CH | CH | CH | CH | C | CH | N | CH | CH | CH | OMe | OMe |
| 389 | S | 1 | CH | CH | CH | CH | C | CH | N | CH | CH | CH | OMe | OMe |
| 390 | $CH_2$ | 1 | CH | CH | CH | CH | C | N | CH | CH | CH | N | OMe | OMe |
| 391 | S | 1 | CH | CH | CH | CH | C | N | CH | CH | CH | N | OMe | OMe |
| 392 | $CH_2$ | 1 | CH | CH | CH | CH | C | N | N | CH | CH | CH | OMe | OMe |
| 393 | S | 1 | CH | CH | CH | CH | C | N | N | CH | CH | CH | OMe | OMe |
| 394 | $CH_2$ | 1 | CH | CH | CH | CH | C | CH | N | CH | N | CH | OMe | absent |
| 395 | S | 1 | CH | CH | CH | CH | C | CH | N | CH | N | CH | OMe |  |
| 396 | $CH_2$ | 1 | CH | CH | CH | CH | C | CH | CH | N | CH | N | absent | OMe |
| 397 | S | 1 | CH | CH | CH | CH | C | CH | CH | N | CH | N |  | OMe |
| 398 | $CH_2$ | 1 | CH | CH | CH | CH | C | CH | CH | N | CH | CH | absent | OMe |
| 399 | S | 1 | CH | CH | CH | CH | C | CH | CH | N | CH | CH |  | OMe |
| 400 | $CH_2$ | 1 | N | CH | CH | CH | C | CH | CH | CH | CH | CH | OMe | OMe |
| 401 | S | 1 | N | CH | CH | CH | C | CH | CH | CH | CH | CH | OMe | OMe |
| 402 | $CH_2$ | 1 | N | CH | CH | CH | C | N | CH | CH | CH | CH | OMe | OMe |
| 403 | S | 1 | N | CH | CH | CH | C | N | CH | CH | CH | CH | OMe | OMe |
| 404 | $CH_2$ | 1 | N | CH | CH | CH | C | CH | N | CH | CH | CH | OMe | OMe |
| 405 | S | 1 | N | CH | CH | CH | C | CH | N | CH | CH | CH | OMe | OMe |
| 406 | $CH_2$ | 1 | N | CH | CH | CH | C | N | CH | CH | CH | N | OMe | OMe |
| 407 | S | 1 | N | CH | CH | CH | C | N | CH | CH | CH | N | OMe | OMe |
| 408 | $CH_2$ | 1 | N | CH | CH | CH | C | CH | CH | N | CH | N | absent | OMe |
| 409 | S | 1 | N | CH | CH | CH | C | CH | CH | N | CH | N |  | OMe |
| 410 | $CH_2$ | 1 | N | CH | CH | CH | C | N | CH | CH | CH | CH | OMe | OMe |
| 411 | S | 1 | N | CH | CH | CH | C | N | CH | CH | CH | CH | OMe | OMe |
| 412 | $CH_2$ | 1 | N | N | CH | CH | C | CH | CH | N | CH | N | absent | OMe |
| 413 | S | 1 | N | N | CH | CH | C | CH | CH | N | CH | N |  | OMe |
| 414 | $CH_2$ | 1 | N | N | CH | CH | C | CH | CH | CH | CH | CH | OMe | OMe |
| 415 | S | 1 | N | N | CH | CH | C | CH | CH | CH | CH | CH | OMe | OMe |
| 416 | $CH_2$ | 1 | CH | N | CH | CH | C | CH | CH | CH | CH | CH | OMe | OMe |
| 417 | S | 1 | CH | N | CH | CH | C | CH | CH | CH | CH | CH | OMe | OMe |
| 418 | $CH_2$ | 1 | CH | N | CH | CH | C | N | CH | CH | CH | CH | OMe | OMe |
| 419 | S | 1 | CH | N | CH | CH | C | N | CH | CH | CH | CH | OMe | OMe |
| 420 | $CH_2$ | 1 | CH | N | CH | CH | C | CH | N | CH | CH | CH | OMe | OMe |
| 421 | S | 1 | CH | N | CH | CH | C | CH | N | CH | CH | CH | OMe | OMe |

-continued

| Comp | $X_1$ | n | $Y_1$ | $Y_2$ | $Y_3$ | $Y_4$ | $Y_5$ | $Y_6$ | $Y_7$ | $Y_8$ | $Y_9$ | $Y_{10}$ | $R_5$ | $R_6$ |
|---|---|---|---|---|---|---|---|---|---|---|---|---|---|---|
| 422 | $CH_2$ | 1 | CH | N | CH | CH | C | CH | N | CH | N | CH | OMe | absent |
| 423 | S | 1 | CH | N | CH | CH | C | CH | N | CH | N | CH | OMe | |
| 424 | $CH_2$ | 1 | CH | N | CH | CH | C | N | CH | CH | N | CH | OMe | OMe |
| 425 | S | 1 | CH | N | CH | CH | C | N | CH | CH | N | CH | OMe | OMe |
| 426 | $CH_2$ | 1 | CH | N | CH | CH | C | CH | CH | N | CH | N | absent | OMe |
| 427 | S | 1 | CH | N | CH | CH | C | CH | CH | N | CH | N | | OMe |
| 428 | $CH_2$ | 1 | CH | N | CH | CH | C | CH | CH | N | CH | CH | OMe | absent |
| 429 | S | 1 | CH | N | CH | CH | C | CH | CH | N | CH | CH | OMe | |
| 430 | $CH_2$ | 1 | N | CH | N | CH | C | CH | CH | CH | CH | CH | OMe | OMe |
| 431 | S | 1 | N | CH | N | CH | C | CH | CH | CH | CH | CH | OMe | OMe |
| 432 | $CH_2$ | 1 | N | CH | N | CH | C | N | CH | CH | CH | CH | OMe | OMe |
| 433 | S | 1 | N | CH | N | CH | C | N | CH | CH | CH | CH | OMe | OMe |
| 434 | $CH_2$ | 1 | N | CH | N | CH | C | CH | N | CH | CH | CH | OMe | OMe |
| 435 | S | 1 | N | CH | N | CH | C | CH | N | CH | CH | CH | OMe | OMe |
| 436 | $CH_2$ | 1 | CH | N | CH | N | C | CH | CH | CH | CH | CH | OMe | OMe |
| 437 | S | 1 | CH | N | CH | N | C | CH | CH | CH | CH | CH | OMe | OMe |
| 438 | $CH_2$ | 1 | CH | CH | N | N | C | CH | CH | CH | CH | CH | OMe | OMe |
| 439 | S | 1 | CH | CH | N | N | C | CH | CH | CH | CH | CH | OMe | OMe |
| 440 | $CH_2$ | 1 | CH | CH | CH | N | C | CH | CH | CH | CH | CH | OMe | OMe |
| 441 | S | 1 | CH | CH | CH | N | C | CH | CH | CH | CH | CH | OMe | OMe |
| 442 | $CH_2$ | 1 | CH | CH | CH | N | C | CH | CH | N | CH | CH | absent | OMe |
| 443 | S | 1 | CH | CH | CH | N | C | CH | CH | N | CH | CH | | OMe |

In a further embodiment, the present invention provides compounds of formula (IVa) and (IVb), wherein $X_1$, o, Z, $Y_1$, $Y_2$, $Y_3$, $Y_4$, $Y_5$, $Y_6$, $Y_7$, $Y_8$, $Y_9$, $Y_{10}$, $R_5$, and $R_6$ are as defined in examples 444 to 795:

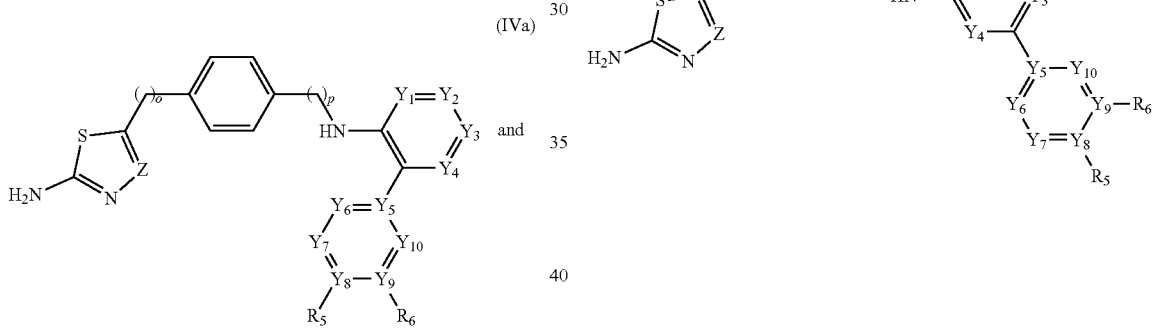

(IVa) and (IVb)

In both, formulae (IVa) and (IVb), o is 0.

| Comp | p | Z | $Y_1$ | $Y_2$ | $Y_3$ | $Y_4$ | $Y_5$ | $Y_6$ | $Y_7$ | $Y_8$ | $Y_9$ | $Y_{10}$ | $R_5$ | $R_6$ |
|---|---|---|---|---|---|---|---|---|---|---|---|---|---|---|
| 444 | 0 | CH | CH | CH | CH | CH | C | CH | CH | CH | CH | CH | H | H |
| 445 | 0 | N | CH | CH | CH | CH | C | CH | CH | CH | CH | CH | H | H |
| 446 | 0 | CH | CH | CH | CH | CH | C | N | CH | CH | CH | CH | H | H |
| 447 | 0 | N | CH | CH | CH | CH | C | N | CH | CH | CH | CH | H | H |
| 448 | 0 | CH | CH | CH | CH | CH | C | CH | N | CH | CH | CH | H | H |
| 449 | 0 | N | CH | CH | CH | CH | C | CH | N | CH | CH | CH | H | H |
| 450 | 0 | CH | CH | CH | CH | CH | C | N | CH | CH | CH | N | H | H |
| 451 | 0 | N | CH | CH | CH | CH | C | N | CH | CH | CH | N | H | H |
| 452 | 0 | CH | CH | CH | CH | CH | C | N | N | CH | CH | CH | H | H |
| 453 | 0 | N | CH | CH | CH | CH | C | N | N | CH | CH | CH | H | H |
| 454 | 0 | CH | CH | CH | CH | CH | C | CH | N | CH | N | CH | H | absent |
| 455 | 0 | N | CH | CH | CH | CH | C | CH | N | CH | N | CH | | H |
| 456 | 0 | CH | CH | CH | CH | CH | C | CH | CH | N | CH | N | absent | H |
| 457 | 0 | N | CH | CH | CH | CH | C | CH | CH | N | CH | N | | H |
| 458 | 0 | CH | CH | CH | CH | CH | C | CH | CH | N | CH | CH | absent | H |
| 459 | 0 | N | CH | CH | CH | CH | C | CH | CH | N | CH | CH | | H |
| 460 | 0 | CH | N | CH | CH | CH | C | CH | CH | CH | CH | CH | H | H |
| 461 | 0 | N | N | CH | CH | CH | C | CH | CH | CH | CH | CH | H | H |
| 462 | 0 | CH | N | CH | CH | CH | C | N | CH | CH | CH | CH | H | H |
| 463 | 0 | N | N | CH | CH | CH | C | N | CH | CH | CH | CH | H | H |
| 464 | 0 | CH | N | CH | CH | CH | C | CH | N | CH | CH | CH | H | H |
| 465 | 0 | N | N | CH | CH | CH | C | CH | N | CH | CH | CH | H | H |
| 466 | 0 | CH | N | CH | CH | CH | C | N | CH | CH | CH | N | H | H |
| 467 | 0 | N | N | CH | CH | CH | C | N | CH | CH | CH | N | H | H |
| 468 | 0 | CH | N | CH | CH | CH | C | CH | CH | N | CH | N | absent | H |

| Comp | p | Z | Y₁ | Y₂ | Y₃ | Y₄ | Y₅ | Y₆ | Y₇ | Y₈ | Y₉ | Y₁₀ | R₅ | R₆ |
|---|---|---|---|---|---|---|---|---|---|---|---|---|---|---|
| 469 | 0 | N | N | CH | CH | CH | C | CH | CH | N | CH | N | | H |
| 470 | 0 | CH | N | CH | CH | CH | C | N | CH | CH | CH | CH | H | H |
| 471 | 0 | N | N | CH | CH | CH | C | N | CH | CH | CH | CH | H | H |
| 472 | 0 | CH | N | N | CH | CH | C | CH | CH | N | CH | N | absent | H |
| 473 | 0 | N | N | N | CH | CH | C | CH | CH | N | CH | N | | H |
| 474 | 0 | CH | N | N | CH | CH | C | CH | CH | CH | CH | CH | H | H |
| 475 | 0 | N | N | N | CH | CH | C | CH | CH | CH | CH | CH | H | H |
| 476 | 0 | CH | CH | N | CH | CH | C | CH | CH | CH | CH | CH | H | H |
| 477 | 0 | N | CH | N | CH | CH | C | CH | CH | CH | CH | CH | H | H |
| 478 | 0 | CH | CH | N | CH | CH | C | N | CH | CH | CH | CH | H | H |
| 479 | 0 | N | CH | N | CH | CH | C | N | CH | CH | CH | CH | H | H |
| 480 | 0 | CH | CH | N | CH | CH | C | CH | N | CH | CH | CH | H | H |
| 481 | 0 | N | CH | N | CH | CH | C | CH | N | CH | CH | CH | H | H |
| 482 | 0 | CH | CH | N | CH | CH | C | CH | N | CH | N | CH | H | absent |
| 483 | 0 | N | CH | N | CH | CH | C | CH | N | CH | N | CH | H | |
| 484 | 0 | CH | CH | N | CH | CH | C | N | CH | CH | N | CH | H | H |
| 485 | 0 | N | CH | N | CH | CH | C | N | CH | CH | N | CH | H | H |
| 486 | 0 | CH | CH | N | CH | CH | C | CH | CH | N | CH | N | absent | H |
| 487 | 0 | N | CH | N | CH | CH | C | CH | CH | N | CH | N | | H |
| 488 | 0 | CH | CH | N | CH | CH | C | CH | CH | N | CH | CH | absent | H |
| 489 | 0 | N | CH | N | CH | CH | C | CH | CH | N | CH | CH | | H |
| 490 | 0 | CH | N | CH | N | CH | C | CH | CH | CH | CH | CH | H | H |
| 491 | 0 | N | N | CH | N | CH | C | CH | CH | CH | CH | CH | H | H |
| 492 | 0 | CH | N | CH | N | CH | C | N | CH | CH | CH | CH | H | H |
| 493 | 0 | N | N | CH | N | CH | C | N | CH | CH | CH | CH | H | H |
| 494 | 0 | CH | N | CH | N | CH | C | CH | N | CH | CH | CH | H | H |
| 495 | 0 | N | N | CH | N | CH | C | CH | N | CH | CH | CH | H | H |
| 496 | 0 | CH | CH | N | CH | N | C | CH | CH | CH | CH | CH | H | H |
| 497 | 0 | N | CH | N | CH | N | C | CH | CH | CH | CH | CH | H | H |
| 498 | 0 | CH | CH | CH | N | N | C | CH | CH | CH | CH | CH | H | H |
| 499 | 0 | N | CH | CH | N | N | C | CH | CH | CH | CH | CH | H | H |
| 500 | 0 | CH | CH | CH | CH | N | C | CH | CH | CH | CH | CH | H | H |
| 501 | 0 | N | CH | CH | CH | N | C | CH | CH | CH | CH | CH | H | H |
| 502 | 0 | CH | CH | CH | CH | N | C | CH | CH | N | CH | CH | absent | H |
| 503 | 0 | N | CH | CH | CH | N | C | CH | CH | N | CH | CH | | H |
| 504 | 0 | CH | CH | CH | CH | CH | C | CH | CH | CH | CH | CH | F | H |
| 505 | 0 | N | CH | CH | CH | CH | C | CH | CH | CH | CH | CH | F | H |
| 506 | 0 | CH | CH | CH | CH | CH | C | N | CH | CH | CH | CH | F | H |
| 507 | 0 | N | CH | CH | CH | CH | C | N | CH | CH | CH | CH | F | H |
| 508 | 0 | CH | CH | CH | CH | CH | C | CH | N | CH | CH | CH | F | H |
| 509 | 0 | N | CH | CH | CH | CH | C | CH | N | CH | CH | CH | F | H |
| 510 | 0 | CH | CH | CH | CH | CH | C | N | CH | CH | CH | N | F | H |
| 511 | 0 | N | CH | CH | CH | CH | C | N | CH | CH | CH | N | F | H |
| 512 | 0 | CH | CH | CH | CH | CH | C | N | N | CH | CH | CH | F | H |
| 513 | 0 | N | CH | CH | CH | CH | C | N | N | CH | CH | CH | F | H |
| 514 | 0 | CH | CH | CH | CH | CH | C | CH | N | CH | N | CH | F | absent |
| 515 | 0 | N | CH | CH | CH | CH | C | CH | N | CH | N | CH | F | |
| 516 | 0 | CH | CH | CH | CH | CH | C | CH | CH | N | CH | N | absent | |
| 517 | 0 | N | CH | CH | CH | CH | C | CH | CH | N | CH | N | | |
| 518 | 0 | CH | CH | CH | CH | CH | C | CH | CH | N | CH | CH | absent | H |
| 519 | 0 | N | CH | CH | CH | CH | C | CH | CH | N | CH | CH | | H |
| 520 | 0 | CH | N | CH | CH | CH | C | CH | CH | CH | CH | CH | F | H |
| 521 | 0 | N | N | CH | CH | CH | C | CH | CH | CH | CH | CH | F | H |
| 522 | 0 | CH | N | CH | CH | CH | C | N | CH | CH | CH | CH | F | H |
| 523 | 0 | N | N | CH | CH | CH | C | N | CH | CH | CH | CH | F | H |
| 524 | 0 | CH | N | CH | CH | CH | C | CH | N | CH | CH | CH | F | H |
| 525 | 0 | N | N | CH | CH | CH | C | CH | N | CH | CH | CH | F | H |
| 526 | 0 | CH | N | CH | CH | CH | C | N | CH | CH | CH | N | F | H |
| 527 | 0 | N | N | CH | CH | CH | C | N | CH | CH | CH | N | F | H |
| 528 | 0 | CH | N | CH | CH | CH | C | CH | CH | N | CH | N | absent | H |
| 529 | 0 | N | N | CH | CH | CH | C | CH | CH | N | CH | N | | H |
| 530 | 0 | CH | N | N | CH | CH | C | CH | CH | CH | CH | CH | F | H |
| 531 | 0 | N | N | N | CH | CH | C | CH | CH | CH | CH | CH | F | H |
| 532 | 0 | CH | N | N | CH | CH | C | CH | CH | N | CH | N | absent | H |
| 533 | 0 | N | N | N | CH | CH | C | CH | CH | N | CH | N | | H |
| 534 | 0 | CH | CH | N | CH | CH | C | CH | CH | CH | CH | CH | F | H |
| 535 | 0 | N | CH | N | CH | CH | C | CH | CH | CH | CH | CH | F | H |
| 536 | 0 | CH | CH | N | CH | CH | C | N | CH | CH | CH | CH | F | H |
| 537 | 0 | N | CH | N | CH | CH | C | N | CH | CH | CH | CH | F | H |
| 538 | 0 | CH | CH | N | CH | CH | C | CH | N | CH | CH | CH | F | H |
| 539 | 0 | N | CH | N | CH | CH | C | CH | N | CH | CH | CH | F | H |
| 540 | 0 | CH | CH | N | CH | CH | C | CH | N | CH | N | CH | H | absent |
| 541 | 0 | N | CH | N | CH | CH | C | N | CH | N | CH | | F | |
| 542 | 0 | CH | CH | N | CH | CH | C | N | CH | N | CH | | F | absent |
| 543 | 0 | N | CH | N | CH | CH | C | N | CH | N | CH | | F | |
| 544 | 0 | CH | CH | N | CH | CH | C | CH | CH | N | CH | N | absent | H |
| 545 | 0 | N | CH | N | CH | CH | C | CH | CH | N | CH | N | | H |

-continued

| Comp | p | Z | $Y_1$ | $Y_2$ | $Y_3$ | $Y_4$ | $Y_5$ | $Y_6$ | $Y_7$ | $Y_8$ | $Y_9$ | $Y_{10}$ | $R_5$ | $R_6$ |
|---|---|---|---|---|---|---|---|---|---|---|---|---|---|---|
| 546 | 0 | CH | N | CH | N | CH | C | CH | CH | CH | CH | CH | F | H |
| 547 | 0 | N | N | CH | N | CH | C | CH | CH | CH | CH | CH | F | H |
| 548 | 0 | CH | N | CH | N | CH | C | N | CH | CH | CH | CH | F | H |
| 549 | 0 | N | N | CH | N | CH | C | N | CH | CH | CH | CH | F | H |
| 550 | 0 | CH | N | CH | N | CH | C | CH | N | CH | CH | CH | F | H |
| 551 | 0 | N | N | CH | N | CH | C | CH | N | CH | CH | CH | F | H |
| 552 | 0 | CH | CH | N | CH | N | C | CH | CH | CH | CH | CH | F | H |
| 553 | 0 | N | CH | N | CH | N | C | CH | CH | CH | CH | CH | F | H |
| 554 | 0 | CH | CH | CH | N | N | C | CH | CH | CH | CH | CH | F | H |
| 555 | 0 | N | CH | CH | N | N | C | CH | CH | CH | CH | CH | F | H |
| 556 | 0 | CH | CH | CH | CH | N | C | CH | CH | CH | CH | CH | F | H |
| 557 | 0 | N | CH | CH | CH | N | C | CH | CH | CH | CH | CH | F | H |
| 558 | 0 | CH | CH | CH | CH | N | C | CH | N | CH | CH | CH | F | H |
| 559 | 0 | N | CH | CH | CH | N | C | CH | N | CH | CH | CH | F | H |
| 560 | 0 | CH | CH | CH | CH | CH | C | CH | CH | CH | CH | CH | OMe | OMe |
| 561 | 0 | N | CH | CH | CH | CH | C | CH | CH | CH | CH | CH | OMe | OMe |
| 562 | 0 | CH | CH | CH | CH | CH | C | N | CH | CH | CH | CH | OMe | OMe |
| 563 | 0 | N | CH | CH | CH | CH | C | N | CH | CH | CH | CH | OMe | OMe |
| 564 | 0 | CH | CH | CH | CH | CH | C | CH | N | CH | CH | CH | OMe | OMe |
| 565 | 0 | N | CH | CH | CH | CH | C | CH | N | CH | CH | CH | OMe | OMe |
| 566 | 0 | CH | CH | CH | CH | CH | C | N | CH | CH | CH | N | OMe | OMe |
| 567 | 0 | N | CH | CH | CH | CH | C | N | CH | CH | CH | N | OMe | OMe |
| 568 | 0 | CH | CH | CH | CH | CH | C | N | N | CH | CH | CH | OMe | OMe |
| 569 | 0 | N | CH | CH | CH | CH | C | N | N | CH | CH | CH | OMe | OMe |
| 570 | 0 | CH | CH | CH | CH | CH | C | CH | N | CH | N | CH | OMe | absent |
| 571 | 0 | N | CH | CH | CH | CH | C | CH | N | CH | N | CH | OMe | |
| 572 | 0 | CH | CH | CH | CH | CH | C | CH | CH | N | CH | N | absent | OMe |
| 573 | 0 | N | CH | CH | CH | CH | C | CH | CH | N | CH | N | | OMe |
| 574 | 0 | CH | CH | CH | CH | CH | C | CH | CH | N | CH | CH | absent | OMe |
| 575 | 0 | N | CH | CH | CH | CH | C | CH | CH | N | CH | CH | | OMe |
| 576 | 0 | CH | N | CH | CH | CH | C | CH | CH | CH | CH | CH | OMe | OMe |
| 577 | 0 | N | N | CH | CH | CH | C | CH | CH | CH | CH | CH | OMe | OMe |
| 578 | 0 | CH | N | CH | CH | CH | C | N | CH | CH | CH | CH | OMe | OMe |
| 579 | 0 | N | N | CH | CH | CH | C | N | CH | CH | CH | CH | OMe | OMe |
| 580 | 0 | CH | N | CH | CH | CH | C | CH | N | CH | CH | CH | OMe | OMe |
| 581 | 0 | N | N | CH | CH | CH | C | CH | N | CH | CH | CH | OMe | OMe |
| 582 | 0 | CH | N | CH | CH | CH | C | N | CH | CH | CH | N | OMe | OMe |
| 583 | 0 | N | N | CH | CH | CH | C | N | CH | CH | CH | N | OMe | OMe |
| 584 | 0 | CH | N | CH | CH | CH | C | CH | CH | N | CH | N | absent | OMe |
| 585 | 0 | N | N | CH | CH | CH | C | CH | CH | N | CH | N | | OMe |
| 586 | 0 | CH | N | CH | CH | CH | C | N | CH | N | CH | CH | OMe | OMe |
| 587 | 0 | N | N | CH | CH | CH | C | N | CH | CH | CH | CH | OMe | OMe |
| 588 | 0 | CH | N | N | CH | CH | C | CH | CH | N | CH | N | absent | OMe |
| 589 | 0 | N | N | N | CH | CH | C | CH | CH | N | CH | N | | OMe |
| 590 | 0 | CH | N | N | CH | CH | C | CH | CH | CH | CH | CH | OMe | OMe |
| 591 | 0 | N | N | N | CH | CH | C | CH | CH | CH | CH | CH | OMe | OMe |
| 592 | 0 | CH | CH | N | CH | CH | C | CH | CH | CH | CH | CH | OMe | OMe |
| 593 | 0 | N | CH | N | CH | CH | C | CH | CH | CH | CH | CH | OMe | OMe |
| 594 | 0 | CH | CH | N | CH | CH | C | N | CH | CH | CH | CH | OMe | OMe |
| 595 | 0 | N | CH | N | CH | CH | C | N | CH | CH | CH | CH | OMe | OMe |
| 596 | 0 | CH | CH | N | CH | CH | C | CH | N | CH | CH | CH | OMe | OMe |
| 597 | 0 | N | CH | N | CH | CH | C | CH | N | CH | CH | CH | OMe | OMe |
| 598 | 0 | CH | CH | N | CH | CH | C | CH | N | CH | N | CH | OMe | absent |
| 599 | 0 | N | CH | N | CH | CH | C | CH | N | CH | N | CH | OMe | |
| 600 | 0 | CH | CH | N | CH | CH | C | N | CH | CH | N | CH | OMe | OMe |
| 601 | 0 | N | CH | N | CH | CH | C | N | CH | CH | N | CH | OMe | OMe |
| 602 | 0 | CH | CH | N | CH | CH | C | CH | CH | N | CH | N | absent | OMe |
| 603 | 0 | N | CH | N | CH | CH | C | CH | CH | N | CH | N | | OMe |
| 604 | 0 | CH | CH | N | CH | CH | C | CH | CH | N | CH | CH | absent | OMe |
| 605 | 0 | N | CH | N | CH | CH | C | CH | CH | N | CH | CH | | OMe |
| 606 | 0 | CH | N | CH | N | CH | C | CH | CH | CH | CH | CH | OMe | OMe |
| 607 | 0 | N | N | CH | N | CH | C | CH | CH | CH | CH | CH | OMe | OMe |
| 608 | 0 | CH | N | CH | N | CH | C | N | CH | CH | CH | CH | OMe | OMe |
| 609 | 0 | N | N | CH | N | CH | C | N | CH | CH | CH | CH | OMe | OMe |
| 610 | 0 | CH | N | CH | N | CH | C | CH | N | CH | CH | CH | OMe | OMe |
| 611 | 0 | N | N | CH | N | CH | C | CH | N | CH | CH | CH | OMe | OMe |
| 612 | 0 | CH | CH | N | CH | N | C | CH | CH | CH | CH | CH | OMe | OMe |
| 613 | 0 | N | CH | N | CH | N | C | CH | CH | CH | CH | CH | OMe | OMe |
| 614 | 0 | CH | CH | CH | N | N | C | CH | CH | CH | CH | CH | OMe | OMe |
| 615 | 0 | N | CH | CH | N | N | C | CH | CH | CH | CH | CH | OMe | OMe |
| 616 | 0 | CH | CH | CH | CH | N | C | CH | CH | CH | CH | CH | OMe | OMe |
| 617 | 0 | N | CH | CH | CH | N | C | CH | CH | CH | CH | CH | OMe | OMe |
| 618 | 0 | CH | CH | CH | CH | N | C | CH | N | CH | CH | CH | absent | OMe |
| 619 | 0 | N | CH | CH | CH | N | C | CH | N | CH | CH | CH | | OMe |
| 620 | 1 | CH | CH | CH | CH | CH | C | CH | CH | CH | CH | CH | H | H |
| 621 | 1 | N | CH | CH | CH | CH | C | CH | CH | CH | CH | CH | H | H |
| 622 | 1 | CH | CH | CH | CH | CH | C | N | CH | CH | CH | CH | H | H |

-continued

| Comp | p | Z | Y$_1$ | Y$_2$ | Y$_3$ | Y$_4$ | Y$_5$ | Y$_6$ | Y$_7$ | Y$_8$ | Y$_9$ | Y$_{10}$ | R$_5$ | R$_6$ |
|---|---|---|---|---|---|---|---|---|---|---|---|---|---|---|
| 623 | 1 | N | CH | CH | CH | CH | C | N | CH | CH | CH | CH | H | H |
| 624 | 1 | CH | CH | CH | CH | CH | C | CH | N | CH | CH | CH | H | H |
| 625 | 1 | N | CH | CH | CH | CH | C | CH | N | CH | CH | CH | H | H |
| 626 | 1 | CH | CH | CH | CH | CH | C | N | CH | CH | CH | N | H | H |
| 627 | 1 | N | CH | CH | CH | CH | C | N | CH | CH | CH | N | H | H |
| 628 | 1 | CH | CH | CH | CH | CH | C | N | N | CH | CH | CH | H | H |
| 629 | 1 | N | CH | CH | CH | CH | C | N | N | CH | CH | CH | H | H |
| 630 | 1 | CH | CH | CH | CH | CH | C | CH | N | CH | N | CH | H | absent |
| 631 | 1 | N | CH | CH | CH | CH | C | CH | N | CH | N | CH | H | |
| 632 | 1 | CH | CH | CH | CH | CH | C | CH | CH | N | CH | N | absent | H |
| 633 | 1 | N | CH | CH | CH | CH | C | CH | CH | N | CH | N | | H |
| 634 | 1 | CH | CH | CH | CH | CH | C | CH | CH | N | CH | CH | absent | H |
| 635 | 1 | N | CH | CH | CH | CH | C | CH | CH | N | CH | CH | | H |
| 636 | 1 | CH | N | CH | CH | CH | C | CH | CH | CH | CH | CH | H | H |
| 637 | 1 | N | N | CH | CH | CH | C | CH | CH | CH | CH | CH | H | H |
| 638 | 1 | CH | N | CH | CH | CH | C | N | CH | CH | CH | CH | H | H |
| 639 | 1 | N | N | CH | CH | CH | C | N | CH | CH | CH | CH | H | H |
| 640 | 1 | CH | N | CH | CH | CH | C | CH | N | CH | CH | CH | H | H |
| 641 | 1 | N | N | CH | CH | CH | C | CH | N | CH | CH | CH | H | H |
| 642 | 1 | CH | N | CH | CH | CH | C | N | CH | CH | CH | N | H | H |
| 643 | 1 | N | N | CH | CH | CH | C | N | CH | CH | CH | N | H | H |
| 644 | 1 | CH | N | CH | CH | CH | C | CH | CH | N | CH | N | absent | H |
| 645 | 1 | N | N | CH | CH | CH | C | CH | CH | N | CH | N | | H |
| 646 | 1 | CH | N | CH | CH | CH | C | N | CH | CH | CH | CH | H | H |
| 647 | 1 | N | N | CH | CH | CH | C | N | CH | CH | CH | CH | H | H |
| 648 | 1 | CH | N | N | CH | CH | C | CH | CH | N | CH | N | absent | H |
| 649 | 1 | N | N | N | CH | CH | C | CH | CH | N | CH | N | | H |
| 650 | 1 | CH | N | N | CH | CH | C | CH | CH | CH | CH | CH | H | H |
| 651 | 1 | N | N | N | CH | CH | C | CH | CH | CH | CH | CH | H | H |
| 652 | 1 | CH | CH | N | CH | CH | C | CH | CH | CH | CH | CH | H | H |
| 653 | 1 | N | CH | N | CH | CH | C | CH | CH | CH | CH | CH | H | H |
| 654 | 1 | CH | CH | N | CH | CH | C | N | CH | CH | CH | CH | H | H |
| 655 | 1 | N | CH | N | CH | CH | C | N | CH | CH | CH | CH | H | H |
| 656 | 1 | CH | CH | N | CH | CH | C | CH | N | CH | CH | CH | H | H |
| 657 | 1 | N | CH | N | CH | CH | C | CH | N | CH | CH | CH | H | H |
| 658 | 1 | CH | CH | N | CH | CH | C | CH | N | CH | N | CH | H | absent |
| 659 | 1 | N | CH | N | CH | CH | C | CH | N | CH | N | CH | H | |
| 660 | 1 | CH | CH | N | CH | CH | C | N | CH | CH | N | CH | H | H |
| 661 | 1 | N | CH | N | CH | CH | C | N | CH | CH | N | CH | H | H |
| 662 | 1 | CH | CH | N | CH | CH | C | CH | CH | N | CH | N | absent | H |
| 663 | 1 | N | CH | N | CH | CH | C | CH | CH | N | CH | N | | H |
| 664 | 1 | CH | CH | N | CH | CH | C | CH | CH | N | CH | CH | absent | H |
| 665 | 1 | N | CH | N | CH | CH | C | CH | CH | N | CH | CH | | H |
| 666 | 1 | CH | N | CH | N | CH | C | CH | CH | CH | CH | CH | H | H |
| 667 | 1 | N | N | CH | N | CH | C | CH | CH | CH | CH | CH | H | H |
| 668 | 1 | CH | N | CH | N | CH | C | N | CH | CH | CH | CH | H | H |
| 669 | 1 | N | N | CH | N | CH | C | N | CH | CH | CH | CH | H | H |
| 670 | 1 | CH | N | CH | N | CH | C | CH | N | CH | CH | CH | H | H |
| 671 | 1 | N | N | CH | N | CH | C | CH | N | CH | CH | CH | H | H |
| 672 | 1 | CH | CH | N | CH | N | C | CH | CH | CH | CH | CH | H | H |
| 673 | 1 | N | CH | N | CH | N | C | CH | CH | CH | CH | CH | H | H |
| 674 | 1 | CH | CH | CH | N | N | C | CH | CH | CH | CH | CH | H | H |
| 675 | 1 | N | CH | CH | N | N | C | CH | CH | CH | CH | CH | H | H |
| 676 | 1 | CH | CH | CH | CH | N | C | CH | CH | CH | CH | CH | H | H |
| 677 | 1 | N | CH | CH | CH | N | C | CH | CH | CH | CH | CH | H | H |
| 678 | 1 | CH | CH | CH | CH | N | C | CH | CH | N | CH | CH | absent | H |
| 679 | 1 | N | CH | CH | CH | N | C | CH | CH | N | CH | CH | | H |
| 680 | 1 | CH | CH | CH | CH | CH | C | CH | CH | CH | CH | CH | F | H |
| 681 | 1 | N | CH | CH | CH | CH | C | CH | CH | CH | CH | CH | F | H |
| 682 | 1 | CH | CH | CH | CH | CH | C | N | CH | CH | CH | CH | F | H |
| 683 | 1 | N | CH | CH | CH | CH | C | N | CH | CH | CH | CH | F | H |
| 684 | 1 | CH | CH | CH | CH | CH | C | CH | N | CH | CH | CH | F | H |
| 685 | 1 | N | CH | CH | CH | CH | C | CH | N | CH | CH | CH | F | H |
| 686 | 1 | CH | CH | CH | CH | CH | C | N | CH | CH | CH | N | F | H |
| 687 | 1 | N | CH | CH | CH | CH | C | N | CH | CH | CH | N | F | H |
| 688 | 1 | CH | CH | CH | CH | CH | C | N | N | CH | CH | CH | F | H |
| 689 | 1 | N | CH | CH | CH | CH | C | N | N | CH | CH | CH | F | H |
| 690 | 1 | CH | CH | CH | CH | CH | C | CH | N | CH | N | CH | F | absent |
| 691 | 1 | N | CH | CH | CH | CH | C | CH | N | CH | N | CH | F | |
| 692 | 1 | CH | CH | CH | CH | CH | C | CH | CH | N | CH | N | absent | |
| 693 | 1 | N | CH | CH | CH | CH | C | CH | CH | N | CH | N | | |
| 694 | 1 | CH | CH | CH | CH | CH | C | CH | CH | N | CH | CH | absent | H |
| 695 | 1 | N | CH | CH | CH | CH | C | CH | CH | N | CH | CH | | H |
| 696 | 1 | CH | N | CH | CH | CH | C | CH | CH | CH | CH | CH | F | H |
| 697 | 1 | N | N | CH | CH | CH | C | CH | CH | CH | CH | CH | F | H |
| 698 | 1 | CH | N | CH | CH | CH | C | N | CH | CH | CH | CH | F | H |
| 699 | 1 | N | N | CH | CH | CH | C | N | CH | CH | CH | CH | F | H |

-continued

| Comp | p | Z | Y₁ | Y₂ | Y₃ | Y₄ | Y₅ | Y₆ | Y₇ | Y₈ | Y₉ | Y₁₀ | R₅ | R₆ |
|---|---|---|---|---|---|---|---|---|---|---|---|---|---|---|
| 700 | 1 | CH | N | CH | CH | CH | C | CH | N | CH | CH | CH | F | H |
| 701 | 1 | N | N | CH | CH | CH | C | CH | N | CH | CH | CH | F | H |
| 702 | 1 | CH | N | CH | CH | CH | C | N | CH | CH | CH | N | F | H |
| 703 | 1 | N | N | CH | CH | CH | C | N | CH | CH | CH | N | F | H |
| 704 | 1 | CH | N | CH | CH | CH | C | CH | CH | N | CH | N | absent | H |
| 705 | 1 | N | N | CH | CH | CH | C | CH | CH | N | CH | N | | H |
| 706 | 1 | CH | N | N | CH | CH | C | CH | CH | CH | CH | CH | F | H |
| 707 | 1 | N | N | N | CH | CH | C | CH | CH | CH | CH | CH | F | H |
| 708 | 1 | CH | N | N | CH | CH | C | CH | CH | N | CH | N | absent | H |
| 709 | 1 | N | N | N | CH | CH | C | CH | CH | N | CH | N | | H |
| 710 | 1 | CH | CH | N | CH | CH | C | CH | CH | CH | CH | CH | F | H |
| 711 | 1 | N | CH | N | CH | CH | C | CH | CH | CH | CH | CH | F | H |
| 712 | 1 | CH | CH | N | CH | CH | C | N | CH | CH | CH | CH | F | H |
| 713 | 1 | N | CH | N | CH | CH | C | N | CH | CH | CH | CH | F | H |
| 714 | 1 | CH | CH | N | CH | CH | C | CH | N | CH | CH | CH | F | H |
| 715 | 1 | N | CH | N | CH | CH | C | CH | N | CH | CH | CH | F | H |
| 716 | 1 | CH | CH | N | CH | CH | C | CH | N | CH | N | CH | F | absent |
| 717 | 1 | N | CH | N | CH | CH | C | CH | N | CH | N | CH | F | |
| 718 | 1 | CH | CH | N | CH | CH | C | N | CH | CH | N | CH | F | absent |
| 719 | 1 | N | CH | N | CH | CH | C | N | CH | CH | N | CH | F | |
| 720 | 1 | CH | CH | N | CH | CH | C | CH | CH | N | | N | absent | H |
| 721 | 1 | N | CH | N | CH | CH | C | CH | CH | N | | N | | H |
| 722 | 1 | CH | N | CH | N | CH | C | CH | CH | CH | CH | CH | F | H |
| 723 | 1 | N | N | CH | N | CH | C | CH | CH | CH | CH | CH | F | H |
| 724 | 1 | CH | N | CH | N | CH | C | N | CH | CH | CH | CH | F | H |
| 725 | 1 | N | N | CH | N | CH | C | N | CH | CH | CH | CH | F | H |
| 726 | 1 | CH | N | CH | N | CH | C | CH | N | CH | CH | CH | F | H |
| 727 | 1 | N | N | CH | N | CH | C | CH | N | CH | CH | CH | F | H |
| 728 | 1 | CH | CH | N | CH | N | C | CH | CH | CH | CH | CH | F | H |
| 729 | 1 | N | CH | N | CH | N | C | CH | CH | CH | CH | CH | F | H |
| 730 | 1 | CH | CH | CH | N | N | C | CH | CH | CH | CH | CH | F | H |
| 731 | 1 | N | CH | CH | N | N | C | CH | CH | CH | CH | CH | F | H |
| 732 | 1 | CH | CH | CH | CH | N | C | CH | CH | CH | CH | CH | F | H |
| 733 | 1 | N | CH | CH | CH | N | C | CH | CH | CH | CH | CH | F | H |
| 734 | 1 | CH | CH | CH | CH | N | C | CH | N | CH | CH | CH | F | H |
| 735 | 1 | N | CH | CH | CH | N | C | CH | N | CH | CH | CH | F | H |
| 736 | 1 | CH | CH | CH | CH | CH | C | CH | CH | CH | CH | CH | OMe | OMe |
| 737 | 1 | N | CH | CH | CH | CH | C | CH | CH | CH | CH | CH | OMe | OMe |
| 738 | 1 | CH | CH | CH | CH | CH | C | N | CH | CH | CH | CH | OMe | OMe |
| 739 | 1 | N | CH | CH | CH | CH | C | N | CH | CH | CH | CH | OMe | OMe |
| 740 | 1 | CH | CH | CH | CH | CH | C | CH | N | CH | CH | CH | OMe | OMe |
| 741 | 1 | N | CH | CH | CH | CH | C | CH | N | CH | CH | CH | OMe | OMe |
| 742 | 1 | CH | CH | CH | CH | CH | C | N | CH | CH | CH | N | OMe | OMe |
| 743 | 1 | N | CH | CH | CH | CH | C | N | CH | CH | CH | N | OMe | OMe |
| 744 | 1 | CH | CH | CH | CH | CH | C | N | N | CH | CH | CH | OMe | OMe |
| 745 | 1 | N | CH | CH | CH | CH | C | N | N | CH | CH | CH | OMe | OMe |
| 746 | 1 | CH | CH | CH | CH | CH | C | CH | N | CH | N | CH | OMe | absent |
| 747 | 1 | N | CH | CH | CH | CH | C | CH | N | CH | N | CH | OMe | |
| 748 | 1 | CH | CH | CH | CH | CH | C | CH | CH | N | CH | N | absent | OMe |
| 749 | 1 | N | CH | CH | CH | CH | C | CH | CH | N | CH | N | | OMe |
| 750 | 1 | CH | CH | CH | CH | CH | C | CH | CH | N | CH | CH | absent | OMe |
| 751 | 1 | N | CH | CH | CH | CH | C | CH | CH | N | CH | CH | | OMe |
| 752 | 1 | CH | N | CH | CH | CH | C | CH | CH | CH | CH | CH | OMe | OMe |
| 753 | 1 | N | N | CH | CH | CH | C | CH | CH | CH | CH | CH | OMe | OMe |
| 754 | 1 | CH | N | CH | CH | CH | C | N | CH | CH | CH | CH | OMe | OMe |
| 755 | 1 | N | N | CH | CH | CH | C | N | CH | CH | CH | CH | OMe | OMe |
| 756 | 1 | CH | N | CH | CH | CH | C | CH | N | CH | CH | CH | OMe | OMe |
| 757 | 1 | N | N | CH | CH | CH | C | CH | N | CH | CH | CH | OMe | OMe |
| 758 | 1 | CH | N | CH | CH | CH | C | N | CH | CH | CH | N | OMe | OMe |
| 759 | 1 | N | N | CH | CH | CH | C | N | CH | CH | CH | N | OMe | OMe |
| 760 | 1 | CH | N | CH | CH | CH | C | CH | CH | N | CH | N | absent | OMe |
| 761 | 1 | N | N | CH | CH | CH | C | CH | CH | N | CH | N | | OMe |
| 762 | 1 | CH | N | N | CH | CH | C | N | CH | CH | CH | CH | OMe | OMe |
| 763 | 1 | N | N | N | CH | CH | C | N | CH | CH | CH | CH | OMe | OMe |
| 764 | 1 | CH | N | N | CH | CH | C | CH | CH | N | CH | N | absent | OMe |
| 765 | 1 | N | N | N | CH | CH | C | CH | CH | N | CH | N | | OMe |
| 766 | 1 | CH | N | N | CH | CH | C | CH | CH | CH | CH | CH | OMe | OMe |
| 767 | 1 | N | N | N | CH | CH | C | CH | CH | CH | CH | CH | OMe | OMe |
| 768 | 1 | CH | CH | N | CH | CH | C | CH | CH | CH | CH | CH | OMe | OMe |
| 769 | 1 | N | CH | N | CH | CH | C | CH | CH | CH | CH | CH | OMe | OMe |
| 770 | 1 | CH | CH | N | CH | CH | C | N | CH | CH | CH | CH | OMe | OMe |
| 771 | 1 | N | CH | N | CH | CH | C | N | CH | CH | CH | CH | OMe | OMe |
| 772 | 1 | CH | CH | N | CH | CH | C | CH | N | CH | CH | CH | OMe | OMe |
| 773 | 1 | N | CH | N | CH | CH | C | CH | N | CH | CH | CH | OMe | OMe |
| 774 | 1 | CH | CH | N | CH | CH | C | CH | N | CH | N | CH | OMe | absent |
| 775 | 1 | N | CH | N | CH | CH | C | CH | N | CH | N | CH | OMe | |
| 776 | 1 | CH | CH | N | CH | CH | C | N | CH | CH | N | CH | OMe | OMe |

| Comp | p | Z | Y₁ | Y₂ | Y₃ | Y₄ | Y₅ | Y₆ | Y₇ | Y₈ | Y₉ | Y₁₀ | R₅ | R₆ |
|---|---|---|---|---|---|---|---|---|---|---|---|---|---|---|
| 777 | 1 | N | CH | N | CH | CH | C | N | CH | CH | N | CH | OMe | OMe |
| 778 | 1 | CH | CH | N | CH | CH | C | CH | CH | N | CH | N | absent | OMe |
| 779 | 1 | N | CH | N | CH | CH | C | CH | CH | N | CH | N | | OMe |
| 780 | 1 | CH | CH | N | CH | CH | C | CH | CH | N | CH | CH | absent | OMe |
| 781 | 1 | N | CH | N | CH | CH | C | CH | CH | N | CH | CH | | OMe |
| 782 | 1 | CH | N | CH | N | CH | C | CH | CH | CH | CH | CH | OMe | OMe |
| 783 | 1 | N | N | CH | N | CH | C | CH | CH | CH | CH | CH | OMe | OMe |
| 784 | 1 | CH | N | CH | N | CH | C | N | CH | CH | CH | CH | OMe | OMe |
| 785 | 1 | N | N | CH | N | CH | C | N | CH | CH | CH | CH | OMe | OMe |
| 786 | 1 | CH | N | CH | N | CH | C | CH | N | CH | CH | CH | OMe | OMe |
| 787 | 1 | N | N | CH | N | CH | C | CH | N | CH | CH | CH | OMe | OMe |
| 788 | 1 | CH | CH | N | CH | N | C | CH | CH | CH | CH | CH | OMe | OMe |
| 789 | 1 | N | CH | N | CH | N | C | CH | CH | CH | CH | CH | OMe | OMe |
| 790 | 1 | CH | CH | CH | N | N | C | CH | CH | CH | CH | CH | OMe | OMe |
| 791 | 1 | N | CH | CH | N | N | C | CH | CH | CH | CH | CH | OMe | OMe |
| 792 | 1 | CH | CH | CH | CH | N | C | CH | CH | CH | CH | CH | OMe | OMe |
| 793 | 1 | N | CH | CH | CH | N | C | CH | CH | CH | CH | CH | OMe | OMe |
| 794 | 1 | CH | CH | CH | CH | N | C | CH | CH | N | CH | CH | absent | OMe |
| 795 | 1 | N | CH | CH | CH | N | C | CH | CH | N | CH | CH | | OMe |

In a further embodiment, the present invention provides compounds of formula (IVa) and (IVb), wherein X₁, o, Z, Y₁, Y₂, Y₃, Y₄, Y₅, Y₆, Y₇, Y₈, Y₉, Y₁₀, R₅, and R₆ are as defined in examples 1289 to 1296:

In a further embodiment, the present invention provides compounds of formula (Va) and (Vb), wherein o, Y₁, Y₂, Y₃, Y₄, Y₅, Y₈, Y₇, Y₈, Y₉, Y₁₀, R₅, and R₆ are as defined in examples 796 to 971:

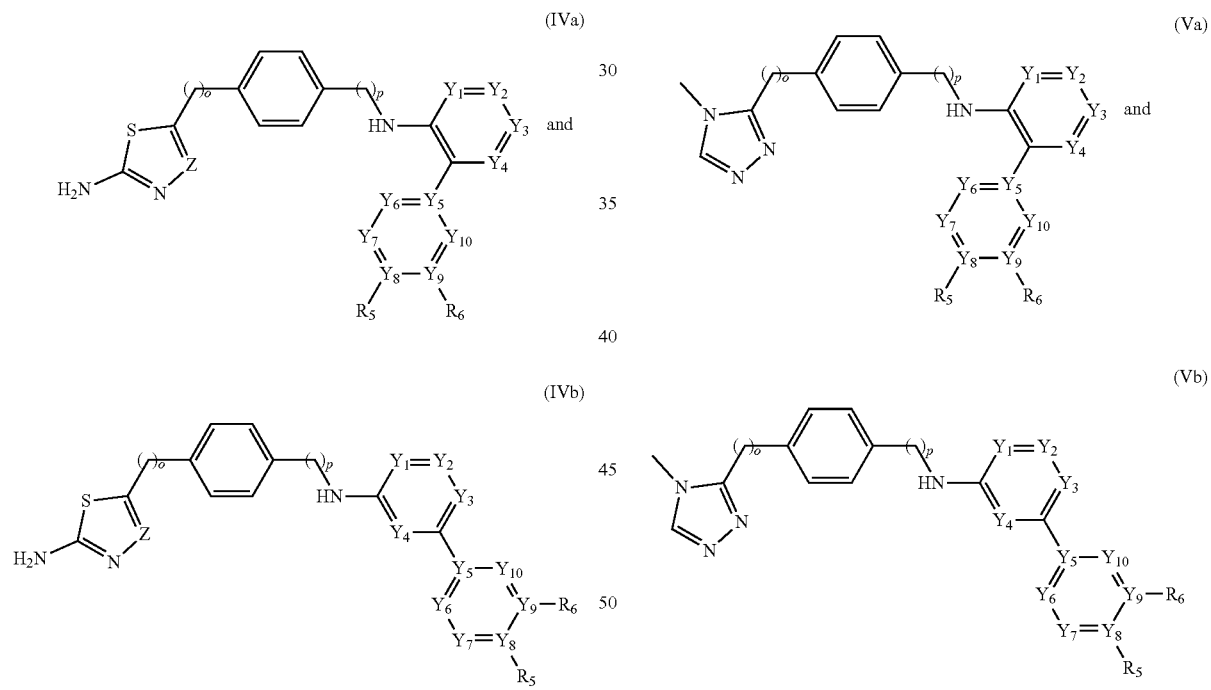

In both, formulae (IVa) and (Vb), o is 0.

In both, formulae (Va) and (Vb), o is 0.

| Comp | p | Z | Y₁ | Y₂ | Y₃ | Y₄ | Y₅ | Y₆ | Y₇ | Y₈ | Y₉ | Y₁₀ | R₅ | R₆ |
|---|---|---|---|---|---|---|---|---|---|---|---|---|---|---|
| 1289 | 0 | N | CH | CH | CH | CH | C | CH | CH | CH | CH | CH | OMe | H |
| 1290 | 0 | N | N | CH | CH | CH | C | CH | CH | CH | CH | CH | OMe | H |
| 1291 | 0 | N | CH | CH | N | CH | C | CH | CH | CH | CH | CH | OMe | H |
| 1292 | 0 | N | CH | CH | N | CH | C | CH | CH | CH | CH | CH | OMe | OMe |
| 1293 | 0 | N | N | CH | CH | N | C | CH | CH | CH | CH | CH | F | H |
| 1294 | 0 | N | CH | CH | CH | C | CH | CH | CH | CH | CH | CH | O-Phenyl | H |
| 1295 | 0 | N | CH | CH | CH | CH | C | CH | CH | CH | CH | CH | propoxy | H |
| 1296 | 0 | N | CH | CH | CH | CH | C | CH | CH | CH | CH | CH | propan-2-yloxy | H |

| Comp | p | Y₁ | Y₂ | Y₃ | Y₄ | Y₅ | Y₆ | Y₇ | Y₈ | Y₉ | Y₁₀ | R₅ | R₆ |
|---|---|---|---|---|---|---|---|---|---|---|---|---|---|
| 796 | 0 | CH | CH | CH | CH | C | CH | CH | CH | CH | CH | H | H |
| 797 | 0 | CH | CH | CH | CH | C | N | CH | CH | CH | CH | H | H |
| 798 | 0 | CH | CH | CH | CH | C | CH | N | CH | CH | CH | H | H |
| 799 | 0 | CH | CH | CH | CH | C | N | CH | CH | CH | N | H | H |
| 800 | 0 | CH | CH | CH | CH | C | N | N | CH | CH | CH | H | H |
| 801 | 0 | CH | CH | CH | CH | C | CH | N | CH | N | CH | H | absent |
| 802 | 0 | CH | CH | CH | CH | C | CH | CH | N | CH | N | absent | H |
| 803 | 0 | CH | CH | CH | CH | C | CH | CH | N | CH | CH | absent | H |
| 804 | 0 | N | CH | CH | CH | C | CH | CH | CH | CH | CH | H | H |
| 805 | 0 | N | CH | CH | CH | C | N | CH | CH | CH | CH | H | H |
| 806 | 0 | N | CH | CH | CH | C | CH | N | CH | CH | CH | H | H |
| 807 | 0 | N | CH | CH | CH | C | N | CH | CH | CH | N | H | H |
| 808 | 0 | N | CH | CH | CH | C | CH | CH | N | CH | N | absent | H |
| 809 | 0 | N | CH | CH | CH | C | N | CH | CH | CH | CH | H | H |
| 810 | 0 | N | N | CH | CH | C | CH | CH | N | CH | N | absent | H |
| 811 | 0 | N | N | CH | CH | C | CH | CH | CH | CH | CH | H | H |
| 812 | 0 | CH | N | CH | CH | C | CH | CH | CH | CH | CH | H | H |
| 813 | 0 | CH | N | CH | CH | C | N | CH | CH | CH | CH | H | H |
| 814 | 0 | CH | N | CH | CH | C | CH | N | CH | CH | CH | H | H |
| 815 | 0 | CH | N | CH | CH | C | CH | N | CH | N | CH | H | absent |
| 816 | 0 | CH | N | CH | CH | C | N | CH | N | CH | CH | H | H |
| 817 | 0 | CH | N | CH | CH | C | CH | CH | N | CH | N | absent | H |
| 818 | 0 | CH | N | CH | CH | C | CH | CH | N | CH | CH | absent | H |
| 819 | 0 | N | CH | N | CH | C | CH | CH | CH | CH | CH | H | H |
| 820 | 0 | N | CH | N | CH | C | N | CH | CH | CH | CH | H | H |
| 821 | 0 | N | CH | N | CH | C | CH | N | CH | CH | CH | H | H |
| 822 | 0 | CH | N | CH | N | C | CH | CH | CH | CH | CH | H | H |
| 823 | 0 | CH | CH | N | N | C | CH | CH | CH | CH | CH | H | H |
| 824 | 0 | CH | CH | CH | N | C | CH | CH | CH | CH | CH | H | H |
| 825 | 0 | CH | CH | CH | N | C | CH | CH | N | CH | CH | absent | H |
| 826 | 0 | CH | CH | CH | CH | C | CH | CH | CH | CH | CH | F | H |
| 827 | 0 | CH | CH | CH | CH | C | N | CH | CH | CH | CH | F | H |
| 828 | 0 | CH | CH | CH | CH | C | CH | N | CH | CH | CH | F | H |
| 829 | 0 | CH | CH | CH | CH | C | N | CH | CH | CH | N | F | H |
| 830 | 0 | CH | CH | CH | CH | C | N | N | CH | CH | CH | F | H |
| 831 | 0 | CH | CH | CH | CH | C | CH | N | CH | N | CH | F | absent |
| 832 | 0 | CH | CH | CH | CH | C | CH | CH | N | CH | N | absent | |
| 833 | 0 | CH | CH | CH | CH | C | CH | CH | N | CH | CH | absent | H |
| 834 | 0 | N | CH | CH | CH | C | CH | CH | CH | CH | CH | F | H |
| 835 | 0 | N | CH | CH | CH | C | N | CH | CH | CH | CH | F | H |
| 836 | 0 | N | CH | CH | CH | C | CH | N | CH | CH | CH | F | H |
| 837 | 0 | N | CH | CH | CH | C | N | CH | CH | CH | N | F | H |
| 838 | 0 | N | CH | CH | CH | C | CH | CH | N | CH | N | absent | H |
| 839 | 0 | N | CH | N | CH | C | CH | CH | CH | CH | CH | F | H |
| 840 | 0 | N | N | CH | CH | C | CH | CH | N | CH | N | absent | H |
| 841 | 0 | CH | N | CH | CH | C | CH | CH | CH | CH | CH | F | H |
| 842 | 0 | CH | N | CH | CH | C | N | CH | CH | CH | CH | F | H |
| 843 | 0 | CH | N | CH | CH | C | CH | N | CH | CH | CH | F | H |
| 844 | 0 | CH | N | CH | CH | C | CH | N | CH | N | CH | F | absent |
| 845 | 0 | CH | N | CH | CH | C | N | CH | N | CH | CH | F | absent |
| 846 | 0 | CH | N | CH | CH | C | CH | CH | N | CH | N | absent | H |
| 847 | 0 | N | CH | N | CH | C | CH | CH | CH | CH | CH | F | H |
| 848 | 0 | N | CH | N | CH | C | N | CH | CH | CH | CH | F | H |
| 849 | 0 | N | CH | N | CH | C | CH | N | CH | CH | CH | F | H |
| 850 | 0 | CH | N | CH | N | C | CH | CH | CH | CH | CH | F | H |
| 851 | 0 | CH | CH | N | N | C | CH | CH | CH | CH | CH | F | H |
| 852 | 0 | CH | CH | CH | N | C | CH | CH | CH | CH | CH | F | H |
| 853 | 0 | CH | CH | CH | N | C | CH | N | CH | CH | CH | F | H |
| 854 | 0 | CH | CH | CH | CH | C | CH | CH | CH | CH | CH | OMe | OMe |
| 855 | 0 | CH | CH | CH | CH | C | N | CH | CH | CH | CH | OMe | OMe |
| 856 | 0 | CH | CH | CH | CH | C | CH | N | CH | CH | CH | OMe | OMe |
| 857 | 0 | CH | CH | CH | CH | C | N | CH | CH | CH | N | OMe | OMe |
| 858 | 0 | CH | CH | CH | CH | C | N | N | CH | CH | CH | OMe | OMe |
| 859 | 0 | CH | CH | CH | CH | C | CH | N | CH | N | CH | OMe | absent |
| 860 | 0 | CH | CH | CH | CH | C | CH | CH | N | CH | N | absent | OMe |
| 861 | 0 | CH | CH | CH | CH | C | CH | CH | N | CH | CH | absent | OMe |
| 862 | 0 | N | CH | CH | CH | C | CH | CH | CH | CH | CH | OMe | OMe |
| 863 | 0 | N | CH | CH | CH | C | N | CH | CH | CH | CH | OMe | OMe |
| 864 | 0 | N | CH | CH | CH | C | CH | N | CH | CH | CH | OMe | OMe |
| 865 | 0 | N | CH | CH | CH | C | N | CH | CH | CH | N | OMe | OMe |
| 866 | 0 | N | CH | CH | CH | C | CH | CH | N | CH | N | absent | OMe |
| 867 | 0 | N | CH | CH | CH | C | N | CH | CH | CH | CH | OMe | OMe |
| 868 | 0 | N | N | CH | CH | C | CH | CH | N | CH | N | absent | OMe |
| 869 | 0 | N | N | CH | CH | C | CH | CH | CH | CH | CH | OMe | OMe |
| 870 | 0 | CH | N | CH | CH | C | CH | CH | CH | CH | CH | OMe | OMe |
| 871 | 0 | CH | N | CH | CH | C | N | CH | CH | CH | CH | OMe | OMe |
| 872 | 0 | CH | N | CH | CH | C | CH | N | CH | CH | CH | OMe | OMe |
| 873 | 0 | CH | N | CH | CH | C | CH | N | CH | N | CH | OMe | absent |
| 874 | 0 | CH | N | CH | CH | C | N | CH | N | CH | CH | OMe | OMe |

-continued

| Comp | p | $Y_1$ | $Y_2$ | $Y_3$ | $Y_4$ | $Y_5$ | $Y_6$ | $Y_7$ | $Y_8$ | $Y_9$ | $Y_{10}$ | $R_5$ | $R_6$ |
|---|---|---|---|---|---|---|---|---|---|---|---|---|---|
| 875 | 0 | CH | N | CH | CH | C | CH | CH | N | CH | N | absent | OMe |
| 876 | 0 | CH | N | CH | CH | C | CH | CH | N | CH | CH | absent | OMe |
| 877 | 0 | N | CH | N | CH | C | CH | CH | CH | CH | CH | OMe | OMe |
| 878 | 0 | N | CH | N | CH | C | N | CH | CH | CH | CH | OMe | OMe |
| 879 | 0 | N | CH | N | CH | C | CH | N | CH | CH | CH | OMe | OMe |
| 880 | 0 | CH | N | CH | N | C | CH | CH | CH | CH | CH | OMe | OMe |
| 881 | 0 | CH | CH | N | N | C | CH | CH | CH | CH | CH | OMe | OMe |
| 882 | 0 | CH | CH | CH | N | C | CH | CH | CH | CH | CH | OMe | OMe |
| 883 | 0 | CH | CH | CH | N | C | CH | CH | N | CH | CH | absent | OMe |
| 884 | 1 | CH | CH | CH | CH | C | CH | CH | CH | CH | CH | H | H |
| 885 | 1 | CH | CH | CH | CH | C | N | CH | CH | CH | CH | H | H |
| 886 | 1 | CH | CH | CH | CH | C | CH | N | CH | CH | CH | H | H |
| 887 | 1 | CH | CH | CH | CH | C | N | CH | CH | CH | N | H | H |
| 888 | 1 | CH | CH | CH | CH | C | N | N | CH | CH | CH | H | H |
| 889 | 1 | CH | CH | CH | CH | C | CH | N | CH | N | CH | H | absent |
| 890 | 1 | CH | CH | CH | CH | C | CH | CH | N | CH | N | absent | H |
| 891 | 1 | CH | CH | CH | CH | C | CH | CH | N | CH | CH | absent | H |
| 892 | 1 | N | CH | CH | CH | C | CH | CH | CH | CH | CH | H | H |
| 893 | 1 | N | CH | CH | CH | C | N | CH | CH | CH | CH | H | H |
| 894 | 1 | N | CH | CH | CH | C | CH | N | CH | CH | CH | H | H |
| 895 | 1 | N | CH | CH | CH | C | N | CH | CH | CH | N | H | H |
| 896 | 1 | N | CH | CH | CH | C | CH | CH | N | CH | N | absent | H |
| 897 | 1 | N | CH | CH | CH | C | N | CH | CH | CH | CH | H | H |
| 898 | 1 | N | N | CH | CH | C | CH | CH | N | CH | N | absent | H |
| 899 | 1 | N | N | CH | CH | C | CH | CH | CH | CH | CH | H | H |
| 900 | 1 | CH | N | CH | CH | C | CH | CH | CH | CH | CH | H | H |
| 901 | 1 | CH | N | CH | CH | C | N | CH | CH | CH | CH | H | H |
| 902 | 1 | CH | N | CH | CH | C | CH | N | CH | CH | CH | H | H |
| 903 | 1 | CH | N | CH | CH | C | CH | N | CH | N | CH | H | absent |
| 904 | 1 | CH | N | CH | CH | C | N | CH | CH | N | CH | H | H |
| 905 | 1 | CH | N | CH | CH | C | CH | CH | N | CH | N | absent | H |
| 906 | 1 | CH | N | CH | CH | C | CH | CH | N | CH | CH | absent | H |
| 907 | 1 | N | CH | N | CH | C | CH | CH | CH | CH | CH | H | H |
| 908 | 1 | N | CH | N | CH | C | N | CH | CH | CH | CH | H | H |
| 909 | 1 | N | CH | N | CH | C | CH | N | CH | CH | CH | H | H |
| 910 | 1 | CH | N | CH | N | C | CH | CH | CH | CH | CH | H | H |
| 911 | 1 | CH | CH | N | N | C | CH | CH | CH | CH | CH | H | H |
| 912 | 1 | CH | CH | CH | N | C | CH | CH | CH | CH | CH | H | H |
| 913 | 1 | CH | CH | CH | N | C | CH | CH | N | CH | CH | absent | H |
| 914 | 1 | CH | CH | CH | CH | C | CH | CH | CH | CH | CH | F | H |
| 915 | 1 | CH | CH | CH | CH | C | N | CH | CH | CH | CH | F | H |
| 916 | 1 | CH | CH | CH | CH | C | CH | N | CH | CH | CH | F | H |
| 917 | 1 | CH | CH | CH | CH | C | N | CH | CH | CH | N | F | H |
| 918 | 1 | CH | CH | CH | CH | C | N | N | CH | CH | CH | F | H |
| 919 | 1 | CH | CH | CH | CH | C | CH | N | CH | N | CH | F | absent |
| 920 | 1 | CH | CH | CH | CH | C | CH | CH | N | CH | N | absent | H |
| 921 | 1 | CH | CH | CH | CH | C | CH | CH | N | CH | CH | absent | H |
| 922 | 1 | N | CH | CH | CH | C | CH | CH | CH | CH | CH | F | H |
| 923 | 1 | N | CH | CH | CH | C | N | CH | CH | CH | CH | F | H |
| 924 | 1 | N | CH | CH | CH | C | CH | N | CH | CH | CH | F | H |
| 925 | 1 | N | CH | CH | CH | C | N | CH | CH | CH | N | F | H |
| 926 | 1 | N | CH | CH | CH | C | CH | CH | N | CH | N | absent | H |
| 927 | 1 | N | N | CH | CH | C | CH | CH | CH | CH | CH | F | H |
| 928 | 1 | N | N | CH | CH | C | CH | CH | N | CH | N | absent | H |
| 929 | 1 | CH | N | CH | CH | C | CH | CH | CH | CH | CH | F | H |
| 930 | 1 | CH | N | CH | CH | C | N | CH | CH | CH | CH | F | H |
| 931 | 1 | CH | N | CH | CH | C | CH | N | CH | CH | CH | F | H |
| 932 | 1 | CH | N | CH | CH | C | CH | N | CH | N | CH | F | absent |
| 933 | 1 | CH | N | CH | CH | C | N | CH | CH | N | CH | F | absent |
| 934 | 1 | CH | N | CH | CH | C | CH | CH | N | CH | N | absent | H |
| 935 | 1 | N | CH | N | CH | C | CH | CH | CH | CH | CH | F | H |
| 936 | 1 | N | CH | N | CH | C | N | CH | CH | CH | CH | F | H |
| 937 | 1 | N | CH | N | CH | C | CH | N | CH | CH | CH | F | H |
| 938 | 1 | CH | N | CH | N | C | CH | CH | CH | CH | CH | F | H |
| 939 | 1 | CH | CH | N | N | C | CH | CH | CH | CH | CH | F | H |
| 940 | 1 | CH | CH | CH | N | C | CH | CH | CH | CH | CH | F | H |
| 941 | 1 | CH | CH | CH | N | C | CH | N | CH | CH | CH | F | H |
| 942 | 1 | CH | CH | CH | CH | C | CH | CH | CH | CH | CH | OMe | OMe |
| 943 | 1 | CH | CH | CH | CH | C | N | CH | CH | CH | CH | OMe | OMe |
| 944 | 1 | CH | CH | CH | CH | C | CH | N | CH | CH | CH | OMe | OMe |
| 945 | 1 | CH | CH | CH | CH | C | N | CH | CH | CH | N | OMe | OMe |
| 946 | 1 | CH | CH | CH | CH | C | N | N | CH | CH | CH | OMe | OMe |
| 947 | 1 | CH | CH | CH | CH | C | CH | N | CH | N | CH | OMe | absent |
| 948 | 1 | CH | CH | CH | CH | C | CH | CH | N | CH | N | absent | OMe |
| 949 | 1 | CH | CH | CH | CH | C | CH | CH | N | CH | CH | absent | OMe |
| 950 | 1 | N | CH | CH | CH | C | CH | CH | CH | CH | CH | OMe | OMe |
| 951 | 1 | N | CH | CH | CH | C | N | CH | CH | CH | CH | OMe | OMe |

-continued

| Comp | p | Y₁ | Y₂ | Y₃ | Y₄ | Y₅ | Y₆ | Y₇ | Y₈ | Y₉ | Y₁₀ | R₅ | R₆ |
|---|---|---|---|---|---|---|---|---|---|---|---|---|---|
| 952 | 1 | N | CH | CH | CH | C | CH | N | CH | CH | CH | OMe | OMe |
| 953 | 1 | N | CH | CH | CH | C | N | CH | CH | CH | N | OMe | OMe |
| 954 | 1 | N | CH | CH | CH | C | CH | CH | N | CH | N | absent | OMe |
| 955 | 1 | N | CH | CH | CH | C | N | CH | CH | CH | CH | OMe | OMe |
| 956 | 1 | N | N | CH | CH | C | CH | CH | N | CH | N | absent | OMe |
| 957 | 1 | N | N | CH | CH | C | CH | CH | CH | CH | CH | OMe | OMe |
| 958 | 1 | CH | N | CH | CH | C | CH | CH | CH | CH | CH | OMe | OMe |
| 959 | 1 | CH | N | CH | CH | C | N | CH | CH | CH | CH | OMe | OMe |
| 960 | 1 | CH | N | CH | CH | C | CH | N | CH | CH | CH | OMe | OMe |
| 961 | 1 | CH | N | CH | CH | C | CH | N | CH | N | CH | OMe | absent |
| 962 | 1 | CH | N | CH | CH | C | N | CH | CH | N | CH | OMe | OMe |
| 963 | 1 | CH | N | CH | CH | C | CH | CH | N | CH | N | absent | OMe |
| 964 | 1 | CH | N | CH | CH | C | CH | CH | N | CH | CH | absent | OMe |
| 965 | 1 | N | CH | N | CH | C | CH | CH | CH | CH | CH | OMe | OMe |
| 966 | 1 | N | CH | N | CH | C | N | CH | CH | CH | CH | OMe | OMe |
| 967 | 1 | N | CH | N | CH | C | CH | N | CH | CH | CH | OMe | OMe |
| 968 | 1 | CH | N | CH | N | C | CH | CH | CH | CH | CH | OMe | OMe |
| 969 | 1 | CH | CH | N | N | C | CH | CH | CH | CH | CH | OMe | OMe |
| 970 | 1 | CH | CH | CH | N | C | CH | CH | CH | CH | CH | OMe | OMe |
| 971 | 1 | CH | CH | CH | N | C | CH | CH | N | CH | CH | absent | OMe |

In a further embodiment, the present invention provides compounds of formula (Va) and (Vb), wherein o, Y₁, Y₂, Y₃, Y₄, Y₅, Y₆, Y₇, Y₈, Y₉, Y₁₀, R₅, and R₆ are as defined in examples 1297 to 1300:

In a further embodiment, the present invention provides compounds of formula (VI), wherein X₁, n, Z, R₅, and R₆ are as defined in examples 972 to 977:

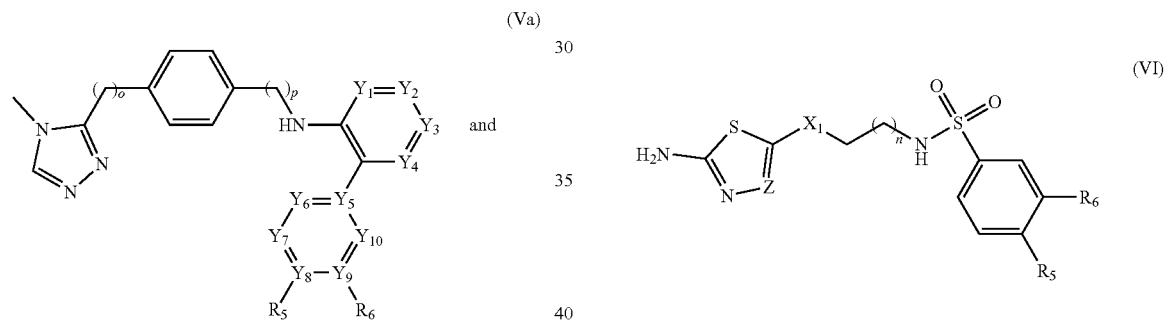

In both, formulae (Va) and (Vb), o is 0.

| Comp | X₁ | Z | n | R₅ | R₆ |
|---|---|---|---|---|---|
| 972 | CH₂ | CH | 1 | F | H |
| 973 | CH₂ | N | 1 | F | H |
| 974 | S | N | 1 | F | H |
| 975 | CH₂ | CH | 1 | OMe | OMe |
| 976 | CH₂ | N | 1 | OMe | OMe |
| 977 | S | N | 1 | OMe | OMe |

In a further embodiment, the present invention provides compounds of formula (VII), wherein X₁, n, Z, R₂, R₅, and R₆ are as defined in examples 978 to 54:

| Comp | p | Y₁ | Y₂ | Y₃ | Y₄ | Y₅ | Y₆ | Y₇ | Y₈ | Y₉ | Y₁₀ | R₅ | R₆ |
|---|---|---|---|---|---|---|---|---|---|---|---|---|---|
| 1297 | 0 | CH | CH | CH | CH | C | CH | CH | CH | CH | CH | OMe | H |
| 1298 | 0 | CH | CH | CH | N | C | CH | CH | CH | CH | CH | OMe | H |
| 1299 | 0 | CH | CH | CH | CH | C | CH | CH | CH | CH | CH | O-Phenyl | H |
| 1300 | 0 | CH | CH | N | CH | C | CH | CH | CH | CH | CH | OMe | OMe |

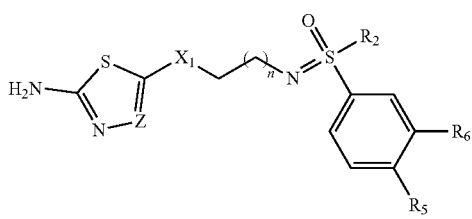

(VII)

| Comp | $X_1$ | Z | n | $R_2$ | $R_5$ | $R_6$ |
|---|---|---|---|---|---|---|
| 978 | $CH_2$ | CH | 1 | Me | F | H |
| 979 | $CH_2$ | N | 1 | Me | F | H |
| 980 | S | N | 1 | Me | F | H |
| 981 | $CH_2$ | CH | 1 | Me | OMe | OMe |
| 982 | $CH_2$ | N | 1 | Me | OMe | OMe |
| 983 | S | N | 1 | Me | OMe | OMe |
| 984 | $CH_2$ | CH | 1 | Cyclopropyl | F | H |
| 985 | $CH_2$ | N | 1 | Cyclopropyl | F | H |
| 986 | S | N | 1 | Cyclopropyl | F | H |
| 987 | $CH_2$ | CH | 1 | Cyclopropyl | OMe | OMe |
| 988 | $CH_2$ | N | 1 | Cyclopropyl | OMe | OMe |
| 989 | S | N | 1 | Cyclopropyl | OMe | OMe |

In a further embodiment, the present invention provides compounds of formula (VIII), wherein $X_1$, n, $R_5$, and $R_6$ are as defined in examples 990 to 993:

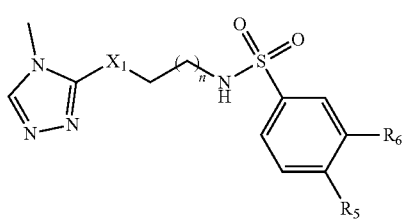

(VIII)

| Comp | $X_1$ | n | R5 | R6 |
|---|---|---|---|---|
| 990 | $CH_2$ | 1 | F | H |
| 991 | S | 1 | F | H |
| 992 | $CH_2$ | 1 | OMe | OMe |
| 993 | S | 1 | OMe | OMe |

In a further embodiment, the present invention provides compounds of formula (IX), wherein $X_1$, n, $R_2$, $R_5$, and $R_6$ are as defined in examples 994 to 1001:

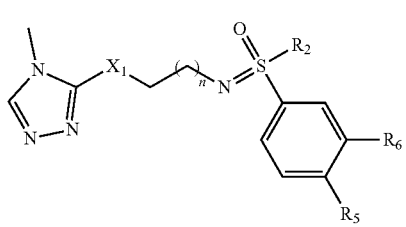

(IX)

| Comp | $X_1$ | n | $R_2$ | $R_5$ | $R_6$ |
|---|---|---|---|---|---|
| 994 | $CH_2$ | 1 | Me | F | H |
| 995 | S | 1 | Me | F | H |
| 996 | $CH_2$ | 1 | Me | OMe | OMe |
| 997 | S | 1 | Me | OMe | OMe |
| 998 | $CH_2$ | 1 | Cyclopropyl | F | H |
| 999 | S | 1 | Cyclopropyl | F | H |
| 1000 | $CH_2$ | 1 | Cyclopropyl | OMe | OMe |
| 1001 | S | 1 | Cyclopropyl | OMe | OMe |

In a further embodiment, the present invention provides compounds of formula (X), wherein o, $R_5$, and $R_6$ are as defined in examples 1002 to 1005:

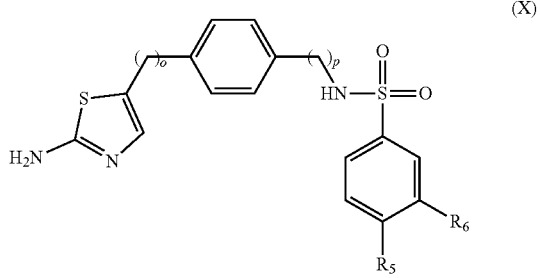

(X)

| o is 0. | | | |
|---|---|---|---|
| Comp | p | $R_5$ | $R_6$ |
| 1002 | 0 | F | H |
| 1003 | 0 | OMe | OMe |
| 1004 | 1 | F | H |
| 1005 | 1 | OMe | OMe |

In a further embodiment, the present invention provides compounds of formula (XI), wherein o, $R_2$, $R_5$, and $R_6$ are as defined in examples 1006 to 1013:

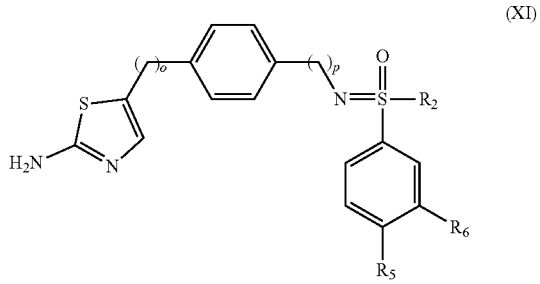

(XI)

| o is 0. | | | | |
|---|---|---|---|---|
| Comp | p | $R_2$ | $R_5$ | $R_6$ |
| 1006 | 0 | Me | F | H |
| 1007 | 0 | Me | OMe | OMe |
| 1008 | 0 | Cyclopropyl | F | H |
| 1009 | 0 | Cyclopropyl | OMe | OMe |
| 1010 | 1 | Me | F | H |
| 1011 | 1 | Me | OMe | OMe |
| 1012 | 1 | Cyclopropyl | F | H |
| 1013 | 1 | Cyclopropyl | OMe | OMe |

In a further embodiment, the present invention provides compounds of formula (XIIa) and (XIIb), wherein Z, $Y_1$, $Y_2$, $Y_3$, $Y_4$, $Y_5$, $Y_6$, $Y_7$, $Y_8$, $Y_9$, $Y_{10}$, $R_5$, and $R_6$ are as defined in examples 1014 to 1189:

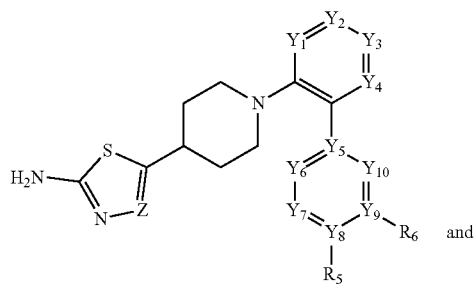

(XIIa)

and

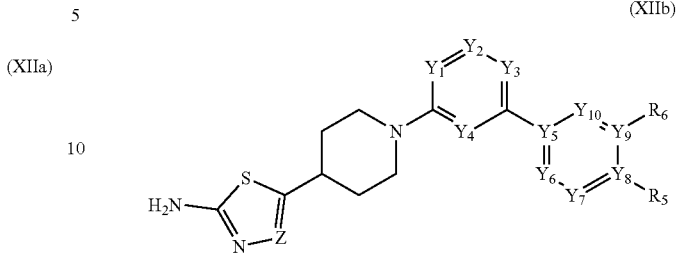

(XIIb)

| Comp | Z | $Y_1$ | $Y_2$ | $Y_3$ | $Y_4$ | $Y_5$ | $Y_6$ | $Y_7$ | $Y_8$ | $Y_9$ | $Y_{10}$ | $R_5$ | $R_6$ |
|---|---|---|---|---|---|---|---|---|---|---|---|---|---|
| 1014 | CH | CH | CH | CH | CH | C | CH | CH | CH | CH | CH | H | H |
| 1015 | N | CH | CH | CH | CH | C | CH | CH | CH | CH | CH | H | H |
| 1016 | CH | CH | CH | CH | CH | C | N | CH | CH | CH | CH | H | H |
| 1017 | N | CH | CH | CH | CH | C | N | CH | CH | CH | CH | H | H |
| 1018 | CH | CH | CH | CH | CH | C | CH | N | CH | CH | CH | H | H |
| 1019 | N | CH | CH | CH | CH | C | CH | N | CH | CH | CH | H | H |
| 1020 | CH | CH | CH | CH | CH | C | N | CH | CH | CH | N | H | H |
| 1021 | N | CH | CH | CH | CH | C | N | CH | CH | CH | N | H | H |
| 1022 | CH | CH | CH | CH | CH | C | N | N | CH | CH | CH | H | H |
| 1023 | N | CH | CH | CH | CH | C | N | N | CH | CH | CH | H | H |
| 1024 | CH | CH | CH | CH | CH | C | CH | N | CH | N | CH | H | absent |
| 1025 | N | CH | CH | CH | CH | C | CH | N | CH | N | CH | H | |
| 1026 | CH | CH | CH | CH | CH | C | CH | CH | N | CH | N | absent | H |
| 1027 | N | CH | CH | CH | CH | C | CH | CH | N | CH | N | | H |
| 1028 | CH | CH | CH | CH | CH | C | CH | CH | N | CH | CH | absent | H |
| 1029 | N | CH | CH | CH | CH | C | CH | CH | N | CH | CH | | H |
| 1030 | CH | N | CH | CH | CH | C | CH | CH | CH | CH | CH | H | H |
| 1031 | N | N | CH | CH | CH | C | CH | CH | CH | CH | CH | H | H |
| 1032 | CH | N | CH | CH | CH | C | N | CH | CH | CH | CH | H | H |
| 1033 | N | N | CH | CH | CH | C | N | CH | CH | CH | CH | H | H |
| 1034 | CH | N | CH | CH | CH | C | CH | N | CH | CH | CH | H | H |
| 1035 | N | N | CH | CH | CH | C | CH | N | CH | CH | CH | H | H |
| 1036 | CH | N | CH | CH | CH | C | N | CH | CH | CH | N | H | H |
| 1037 | N | N | CH | CH | CH | C | N | CH | CH | CH | N | H | H |
| 1038 | CH | N | CH | CH | CH | C | CH | CH | N | CH | N | absent | H |
| 1039 | N | N | CH | CH | CH | C | CH | CH | N | CH | N | | H |
| 1040 | CH | N | CH | CH | CH | C | N | CH | CH | CH | CH | H | H |
| 1041 | N | N | CH | CH | CH | C | N | CH | CH | CH | CH | H | H |
| 1042 | CH | N | N | CH | CH | C | CH | CH | N | CH | N | absent | H |
| 1043 | N | N | N | CH | CH | C | CH | CH | N | CH | N | | H |
| 1044 | CH | N | N | CH | CH | C | CH | CH | CH | CH | CH | H | H |
| 1045 | N | N | N | CH | CH | C | CH | CH | CH | CH | CH | H | H |
| 1046 | CH | CH | N | CH | CH | C | CH | CH | CH | CH | CH | H | H |
| 1047 | N | CH | N | CH | CH | C | CH | CH | CH | CH | CH | H | H |
| 1048 | CH | CH | N | CH | CH | C | N | CH | CH | CH | CH | H | H |
| 1049 | N | CH | N | CH | CH | C | N | CH | CH | CH | CH | H | H |
| 1050 | CH | CH | N | CH | CH | C | CH | N | CH | CH | CH | H | H |
| 1051 | N | CH | N | CH | CH | C | CH | N | CH | CH | CH | H | H |
| 1052 | CH | CH | N | CH | CH | C | CH | N | CH | N | CH | H | absent |
| 1053 | N | CH | N | CH | CH | C | CH | N | CH | N | CH | H | |
| 1054 | CH | CH | N | CH | CH | C | N | CH | CH | N | CH | H | H |
| 1055 | N | CH | N | CH | CH | C | N | CH | CH | N | CH | H | H |
| 1056 | CH | CH | N | CH | CH | C | CH | CH | N | CH | N | absent | H |
| 1057 | N | CH | N | CH | CH | C | CH | CH | N | CH | N | | H |
| 1058 | CH | CH | N | CH | CH | C | CH | CH | N | CH | CH | absent | H |
| 1059 | N | CH | N | CH | CH | C | CH | CH | N | CH | CH | | H |
| 1060 | CH | N | CH | N | CH | C | CH | CH | CH | CH | CH | H | H |
| 1061 | N | N | CH | N | CH | C | CH | CH | CH | CH | CH | H | H |
| 1062 | CH | N | CH | N | CH | C | N | CH | CH | CH | CH | H | H |
| 1063 | N | N | CH | N | CH | C | N | CH | CH | CH | CH | H | H |
| 1064 | CH | N | CH | N | CH | C | CH | N | CH | CH | CH | H | H |
| 1065 | N | N | CH | N | CH | C | CH | N | CH | CH | CH | H | H |
| 1066 | CH | CH | N | CH | N | C | CH | CH | CH | CH | CH | H | H |
| 1067 | N | CH | N | CH | N | C | CH | CH | CH | CH | CH | H | H |

-continued

| Comp | Z | $Y_1$ | $Y_2$ | $Y_3$ | $Y_4$ | $Y_5$ | $Y_6$ | $Y_7$ | $Y_8$ | $Y_9$ | $Y_{10}$ | $R_5$ | $R_6$ |
|---|---|---|---|---|---|---|---|---|---|---|---|---|---|
| 1068 | CH | CH | CH | N | N | C | CH | CH | CH | CH | CH | H | H |
| 1069 | N | CH | CH | N | N | C | CH | CH | CH | CH | CH | H | H |
| 1070 | CH | CH | CH | CH | N | C | CH | CH | CH | CH | CH | H | H |
| 1071 | N | CH | CH | CH | N | C | CH | CH | CH | CH | CH | H | H |
| 1072 | CH | CH | CH | CH | N | C | CH | CH | N | CH | CH | absent | H |
| 1073 | N | CH | CH | CH | N | C | CH | CH | N | CH | CH | | H |
| 1074 | CH | CH | CH | CH | CH | C | CH | CH | CH | CH | CH | F | H |
| 1075 | N | CH | CH | CH | CH | C | CH | CH | CH | CH | CH | F | H |
| 1076 | CH | CH | CH | CH | CH | C | N | CH | CH | CH | CH | F | H |
| 1077 | N | CH | CH | CH | CH | C | N | CH | CH | CH | CH | F | H |
| 1078 | CH | CH | CH | CH | CH | C | CH | N | CH | CH | CH | F | |
| 1079 | N | CH | CH | CH | CH | C | CH | N | CH | CH | CH | F | H |
| 1080 | CH | CH | CH | CH | CH | C | N | CH | CH | CH | N | F | H |
| 1081 | N | CH | CH | CH | CH | C | N | CH | CH | CH | N | F | H |
| 1082 | CH | CH | CH | CH | CH | C | N | N | CH | CH | CH | F | H |
| 1083 | N | CH | CH | CH | CH | C | N | N | CH | CH | CH | F | H |
| 1084 | CH | CH | CH | CH | CH | C | CH | N | CH | N | CH | F | absent |
| 1085 | N | CH | CH | CH | CH | C | CH | N | CH | N | CH | F | |
| 1086 | CH | CH | CH | CH | CH | C | CH | CH | N | CH | N | absent | |
| 1087 | N | CH | CH | CH | CH | C | CH | CH | N | CH | N | | |
| 1088 | CH | CH | CH | CH | CH | C | CH | CH | N | CH | CH | absent | H |
| 1089 | N | CH | CH | CH | CH | C | CH | CH | N | CH | CH | | H |
| 1090 | CH | N | CH | CH | CH | C | CH | CH | CH | CH | CH | F | H |
| 1091 | N | N | CH | CH | CH | C | CH | CH | CH | CH | CH | F | H |
| 1092 | CH | N | CH | CH | CH | C | N | CH | CH | CH | CH | F | H |
| 1093 | N | N | CH | CH | CH | C | N | CH | CH | CH | CH | F | H |
| 1094 | CH | N | CH | CH | CH | C | CH | N | CH | CH | CH | F | H |
| 1095 | N | N | CH | CH | CH | C | CH | N | CH | CH | CH | F | H |
| 1096 | CH | N | CH | CH | CH | C | N | CH | CH | CH | N | F | H |
| 1097 | N | N | CH | CH | CH | C | N | CH | CH | CH | N | F | H |
| 1098 | CH | N | CH | CH | CH | C | CH | CH | N | CH | N | absent | H |
| 1099 | N | N | CH | CH | CH | C | CH | CH | N | CH | N | | H |
| 1100 | CH | N | N | CH | CH | C | CH | CH | CH | CH | CH | F | H |
| 1101 | N | N | N | CH | CH | C | CH | CH | CH | CH | CH | F | H |
| 1102 | CH | N | N | CH | CH | C | CH | CH | N | CH | N | absent | H |
| 1103 | N | N | N | CH | CH | C | CH | CH | N | CH | N | | H |
| 1104 | CH | CH | N | CH | CH | C | CH | CH | CH | CH | CH | F | H |
| 1105 | N | CH | N | CH | CH | C | CH | CH | CH | CH | CH | F | H |
| 1106 | CH | CH | N | CH | CH | C | N | CH | CH | CH | CH | F | H |
| 1107 | N | CH | N | CH | CH | C | N | CH | CH | CH | CH | F | H |
| 1108 | CH | CH | N | CH | CH | C | CH | N | CH | CH | CH | F | H |
| 1109 | N | CH | N | CH | CH | C | CH | N | CH | CH | CH | F | H |
| 1110 | CH | CH | N | CH | CH | C | CH | N | CH | N | CH | F | absent |
| 1111 | N | CH | N | CH | CH | C | CH | N | CH | N | CH | F | |
| 1112 | CH | CH | N | CH | CH | C | N | CH | N | CH | CH | F | absent |
| 1113 | N | CH | N | CH | CH | C | N | CH | N | CH | CH | F | |
| 1114 | CH | CH | N | CH | CH | C | CH | CH | N | CH | N | absent | H |
| 1115 | N | CH | N | CH | CH | C | CH | CH | N | CH | N | | H |
| 1116 | CH | N | CH | N | CH | C | CH | CH | CH | CH | CH | F | H |
| 1117 | N | N | CH | N | CH | C | CH | CH | CH | CH | CH | F | H |
| 1118 | CH | N | CH | N | CH | C | N | CH | CH | CH | CH | F | H |
| 1119 | N | N | CH | N | CH | C | N | CH | CH | CH | CH | F | H |
| 1120 | CH | N | CH | N | CH | C | CH | N | CH | CH | CH | F | H |
| 1121 | N | N | CH | N | CH | C | CH | N | CH | CH | CH | F | H |
| 1122 | CH | CH | N | CH | N | C | CH | CH | CH | CH | CH | F | H |
| 1123 | N | CH | N | CH | N | C | CH | CH | CH | CH | CH | F | H |
| 1124 | CH | CH | CH | N | N | C | CH | CH | CH | CH | CH | F | H |
| 1125 | N | CH | CH | N | N | C | CH | CH | CH | CH | CH | F | H |
| 1126 | CH | CH | CH | CH | N | C | CH | CH | CH | CH | CH | F | H |
| 1127 | N | CH | CH | CH | N | C | CH | CH | CH | CH | CH | F | H |
| 1128 | CH | CH | CH | CH | N | C | CH | N | CH | CH | CH | F | H |
| 1129 | N | CH | CH | CH | N | C | CH | N | CH | CH | CH | F | H |
| 1130 | CH | CH | CH | CH | CH | C | CH | CH | CH | CH | CH | OMe | OMe |
| 1131 | N | CH | CH | CH | CH | C | CH | CH | CH | CH | CH | OMe | OMe |
| 1132 | CH | CH | CH | CH | CH | C | N | CH | CH | CH | CH | OMe | OMe |
| 1133 | N | CH | CH | CH | CH | C | N | CH | CH | CH | CH | OMe | OMe |
| 1134 | CH | CH | CH | CH | CH | C | CH | N | CH | CH | CH | OMe | OMe |
| 1135 | N | CH | CH | CH | CH | C | CH | N | CH | CH | CH | OMe | OMe |
| 1136 | CH | CH | CH | CH | CH | C | N | CH | CH | CH | N | OMe | OMe |
| 1137 | N | CH | CH | CH | CH | C | N | CH | CH | CH | N | OMe | OMe |
| 1138 | CH | CH | CH | CH | CH | C | N | N | CH | CH | CH | OMe | OMe |
| 1139 | N | CH | CH | CH | CH | C | N | N | CH | CH | CH | OMe | OMe |
| 1140 | CH | CH | CH | CH | CH | C | CH | N | CH | N | CH | OMe | absent |
| 1141 | N | CH | CH | CH | CH | C | CH | N | CH | N | CH | OMe | |
| 1142 | CH | CH | CH | CH | CH | C | CH | CH | N | CH | N | absent | OMe |
| 1143 | N | CH | CH | CH | CH | C | CH | CH | N | CH | N | | OMe |
| 1144 | CH | CH | CH | CH | CH | C | CH | CH | N | CH | CH | absent | OMe |

| Comp | Z | $Y_1$ | $Y_2$ | $Y_3$ | $Y_4$ | $Y_5$ | $Y_6$ | $Y_7$ | $Y_8$ | $Y_9$ | $Y_{10}$ | $R_5$ | $R_6$ |
|---|---|---|---|---|---|---|---|---|---|---|---|---|---|
| 1145 | N | CH | CH | CH | CH | C | CH | CH | N | CH | CH | | OMe |
| 1146 | CH | N | CH | CH | CH | C | CH | CH | CH | CH | CH | OMe | OMe |
| 1147 | N | N | CH | CH | CH | C | CH | CH | CH | CH | CH | OMe | OMe |
| 1148 | CH | N | CH | CH | CH | C | N | CH | CH | CH | CH | OMe | OMe |
| 1149 | N | N | CH | CH | CH | C | N | CH | CH | CH | CH | OMe | OMe |
| 1150 | CH | N | CH | CH | CH | C | CH | N | CH | CH | CH | OMe | OMe |
| 1151 | N | N | CH | CH | CH | C | CH | N | CH | CH | CH | OMe | OMe |
| 1152 | CH | N | CH | CH | CH | C | N | CH | CH | CH | N | OMe | OMe |
| 1153 | N | N | CH | CH | CH | C | N | CH | CH | CH | N | OMe | OMe |
| 1154 | CH | N | CH | CH | CH | C | CH | CH | N | CH | N | absent | OMe |
| 1155 | N | N | CH | CH | CH | C | CH | CH | N | CH | N | | OMe |
| 1156 | CH | N | CH | CH | CH | C | N | CH | CH | CH | CH | OMe | OMe |
| 1157 | N | N | CH | CH | CH | C | N | CH | CH | CH | CH | OMe | OMe |
| 1158 | CH | N | N | CH | CH | C | CH | CH | N | CH | N | absent | OMe |
| 1159 | N | N | N | CH | CH | C | CH | CH | N | CH | N | | OMe |
| 1160 | CH | N | N | CH | CH | C | CH | CH | CH | CH | CH | OMe | OMe |
| 1161 | N | N | N | CH | CH | C | CH | CH | CH | CH | CH | OMe | OMe |
| 1162 | CH | CH | N | CH | CH | C | CH | CH | CH | CH | CH | OMe | OMe |
| 1163 | N | CH | N | CH | CH | C | CH | CH | CH | CH | CH | OMe | OMe |
| 1164 | CH | CH | N | CH | CH | C | N | CH | CH | CH | CH | OMe | OMe |
| 1165 | N | CH | N | CH | CH | C | N | CH | CH | CH | CH | OMe | OMe |
| 1166 | CH | CH | N | CH | CH | C | CH | N | CH | CH | CH | OMe | OMe |
| 1167 | N | CH | N | CH | CH | C | CH | N | CH | CH | CH | OMe | OMe |
| 1168 | CH | CH | N | CH | CH | C | CH | N | CH | N | CH | OMe | absent |
| 1169 | N | CH | N | CH | CH | C | CH | N | CH | N | CH | OMe | |
| 1170 | CH | CH | N | CH | CH | C | N | CH | CH | N | CH | OMe | OMe |
| 1171 | N | CH | N | CH | CH | C | N | CH | CH | N | CH | OMe | OMe |
| 1172 | CH | CH | N | CH | CH | C | CH | CH | N | CH | N | absent | OMe |
| 1173 | N | CH | N | CH | CH | C | CH | CH | N | CH | N | | OMe |
| 1174 | CH | CH | N | CH | CH | C | CH | CH | N | CH | CH | absent | OMe |
| 1175 | N | CH | N | CH | CH | C | CH | CH | N | CH | CH | | OMe |
| 1176 | CH | N | CH | N | CH | C | CH | CH | CH | CH | CH | OMe | OMe |
| 1177 | N | N | CH | N | CH | C | CH | CH | CH | CH | CH | OMe | OMe |
| 1178 | CH | N | CH | N | CH | C | N | CH | CH | CH | CH | OMe | OMe |
| 1179 | N | N | CH | N | CH | C | N | CH | CH | CH | CH | OMe | OMe |
| 1180 | CH | N | CH | N | CH | C | CH | N | CH | CH | CH | OMe | OMe |
| 1181 | N | N | CH | N | CH | C | CH | N | CH | CH | CH | OMe | OMe |
| 1182 | CH | CH | N | CH | N | C | CH | CH | CH | CH | CH | OMe | OMe |
| 1183 | N | CH | N | CH | N | C | CH | CH | CH | CH | CH | OMe | OMe |
| 1184 | CH | CH | CH | N | N | C | CH | CH | CH | CH | CH | OMe | OMe |
| 1185 | N | CH | CH | N | N | C | CH | CH | CH | CH | CH | OMe | OMe |
| 1186 | CH | CH | CH | CH | N | C | CH | CH | CH | CH | CH | OMe | OMe |
| 1187 | N | CH | CH | CH | N | C | CH | CH | CH | CH | CH | OMe | OMe |
| 1188 | CH | CH | CH | CH | N | C | CH | CH | N | CH | CH | absent | OMe |
| 1189 | N | CH | CH | CH | N | C | CH | CH | N | CH | CH | | OMe |

In a further embodiment, the present invention provides compounds of formula (XIII), wherein Z, $R_5$, and $R_6$ are as defined in examples 1190 to 1193:

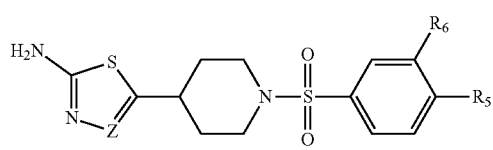

(XIII)

| Comp | Z | $R_5$ | $R_6$ |
|---|---|---|---|
| 1190 | CH | F | H |
| 1191 | N | F | H |
| 1192 | CH | OMe | OMe |
| 1193 | N | OMe | OMe |

In a further embodiment, the present invention provides compounds of formula (XIV), wherein $R_5$, and $R_6$ are as defined in examples 1194 to 1195:

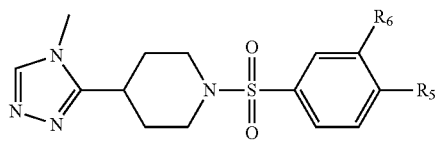

(XIV)

| Comp | $R_5$ | $R_6$ |
|---|---|---|
| 1194 | F | H |
| 1195 | OMe | OMe |

In a further embodiment, the present invention provides compounds of formula (XVa) and (XVb), wherein $Y_1$, $Y_2$, $Y_3$, $Y_4$, $Y_5$, $Y_6$, $Y_7$, $Y_8$, $Y_9$, $Y_{10}$, $R_5$, and $R_6$ are as defined in examples 1196 to 1282:

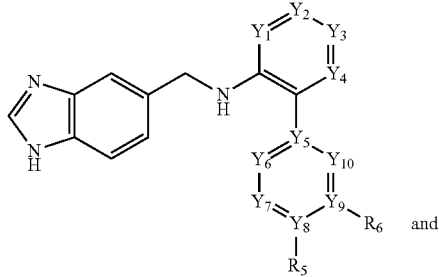

(XVa)

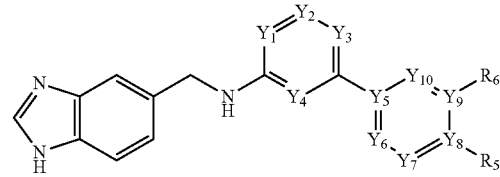

(XVb)

| Comp | Y₁ | Y₂ | Y₃ | Y₄ | Y₅ | Y₆ | Y₇ | Y₈ | Y₉ | Y₁₀ | R₅ | R₆ |
|---|---|---|---|---|---|---|---|---|---|---|---|---|
| 1196 | CH | CH | CH | CH | C | CH | CH | CH | CH | CH | H | H |
| 1197 | CH | CH | CH | CH | C | N | CH | CH | CH | CH | H | H |
| 1198 | CH | CH | CH | CH | C | CH | N | CH | CH | CH | H | H |
| 1199 | CH | CH | CH | CH | C | N | CH | CH | CH | N | H | H |
| 1200 | CH | CH | CH | CH | C | N | N | CH | CH | CH | H | H |
| 1201 | CH | CH | CH | CH | C | CH | N | CH | N | CH | H | absent |
| 1202 | CH | CH | CH | CH | C | CH | CH | N | CH | N | absent | H |
| 1203 | CH | CH | CH | CH | C | CH | CH | N | CH | CH | absent | H |
| 1204 | N | CH | CH | CH | C | CH | CH | CH | CH | CH | H | H |
| 1205 | N | CH | CH | CH | C | N | CH | CH | CH | CH | H | H |
| 1206 | N | CH | CH | CH | C | CH | N | CH | CH | CH | H | H |
| 1207 | N | CH | CH | CH | C | N | CH | CH | CH | N | H | H |
| 1208 | N | CH | CH | CH | C | CH | CH | N | CH | N | absent | H |
| 1209 | N | CH | CH | CH | C | N | CH | CH | CH | CH | H | H |
| 1210 | N | N | CH | CH | C | CH | CH | N | CH | N | absent | H |
| 1211 | N | N | CH | CH | C | CH | CH | CH | CH | CH | H | H |
| 1212 | CH | N | CH | CH | C | CH | CH | CH | CH | CH | H | H |
| 1213 | CH | N | CH | CH | C | N | CH | CH | CH | CH | H | H |
| 1214 | CH | N | CH | CH | C | CH | N | CH | CH | CH | H | H |
| 1215 | CH | N | CH | CH | C | CH | N | CH | N | CH | H | absent |
| 1216 | CH | N | CH | CH | C | N | CH | CH | N | CH | H | H |
| 1217 | CH | N | CH | CH | C | CH | CH | N | CH | N | absent | H |
| 1218 | CH | N | CH | CH | C | CH | CH | N | CH | CH | absent | H |
| 1219 | N | CH | N | CH | C | CH | CH | CH | CH | CH | H | H |
| 1220 | N | CH | N | CH | C | N | CH | CH | CH | CH | H | H |
| 1221 | N | CH | N | CH | C | CH | N | CH | CH | CH | H | H |
| 1222 | CH | N | CH | N | C | CH | CH | CH | CH | CH | H | H |
| 1223 | CH | CH | N | N | C | CH | CH | CH | CH | CH | H | H |
| 1224 | CH | CH | CH | N | C | CH | CH | CH | CH | CH | H | H |
| 1225 | CH | CH | CH | N | C | CH | CH | N | CH | CH | absent | H |
| 1226 | CH | CH | CH | CH | C | CH | CH | CH | CH | CH | F | H |
| 1227 | CH | CH | CH | CH | C | N | CH | CH | CH | CH | F | H |
| 1228 | CH | CH | CH | CH | C | CH | N | CH | CH | CH | F | H |
| 1229 | CH | CH | CH | CH | C | N | CH | CH | CH | N | F | H |
| 1230 | CH | CH | CH | CH | C | N | N | CH | CH | CH | F | H |
| 1231 | CH | CH | CH | CH | C | CH | N | CH | N | CH | F | absent |
| 1232 | CH | CH | CH | CH | C | CH | CH | N | CH | N | absent | H |
| 1233 | CH | CH | CH | CH | C | CH | CH | N | CH | CH | absent | H |
| 1234 | N | CH | CH | CH | C | CH | CH | CH | CH | CH | F | H |
| 1235 | N | CH | CH | CH | C | N | CH | CH | CH | CH | F | H |
| 1236 | N | CH | CH | CH | C | CH | N | CH | CH | CH | F | H |
| 1237 | N | CH | CH | CH | C | N | CH | CH | CH | N | F | H |
| 1238 | N | CH | CH | CH | C | CH | CH | N | CH | N | absent | H |
| 1239 | N | N | CH | CH | C | CH | CH | CH | CH | CH | F | H |
| 1240 | N | N | CH | CH | C | CH | CH | N | CH | N | absent | H |
| 1241 | CH | N | CH | CH | C | CH | CH | CH | CH | CH | F | H |
| 1242 | CH | N | CH | CH | C | N | CH | CH | CH | CH | F | H |
| 1243 | CH | N | CH | CH | C | CH | N | CH | CH | CH | F | H |
| 1244 | CH | N | CH | CH | C | CH | N | CH | N | CH | F | absent |
| 1245 | CH | N | CH | CH | C | N | CH | N | CH | CH | F | absent |
| 1246 | CH | N | CH | CH | C | CH | CH | N | CH | N | absent | H |
| 1247 | N | CH | N | CH | C | CH | CH | CH | CH | CH | F | H |
| 1248 | N | CH | N | CH | C | N | CH | CH | CH | CH | F | H |
| 1249 | N | CH | N | CH | C | CH | N | CH | CH | CH | F | H |
| 1250 | CH | N | CH | N | C | CH | CH | CH | CH | CH | F | H |
| 1251 | CH | CH | N | N | C | CH | CH | CH | CH | CH | F | H |
| 1252 | CH | CH | CH | N | C | CH | CH | CH | CH | CH | F | H |
| 1253 | CH | CH | CH | N | C | CH | CH | CH | CH | CH | F | H |
| 1254 | CH | CH | CH | CH | C | CH | CH | CH | CH | CH | OMe | OMe |
| 1255 | CH | CH | CH | CH | C | N | CH | CH | CH | CH | OMe | OMe |
| 1256 | CH | CH | CH | CH | C | CH | N | CH | CH | CH | OMe | OMe |

| Comp | Y$_1$ | Y$_2$ | Y$_3$ | Y$_4$ | Y$_5$ | Y$_6$ | Y$_7$ | Y$_8$ | Y$_9$ | Y$_{10}$ | R$_5$ | R$_6$ |
|---|---|---|---|---|---|---|---|---|---|---|---|---|
| 1257 | CH | CH | CH | CH | C | N | CH | CH | CH | N | OMe | OMe |
| 1258 | CH | CH | CH | CH | C | N | N | CH | CH | CH | OMe | OMe |
| 1259 | CH | CH | CH | CH | C | CH | N | CH | N | CH | OMe | absent |
| 1260 | CH | CH | CH | CH | C | CH | CH | N | CH | N | absent | OMe |
| 1261 | CH | CH | CH | CH | C | CH | CH | N | CH | CH | absent | OMe |
| 1262 | N | CH | CH | CH | C | CH | CH | CH | CH | CH | OMe | OMe |
| 1263 | N | CH | CH | CH | C | N | CH | CH | CH | CH | OMe | OMe |
| 1264 | N | CH | CH | CH | C | CH | N | CH | CH | CH | OMe | OMe |
| 1265 | N | CH | CH | CH | C | N | CH | CH | CH | N | OMe | OMe |
| 1266 | N | CH | CH | CH | C | CH | CH | N | CH | N | absent | OMe |
| 1267 | N | CH | CH | CH | C | N | CH | CH | CH | CH | OMe | OMe |
| 1268 | N | N | CH | CH | C | CH | CH | N | CH | N | absent | OMe |
| 1269 | N | N | CH | CH | C | CH | CH | CH | CH | CH | OMe | OMe |
| 1270 | CH | N | CH | CH | C | CH | CH | CH | CH | CH | OMe | OMe |
| 1271 | CH | N | CH | CH | C | N | CH | CH | CH | CH | OMe | OMe |
| 1272 | CH | N | CH | CH | C | CH | N | CH | CH | CH | OMe | OMe |
| 1273 | CH | N | CH | CH | C | CH | N | CH | N | CH | OMe | absent |
| 1274 | CH | N | CH | CH | C | N | CH | CH | N | CH | OMe | OMe |
| 1275 | CH | N | CH | CH | C | CH | CH | N | CH | N | absent | OMe |
| 1276 | CH | N | CH | CH | C | CH | CH | N | CH | CH | absent | OMe |
| 1277 | N | CH | N | CH | C | CH | CH | CH | CH | CH | OMe | OMe |
| 1278 | N | CH | N | CH | C | N | CH | CH | CH | CH | OMe | OMe |
| 1279 | N | CH | N | CH | C | CH | N | CH | CH | CH | OMe | OMe |
| 1280 | CH | N | CH | N | C | CH | CH | CH | CH | CH | OMe | OMe |
| 1281 | CH | CH | N | N | C | CH | CH | CH | CH | CH | OMe | OMe |
| 1282 | CH | CH | CH | N | C | CH | CH | CH | CH | CH | OMe | OMe |

In a further embodiment, the present invention provides compounds of formula (XVa) and (XVb), wherein Y$_1$, Y$_2$, Y$_3$, Y$_4$, Y$_5$, Y$_6$, Y$_7$, Y$_8$, Y$_9$, Y$_{10}$, R$_5$, and R$_6$ are as defined in examples 1310 to 1319:

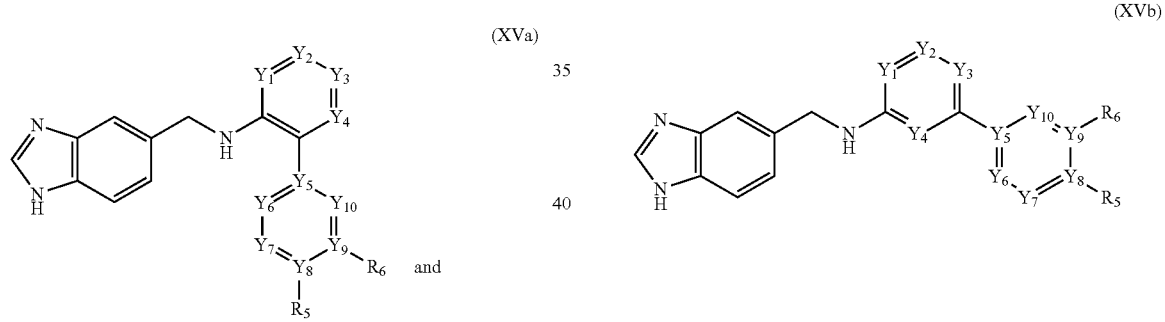

| Comp | Y$_1$ | Y$_2$ | Y$_3$ | Y$_4$ | Y$_5$ | Y$_6$ | Y$_7$ | Y$_8$ | Y$_9$ | Y$_{10}$ | R$_5$ | R$_6$ |
|---|---|---|---|---|---|---|---|---|---|---|---|---|
| 1301 | CH | CH | CH | CH | C | CH | CH | CH | CH | CH | OMe | H |
| 1302 | CH | CH | CH | N | C | CH | CH | CH | CH | CH | OMe | H |
| 1303 | N | CH | CH | CH | C | CH | CH | CH | CH | CH | OMe | H |
| 1304 | CH | CH | N | CH | C | CH | CH | CH | CH | CH | OMe | H |
| 1305 | CH | N | CH | CH | C | CH | CH | CH | CH | CH | OMe | H |
| 1306 | N | CH | N | CH | C | CH | CH | CH | CH | CH | OMe | H |
| 1307 | N | CH | CH | N | C | CH | CH | CH | CH | CH | OMe | H |
| 1308 | CH | CH | N | CH | C | CH | CH | CH | CH | CH | OMe | OMe |
| 1309 | N | CH | CH | N | C | CH | CH | CH | CH | CH | OMe | OMe |
| 1310 | N | CH | CH | N | C | CH | CH | CH | CH | CH | F | H |
| 1311 | CH | CH | CH | CH | C | CH | CH | CH | CH | CH | O-phenyl | H |
| 1312 | CH | CH | CH | CH | C | CH | CH | CH | CH | CH | O-cyclohexyl | H |
| 1313 | CH | CH | CH | CH | C | CH | CH | CH | CH | CH | propyloxy | H |
| 1314 | CH | CH | CH | CH | C | CH | CH | CH | CH | CH | propan-2-yloxy | H |
| 1315 | CH | CH | CH | CH subst. with Me | C | CH | CH | CH | CH | CH | OMe | H |
| 1316 | CH | CH | CH | CH subst. with Me | C | CH | CH | CH | CH | CH | OMe | OMe |
| 1317 | CH | CH | CH | CH subst. with F | C | CH | CH | CH | CH | CH | Cl | OMe |
| 1318 | CH | CH | CH | CH subst. with F | C | CH | CH | CH | CH | CH | OMe | OMe |

-continued

| Comp | Y₁ | Y₂ | Y₃ | Y₄ | Y₅ | Y₆ | Y₇ | Y₈ | Y₉ | Y₁₀ | R₅ | R₆ |
|---|---|---|---|---|---|---|---|---|---|---|---|---|
| 1319 | CH | CH | CH | CH subst. with F | C | CH | CH | CH | CH | CH | F | H |

In a further embodiment, the present invention provides compounds of formula (XVI), wherein $R_5$, and $R_6$ are as defined in examples 1283 to 1284:

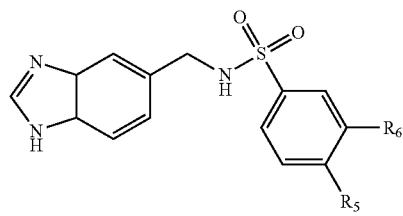

(XVI)

| Comp | R5 | R6 |
|---|---|---|
| 1283 | F | H |
| 1284 | OMe | OMe |

In a further embodiment, the present invention provides compounds of formula (XVII), wherein $R_2$, $R_5$, and $R_6$ are as defined in examples 1285 to 1288:

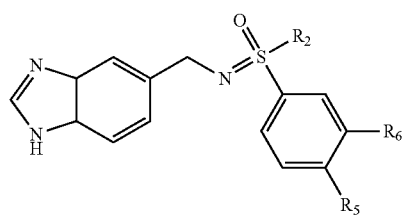

(XVII)

| Comp | R2 | R5 | R6 |
|---|---|---|---|
| 1285 | Me | F | H |
| 1286 | Me | OMe | OMe |
| 1287 | Cyclopropy | F | H |
| 1288 | Cyclopropy | OMe | OMe |

In a further embodiment, the present invention provides compounds of formula (XVIII), wherein $X_1$, n, $R_5$, and $R_6$ are as defined in examples 1320 to 1323:

(XVIII)

| Comp | X₁ | n | R5 | R6 |
|---|---|---|---|---|
| 1320 | CH₂ | 1 | F | H |
| 1321 | S | 1 | F | H |
| 1322 | CH₂ | 1 | OMe | OMe |
| 1323 | S | 1 | OMe | OMe |

In a preferred embodiment, the present invention provides compounds of formula (I), or a pharmaceutically acceptable salt, solvate or polymorph thereof, including all tautomers and stereoisomers thereof, wherein said compound of formula (I) is selected from:

| Example Compound | Synthesis Example | Compound Name | Structure | Formula | Mol Weight | hQC K$_i$ [μM] pH6 | hQC K$_i$ [μM] pH8 |
|---|---|---|---|---|---|---|---|
| 93 | A2 | 5-[3-({4'-fluoro-[1,1'-biphenyl]-2-yl}amino)propyl]-1,3,4-thiadiazol-2-amine | 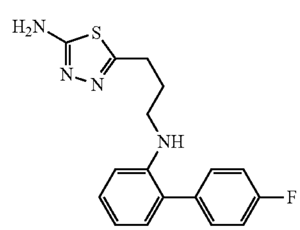 [SMILES: Nc1nnc(CCCNc2ccccc2-c2ccc(F)cc2)s1] | C₁₇H₁₇FN₄S | 328.40 | 2.6 | 1102 |

-continued

| Example Compound | Synthesis Example | Compound Name | Structure | Formula | Mol Weight | hQC K$_i$ [μM] pH6 | hQC K$_i$ [μM] pH8 |
|---|---|---|---|---|---|---|---|
| 94 | A3 | 5-{[2-({4'-fluoro-[1,1'-biphenyl]-2-yl}amino)ethyl]sulfanyl}-1,3,4-thiadiazol-2-amine | 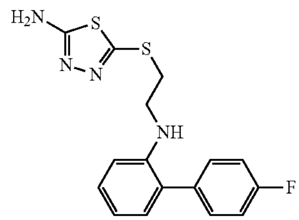 [SMILES: Nc1nnc(SCCNc2ccccc2-c2ccc(F)cc2)s1] | C$_{16}$H$_{15}$FN$_4$S$_2$ | 346.44 | 2.97 | 11.51 |
| 178 | A4 | 5-{[2-({3',4'-dimethoxy-[1,1'-biphenyl]-2-yl}amino)ethyl]sulfanyl}-1,3,4-thiadiazol-2-amine | 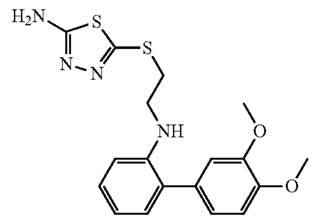 [SMILES: COc1ccc(-c2ccccc2NCCSc2nnc(N)s2)cc1OC] | C$_{18}$H$_{20}$N$_4$O$_2$S$_2$ | 388.50 | 1.10 | 0.97 |
| 328 | B1 | 4'-fluoro-N-[3-(4-methyl-4H-1,2,4-triazol-3-yl)propyl]-[1,1'-biphenyl]-2-amine | 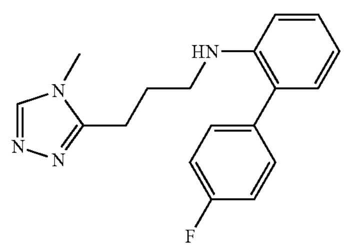 [SMILES: Cn1cnnc1CCCNc1ccccc1-c1ccc(F)cc1] | C$_{18}$H$_{19}$FN$_4$ | 310.36 | 1.97 | 2.86 |
| 384 | B3 | 3',4'-dimethoxy-N-[3-(4-methyl-4H-1,2,4-triazol-3-yl)propyl]-[1,1'-biphenyl]-2-amine | 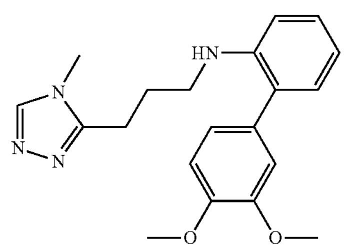 [SMILES: COc1ccc(-c2ccccc2NCCCc2nncn2C)cc1OC] | C$_{20}$H$_{24}$N$_4$O$_2$ | 352.43 | 0.13 | 0.26 |
| 505 | C2 | 5-[4-({4'-fluoro-[1,1-biphenyl]-2-yl}amino)phenyl]-1,3,4-thiadiazol-2-amine | 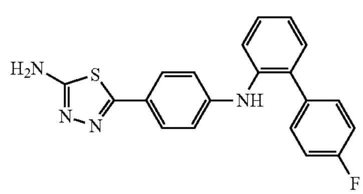 [SMILES: Nc1nnc(-c2ccc(Nc3ccccc3-c3ccc(F)cc3)cc2)s1] | C$_{20}$H$_{15}$FN$_4$S | 362.42 | 1.52 | 1.81 |
| 561 | C3 | 5-(4-{[2-(3,4-dimethoxyphenyl)phenyl]amino}phenyl)-1,3,4-thiadiazol-2-amine | 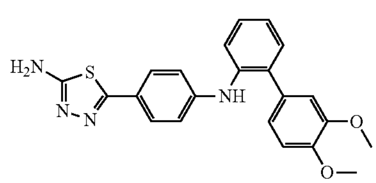 [SMILES: COc1ccc(-c2ccccc2Nc2ccc(-c3nnc(N)s3)cc2)cc1OC] | C$_{22}$H$_{20}$N$_4$O$_2$S | 404.48 | 0.42 | 1.09 |
| 1289 | C4 | 5-(4-{[2-(4-methoxyphenyl)phenyl]amino}phenyl)-1,3,4-thiadiazol-2-amine | 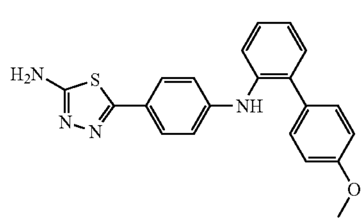 [SMILES: COc1ccc(-c2ccccc2Nc2ccc(-c3nnc(N)s3)cc2)cc1] | C$_{21}$H$_{18}$N$_4$OS | 374.46 | 1.87 | 1.48 |

-continued

| Example Compound | Synthesis Example | Compound Name | Structure | Formula | Mol Weight | hQC $K_i$ [μM] pH6 | hQC $K_i$ [μM] pH8 |
|---|---|---|---|---|---|---|---|
| 1290 | C5 | N-[4-(5-amino-1,3,4-thiadiazol-2-yl)phenyl]-3-(4-methoxyphenyl)pyridin-2-amine | 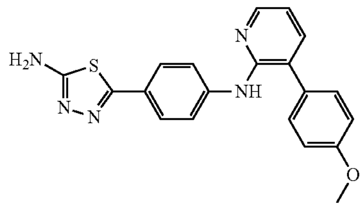 [SMILES: COc1ccc(-c2cccnc2Nc2ccc(-c3nnc(N)s3)cc2)cc1] | $C_{20}H_{17}N_5OS$ | 375.44 | 4.17 | 4.70 |
| 1291 | C6 | N-[4-(5-amino-1,3,4-thiadiazol-2-yl)phenyl]-3-(4-methoxyphenyl)pyridin-4-amine | 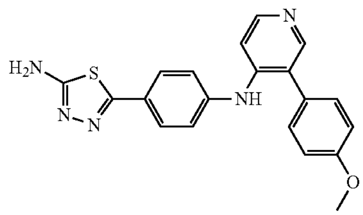 [SMILES: COc1ccc(-c2cnccc2Nc2ccc(-c3nnc(N)s3)cc2)cc1] | $C_{20}H_{17}N_5OS$ | 375.44 | 7.16 | 4.22 |
| 1292 | C7 | N-[4-(5-amino-1,3,4-thiadiazol-2-yl)phenyl]-3-(3,4-dimethoxyphenyl)pyridin-4-amine | 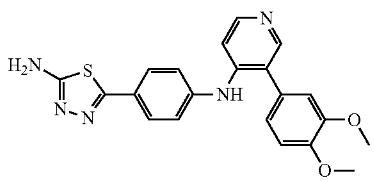 [SMILES: COc1ccc(-c2cnccc2Nc2ccc(-c3nnc(N)s3)cc2)cc1OC] | $C_{21}H_{19}N_5O_2S$ | 405.47 | 54.69 | 7.46 |
| 521 | C8 | N-[4-(5-amino-1,3,4-thiadiazol-2-yl)phenyl]-3-(4-fluorophenyl)pyridin-2-amine | 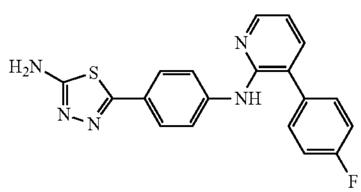 [SMILES: Nc1nnc(-c2ccc(Nc3ncccc3-c3ccc(F)cc3)cc2)s1] | $C_{19}H_{14}FN_5S$ | 363.41 | 2.69 | 4.27 |
| 1293 | C9 | N-[4-(5-amino-1,3,4-thiadiazol-2-yl)phenyl]-3-(4-fluorophenyl)pyrazin-2-amine | 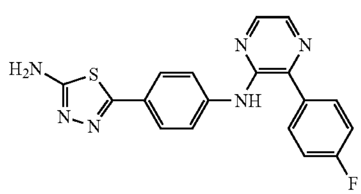 [SMILES: Nc1nnc(-c2ccc(Nc3nccnc3-c3ccc(F)cc3)cc2)s1] | $C_{18}H_{13}FN_6S$ | 364.39 | 1.66 | 6.89 |
| 1294 | C10 | 5-(4-{[2-(4-phenoxyphenyl)phenyl]amino}phenyl)-1,3,4-thiadiazol-2-amine | 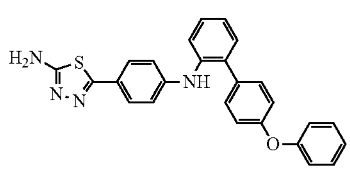 [SMILES: Nc1nnc(-c2ccc(Nc3ccccc3-c3ccc(Oc4ccccc4)cc3)cc2)s1] | $C_{26}H_{20}N_4OS$ | 436.52 | 4.37 | 2.23 |
| 1295 | C11 | 5-(4-{[2-(4-propoxyphenyl)phenyl]amino}phenyl)-1,3,4-thiadiazol-2-amine | 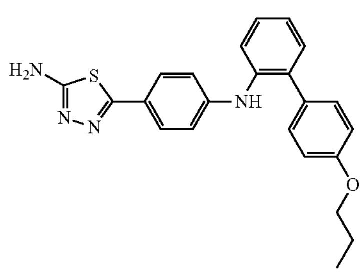 [SMILES: CCCOc1ccc(-c2ccccc2Nc2ccc(-c3nnc(N)s3)cc2)cc1] | $C_{23}H_{22}N_4OS$ | 402.51 | 2.15 | 2.36 |

-continued

| Example Compound | Synthesis Example | Compound Name | Structure | Formula | Mol Weight | hQC $K_i$ [μM] pH6 | hQC $K_i$ [μM] pH8 |
|---|---|---|---|---|---|---|---|
| 1296 | C12 | 5-[4-({2-[4-(propan-2-yloxy)phenyl]phenyl}amino)phenyl]-1,3,4-thiadiazol-2-amine | 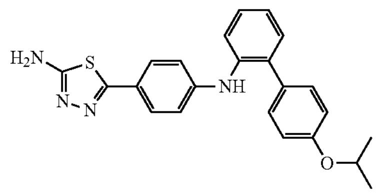 [SMILES: CC(C)Oc1ccc(-c2ccccc2Nc2ccc(-c3nnc(N)s3)cc2)cc1] | $C_{23}H_{22}N_4OS$ | 402.51 | 1.51 | 3.27 |
| 826 | D1 | 4'-fluoro-N-[4-(4-methyl-4H-1,2,4-triazol-3-yl)phenyl]-[1,1'-biphenyl]-2-amine | 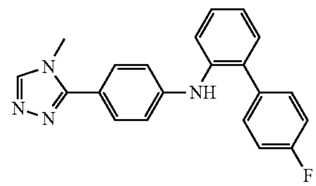 [SMILES: Cn1cnnc1-c1ccc(Nc2ccccc2-c2ccc(F)cc2)cc1] | $C_{21}H_{17}FN_4$ | 344.38 | 1.44 | 1.74 |
| 854 | D2 | 3',4'-dimethoxy-N-[4-(4-methyl-4H-1,2,4-triazol-3-yl)phenyl]-[1,1'-biphenyl]-2-amine | 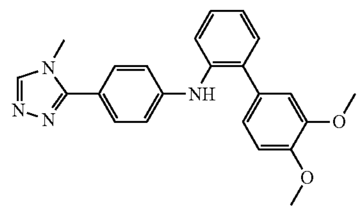 [SMILES: COc1ccc(-c2ccccc2Nc2ccc(-c3nncn3C)cc2)cc1OC] | $C_{23}H_{22}N_4O_2$ | 386.45 | 0.44 | 1.48 |
| 1297 | D3 | N-[2-(4-methoxyphenyl)phenyl]-4-(4-methyl-4H-1,2,4-triazol-3-yl)aniline | 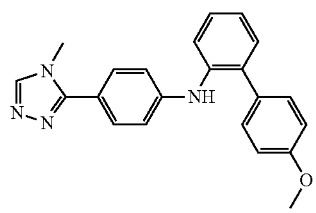 [SMILES: COc1ccc(-c2ccccc2Nc2ccc(-c3nncn3C)cc2)cc1] | $C_{22}H_{20}N_4O$ | 356.42 | 0.99 | 1.69 |
| 1298 | D4 | 2-(4-methoxyphenyl)-N-[4-(4-methyl-4H-1,2,4-triazol-3-yl)phenyl]pyridin-3-amine | 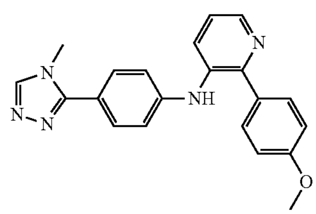 [SMILES: COc1ccc(-c2ncccc2Nc2ccc(-c3nncn3C)cc2)cc1] | $C_{21}H_{19}N_5O$ | 357.40 | 1.70 | 3.37 |
| 852 | D5 | 2-(4-fluorophenyl)-N-[4-(4-methyl-4H-1,2,4-triazol-3-yl)phenyl]pyridin-3-amine | 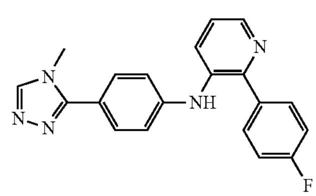 [SMILES: Cn1cnnc1-c1ccc(Nc2cccnc2-c2ccc(F)cc2)cc1] | $C_{20}H_{16}FN_5$ | 345.37 | 2.69 | 5.05 |
| 1299 | D6 | 4-(4-methyl-4H-1,2,4-triazol-3-yl)-N-[2-(4-phenoxyphenyl)phenyl]aniline | 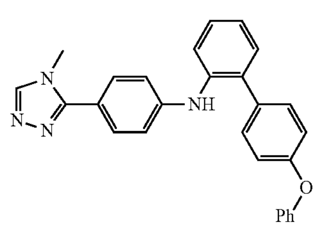 [SMILES: Cn1cnnc1-c1ccc(Nc2ccccc2-c2ccc(Oc3ccccc3)cc2)cc1] | $C_{27}H_{22}N_4O$ | 418.48 | 1.33 | 1.81 |

-continued

| Example Compound | Synthesis Example | Compound Name | Structure | Formula | Mol Weight | hQC $K_i$ [μM] pH6 | hQC $K_i$ [μM] pH8 |
|---|---|---|---|---|---|---|---|
| 1300 | D7 | 3-(3,4-dimethoxyphenyl)-N-[4-(4-methyl-4H-1,2,4-triazol-3-yl)phenyl]pyridin-4-amine | 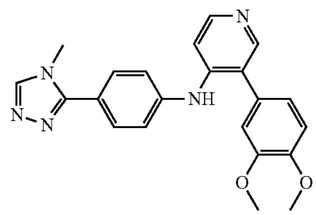 [SMILES: COc1ccc(-c2cnccc2Nc2ccc(-c3nncn3C)cc2)cc1OC] | $C_{22}H_{21}N_5O_2$ | 387.43 | Not determined | 10.07 |
| 973 | E2 | N-[3-(5-amino-1,3,4-thiadiazol-2-yl)propyl]-4-fluorobenzene-1-sulfonamide | 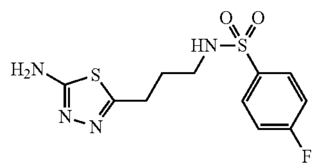 [SMILES: Nc1nnc(CCCNS(=O)(=O)c2ccc(F)cc2)s1] | $C_{11}H_{13}FN_4O_2S_2$ | 316.37 | 18.08 | 9.38 |
| 974 | E3 | N-{2-[(5-amino-1,3,4-thiadiazol-2-yl)sulfanyl]ethyl}-4-fluorobenzene-1-sulfonamide | 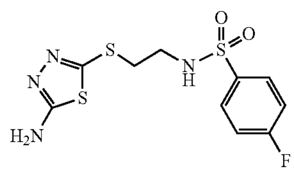 [SMILES: Nc1nnc(SCCNS(=O)(=O)c2ccc(F)cc2)s1] | $C_{10}H_{11}FN_4O_2S_3$ | 334.41 | 19.91 | 26.48 |
| 979 | F2 | 5-(3-{[(4-fluorophenyl)(methyl)oxo-λω-sulfanylidene]amino}propyl)-1,3,4-thiadiazol-2-amine | 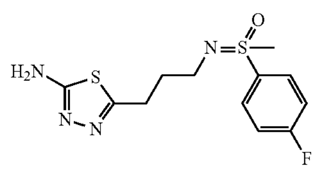 [SMILES: CS(=O)(=NCCCc1nnc(N)s1)c1ccc(F)cc1] | $C_{12}H_{15}FN_4OS_2$ | 314.40 | 11.41 | 11.70 |
| 990 | G1 | 4-fluoro-N-[3-(4-methyl-4H-1,2,4-triazol-3-yl)propyl]benzene-1-sulfonamide | 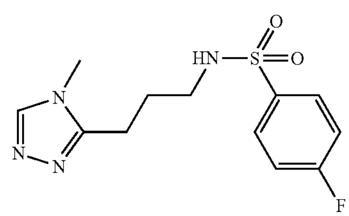 [SMILES: Cn1cnnc1CCCNS(=O)(=O)c1ccc(F)cc1] | $C_{12}H_{15}FN_4O_2S$ | 298.33 | — | — |
| 991 | G2 | 4-fluoro-N-{2-[(4-methyl-4H-1,2,4-triazol-3-yl)sulfanyl]ethyl}benzene-1-sulfonamide | 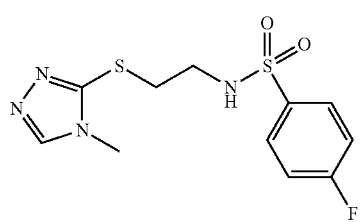 [SMILES: Cn1cnnc1SCCNS(=O)(=O)c1ccc(F)cc1] | $C_{11}H_{13}FN_4O_2S_2$ | 316.37 | 8.84 | 11.49 |
| 1332 | G5 | [(3,4-dimethoxyphenyl)sulfamoyl]({2-[(4-methyl-4H-1,2,4-triazol-3-yl)sulfanyl]ethyl})amine | 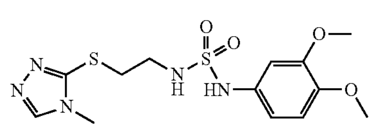 [SMILES: COc1ccc(NS(=O)(=O)NCCSc2nncn2C)cc1OC] | $C_{13}H_{19}N_5O_4S_2$ | 373.45 | 13.63 | 11.76 |
| 1002 | I1 | N-[4-(2-amino-1,3-thiazol-5-yl)phenyl]-4-fluorobenzene-1-sulfonamide | 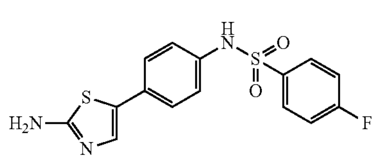 [SMILES: Nc1ncc(-c2ccc(NS(=O)(=O)c3ccc(F)cc3)cc2)s1] | $C_{15}H_{12}FN_3O_2S_2$ | 349.40 | 2.93 | 2.64 |

-continued

| Example Compound | Synthesis Example | Compound Name | Structure | Formula | Mol Weight | hQC $K_i$ [μM] pH6 | hQC $K_i$ [μM] pH8 |
|---|---|---|---|---|---|---|---|
| 1003 | I2 | N-[4-(2-amino-1,3-thiazol-5-yl)phenyl]-3,4-dimethoxybenzene-1-sulfonamide | 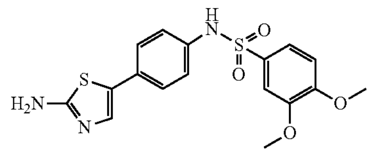 [SMILES: COc1ccc(S(=O)(=O)Nc2ccc(-c3cnc(N)s3)cc2)cc1OC] | $C_{17}H_{17}N_3O_4S_2$ | 391.46 | 0.20 | 0.34 |
| 1075 | L2 | 5-(1-{4'-fluoro-[1,1'-biphenyl]-2-yl}piperidin-4-yl)-1,3,4-thiadiazol-2-amine | 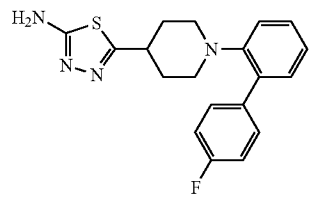 [SMILES: Nc1nnc(C2CCN(c3ccccc3-c3ccc(F)cc3)CC2)s1] | $C_{19}H_{19}FN_4S$ | 354.44 | 0.09 | 0.248 |
| 1190 | M1 | 5-[1-(4-fluorobenzenesulfonyl)piperidin-4-yl]-1,3-thiazol-amine | 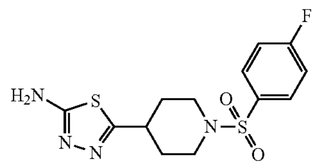 [SMILES: Nc1nnc(C2CCN(S(=O)(=O)c3ccc(F)cc3)CC2)s1] | $C_{14}H_{16}FN_3O_2S_2$ | 341.42 | 1.32 | 1.70 |
| 1191 | M2 | 5-[1-(4-fluorobenzenesulfonyl)piperidin-4-yl]-1,3,4-thiadiazol-2-amine | 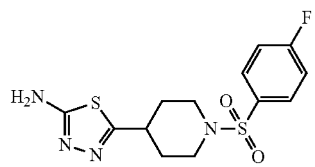 [SMILES: Nc1nnc(C2CCN(S(=O)(=O)c3ccc(F)cc3)CC2)s1] | $C_{13}H_{15}FN_4O_2S_2$ | 342.41 | 1.18 | 1.60 |
| 1194 | N1 | 1-(4-fluorobenzenesulfonyl)-4-(4-methyl-4H-1,2,4-triazol-3-yl)piperidine | 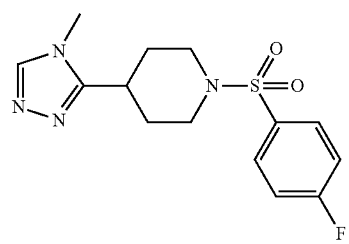 [SMILES: Cn1cnnc1C1CCN(S(=O)(=O)c2ccc(F)cc2)CC1] | $C_{14}H_{17}FN_4O_2S$ | 324.37 | 3.05 | 3.30 |
| 1226 | O1 | N-[(1H-1,3-benzodiazol-5-yl)methyl]-4'-fluoro-[1,1'-biphenyl]-2-amine | 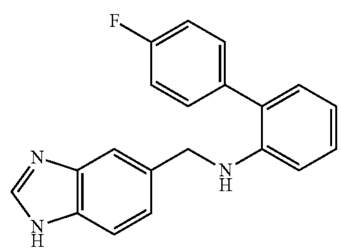 [SMILES: Fc1ccc(-c2ccccc2NCc2ccc3[nH]cnc3c2)cc1] | $C_{20}H_{16}FN_3$ | 317.35 | 5.91 | 5.29 |
| 1254 | O2 | N-[(1H-1,3-benzodiazol-5-yl)methyl]-3',4'-dimethoxy-[1,1'-biphenyl]-2-amine | 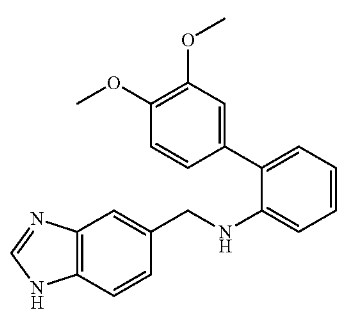 [SMILES: COc1ccc(-c2ccccc2NCc2ccc3[nH]cnc3c2)cc1OC] | $C_{22}H_{21}N_3O_2$ | 359.42 | 0.12 | 0.27 |

-continued

| Example Compound | Synthesis Example | Compound Name | Structure | Formula | Mol Weight | hQC $K_i$ [μM] pH6 | hQC $K_i$ [μM] pH8 |
|---|---|---|---|---|---|---|---|
| 1301 | O3 | N-(1H-1,3-benzodiazol-5-ylmethyl)-2-(4-methoxyphenyl)amine | 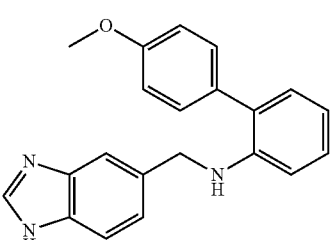 | $C_{21}H_{19}N_3O$ | 329.39 | 1.44 | 1.65 |
| 1302 | O4 | N-(1H-1,3-benzodiazol-5-ylmethyl)-2-(4-methoxyphenyl)pyridin-3-amine | 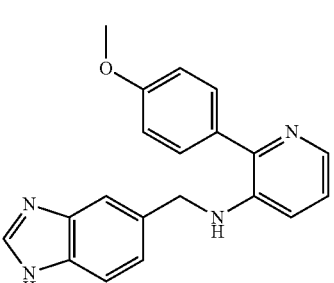 | $C_{20}H_{18}N_4O$ | 330.38 | 9.52 | 2.96 |
| 1303 | O5 | N-(1H-1,3-benzodiazol-5-ylmethyl)-3-(4-methoxyphenyl)pyridin-2-amine | 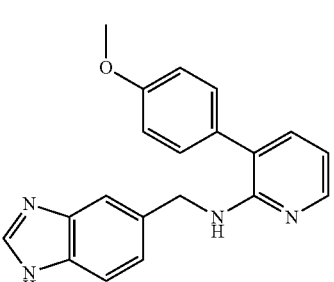 | $C_{20}H_{18}N_4O$ | 330.38 | 2.74 | 2.41 |
| 1304 | O6 | N-(1H-1,3-benzodiazol-5-ylmethyl)-3-(4-methoxyphenyl)pyridin-4-amine | 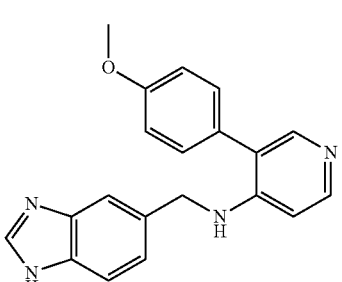 | $C_{20}H_{18}N_4O$ | 330.38 | 15.05 | 10.85 |
| 1305 | O7 | N-(1H-1,3-benzodiazol-5-ylmethyl)-4-(4-methoxyphenyl)pyridin-3-amine | 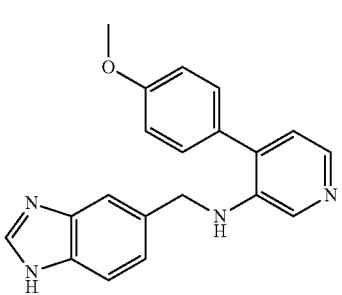 [SMILES: COc1ccc(-c2ccncc2NCc2ccc3[nH]cnc3c2)cc1] | $C_{20}H_{18}N_4O$ | 330.38 | 11.14 | 4.24 |

-continued

| Example Compound | Synthesis Example | Compound Name | Structure | Formula | Mol Weight | hQC $K_i$ [μM] pH6 | hQC $K_i$ [μM] pH8 |
|---|---|---|---|---|---|---|---|
| 1306 | O8 | N-(1H-1,3-benzodiazol-5-ylmethyl)-5-(4-methoxyphenyl)pyrimidin-4-amine | 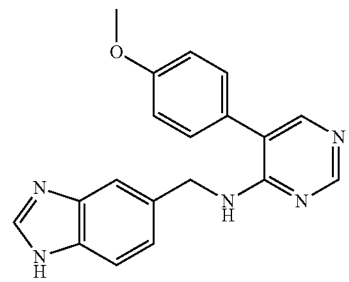 [SMILES: COc1ccc(-c2cncnc2NCc2ccc3[nH]cnc3c2)cc1] | $C_{19}H_{17}N_5O$ | 331.37 | Not determined | 18.31 |
| 1307 | O9 | N-(1H-1,3-benzodiazol-5-ylmethyl)-3-(4-methoxyphenyl)pyrazin-2-amine | 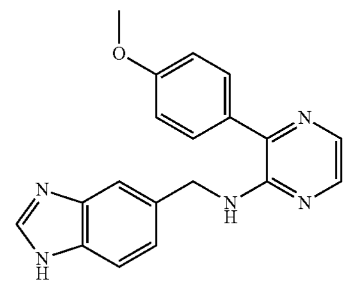 [SMILES: COc1ccc(-c2nccnc2NCc2ccc3[nH]cnc3c2)cc1] | $C_{19}H_{17}N_5O$ | 331.37 | 1.90 | 2.21 |
| 1308 | O10 | N-(1H-1,3-benzodiazol-5-ylmethyl)-3-(3,4-dimethoxyphenyl)pyridin-4-amine | 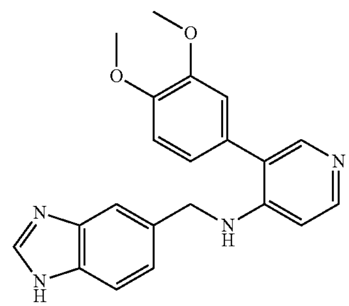 [SMILES: COc1ccc(-c2cnccc2NCc2ccc3[nH]cnc3c2)cc1OC] | $C_{21}H_{20}N_4O_2$ | 360.40 | 1.63 | 0.88 |
| 1262 | O11 | N-(1H-1,3-benzodiazol-5-ylmethyl)-3-(3,4-dimethoxyphenyl)pyridin-2-amine | 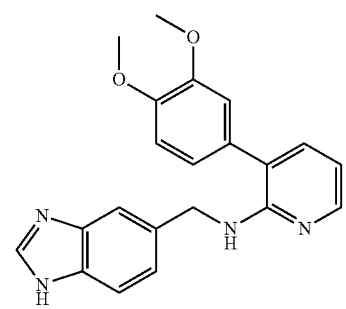 [SMILES: COc1ccc(-c2cccnc2NCc2ccc3[nH]cnc3c2)cc1OC] | $C_{21}H_{20}N_4O_2$ | 360.40 | 0.10 | 0.23 |
| 1309 | O12 | N-(1H-1,3-benzodiazol-5-ylmethyl)-3-(3,4-dimethoxyphenyl)pyrazin-2-amine | 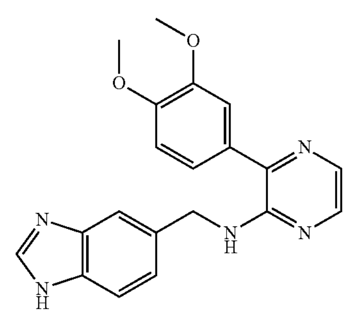 [SMILES: COc1ccc(-c2nccnc2NCc2ccc3[nH]cnc3c2)cc1OC] | $C_{20}H_{19}N_5O_2$ | 361.39 | 0.13 | 0.42 |

-continued

| Example Compound | Synthesis Example | Compound Name | Structure | Formula | Mol Weight | hQC $K_i$ [μM] pH6 | hQC $K_i$ [μM] pH8 |
|---|---|---|---|---|---|---|---|
| 1252 | O13 | N-(1H-1,3-benzodiazol-5-ylmethyl)-2-(4-fluorophenyl)pyridin-3-amine | 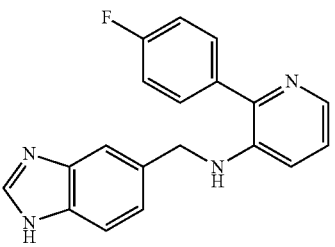 [SMILES: Fc1ccc(-c2ncccc2NCc2ccc3[nH]cnc3c2)cc1] | $C_{19}H_{15}FN_4$ | 318.34 | 145.42 | 21.96 |
| 1234 | O14 | N-(1H-1,3-benzodiazol-5-ylmethyl)-3-(4-fluorophenyl)pyridin-2-amine | 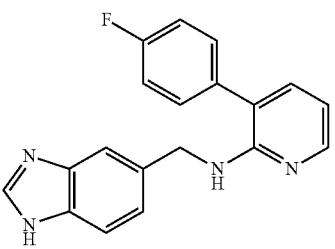 | $C_{19}H_{15}FN_4$ | 318.34 | 58.79 | 12.28 |
| 1310 | O15 | N-(1H-1,3-benzodiazol-5-ylmethyl)-3-(4-fluorophenyl)pyrazin-2-amine | 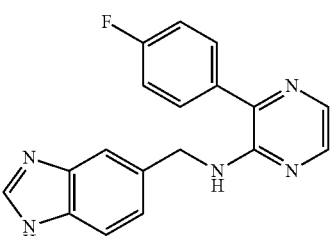 | $C_{18}H_{14}FN_5$ | 319.33 | 10.52 | 11.74 |
| 1311 | O16 | N-(1H-1,3-benzodiazol-5-ylmethyl)-2-(4-phenoxyphenyl)aniline | 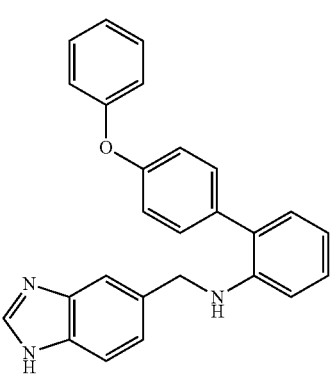 [SMILES: c1ccc(Oc2ccc(-c3ccccc3NCc3ccc4[nH]cnc4c3)cc2)cc1] | $C_{26}H_{21}N_3O$ | 391.46 | 4.34 | 2.11 |
| 1312 | O17 | N-(1H-1,3-benzodiazol-5-ylmethyl)-2-[4-(cyclohexyloxy)phenyl]aniline | 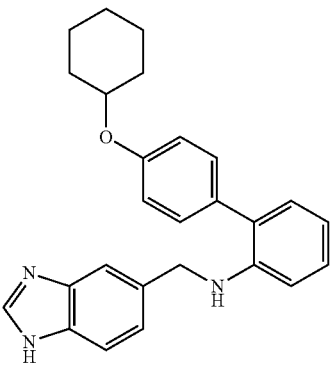 [SMILES: c1ccc(-c2ccc(OC3CCCCC3)cc2)c(NCc2ccc3[nH]cnc3c2)c1] | $C_{26}H_{27}N_3O$ | 397.51 | 2.03 | 4.17 |

-continued

| Example Compound | Synthesis Example | Compound Name | Structure | Formula | Mol Weight | hQC $K_i$ [μM] pH6 | hQC $K_i$ [μM] pH8 |
|---|---|---|---|---|---|---|---|
| 1313 | O18 | N-(1H-1,3-benzodiazol-5-ylmethyl)-2-(4-propoxyphenyl)aniline | 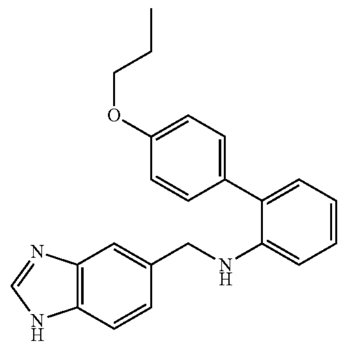 [SMILES: CCCOc1ccc(-c2ccccc2NCc2ccc3[nH]cnc3c2)cc1] | $C_{23}H_{23}N_3O$ | 357.44 | 3.59 | 2.64 |
| 1314 | O19 | N-(1H-1,3-benzodiazol-5-ylmethyl)-2-[4-(propan-2-yloxy)phenyl]aniline | 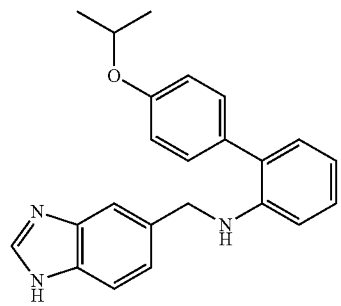 [SMILES: CC(C)Oc1ccc(-c2ccccc2NCc2ccc3[nH]cnc3c2)cc1] | $C_{23}H_{23}N_3O$ | 357.44 | 1.53 | 3.39 |
| 1315 | O20 | N-(1H-1,3-benzodiazol-5-ylmethyl)-2-(4-methoxyphenyl)-3-methylaniline | 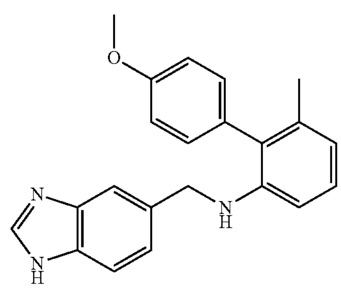 [SMILES: COc1ccc(-c2c(C)cccc2NCc2ccc3[nH]cnc3c2)cc1] | C22H21N3O | 343.42 | 2.38 | 1.64 |
| 1316 | O21 | N-(1H-1,3-benzodiazol-5-ylmethyl)-2-(3,4-dimethoxyphenyl)-3-methylaniline | 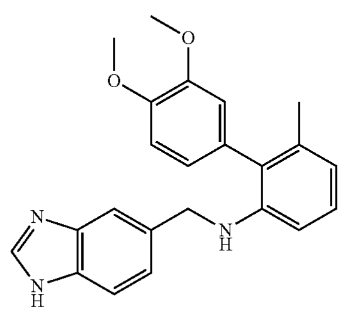 [SMILES: COc1ccc(-c2c(C)cccc2NCc2ccc3[nH]cnc3c2)cc1OC] | C23H23N3O2: | 373.45 | 0.43 | 0.42 |
| 1317 | O22 | N-(1H-1,3-benzodiazol-5-ylmethyl)-2-(4-chlorophenyl)-3-fluoroaniline | 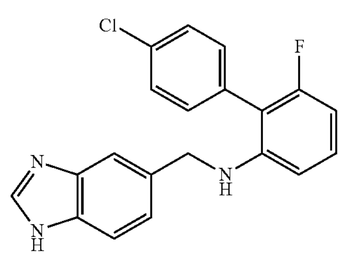 [SMILES: Fc1cccc(NCc2ccc3[nH]cnc3c2)c1-c1ccc(Cl)cc1] | C20H15ClFN3 | 351.8 | 4.89 | 6.83 |

| Example Compound | Synthesis Example | Compound Name | Structure | Formula | Mol Weight | hQC $K_i$ [μM] pH6 | hQC $K_i$ [μM] pH8 |
|---|---|---|---|---|---|---|---|
| 1318 | O23 | N-(1H-1,3-benzodiazol-5-ylmethyl)-2-(3,4-dimethoxyphenyl)-3-fluoroaniline | 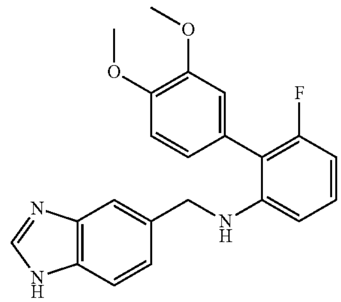 [SMILES: COc1ccc(-c2c(F)cccc2NCc2ccc3[nH]cnc3c2)cc1OC] | C22H20FN3O2 | 377.41 | 0.055 | 0.10 |
| 1319 | O24 | N-(1H-1,3-benzodiazol-5-ylmethyl)-3-fluoro-2-(4-fluoropheny)aniline | 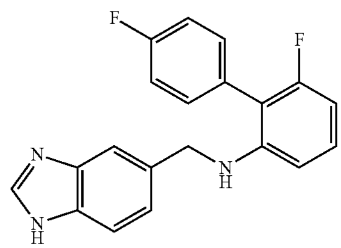 [SMILES: Fc1ccc(-c2c(F)cccc2NCc2ccc3[nH]cnc3c2)cc1] | C20H15F2N3 | 335.35 | 5.81 | 9.41 |
| 1283 | P1 | N-[(1H-1,3-benzodiazol-5-yl)methyl]-4-fluorobenzene-1-sulfonamide | 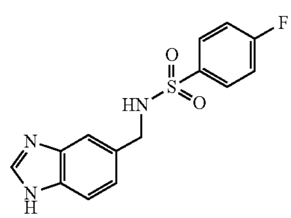 [SMILES: O=S(=O)(NCc1ccc2[nH]cnc2c1)c1ccc(F)cc1] | $C_{14}H_{12}FN_3O_2S$ | 305.32 | 38.34 | 24.74 |
| 1285 | Q1 | [(1H-1,3-benzodiazol-5-yl)methyl][(4-fluorophenyl)(methyl)oxo-λω-sulfanylidene]amine | 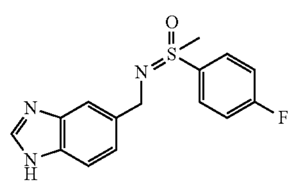 [SMILES: CS(=O)(=NCc1ccc2[nH]cnc2c1)c1ccc(F)cc1] | $C_{15}H_{14}FN_3OS$ | 303.35 | 8.05 | 5.18 |

SYNTHESIS OF THE EXAMPLES

Synthesis Method A

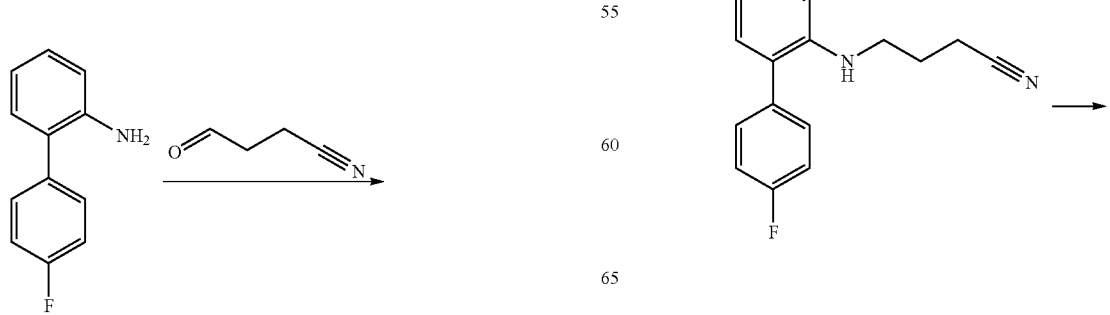

-continued

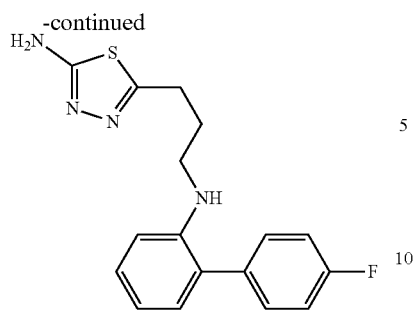

4-({4'-fluoro-[1,1'-biphenyl]-2-yl}amino)butanenitrile 4'-fluoro-[1,1'-biphenyl]-2-amine (0.5 g, 2.7 mmol), sodium cyanoborohydride (0.25 g, 4.0 mmol) and 4-oxobutanenitrile (0.44 g, 5.3 mmol) were dissolved in dry MeOH (15 mL) and acetic acid was added (0.5 mL). Reaction was stirred over 2 h until full consumption of amine was observed via UPLC analysis. After this time reaction mixture was diluted with saturated sodium bicarbonate solution (40 mL) and extracted with ethyl acetate (3×20 mL). Combined organic layers were dried over sodium sulfate, filtered and evaporated and purified via column chromatography using ethyl acetate in hexanes 10-20% as eluent to give pure title compound (0.17 g, 12%).

5-[3-({4'-fluoro-[1,1'-biphenyl]-2-yl}amino)propyl]-1,3,4-thiadiazol-2-amine (A2) 4-({4'-fluoro-[1,1'-biphenyl]-2-yl}amino)butanenitrile (0.16 g, 0.6 mmol) and tiosemicarbazide (0.06 g, 0.7 mmol) were dissolved in trifluoroacetic acid (1.3 mL). Reaction was monitored via UPLC analysis. After completion of the reaction, solvent was removed in vacuo and crude material was purified via column chromatography using MeOH in DCM 0-2% as eluent to give pure title compound (70 mg, 33%). LCMS-Method 10 (200 nm); RT=5.81 min, 95.2% purity, [M+1]=329.2, $^1$H NMR (300 MHz, DMSO-$d_6$) δ 7.46-7.36 (m, 2H), 7.32-7.23 (m, 2H), 7.20-7.11 (m, 1H), 7.05-6.89 (m, 3H), 6.76-6.55 (m, 2H), 4.61 (t, J=5.9 Hz, 1H), 3.10 (q, J=6.6 Hz, 2H), 2.82 (t, J=7.5 Hz, 2H), 1.85 (p, J=7.2 Hz, 2H).

Synthesis Method B

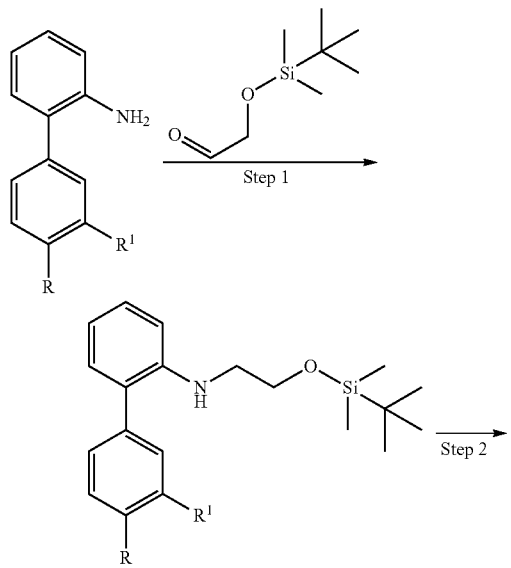

-continued

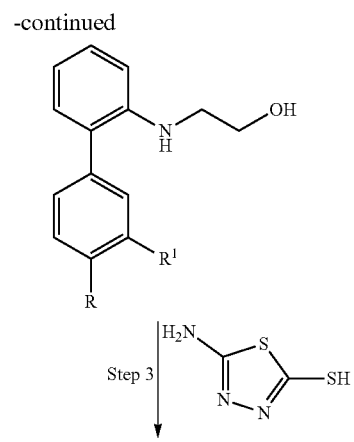

Step 3

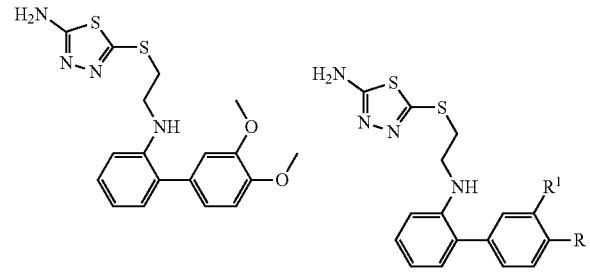

A3: R = F, R$^1$ = H
A4: R = R$^1$ = OMe

Step 1

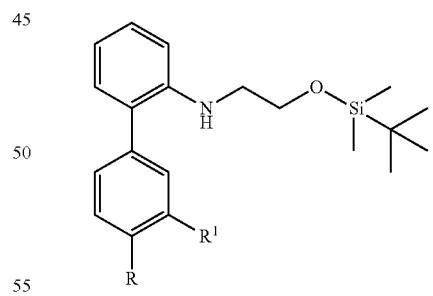

2-substituted aniline (1.0 eq.), sodium cyanoborohydride (1.5 eq.) and t-butyldimethylsilyloxyacetaldehyde (2.0 eq.) were dissolved in dry MeOH (30.0 vol.) and acetic acid was added (1.0 vol.). Reaction was stirred over 1-2 h until full consumption of amine was observed via UPLC analysis. After this time reaction mixture was diluted with saturated sodium bicarbonate solution (40 mL) and extracted with ethyl acetate (3×20 mL). Combined organic layers were dried over sodium sulfate, filtered and evaporated, used in next step without further purification.

Step 2

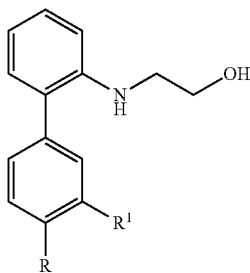

Product from step 1 (1.0 eq.) and tetrabutylammonium fluoride trihydrate (1.05 eq.) were dissolved in THF (40.0 vol.). Reaction was monitored via UPLC analysis. After completion the reaction, solvent was removed in vacuo and crude material was taken to step 3.

5-{[2-({4'-fluoro-[1,1'-b]phenyl]-2-yl}amino)ethyl]sulfanyl}-1,3,4-thiadiazol-2-amine (A3). To solution of 2-({4'-fluoro-[1,1'-biphenyl]-2-yl}amino)ethan-1-ol (0.58 g, 2.5 mmol), 2-amino-5-mercapto-thiadiazole (0.50 g, 3.8 mmol) and triphenylphosphine (1.18 g, 4.5 mmol) in anhydrous THF (16.0 mL) diethyleneazodicarboxylate (0.66 g, 3.8 mmol) was added dropwise. Reaction mixture was stirred overnight at room temperature. After this time solvents were removed in vacuo. Crude product was purified via column chromatography using 0-3% MeOH in DCM and additional repurified via preparative TLC method using MeOH in DCM as eluent. Final re-purification was performed via preparative HPLC method to give pure product (40 mg. 7%) LCMS-Method 7 (200 nm): RT=5.81 min, 98.7% purity, [M]=346.0, $^1$H NMR (300 MHz, Methanol-$d_4$) δ 7.48-7.31 (m, 1H), 7.27-7.10 (m, 2H), 7.01 (dd, J=7.4, 1.6 Hz, 1H), 6.84-6.52 (m, 1H), 3.47 (t, J=6.6 Hz, 1H), 3.26 (t, J=6.6 Hz, 1H).

5-{[2-({3',4'-dimethoxy-[1,1'-biphenyl]-2-yl}amino)ethyl]sulfanyl}-1,3,4-thiadiazol-2-amine (A4). To solution of 2-({3',4'-dimethoxy-[1,1'-biphenyl]-2-yl}amino)ethan-1-ol (0.9 g, 8.3 mmol), 2-amino-5-mercapto-thiadiazole (1.0 g, 7.5 mmol) and triphenylphosphine (2.17 g, 8.3 mmol) in anhydrous THF (10.0 mL) diethyleneazadicarboxylate (2.25 g, 9.8 mmol) was added dropwise in 5 mL of anhydrous tetrahydrofurane. Reaction mixture was stirred overnight at room temperature. After this time solvents were removed in vacuo. Crude product was purified via column chromatography using 0-3% MeOH in DCM and re-purified via preparative HPLC method to give pure product (80 mg, 7%) LCMS-Method 7 (205 nm): RT=5.27 min, 98.1% purity, [M]=386.9. $^1$H NMR (300 MHz, DMSO-$d_6$) δ 7.30 (s, 1H), 7.14 (td, J=7.8, 7.3, 1.7 Hz, 1H), 7.09-6.96 (m, 2H), 6.89 (dd, J=8.2, 2.0 Hz, 0H), 6.75-6.61 (m, 1H), 4.94 (t, J=6.0 Hz, 1H), 3.79 (d, J=1.8 Hz, 3H), 3.38 (d, J=6.5 Hz, 1H), 3.24 (t, J=6.4 Hz, 1H).

Synthesis Method C

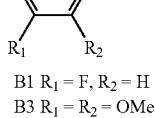

B1 $R_1$ = F, $R_2$ = H
B3 $R_1$ = $R_2$ = OMe

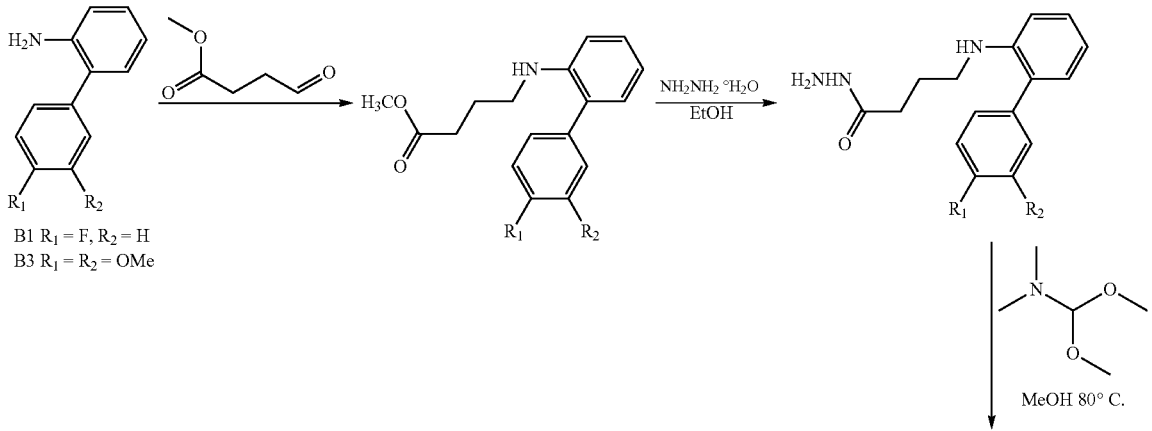

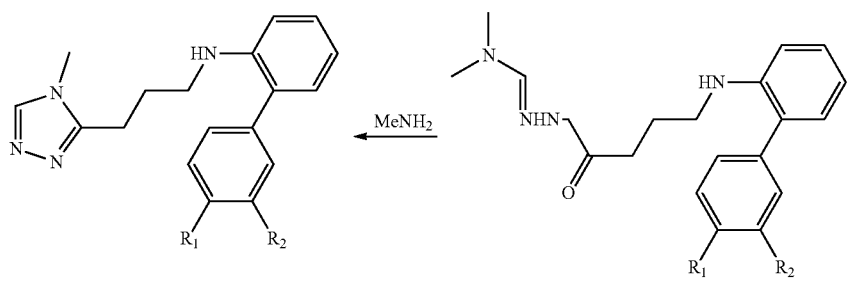

Step 1

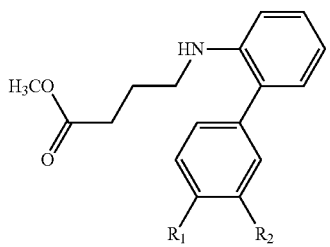

To the solution of amine (4.27 mmol) in MeOH (25.0 mL) methyl 4-oxobutanoate (0.99 g, 8.54 mmol) and acetic acid (0.8 mL) was added. The reaction mixture was stirred for 1.5 hours at ambient temperature. After that time NaBH$_3$CN (0.40 mg, 6.41 mmol) was added and the mixture was stirred for 1 h. Reaction was quenched with saturated solution of NaHCO$_3$. The water layer was extracted with DCM (3×20 mL). Combined organic layers were dried over sodium sulfate, filtered, evaporated to provide the product.

methyl 4-(4'-fluoro-[1,1'-biphenyl]-2-yl)amino)butanoate (0.875 g, 71%) 4'-fluoro-[1,1'-biphenyl]-2-amine was used. Crude (1.47 g) was purified via column chromatography using 100% DCM as eluent. UPLC (254 nm): RT=4.14 min, 76% purity, [M+H]=288.20.

methyl 4-((3',4'-dimethoxy-[1,1'-biphenyl]-2-yl)amino)butanoate (1.00 g, 71%) 3',4'-dimethoxy-[1,1'-biphenyl]-2-amine was used. Crude product was purified via column chromatography using 0-20% EA in hexane as eluent.

Step 2

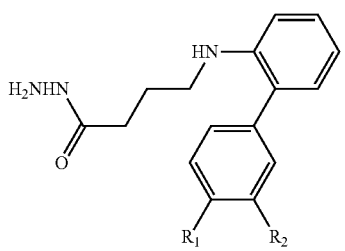

To the solution of corresponding starting material (3.04 mmol) in EtOH (30 mL) 50% hydrazine in H$_2$O (5.0 eq) was added. Reaction mixture was stirred for 18 hour at 80° C. After that time the solvent was evaporated to give pure compound.

4-(4'-fluoro-[1,1'-biphenyl]-2-yl)amino)butanehydrazide (0.85 g, 96%). Methyl 4-({4'-fluoro-[1,1'-biphenyl]-2-yl}amino)butanoate (0.875 g. 3.04 mmol) as starting material was used. UPLC (254 nm): RT=3.06 min, [M+H]= 288.35.

4-({3',4'-dimethoxy-[1,1'-biphenyl]-2-yl}amino)butane-hydrazide (0.97 g, 97%). Methyl 4-({3',4'-dimethoxy-[1,1'-biphenyl]-2-yl}amino)butanoate (1.0 g, 3.04 mmol) as starting material was used. UPLC (254 nm): RT=2.82 min, [M+H]=330.30.

Step 3

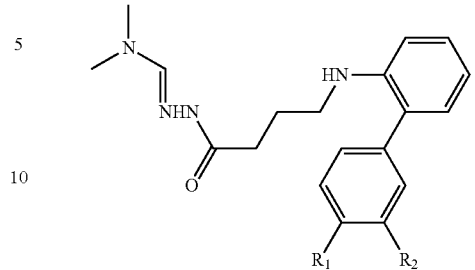

To the solution of corresponding starting material (2.6 mmol) in MeOH (8 mL) N,N-dimethylformamide dimethylacetal (311 mg, 2.6 mmol) was added. Reaction mixture was stirred for 1 hour at 80° C. After that time solvent was evaporated to obtain desired product.

N'-[(1E)-(dimethylamino)methylidene]-4-({4'-fluoro-[1,1'-biphenyl]-2-yl}amino)butane-hydrazide (0.894 g, 100%). 4-({4'-fluoro-[1,1'-biphenyl]-2-yl}amino)butanehydrazide (0.75 g, 2.61 mmol) was used as starting material. UPLC (254 nm): RT=3.40 min, [M+H]=343.15.

4-({3',4'-dimethoxy-[1,1'-biphenyl]-2-yl}amino)-N'-[(1E)-(dimethylamino)methylidene]-butanehydrazide (1.014 g, 100%). 4-({3',4'-dimethoxy-[1,1'-biphenyl]-2-yl}amino)butane-hydrazide (0.869 g, 2.64 mmol) was used as starting material. UPLC (254 nm): RT=3.40 min, [M+H]= 385.30.

Step 4

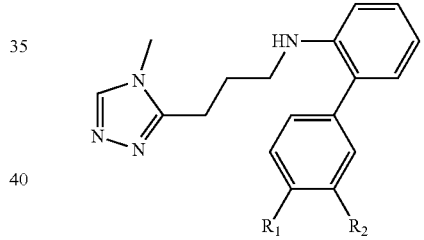

MeNH$_2$ 2M in THF (20 eq) was added to the solution of corresponding starting material in anhydrous THF (10.0 mL) under argon atmosphere. Reaction mixture was cooled to 0° C. and acetic acid (2 mL) was carefully added. Reaction mixture was stirred for 18 hours at 100° C. After that time reaction was cooled to room temperature and water (5 mL) was added. Layers were separated and water layer was extracted three times with EA (3×20 mL). Combined organic layers were dried over sodium sulfate, filtered and evaporated. Crude product was purified via column chromatography using 0-4% MeOH in DCM as eluent and then re-purified via preparative HPLC. Fraction containing the title compound in pure form was concentrated to give the product.

4'-fluoro-N-[3-(4-methyl-4H-1,2,4-triazol-3-yl)propyl]-[1,1'-biphenyl]-2-amine (B1) (101 mg, 11%) N'-[(1E)-(dimethylamino)methylidene]-4-({4'-fluoro-[1,1'-biphenyl]-2-yl}amino)butane-hydrazide (1.00 g, 2.92 mmol) was used as starting material. LCMS-Method 2 (220 nm): RT=4.78 min, 98.89% purity. $^1$H NMR (300 MHz, DMSO-d$_6$) δ 8.32 (s, 1H), 7.46-7.36 (m, 2H), 7.32-7.21 (m, 2H), 7.21-7.14 (m, 1H), 6.95 (d, J=1.7 Hz, 1H), 6.72-6.61 (m, 2H). 4.10 (q, J=5.3 Hz, 2H), 3.54 (s, 3H). 2.69 (d, J=7.5 Hz, 2H), 1.95-1.84 (m, 2H).

3',4'-dimethoxy-N-[3-(4-methyl-4H-1,2,4-triazol-3-yl)propyl]-[1,1'-biphenyl]-2-amine (B3) (5 mg, 0.4%). 4-({3',4'-dimethoxy-[1,1'-biphenyl]-2-yl}amino)-N'-[(1E)-(dimethylamino)-methylidene]-butanehydrazide (1.10 g, 2.86 mmol) was used as starting material. LCMS-Method 8 (210 nm): RT=12.12 min, 99.45% purity. $^1$H NMR (300 MHz, DMSO-$d_6$) δ 8.32 (s, 1H), 7.09-6.84 (m, 4H), 6.66 (d, J=7.9 Hz, 2H), 4.11 (q, J=5.4 Hz, 2H), 3.79 (d, J=5.4 Hz, 3H), 3.53 (s, 3H), 3.40 (t, J=7.0 Hz, 2H), 3.18 (d, J=5.3 Hz, 3H), 1.89-1.96 (m, 2H).

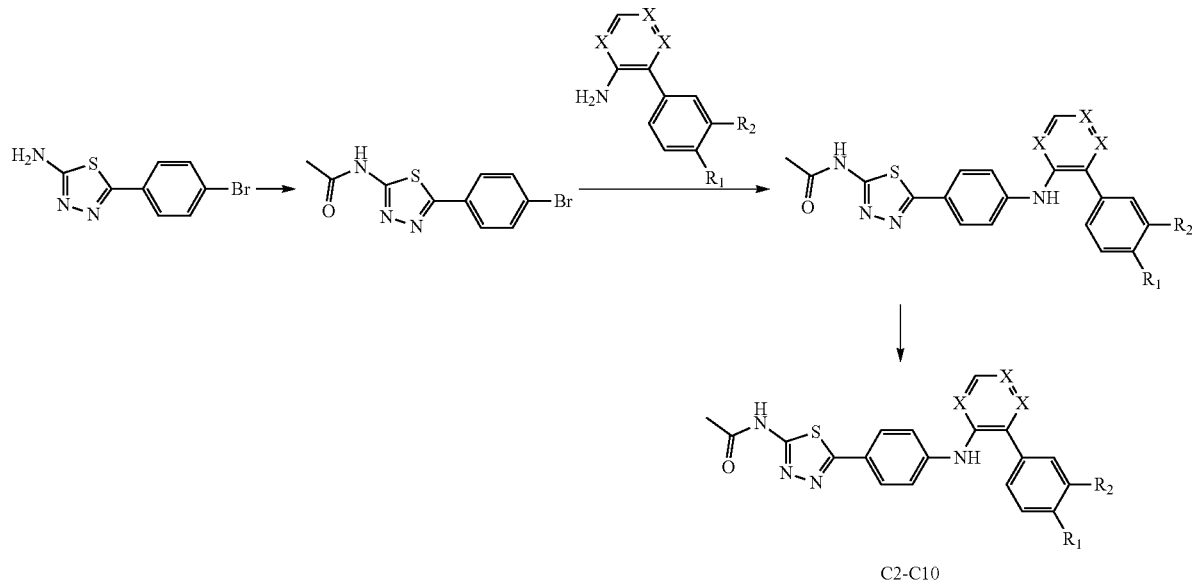

C2-C10

Step 1

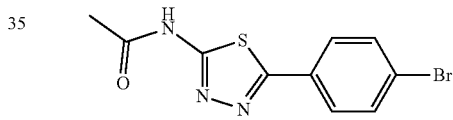

N-[5-(4-bromophenyl)-1,3,4-thiadiazol-2-yl]acetamide 5-(4-bromophenyl)-1,3,4-thiadiazol-2-amine (0.5 g, 2.0 mmol), triethylamine (0.54 mL, 4.0 mmol), were dissolved in DCM (5 mL) and acetyl chloride (0.17 g, 2.15 mmol) was added dropwise at 5° C., reaction was stirred at room temperature over 1h, after this time another portion of triethylamine and acetyl chloride was added at 5° C. and reaction mixture was stirred over additional 30 min. The mixture was diluted with DCM (15.0 mL) and washed with sat. solution of sodium bicarbonate (20 mL), water (20 mL). Title compound was obtained as 1:1 mixture of acetylated (UPLC (254 nm): RT=3.13 min[M+H]=297.9) and diacetylated amine (UPLC (254 nm): RT=3.58 min[M+H]=338.9). (0.40 g, 60%). Used in next step without purification.

Step 2

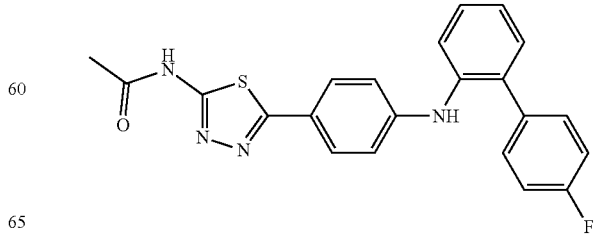

N-(5-[4-({4'-fluoro-[1,1'-biphenyl]-2-yl}amino)phenyl]-1,3,4-thiadiazol-2-yl)acetamide N-[5-(4-bromophenyl)-1,3,4-thiadiazol-2-yl]acetamide (0.2 g, 0.67 mmol), 4'-fluoro-[1,1'-biphenyl]-2-amine (0.12 g, 0.56 mmol), sodium tert-butanolate (0.15 mg, 1.56 mmol) and XantPhos (40 mg, 0.07 mmol) were suspended in 1,4-dioxane (6 ml), Reaction mixture was degassed with argon flow over 20 min and tris(dibenzylideneacetone)dipalladium(0)-chloroform adduct (35 mg, 0.035 mmol) was added. Reaction was stirred overnight at 100° C. After that time reaction mixture was cooled to room temperature, Filtered thru celite, evaporated and purified via column chromatography using MeOH in DCM 0-3% as aluent to give pure product (0.24 g, 88%). UPLC (254 nm): RT=3.78 min. 85% purity, [M+H]=404.8.

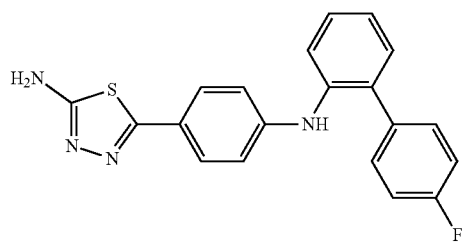 [SMILES: Nc1nnc(-c2ccc(Nc3ccccc3-c3ccc(F)cc3)cc2)s1]

5-[4-({4'-fluoro-[1,1'-biphenyl]-2-yl}amino)phenyl]-1,3,4-thiadiazol-2-amine (C$_2$) To solution of N-{5-[4-({4'-fluoro-[1,1'-biphenyl]-2-yl}amino)phenyl]-1,3,4-thiadiazol-2-yl}acetamide (0.17 g, 0.42 mmol) in methanol (2.5 mL) concentrated hydrochloric acid (2.5 mL) was added dropwise. Reaction mixture was refluxed overnight. After this time reaction was diluted with saturated sodium bicarbonate solution (20 mL) and extracted with DCM (6×15 mL), organic layers were combined, dried over sodium sulfate, filtered and evaporated. Crude product was purified via preparative HPLC method to give pure product (40 mg, 25%) LCMS-Method 6 (200 nm): RT=20.57 min, 91.6% purity, [M+H]=363.14, LCMS (340 nm): RT=20.57 min, 99.2% purity, [M+H]=363.14, 1H NMR (300 MHz, DMSO-d6) δ 7.82 (s, 1H), 7.59-7.33 (m, 7H), 7.27-7.04 (m, 5H), 6.89-6.54 (m, 2H).

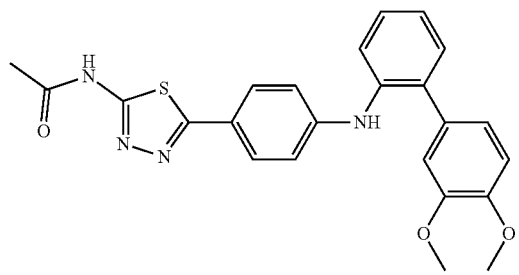 [SMILES: COc1ccc(-c2ccccc2Nc2ccc(-c3nnc(NC(C)=O)s3)cc2)cc1OC]

N-{5-(4-{[2-(3,4-dimethoxyphenyl)phenyl]amino}phenyl)-1,3,4-thiadiazol-2-yl}acetamide N-[5-(4-bromophenyl)-1,3,4-thiadiazol-2-yl]acetamide (100 mg, 0.34 mmol), 2-(3,4-dimethoxyphenyl)aniline (60 mg, 0.28 mmol), sodium tert-butanolate (75 mg, 1.56 mmol) and XantPhos (40 mg, 0.035 mmol) were suspended in 1,4-dioxane (3 ml), Reaction mixture was degassed with argon flow over 20 min and tris(dibenzylideneacetone)dipalladium (0)-chloroform adduct (17 mg, 0.017 mmol) was added. Reaction was stirred overnight at 100° C. After that time reaction mixture was cooled to room temperature, Filtered through celite, evaporated and purified via column chromatography using MeOH in DCM 0-3% as aluent to give pure product (0.2 g, 80%). UPLC (254 nm): RT=3.64 min, 85% purity, [M+H]=447.15.

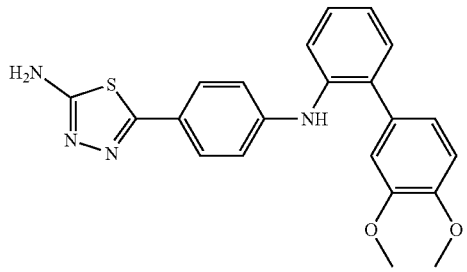 [SMILES: COc1ccc(-c2ccccc2Nc2ccc(-c3nnc(N)s3)cc2)cc1OC]

5-(4-([2-(3,4-dimethoxyphenyl)phenyl]amino)phenyl)-1,3,4-thiadiazol-2-amine (C3). To solution of N-{5-(4-{[2-(3,4-dimethoxyphenyl)phenyl]amino}phenyl)-1,3,4-thiadiazol-2-yl}acetamide (0.20 g, 0.42 mmol) in methanol (3.0 mL) concentrated hydrochloric acid (3.0 mL) was added dropwise. Reaction mixture was refluxed overnight. After this time reaction was diluted with saturated sodium bicarbonate solution (20 mL) and extracted with DCM (6×15 mL), organic layers were combined, dried over sodium sulfate, filtered and evaporated. Crude product was purified via preparative HPLC method to give pure product (44 mg, 25%) LCMS (LCMS-Method 10, 200 nm), RT=5.22 min, 96.1% purity, [M+H]=405.11, 1H NMR (300 MHz, DMSO-d6) δ 7.87 (s, 1H), 7.55-7.31 (m, 6H), 7.37-7.13 (m, 5H), 6.81-6.64 (m, 2H), 3.53 (s, 3H), 3.50 (s, J=7.0 Hz, 3H).

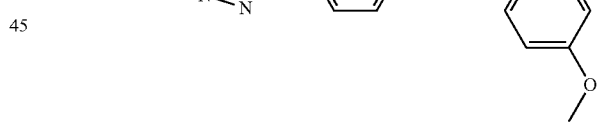

N-[5-(4-{[2-(4-methoxyphenyl)phenyl]amino}phenyl)-1,3,4-thiadiazol-2-yl]acetamide. N-[5-(4-bromophenyl)-1,3,4-thiadiazol-2-yl]acetamide (128 mg, 0.43 mmol), 2-(4-methoxyphenyl)aniline (102 mg, 0.51 mmol), cesium carbonate (279 mg, 0.86 mmol) and XantPhos (50 mg, 0.09 mmol) were suspended in 1,4-dioxane (3.8 mL). Reaction mixture was degassed with argon flow over 20 min and tris(dibenzylideneacetone)dipalladium(0) (35 mg. 0.04 mmol) was added. Reaction was stirred at 100° C. for 96 hours. After that time reaction mixture was cooled to room temperature, Filtered thru celite, evaporated and purified via column chromatography using DCM/MeOH 1:0→98:2 as a eluent to give product as a yellow solid (62.5 mg, 35.01%). UPLC (254 nm): RT=7.14 min, 80.9% purity, [M+H]= 417.10.

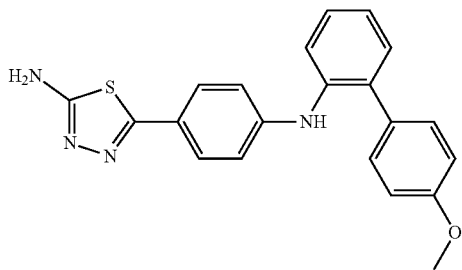 [SMILES: COc1ccc(-c2ccccc2Nc2ccc(-c3nnc(N)s3)cc2)cc1]
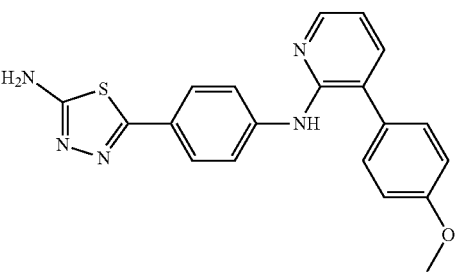

5-(4-{[2-(4-methoxyphenyl)phenyl]amino}phenyl)-1,3,4-thiadiazol-2-amine C4. To solution of N-[5-(4-{[2-(4-methoxyphenyl)phenyl]amino}phenyl)-1,3,4-thiadiazol-2-yl]acetamide (63 mg, 0.15 mmol) in methanol (1.0 mL) concentrated hydrochloric acid (1.0 mL) was added dropwise. Reaction mixture was refluxed overnight. After this time reaction was diluted with saturated sodium bicarbonate solution (20 mL), methanol was evaporated and extraction with ethyl acetate (2×10 mL) was made. Combined organic layers were dried over sodium sulfate, filtered and evaporated. Crude product was purified via preparative TLC eluted with Hex/EtOAc/MeOH 70:25:5 to give desired product as a yellow solid (19.6 mg, 35%). LCMS (LCMS-Method 11, 200 nm): RT=2.75 min, 98.9% purity, [M+H]= 375.21. $^1$H NMR (300 MHz, DMSO-d$_6$) δ 7.74 (s, 1H), 7.50-7.43 (m, 2H), 7.40-7.28 (m, 5H), 7.23-7.14 (m, 3H), 6.98-6.91 (m, 2H), 6.84-6.78 (m, 2H), 3.75 (s, 3H).

N-[4-(5-amino-1,3,4-thiadiazol-2-yl)phenyl]-3-(4-methoxyphenyl)pyridin-2-amine (C5). To solution of N-[5-(4-{[3-(4-methoxyphenyl)pyridin-2-yl]amino}phenyl)-1,3,4-thiadiazol-2-yl]acetamide (114 mg, 0.27 mmol) in methanol (1.7 mL) concentrated hydrochloric acid (1.7 mL) was added dropwise. Reaction mixture was refluxed overnight. After this time reaction was diluted with saturated sodium bicarbonate solution (20 mL), methanol was evaporated and extraction with ethyl acetate (2×15 mL) was made. Combined organic layers were dried over sodium sulfate, filtered and evaporated. Crude product was purified via preparative TLC eluted with DCM/MeOH 9:1 to give desired product as a yellowish solid (16.4 mg, 16%). LCMS-Method 5 (200 nm): RT=1.75 min, 99.3% purity, [M+H]= 376.19. $^1$H NMR (300 MHz, DMSO-d$_6$) δ 8.20 (dd, J=4.9, 1.9 Hz, 1H), 7.96 (s, 1H), 7.67-7.56 (m, 4H), 7.53 (dd, J=7.4, 1.9 Hz, 1H), 7.47-7.40 (m, 2H), 7.25 (s, 2H), 7.10-7.04 (m, 2H), 6.98 (dd, J=7.4, 4.9 Hz, 1H), 3.82 (s, 3H).

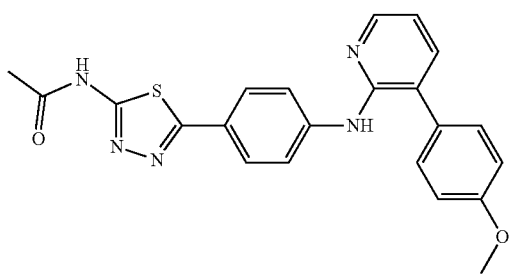 [SMILES: COc1ccc(-c2cccnc2Nc2ccc(-c3nnc(NC(C)=O)s3)cc2)cc1]
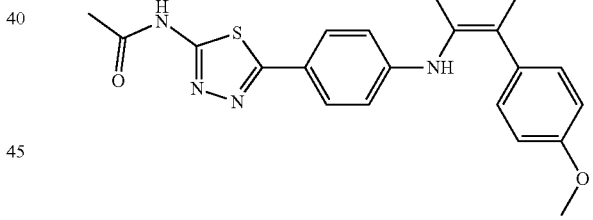

N-[5-(4-([3-(4-methoxyphenyl)pyridin-2-yl]]amino)phenyl)-1,3,4-thiadiazol-2-yl]acetamide. N-[5-(4-bromophenyl)-1,3,4-thiadiazol-2-yl]acetamide (87 mg, 0.29 mmol), 3-(4-methoxyphenyl)pyridin-2-amine (70 mg, 0.35 mmol), cesium carbonate (190 mg, 0.58 mmol) and XantPhos (34 mg, 0.06 mmol) were suspended in 1,4-dioxane (2.6 mL). Reaction mixture was degassed with argon flow over 20 min and tris(dibenzylideneacetone)dipalladium(0) (24 mg, 0.03 mmol) was added. Reaction was stirred at 100° C. for 72 hours. After that time reaction mixture was cooled to room temperature, Filtered thru celite, evaporated and purified via column chromatography using DCM/MeOH 1:0→95:5 as a eluent to give product as a pale-yellow solid (114 mg, 93.6%). UPLC (254 nm): RT=5.35 min. 65% purity, [M+H]= 418.70.

N-[5-(4-{[3-(4-methoxyphenyl)pyridin-4-yl]amino}phenyl)-1,3,4-thiadiazol-2-yl]acetamide. N-[5-(4-bromophenyl)-1,3,4-thiadiazol-2-yl]acetamide (100 mg, 0.34 mmol), 3-(4-methoxyphenyl)pyridin-4-amine (81 mg, 0.40 mmol), cesium carbonate (219 mg, 0.67 mmol) and XantPhos (39 mg, 0.07 mmol) were suspended in 1,4-dioxane (3 mL). Reaction mixture was degassed with argon flow over 20 min and tris(dibenzylideneacetone)dipalladium(0) (27 mg, 0.03 mmol) was added. Reaction was stirred at 100° C. for 72 hours. After that time reaction mixture was cooled to room temperature, Filtered thru celite, evaporated and purified via column chromatography using DCM/MeOH 1:0→95:5 as a eluent to give product as a yellow solid (75 mg, 53.6%). UPLC (310 nm): RT=3.96 min, 93% purity, [M+H]=418.95.

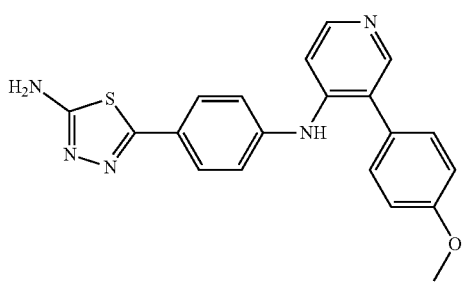 [SMILES: COc1ccc(-c2cnccc2Nc2ccc(-c3nnc(N)s3)cc2)cc1]

N-[4-(5-amino-1,3,4-thiadiazol-2-yl)phenyl]-3-(4-methoxyphenyl)pyridin-4-amine (C6). To solution of N-[5-(4-{[3-(4-methoxyphenyl)pyridin-4-yl]amino}phenyl)-1,3,4-thiadiazol-2-yl]acetamide (75 mg, 0.18 mmol) in methanol (1.12 mL) concentrated hydrochloric acid (1.12 mL) was added dropwise. Reaction mixture was refluxed overnight. After this time reaction was diluted with saturated sodium bicarbonate solution (20 mL), methanol was evaporated and extraction with ethyl acetate (2×15 mL) was made. Combined organic layers were dried over sodium sulfate, filtered and evaporated. Crude product was purified via preparative TLC eluted with DCM/MeOH 9:1. Re-purification was performed via preparative TLC eluted with DCM/MeOH 9:1 to give desired product as a whitish solid (32.0 mg, 47%). LCMS-Method 3 (200 nm): RT=3.01 min, 99.8% purity, [M+H]=376.18. $^1$H NMR (300 MHz, DMSO-$d_6$) δ 8.26-8.20 (m, 2H). 8.00 (s, 1H), 7.66-7.61 (m, 2H), 7.45-7.40 (m, 2H), 7.32-7.18 (m, 5H), 7.07-7.02 (m, 2H), 3.80 (s, 3H).

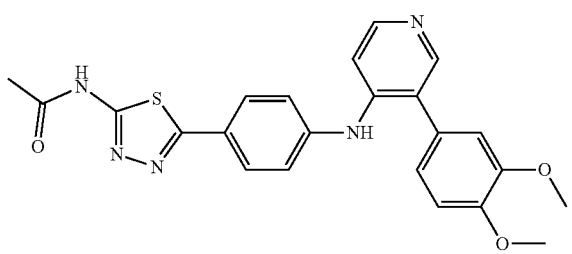 [SMILES: COc1ccc(-c2cnccc2Nc2ccc(-c3nnc(NC(C)=O)s3)cc2)cc1OC]

N-[5-(4-{[3-(3,4-dimethoxyphenyl)pyridin-4-yl]amino}phenyl)-1,3,4-thiadiazol-2-yl]acetamide. N-[5-(4-bromophenyl)-1,3,4-thiadiazol-2-yl]acetamide (100 mg, 0.34 mmol), 3-(3,4-dimethoxyphenyl)pyridin-4-amine (93 mg, 0.40 mmol), cesium carbonate (219 mg, 0.67 mmol) and XantPhos (39 mg, 0.07 mmol) were suspended in 1,4-dioxane (3 mL). Reaction mixture was degassed with argon flow over 20 min and tris(dibenzylideneacetone)dipalladium (0) (27 mg, 0.03 mmol) was added. Reaction was stirred at 100° C. for 72 hours. After that time reaction mixture was cooled to room temperature, Filtered thru celite, evaporated and purified via column chromatography using DCM/MeOH 1:0→95:5 as a eluent to give product as a pale-yellow solid (49 mg, 32.7%). UPLC (310 nm): RT=4.72 min, 100% purity, [M+H]=448.15.

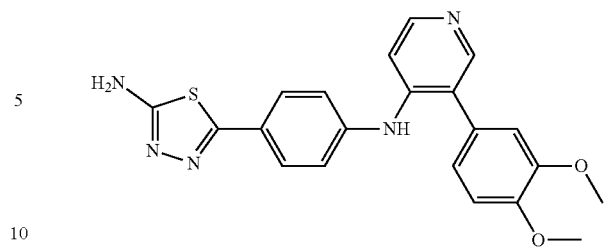

N-[4-(5-amino-1,3,4-thiadiazol-2-yl)phenyl]-3-(3,4-dimethoxyphenyl)pyridin-4-amine (C7). To solution of N-[5-(4-{[3-(3,4-dimethoxyphenyl)pyridin-4-yl]amino}phenyl)-1,3,4-thiadiazol-2-yl]acetamide (49 mg, 0.11 mmol) in methanol (0.75 mL) concentrated hydrochloric acid (0.75 mL) was added dropwise. Reaction mixture was refluxed overnight. After this time reaction was diluted with saturated sodium bicarbonate solution (10 mL), methanol was evaporated and extraction with ethyl acetate (2×10 mL) was made. Combined organic layers were dried over sodium sulfate, filtered and evaporated. Crude product was purified via preparative TLC eluted with DCM/MeOH 95:5 to give desired product as a light yellow solid (11 mg, 24.8%). LCMS-Method 3 (200 nm): RT=2.90 min, 99.6% purity, [M+H]=406.17. $^1$H NMR (300 MHz, DMSO-$d_6$) δ 8.28-8.22 (m, 2H), 8.01 (s, 1H), 7.67-7.60 (m, 2H), 7.33-7.17 (m, 5H), 7.09-6.99 (m, 3H), 3.77 (d, J=12.1 Hz, 6H).

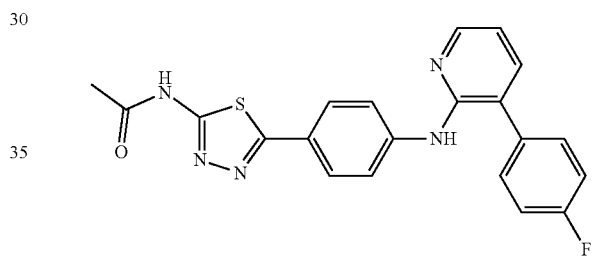

N-[5-(4-{[3-(4-fluorophenyl)pyridin-2-yl]amino}phenyl)-1,3,4-thiadiazol-2-yl]acetamide. N-[5-(4-bromophenyl)-1,3,4-thiadiazol-2-yl]acetamide (100 mg, 0.34 mmol), 3-(4-fluorophenyl)pyridin-2-amine (52 mg, 0.28 mmol), cesium carbonate (219 mg, 0.67 mmol) and XantPhos (39 mg, 0.07 mmol) were suspended in 1,4-dioxane (3 mL). Reaction mixture was degassed with argon flow over 20 min and tris(dibenzylideneacetone)dipalladium (0) (27 mg, 0.03 mmol) was added. Reaction was stirred at 100° C. for 72 hours. After that time reaction mixture was cooled to room temperature, Filtered thru celite, evaporated and purified via column chromatography using DCM/MeOH 1:0→99:1 as a eluent to give product as a yellowish solid (75 mg, 55.6%). UPLC (254 nm): RT=5.92 min, 96.8% purity, [M+H]=406.95.

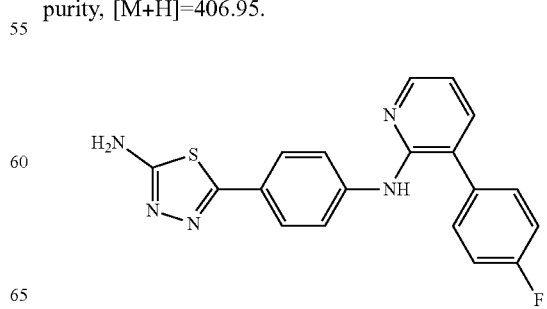

N-[4-(5-amino-1,3,4-thiadiazol-2-yl)phenyl]-3-(4-fluorophenyl)pyridin-2-amine (C8). To solution of N-[5-(4-{[3-(4-fluorophenyl)pyridin-2-yl]amino}phenyl)-1,3,4-thiadiazol-2-yl]acetamide (75 mg, 0.18 mmol) in methanol (1.2 mL) concentrated hydrochloric acid (1.2 mL) was added dropwise. Reaction mixture was refluxed overnight. After this time reaction was diluted with saturated sodium bicarbonate solution (20 mL), methanol was evaporated and extraction with ethyl acetate (2×15 mL) was made. Combined organic layers were dried over sodium sulfate, filtered and evaporated. Crude product was purified via preparative TLC eluted with DCM/MeOH 95:5. Re-purification was performed via preparative TLC eluted with DCM/MeOH 95:5 to give desired product as a yellowish solid (4.3 mg, 6.4%). LCMS-Method 2 (200 nm): RT=4.69 min, 98.9% purity, [M+H]=364.18. ¹H NMR (300 MHz, Methanol-d₄) δ 8.22 (dd, J=5.0, 1.9 Hz, 1H), 7.68-7.61 (m, 2H), 7.60-7.47 (m, 5H), 7.30-7.20 (m, 2H), 7.02 (dd, J=7.4, 5.0 Hz, 1H).

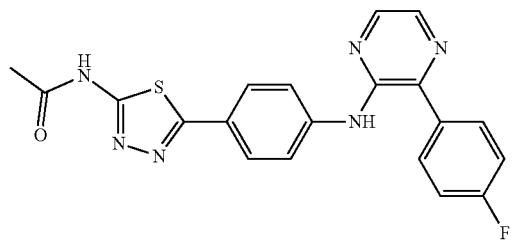 [SMILES: CC(=O)Nc1nnc(-c2ccc(Nc3nccnc3-c3ccc(F)cc3)cc2)s1]

N-[5-(4-{[3-(4-fluorophenyl)pyrazin-2-yl]amino}phenyl)-1,3,4-thiadiazol-2-yl]acetamide. N-[5-(4-bromophenyl)-1,3,4-thiadiazol-2-yl]acetamide (100 mg, 0.34 mmol), 3-(4-fluorophenyl)pyrazin-2-amine (76 mg, 0.40 mmol), cesium carbonate (219 mg, 0.67 mmol) and XantPhos (39 mg, 0.07 mmol) were suspended in 1,4-dioxane (3 mL). Reaction mixture was degassed with argon flow over 20 min and tris(dibenzylideneacetone)dipalladium(0) (27 mg, 0.03 mmol) was added. Reaction was stirred at 100° C. for 72 hours. After that time reaction mixture was cooled to room temperature. Filtered thru celite, evaporated and purified via column chromatography using DCM/MeOH 1:0→97:3 as a eluent to give product as a yellowish solid (68 mg, 49.8%). UPLC (254 nm): RT=5.88 min, 95.5% purity, [M+H]=407.05.

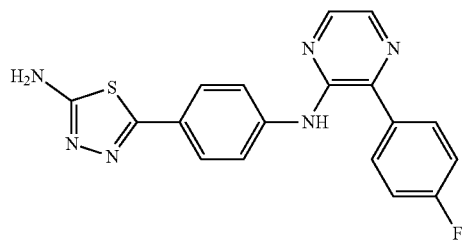 [SMILES: Nc1nnc(-c2ccc(Nc3nccnc3-c3ccc(F)cc3)cc2)s1]

N-[4-(5-amino-1,3,4-thiadiazol-2-yl)phenyl]-3-(4-fluorophenyl)pyrazin-2-amine (C9). To solution of N-[5-(4-{[3-(4-fluorophenyl)pyrazin-2-yl]amino}phenyl)-1,3,4-thiadiazol-2-yl]acetamide (68 mg, 0.17 mmol) in methanol (1 mL) concentrated hydrochloric acid (1 mL) was added dropwise. Reaction mixture was refluxed overnight. After this time reaction was diluted with saturated sodium bicarbonate solution (20 mL), methanol was evaporated and extraction with ethyl acetate (2×15 mL) was made. Combined organic layers were dried over sodium sulfate, filtered and evaporated. Crude product was purified via preparative TLC eluted with DCM/MeOH 9:1. Re-purification was performed via preparative TLC eluted with DCM/MeOH 95:5 to give desired product as a yellow solid (20.2 mg, 33.2%). LCMS-Method 4 (328 nm): RT=2.44 min, 97.0% purity, [M+H]=365.15. ¹H NMR (300 MHz, DMSO-d₆) δ 8.70 (s, 1H), 8.19 (s, 2H), 7.86-7.79 (m, 2H), 7.64 (s, 4H), 7.46-7.27 (m, 4H).

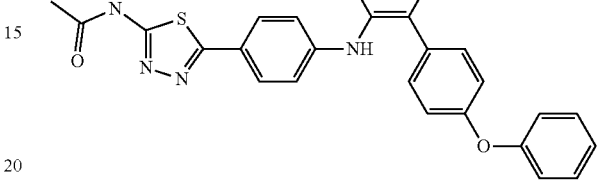

N-[5-(4-{[2-(4-phenoxyphenyl)phenyl]amino}phenyl)-1,3,4-thiadiazol-2-yl]acetamide. N-[5-(4-bromophenyl)-1,3,4-thiadiazol-2-yl]acetamide (100 mg, 0.34 mmol), 2-(4-phenoxyphenyl)aniline (105 mg, 0.40 mmol), cesium carbonate (219 mg, 0.67 mmol) and XantPhos (39 mg, 0.07 mmol) were suspended in 1,4-dioxane (3 mL). Reaction mixture was degassed with argon flow over 20 min and tris(dibenzylideneacetone)dipalladium(0) (27 mg, 0.03 mmol) was added. Reaction was stirred at 100° C. for 72 hours. After that time reaction mixture was cooled to room temperature, Filtered thru celite, evaporated and purified via column chromatography using DCM/MeOH 1:0→98:2 as a eluent to give product as a yellow solid (115 mg, 71.7%). UPLC (254 nm): RT=7.96 min, 88.6% purity, [M+H]=479.15.

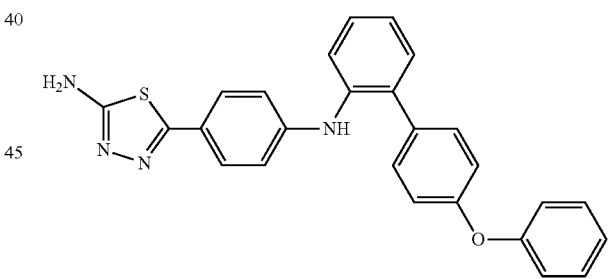

5-(4-{[2-(4-phenoxyphenyl)phenyl]amino}phenyl)-1,3,4-thiadiazol-2-amine (C10). To solution of N-[5-(4-{[2-(4-phenoxyphenyl)phenyl]amino}phenyl)-1,3,4-thiadiazol-2-yl]acetamide (95 mg, 0.20 mmol) in methanol (1.4 mL) concentrated hydrochloric acid (1.4 mL) was added dropwise. Reaction mixture was refluxed overnight. After this time reaction was diluted with saturated sodium bicarbonate solution (20 mL), methanol was evaporated and extraction with ethyl acetate (2×15 mL) was made. Combined organic layers were dried over sodium sulfate, filtered and evaporated. Crude product was purified via preparative TLC eluted with DCM/MeOH 8:2. Re-purification was performed via preparative TLC eluted with Hex/EtOAc/MeOH 70:25:5 to give desired product as a yellowish solid (17.2 mg, 19.9%). LCMS-Method 11 (200 nm): RT=3.57 min, 97.5% purity, [M+H]=437.16. ¹H NMR (300 MHz. Methanol-d₄) δ 7.52-7.43 (m, 2H), 7.41-7.15 (m, 8H), 7.10-7.01 (m, 1H), 6.97-6.84 (m, 4H), 6.82-6.72 (m, 2H).

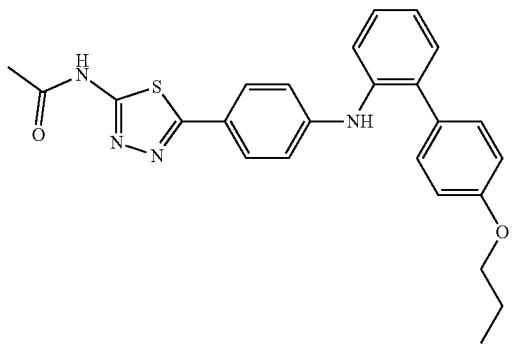 [SMILES: CCCOc1ccc(-c2ccccc2Nc2ccc(-c3nnc(NC(C)=O)s3)cc2)cc1]

N-[5-(4-([2-(4-propoxyphenyl)phenyl]amino)phenyl)-1,3,4-thiadiazol-2-yl]acetamide. N-[5-(4-bromophenyl)-1,3,4-thiadiazol-2-yl]acetamide (120 mg, 0.40 mmol), 2-(4-propoxyphenyl)aniline (110 mg, 0.48 mmol), cesium carbonate (262 mg, 0.80 mmol) and XantPhos (47 mg, 0.08 mmol) were suspended in 1,4-dioxane (3.6 mL). Reaction mixture was degassed with argon flow over 20 min and tris(dibenzylideneacetone)dipalladium(0) (33 mg, 0.04 mmol) was added. Reaction was stirred at 100° C. for 72 hours. After that time reaction mixture was cooled to room temperature, Filtered thru celite, evaporated and purified via column chromatography using DCM/MeOH 1:0→97:3 as a eluent to give product as a yellowish solid (55.7 mg, 31.1%). UPLC (254 nm): RT=8.07 min, 86.8% purity, [M+H]=445.30.

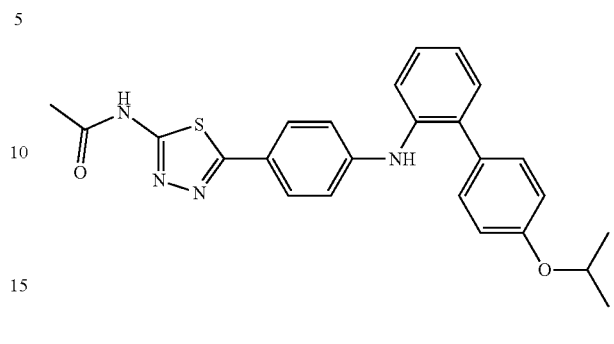

N-(5-[4-(2-[4-(propan-2-yloxy)phenyl]phenyl)amino)phenyl]-1,3,4-thiadiazol-2-yl)acetamide. N-[5-(4-bromophenyl)-1,3,4-thiadiazol-2-yl]acetamide (100 mg, 0.34 mmol), 2-[4-(propan-2-yloxy)phenyl]aniline (91 mg, 0.40 mmol), cesium carbonate (219 mg, 0.67 mmol) and XantPhos (39 mg, 0.07 mmol) were suspended in 1,4-dioxane (3 mL). Reaction mixture was degassed with argon flow over 20 min and tris(dibenzylideneacetone)dipalladium(0) (27 mg, 0.03 mmol) was added. Reaction was stirred at 100° C. for 72 hours. After that time reaction mixture was cooled to room temperature. Filtered thru celite, evaporated and purified via column chromatography using DCM/MeOH 1:0→97:3 as a eluent to give product as a yellowish solid (87.4 mg, 58.6%). UPLC (254 nm): RT=7.59 min, 87.6% purity, [M+H]=445.15.

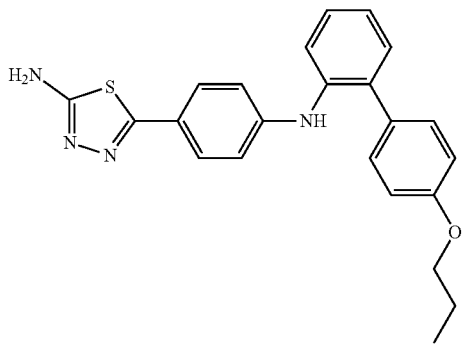 [SMILES: CCCOc1ccc(-c2ccccc2Nc2ccc(-c3nnc(N)s3)cc2)cc1]

5-(4-([2-(4-propoxyphenyl)phenyl]amino)phenyl)-1,3,4-thiadiazol-2-amine (C11). To solution of N-[5-(4-{[2-(4-propoxyphenyl)phenyl]amino}phenyl)-1,3,4-thiadiazol-2-yl]acetamide (56 mg, 0.13 mmol) in methanol (0.84 mL) concentrated hydrochloric acid (0.84 mL) was added dropwise. Reaction mixture was refluxed overnight. After this time reaction was diluted with saturated sodium bicarbonate solution (10 mL), methanol was evaporated and extraction with ethyl acetate (2×10 mL) was made. Combined organic layers were dried over sodium sulfate, filtered and evaporated. Crude product was purified via preparative TLC eluted with Hex/EtOAc/MeOH 70:25:5. Re-purification was performed via maceration with diethyl ether to give desired product as a light brown solid (11 mg, 22%). LCMS-Method 4 (200 nm): RT=3.67 min, 98.9% purity, [M+H]=403.19. ¹H NMR (300 MHz. Methanol-d₄) δ 7.56-7.47 (m, 2H), 7.41-7.27 (m, 5H), 7.17 (td, J=7.3, 1.5 Hz, 1H), 6.96-6.81 (m, 4H), 3.94 (t, J=6.5 Hz, 2H), 1.79 dtd, J=13.8, 7.4, 6.4 Hz, 2H), 1.04 (t, J=7.4 Hz, 3H).

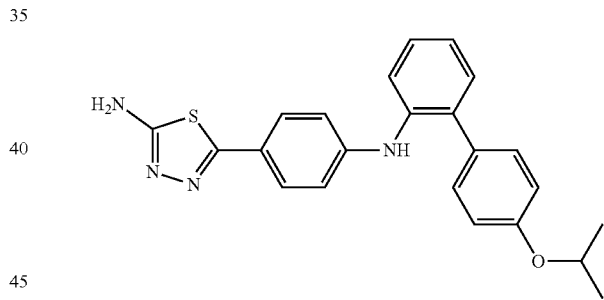

5-[4-({2-[4-{propan-2-yloxy)phenyl]phenyl}amino)phenyl]-1,3,4-thiadiazol-2-amine (C12). To solution of N-{5-[4-((2-[4-(propan-2-yloxy)phenyl]phenyl}amino)phenyl]-1,3,4-thiadiazol-2-yl}acetamide (87 mg, 0.20 mmol) in methanol (1.3 mL) concentrated hydrochloric acid (1.3 mL) was added dropwise. Reaction mixture was refluxed overnight. After this time reaction was diluted with saturated sodium bicarbonate solution (15 mL), methanol was evaporated and extraction with ethyl acetate (2×15 mL) was made. Combined organic layers were dried over sodium sulfate, filtered and evaporated. Crude product was purified via preparative TLC eluted with Hex/EtOAc/MeOH 70:25:5. Re-purification was performed via maceration with methanol, to give desired product as a yellow solid (7 mg, 8.8%). LCMS-Method 4 (200 nm): RT=3.54 min, 97.4% purity, [M+H]=403.20. ¹H NMR (300 MHz, Methanol-d₄) δ 7.55-7.47 (m, 2H), 7.41-7.27 (m, 5H), 7.18 (td, J=7.3, 1.5 Hz, 1H), 6.94-6.81 (m, 4H), 4.59 (dq, J=12.1, 6.1 Hz, 1H), 1.30 (d, J=6.0 Hz, 6H).

Synthesis Method E

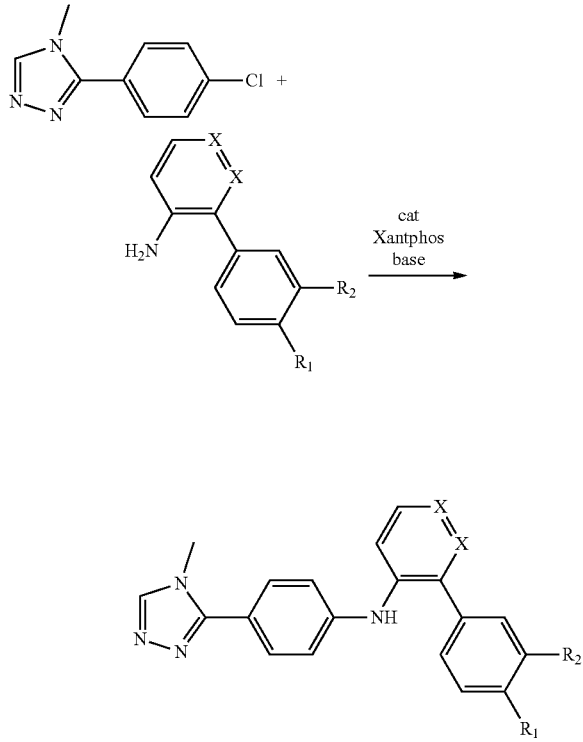

To a solution of 4-(chlorophenyl)-4-methyl-4-H-1,2,4-triazole (100 mg, 0.52 mmol) and corresponding base (1.20 mmol, 2.3 eq) in 1,4-dioxane (3.0 mL) amine (1.0 eq) was added. Reaction mixture was degassed for 30 minutes. Then xantphos (30 mg, 0.05 mmol) and corresponding catalyst were added and the mixture was stirred at 100° C. for 5 days. The reaction mixture was filtrated throw cellite, the filtrate was concentrated and purified via column chromatography using 0-10% MeOH in DCM as eluent. Fractions containing the title compound were combined and concentrated. Product was re-purified via P-TLC using 4% MeOH in DCM as an eluent.

4'-fluoro-N-[4-(4-methyl-4H-1,2,4-triazol-3-yl)phenyl]-[1,1'-biphenyl]-2-amine (D1) (34 mg, 19%). 4'-fluoro-[1,1'-biphenyl]-2-amine (97 mg, 0.52 mmol), t-BuONa (115 mg, 1.2 mmol), chloroform adduct of tris(dibenzylideneacetone) dipalladium(0) (26 mg 0.05 mmol), tetrakis(triphenylphosphine)palladium(0) (30 mg, 0.05 mmol) were used. LCMS-Method 2 (200 nm): RT=5.54 min, 97.6% purity, [M+H]=345.15. $^1$H NMR (300 MHz, DMSO-$d_6$) δ 8.46 (s, 1H), 7.82 (s, 1H), 7.45-7.49 (m, 4H), 7.34-7.40 (m, 3H), 7.17-7.25 (m, 3H), 6.88 (d, J=9.0 Hz, 2H), 3.69 (s, 3H).

3',4'-dimethoxy-N-[4-(4-methyl-4H-1,2,4-triazol-3-yl)phenyl]-[1,1'-biphenyl]-2-amine (D2) (45 mg, 28%). 3',4'-dimethoxy-[1,1'-biphenyl]-4-amine (120 mg, 0.52 mmol), Cs$_2$CO$_3$ (396 mg, 1.2 mmol), chloroform adduct of tris (dibenzylideneacetone)dipalladium(0) (26 mg 0.05 mmol) were used. LCMS-Method 2 (200 nm) RT=4.8 min, 98.7% purity, [M+H]=387.14. $^1$H NMR (300 MHz, DMSO-$d_6$) δ 8.46 (s, 1H), 7.74 (s, 1H), 7.47 (d, J=9 Hz, 2H), 7.31-7.42 (m, 3H), 7.19-7.25 (m, 1H), 6.99 (d, 2H, J=6 Hz), 6.88 (d, 2H, J=9 Hz), 3.76 (s, 3H), 3.68 (s, 3H), 3.62 (s, 3H).

N-[2-(4-methoxyphenyl)phenyl]-4-(4-methyl-4H-1,2,4-triazol-3-yl)aniline (D3). To a solution of 4-(chlorophenyl)-4-methyl-4-H-1,2,4-triazole (73 mg, 0.38 mmol) and Cs$_2$CO$_3$ (285 mg, 0.87 mmol) in 1,4-dioxane (2.25 mL) 2-(4-methoxyphenyl)aniline (75 mg, 0.38 mmol) was added. Reaction mixture was degassed for 30 minutes. Then xantphos (22 mg, 0.04 mmol) and chloroform adduct of tris (dibenzylideneacetone)dipalladium(0) (19 mg 0.02 mmol) were added and the mixture was stirred at 100° C. overnight. The reaction mixture was filtrated through cellite, washed with MeOH. Filtrate was concentrated and purified via column chromatography using 0-10% MeOH in DCM as eluent. Fractions containing the title compound were combined and concentrated. Product was re-purified via P-TLC using 4% MeOH in DCM as an eluent to give desired product as an orange solid (13 mg, 10%). LCMS-Method 2 (200 nm): RT=5.38 min, 94.03% purity, [M+H]=357.21. $^1$H NMR (300 MHz, Methanol-$d_4$) δ 8.48 (s, 1H), 7.45 (d, J=8.8 Hz, 2H), 7.39 (s, 1H), 7.37-7.28 (m, 4H), 7.29-7.13 (m, 1H), 6.94 (dd, J=8.8, 3.3 Hz, 4H), 3.80 (s, 3H), 3.78 (s, 3H).

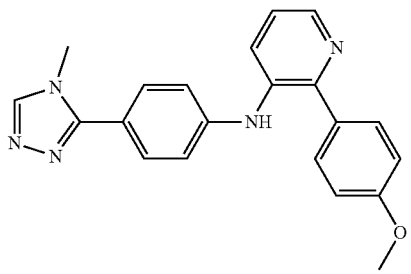 [SMILES: COc1ccc(-c2ncccc2Nc2ccc(-c3nncn3C)cc2)cc1]

2-(4-methoxyphenyl)-N-[4(4-methyl-4H-1,2,4-triazol-3-yl)phenyl]pyridin-3-amine (D4). To a solution of 4-(chlorophenyl)-4-methyl-4-H-1,2,4-triazole (68 mg, 0.35 mmol) and Cs$_2$CO$_3$ (264 mg, 0.81 mmol) in 1,4-dioxane (2.10 mL) 2-(4-methoxyphenyl)pyridin-3-amine (70 mg, 0.35 mmol) was added. Reaction mixture was degassed for 30 minutes. Then xantphos (20 mg, 0.03 mmol) and chloroform adduct of tris(dibenzylideneacetone)dipalladium(0) (18 mg 0.02 mmol) were added and the mixture was stirred at 100° C. overnight. The reaction mixture was filtrated through cellite, washed with MeOH. Filtrate was concentrated and purified via column chromatography using 0-10% MeOH in DCM as eluent. Fractions containing the title compound were combined and concentrated. Product was re-purified via P-TLC using 4% MeOH in DCM as an eluent to give desired product as white solid (35 mg, 28%). LCMS-Method 1 (200 nm): RT=5.58 min, 96.3% purity, [M+H]=358.22. $^1$H NMR (300 MHz, DMSO-$d_6$) δ 8.67 (s, 1H), 8.43 (d, J=5.9 Hz, 1H), 8.24 (s, 1H), 7.84 (d, J=8.8 Hz, 1H), 7.71 (d, J=8.8 Hz, 2H), 7.54 (d, J=8.3 Hz, 2H), 7.39 (dd, J=8.1, 4.7 Hz, 3H), 6.98 (t, J=9.1 Hz, 4H), 3.78 (s. 3H), 3.74 (s, 3H).

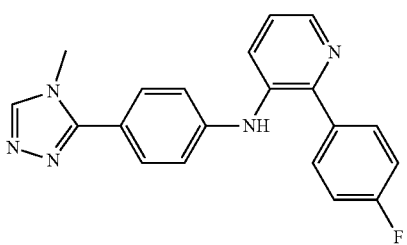 [SMILES: Cn1cnnc1-c1ccc(Nc2cccnc2-c2ccc(F)cc2)cc1]

2-(4-fluorophenyl)-N-[4-(4-methyl-4H-1,2,4-triazol-3-yl)phenyl]pyridin-3-amine (D5). To a solution of 4-(chlorophenyl)-4-methyl-4-H-1,2,4-triazole (77 mg, 0.40 mmol) and $Cs_2CO_3$ (301 mg, 0.92 mmol) in 1,4-dioxane (2.25 mL) 2-(4-fluorophenyl)pyridin-3-amine (75 mg, 0.40 mmol) was added. Reaction mixture was degassed for 30 minutes. Then xantphos (23 mg, 0.04 mmol) and chloroform adduct of tris(dibenzylideneacetone)dipalladium(0) (20 mg 0.02 mmol) were added and the mixture was stirred at 100° C. overnight. The reaction mixture was filtrated through cellite, washed with MeOH. Filtrate was concentrated and purified via column chromatography using 0-10% MeOH in DCM as eluent. Fractions containing the title compound were combined and concentrated. Product was re-purified via P-TLC using 4% MeOH in DCM as an eluent to give desired product as light orange solid (5 mg, 4%). LCMS-Method 1 (205 nm): RT=5.82 min, 99.46% purity, [M+H]=346.22. $^1$H NMR (300 MHz, Methanol-$d_4$) δ 8.50 (s, 1H), 8.37 (dd, J=4.7, 1.5 Hz, 1H), 7.89 (d, J=7.2 Hz, 1H), 7.70 (dd, J=9.1, 5.6 Hz, 2H), 7.51 (d, J=8.8 Hz, 2H), 7.42 (dd, J=8.2, 4.7 Hz, 1H), 7.16 (t, J=8.7 Hz, 2H), 7.01 (d, J=8.8 Hz, 2H), 3.78 (s, 3H).

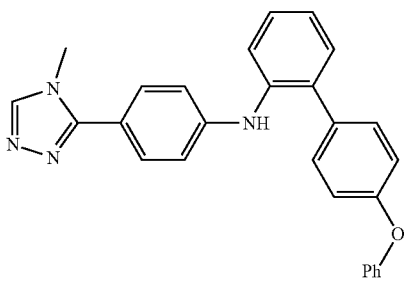 [SMILES: Cn1cnnc1-c1ccc(Nc2ccccc2-c2ccc(Oc3ccccc3)cc2)cc1]

4-(4-methyl-4H-1,2,4-triazol-3-yl)-N-[2-(4-phenoxyphenyl)phenyl]aniline (D6). To a solution of 4-(chlorophenyl)-4-methyl-4-H-1,2,4-triazole (74 mg, 0.38 mmol) and $Cs_2CO_3$ (289 mg, 0.89 mmol) in 1,4-dioxane (3.00 mL) 2-(4-phenoxyphenyl)aniline (100 mg, 0.38 mmol) was added. Reaction mixture was degassed for 30 minutes. Then xantphos (22 mg, 0.04 mmol) and chloroform adduct of tris(dibenzylideneacetone)dipalladium(0) (20 mg 0.02 mmol) were added and the mixture was stirred at 100° C. overnight. The reaction mixture was filtrated through celite, washed with MeOH. Filtrate was concentrated and purified via column chromatography using 0-5% MeOH in DCM as eluent. Fractions containing the title compound were combined and concentrated. Product was re-purified via P-TLC using 4% MeOH in DCM as an eluent to give desired product as white solid (25 mg, 16%). LCMS-Method 5 (200 nm): RT=2.25 min, 99.51% purity. [M+H]=419.20. $^1$H NMR (300 MHz, Methanol-$d_4$) δ 8.47 (s, 1H), 7.74-7.14 (m, 11H), 7.09 (t, J=7.9 Hz, 1H), 7.09-6.77 (m, 6H), 3.75 (s, 3H).

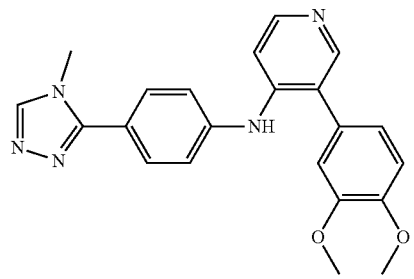 [SMILES: COc1ccc(-c2cnccc2Nc2ccc(-c3nncn3C)cc2)cc1OC]

3-(3,4-dimethoxyphenyl)-N-[4-(4-methyl-4H-1,2,4-triazol-3-yl)phenyl]pyridin-4-amine (D7). To a solution of 4-(chlorophenyl)-4-methyl-4-H-1,2,4-triazole (59 mg, 0.30 mmol) and $Cs_2CO_3$ (230 mg, 0.71 mmol) in 1,4-dioxane (2.10 mL) 3-(3,4-dimethoxyphenyl)pyridin-4-amine (70 mg, 0.30 mmol) was added. Reaction mixture was degassed for 30 minutes. Then xantphos (18 mg, 0.03 mmol) and chloroform adduct of tris(dibenzylideneacetone)dipalladium (0) (16 mg 0.02 mmol) were added and the mixture was stirred at 100° C. overnight. The reaction mixture was filtrated through celite, washed with MeOH. Filtrate was concentrated and purified via column chromatography using 0-10% MeOH in DCM as eluent. Fractions containing the title compound were combined and concentrated. Product was re-purified via P-TLC using 4% MeOH in DCM as an eluent to give desired product as white solid (20 mg, 16%). LCMS-Method 3 (305 nm): RT=2.69 min, 98.21% purity, [M+H]=388.24. $^1$H NMR (300 MHz, Methanol-$d_4$) δ 8.55 (s, 1H), 8.26-8.19 (m, 2H), 7.72-7.58 (m, 2H). 7.43-7.25 (m, 3H), 7.09 (d, J=4.2 Hz, 3H). 3.89 (s, 3H), 3.85 (s, 3H), 3.82 (s. 3H).

Synthesis Method F

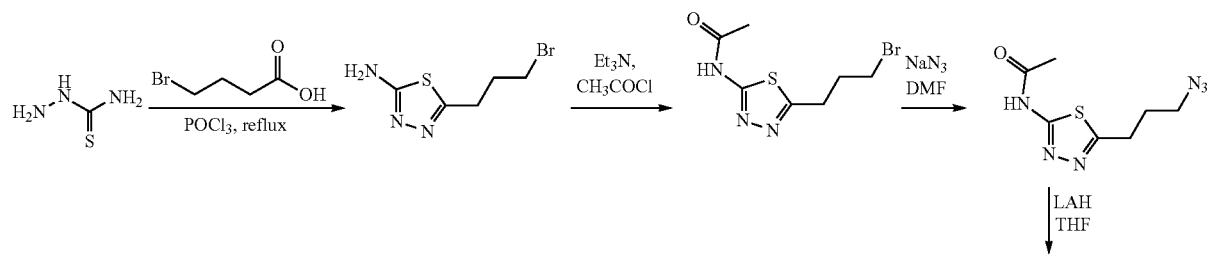

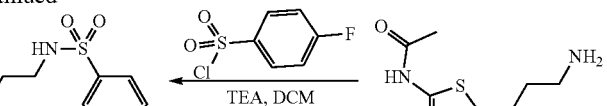

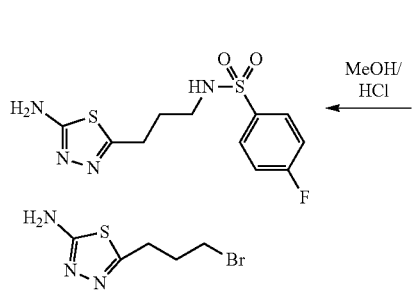

5-(3-bromopropyl)-1,3,4-thiadiazol-2-amine. Phosphoryl chloride (7.37 mL, 79.0 mmol) was added to aminothiourea (2.185 g, 24.0 mmol) and 4-bromobutanoic acid. The mixture was stirred at 85° C. overnight, cooled and poured into ice. Solution of saturated sodium biscarbonate was added the solution and the water layer was extracted three times with EA (3×80 mL). Combined organic layers were dried over sodium sulfate, filtered and evaporated. Crude product was purified via column chromatography using 0-10% DCM in MeOH as eluent. Fractions containing the title compound were combined and concentrated (3.301 g, 62%). UPLC (254 nm): RT=1.91 min, 68% purity, [M−H]=223.7.

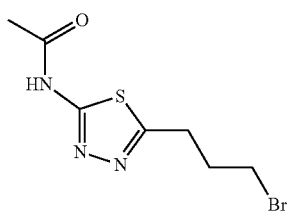

N-[5-(3-bromopropyl)-1,3,4-thiadiazol-2-yl]acetamide. To the solution of 5-(3-bromopropyl)-1,3,4-thiadiazol-2-amine (3.3 g, 14.8 mmol) in anhydrous DCM (35 mL), under argon atmosphere, trietylamine (4.14 mL, 29.7 mmol) and acetylchloride (1.16 mL, 16.3 mmol) were added. Reaction mixture was stirred for 6 hours at ambient temperature. After that time 1M HCl was added (50 mL) and the water layer was extracted three times with DCM (3×80 mL). Combined organic layers were dried over sodium sulfate, filtered, evaporated to provide the pure product (3.144 g, 80%). UPLC (254 nm): RT=2.43 min. 89% purity, [M+H]=265.65.

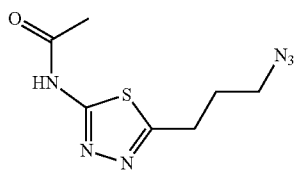

N-[5-(3-azidopropyl)-1,3,4-thiadiazol-2-yl]acetamide. To the solution of N-[5-(3-bromopropyl)-1,3,4-thiadiazol-2-yl]acetamide (1.0 g, 3.8 mmol) in anhydrous DMF (20.0 mL), under argon atmosphere, sodium azide (0.37 g, 5.7 mmol) was added. Reaction mixture was stirred for 2 hours. After that time water (10 mL) was added and the water layer was extracted with DCM (3×80 mL). Combined organic layers were dried over sodium sulfate, filtered and evaporated to provide the pure product (0.6 g, 71%). UPLC (254 nm): RT=2.29 min, 98% purity, [M+H]=227.0.

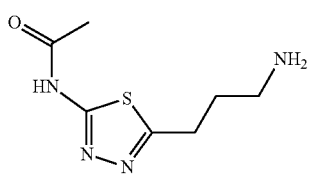

N-[5-(3-aminopropyl)-1,3,4-thiadiazol-2-yl]acetamide. Solution of methyl N-[5-(3-azidopropyl)-1,3,4-thiadiazol-2-yl]acetamide (0.6 g, 2.7 mmol) in anhydrous tetrahydrofuran (7 mL was dropped to the suspension of LAH pellets (0.1 g, 2.8 mmol) in anhydrous THF (5 mL) under argon atmosphere. Reaction mixture was stirred 1h at ambient temperature. After that time LAH (0.1 g. 2.8 mmol) was added. The stirring was continued for 2 hours. After that time 0.2 mL of water was added, followed by addition of 0.4 mL of 20% NaOH and 0.6 mL of water. The suspension was filtered throw cellite and washed with DCM/MeOH 9:1. Evaporation of solvents gave titled compound (0.22 g, 41%). UPLC (254 nm): RT=1.17 min, 57% purity, [M−H]=201.2.

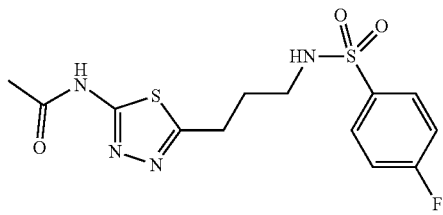 [SMILES: CC(=O)Nc1nnc(CCCNS(=O)(=O)c2ccc(F)cc2)s1]

N-{5-[3-(4-fluorobenzenesulfonamido)propyl]-1,3,4-thiadiazol-2-yl}acetamide. To the solution of 3,4-dichlorobenzenosulfonyl chloride (165 mg, 0.85 mmol) in the mixture of solvents DCM (1.0 mL) and pyridine (1.0 mL) N-[5-(3-aminopropyl)-1,3,4-thiadiazol-2-yl]acetamide (170 mg, 0.85 mmol) was added. The reaction mixture was stirred for 18 hours at ambient temperature. After that time solvents were evaporated and to the residues 1M HCl was added and the water layer was extracted with DCM (3×20 mL). Combined organic layers were dried over sodium sulfate, filtered, evaporated to provide the product (0.02 g, 7%). UPLC (254 nm): RT=2.56 min, 98% purity, [M+H]=358.85.

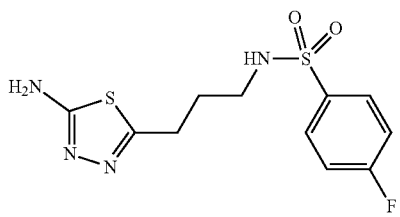 [SMILES: Nc1nnc(CCCNS(=O)(=O)c2ccc(F)cc2)s1]
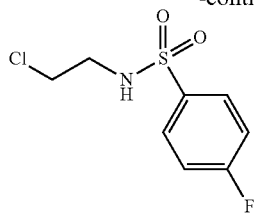

N-[3-(5-amino-1,3,4-thiadiazol-2-yl)propyl]-4-fluorobenzene-1-sulfonamide (E2). N-{5-[3-(4-fluorobenzenesulfonamido)propyl]-1,3,4-thiadiazol-2-yl}acetamide (20 mg, 0.06 mmol) was dissolved in the solution of HCl (2 mL) and MeOH (2 mL). The reaction mixture was stirred for 18 hours at 80° C. After that time solution of sodium biscarbonate was added and the water layer was extracted with DCM (3×10 mL). Combined organic layers were dried over sodium sulfate, filtered and evaporated. Purification of crude product via P-TLC using 4% methanol in dichloromethane as an eluent gave desired product (3 mg, 17%). LCMS-Method 1 (200 nm): RT=2.56 min, 96.0% purity. [M+H]=317.15. $^{1}$H NMR (300 MHz, MeOH-d$_4$) δ 7.87-7.94 (m, 2H), 7.29-7.39 (m, 2H), 2.86-2.97 (m, 4H), 1.82-1.91 (m, 2H).

Synthesis Method G

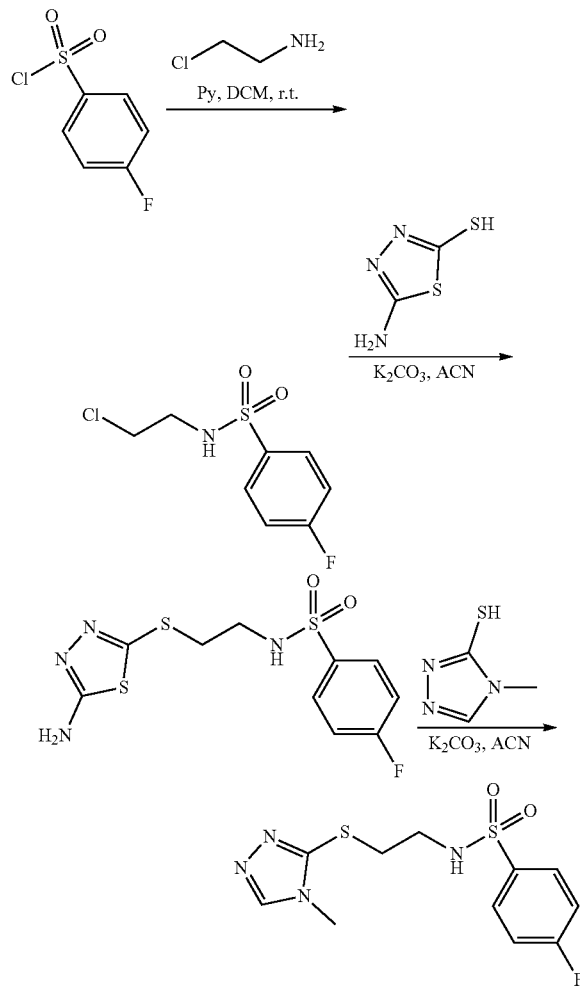

N-(2-chloroethyl)-4-fluorobenzene-1-sulfonamide 2-chloroethylamine hydrochloride (0.25 g, 2.2 mmol), 4-fluorobenzenesulfonyl chloride (0.42 g, 2.2 mmol), were dissolved in DCM (2.5 mL) and pyridine (2.5 mL). Reaction was stirred at room temperature overnight. The mixture was diluted with DCM (15.0 mL) and washed with 1M solution of hydrochloric acid (20 mL). Organic layer was dried over sodium sulfate, filtered and evaporated. Title compound was obtained as yellow oil (0.5 g, 86% yield). $^{1}$H NMR (300 MHz, CDCl$_3$) δ 7.82-7.95 (m, 2H), 7.25-7.33 (m, 2H), 4.92 (t, 1H), 3.54-3.64 (t, 2H), 3.32-3.44 (dt, 2H).

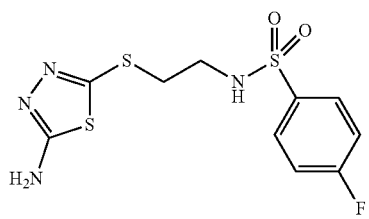 [SMILES: Nc1nnc(SCCNS(=O)(=O)c2ccc(F)cc2)s1]

N-{2-[(5-amino-1,3,4-thiadiazol-2-yl)sulfanyl]ethyl}-4-fluorobenzene-1-sulfonamide (E3) N-(2-chloroethyl)-4-fluorobenzene-1-sulfonamide (0.18 g, 0.75 mmol), 2-Amino-5-mercapto-1,3,4-thiadiazole (0.10 g, 0.75 mmol), potassium carbonate (0.31 g, 2.25 mmol) were dissolved in acetonitrile (2.0 mL) and stirred at 80° C. overnight. After that time reaction mixture was cooled to room temperature, filtered thru celite, evaporated and purified via column chromatography using MeOH in DCM 0-5% as aluent to give pure product (120 mg, 48%) LCMS-Method 2 (200 nm): RT=4.24 min, 99.71% purity, [M+H]=334.97, $^{1}$H NMR (300 MHz, DMSO-d$_6$) δ 7.92 (br s, 1H), 7.80-7.90 (m, 2H), 7.37-7.47 (m, 2H), 7.30 (br s. 2H), 3.07 (m, 4H).

4-fluoro-N-{2-[(4-methyl-4H-1,2,4-triazol-3-yl)sulfanyl]ethyl}benzene-1-sulfonamide (G2) N-(2-chloroethyl)-4-fluorobenzene-1-sulfonamide (0.21 g, 0.87 mmol), 3-mercapto-4-methyl-4H-1,2,4-triazole (0.10 g, 0.87 mmol), potassium carbonate (0.36 g, 2.61 mmol) were dissolved in acetonitrile (2.0 mL) and stirred at 80° C. overnight. After that time reaction mixture was cooled to room temperature, filtered thru celite, evaporated and purified via column chromatography using MeOH in DCM 0-5% as eluent to give pure product (200 mg, 73%) LCMS-Method 2 (200 nm): RT=3.79 min, 97.39% purity, [M+H]=317.05, 1H NMR (300 MHz, DMSO-d6) δ 8.53 (s, 1H), 7.97 (s, 1H), 7.88-7.77 (m, 2H). 7.49-7.35 (m, 2H), 3.53 (s, 3H), 3.21-2.99 (m, 4H).

Synthesis Method H

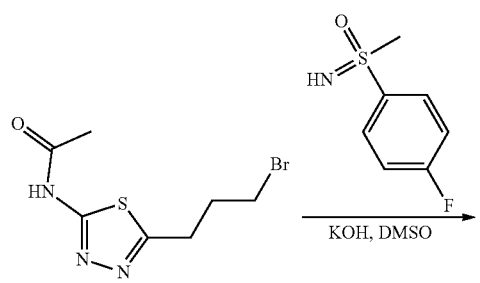

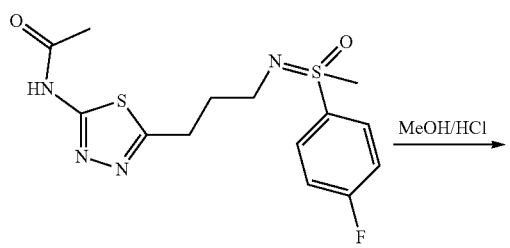

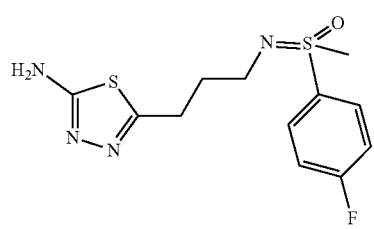

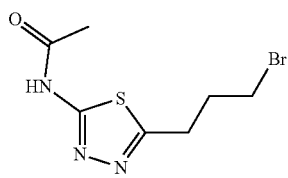

N-[5-(3-bromopropyl)-1,3,4-thiadiazol-2-yl]acetamide was synthesized according to the procedure described for E2.

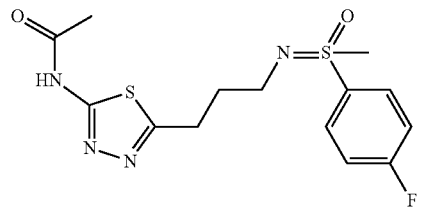 [SMILES: CC(=O)Nc1nnc(CCCN=S(C)(=O)c2ccc(F)cc2)s1]

N-[5-(3-{[(4-fluorophenyl)(methyl)oxo-$\lambda^6$-sulfanylidene]amino}propyl)-1,3,4-thiadiazol-2-yl]acetamide.

To the solution of (4-fluorophenyl)(imino)methyl-$\lambda_6$-sulfanone (0.1 g, 0.58 mmol) in anhydrous DMSO (4 mL), under argon atmosphere, KOH (0.065 g, 1.15 mmol) was added. The suspension was stirred for 1.5 hours at ambient temperature. After that time solution of N-[5-(3-bromopropyl)-1,3,4-thiadiazol-2-yl]acetamide (0.229 g, 0.87 mmol) in anhydrous DMSO (4 mL) was slowly (1.5 hours) dropped. The reaction was quenched with water (5 mL) immediately after the dropping was completed. The water layer was extracted with DCM (10 mL) and after that extracted 5 times with mixture of chloroform/isopropyl alcohol 3:1 (5×20 mL). Combined organic layers were dried over sodium sulfate, filtered, evaporated to provide the pure product (0.06 g, 29%). UPLC (254 nm): RT=2.2 min, 61% purity, [M+H]=357.2

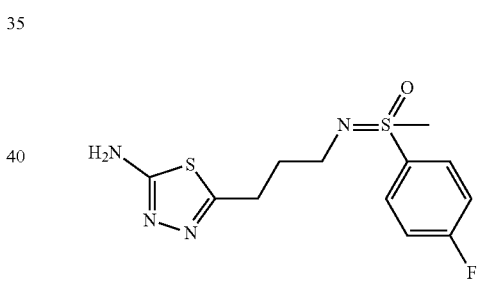

5-(3-{[(4-fluorophenyl)(methyl)oxo-$\lambda^6$-sulfanylidene]amino}propyl)-1,3,4-thiadiazol-2-amine (F2). N-[5-(3-{[(4-fluorophenyl)(methyl)oxo-$\lambda^6$-sulfanylidene]amino}propyl)-1,3,4-thiadiazol-2-yl]acetamide (20 mg, 0.06 mmol) was dissolved in the solution of HCl (2 mL) and MeOH (2 mL). The reaction mixture was stirred for 3 hours at 80° C. After that time solution of sodium biscarbonate was added and the water layer was extracted with DCM (3×10 mL). Combined organic layers were dried over sodium sulfate, filtered and evaporated. Purification of crude product via P-TLC using 4% methanol in dichloromethane as an eluent gave desired product (5 mg, 9%). LCMS (245 nm): RT=5.91 min, 98.88% purity. [M+H]=315.17 $^1$H NMR (300 MHz. CDCl$_3$) δ 7.98-7.87 (m, 2H), 7.22-7.26 (m, 2H), 5.21 (s, 2H), 3.11 (s, 2H), 2.89-3.09 (m, 2H), 1.97-2.00 (m, 2H).

Synthesis Method I

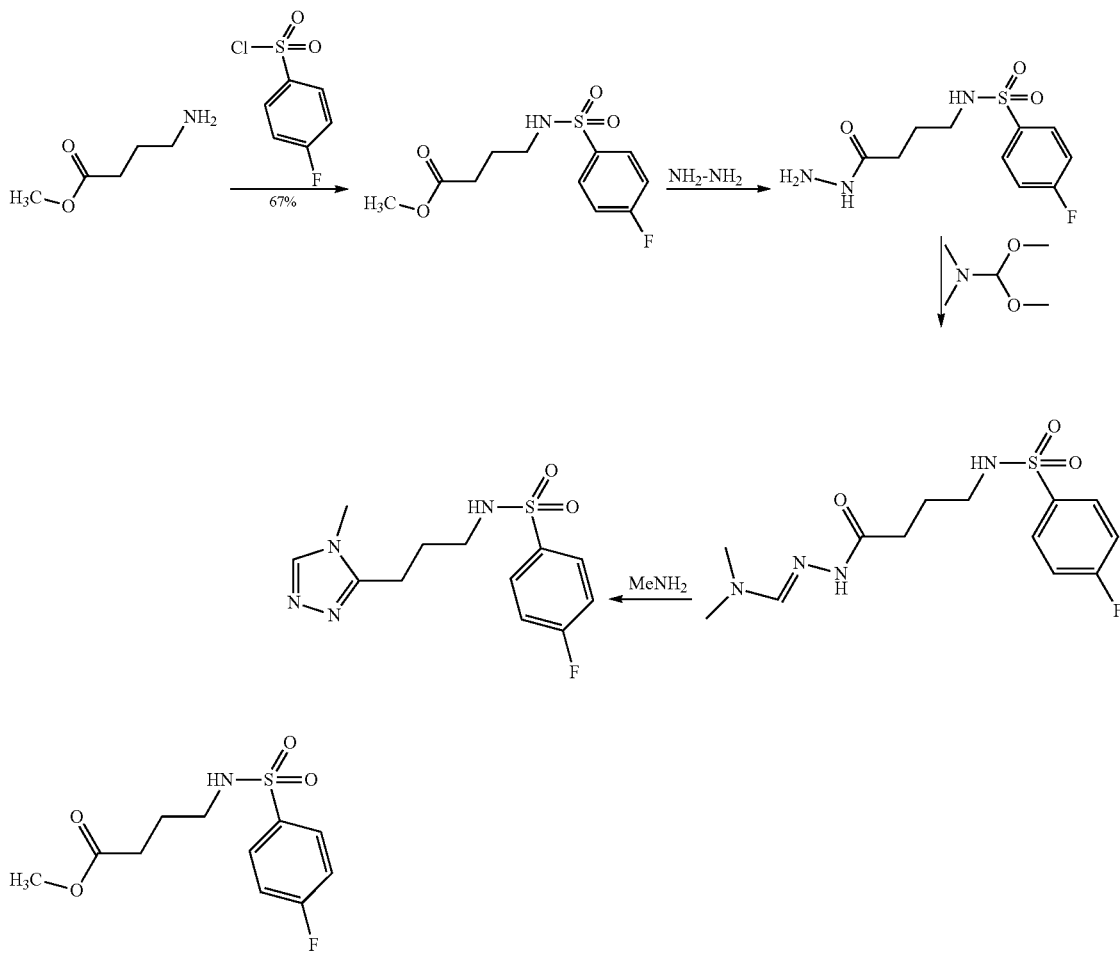

Methyl-4-(4-fluorobenzenesulfonamido)butanoate. To the solution of 3,4-dichlorobenzenosulfonyl chloride (633 mg, 3.25 mmol) in DCM (3.0 mL) trietylamine (1.3 mL, 9.76 mmol) and methyl-4-aminobutanoate hydrochloride (500 mg, 3.25 mmol) was added. The reaction mixture was stirred for 18 hours at ambient temperature. After that time 1M HCl (5 mL) was added and the water layer was extracted with DCM (3×5 mL). Combined organic layers were dried over sodium sulfate, filtered, evaporated to provide the product (0.605 g, 68%). UPLC (254 nm): RT=2.89 min, [M+H]= 275.85.

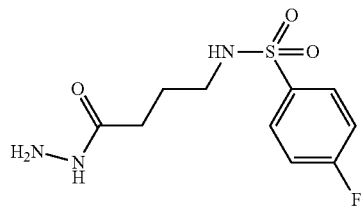 [SMILES: NNC(=O)CCCNS(=O)(=O)c1ccc(F)cc1]

4-Fluoro-N-[3-(hydrazinecarbonyl)propyl]benzene-1-sulfonamide. To the solution of methyl-4-(4-fluorobenzene-sulfonamido)butanoate (605 mg, 2.09 mmol) in EtOH (10 mL) 50% hydrazine in $H_2O$ (0.65 mL, 10.4 mmol) was added. Reaction mixture was stirred for 1 hour at 80° C. After that time the reaction mixture was cooled, water (20 mL) was added and water layer was extracted three times with EA (3×10 mL). Combined organic layers were dried over sodium sulfate, filtered and evaporated to provide the pure product (180 mg, 31%). UPLC (254 nm): RT=1.88 min, 65% purity, [M+H]=276.2.

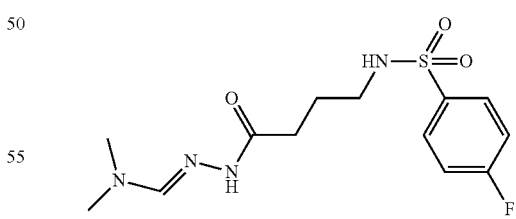

N-(3-(N'-[(1-dimethylamino)methylidene]hydrazinecarbonyl)propyl)-4-fluorobenzene-1-sulfonamide. To the solution of 4-fluoro-N-[3-(hydrazinecarbonyl)propyl]benzene-1-sulfonamide (180 mg, 0.65 mmol) in MeOH (2 mL) N,N-dimethylformamide dimethylacetal (78 mg, 0.65 mmol) was added. Reaction mixture was stirred for 1 hour at 80° C. After that time solvent was evaporated to obtain desired product. (216 mg, 100%). UPLC (254 nm): RT=1.78 min. 60% purity, [M+H]=331.3.

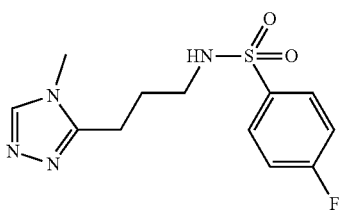 [SMILES: Cn1cnnc1CCCNS(=O)(=O)c1ccc(F)cc1]

4-fluoro-N-[3-(4-methyl-4H-1,2,4-triazol-3-yl)propyl]benzene-1-sulfonamide (G1). MeNH$_2$ 2M in THF (32 mL, 3.3 mmol) was added to the solution of N-(3-{N'-[(1-dimethylamino)methylidene]hydrazinecarbonyl}propyl)-4-fluorobenzene-1-sulfonamide (216 mg, 0.63 mmol) in anhydrous THF (5.0 mL) under argon atmosphere. Reaction mixture was cooled to 0° C. and acetic acid (2 mL) was carefully added. Reaction mixture was stirred for 1 hour at 100° C. After that time reaction was cooled to room temperature and water (5 mL) was added and water layer was extracted three times with EA (3×20 mL). Combined organic layers were dried over sodium sulfate, filtered and evaporated. Crude product was purified via column chromatography using 0-4% MeOH in DCM as eluent. Obtained 40 mg of product was re-purified via P-TLC using 4% MeOH in DCM as an eluent and then re-purified via preparative HPLC. Fraction containing the title compound in pure form was concentrated (3 mg, 2%). LCMS-Method 1 (200 nm): RT=6.17 min, 99.5% purity, [M+H]=299.2. $^1$H NMR (300 MHz, CDCl$_3$) δ 8.09 (s, 1H). 7.84-7.90 (m, 2H), 7.15-7.23 (m, 2H), 5.62 (t. J=5.6 Hz, 1H), 3.64 (s. 3H), 3.12 (q, J=3.1 Hz, 2H), 2.85 (t, J=6.6 Hz, 2H) 2.06-2.15 (m, 2H).

Synthesis Method K

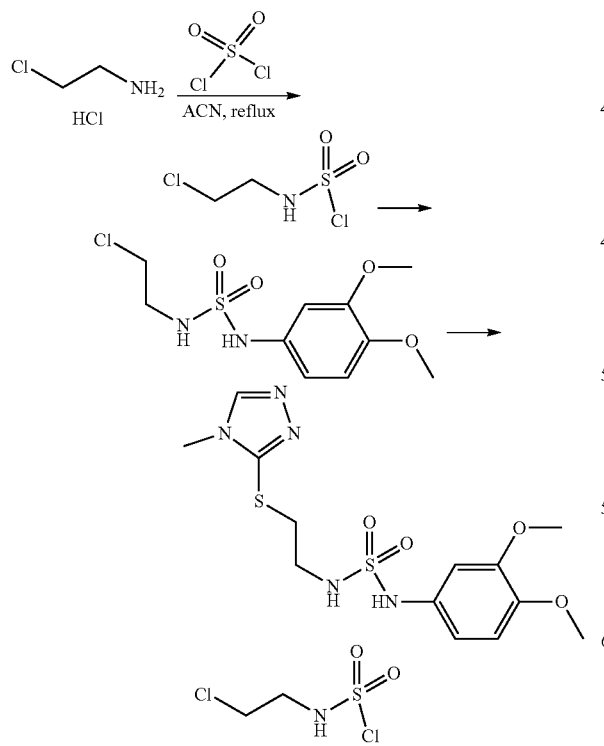

N-(2-chloroethyl)sulfamoyl chloride 2-chloroethylamine hydrochloride (0.50 g, 4.3 mmol), sulfuryl chloride (3.49 g, 2.10 mL. 25.8 mmol), were dissolved in acetonitrile (5.0 mL) Reaction was stirred at 80° C. overnight. The mixture was concentrated and used directly into next step. Title compound was obtained as yellow oil (0.5 g, 86% yield). $^1$H NMR (300 MHz, d$_6$-DMSO) δ 11.0 (bs, 1H), 3.83 (t, 2H), 3.36 (t, 2H)

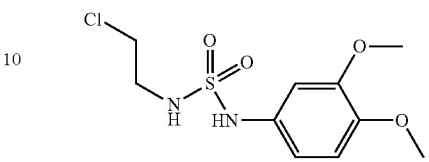

(2-chloroethyl)[(3,4-dimethoxyphenyl)sulfamoyl]amine N-(2-chloroethyl)sulfamoyl chloride (0.14 g, 0.78 mmol) and 3,4-dimetoxyaniline (0.12 g, 0.78 mmol) were dissolved in DCM (1.2 mL) and pyridine (1.2 mL). Reaction was stirred at room temperature overnight. After that time reaction mixture was cooled to room temperature. The mixture was diluted with DCM (15.0 mL) and washed with 1M solution of hydrochloric acid (20 mL). Organic layer was dried over sodium sulfate, filtered and evaporated. Title compound was obtained as yellow oil (0.23 g. 100% yield). Compound was used in the next step without further purification. UPLC (280 nm): RT=3.14 min, 11% purity. [M+H]= 294.95

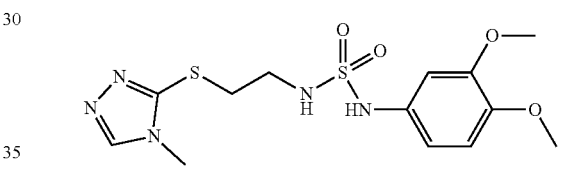

[(3,4-dimethoxyphenyl)sulfamoyl]((2-[(4-methyl-4H-1,2,4-triazol-3-yl)sulfanyl]ethyl))amine (G5) (2-chloroethyl)[(3,4-dimethoxyphenyl)sulfamoyl]amine (0.085 g, 0.74 mmol), 3-mercapto-4-methyl-4H-1,2,4-triazole (0.22 g, 0.74 mmol), potassium carbonate (0.31 g, 2.21 mmol) were dissolved in acetonitrile (1.7 mL) and stirred at 80° C. for 3 hours. After that time reaction mixture was cooled to room temperature, filtered thru celite, evaporated and purified via column chromatography using MeOH in DCM 0-5% as eluent to give pure product (8 mg, 3%) LCMS-Method 2 (200 nm): RT=3.08 min, 99.1% purity, [M+H]=374.03, 1H NMR (400 MHz, DMSO-d6) δ 7.57 (s, 1H), 6.96-6.75 (m, 2H), 6.72-6.63 (m, 1H), 3.71 (d, J=2.7 Hz, 6H), 3.51 (s, 3H), 3.23-3.08 (m, 4H).

Synthesis Method L

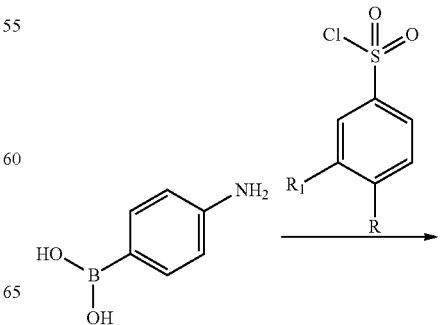

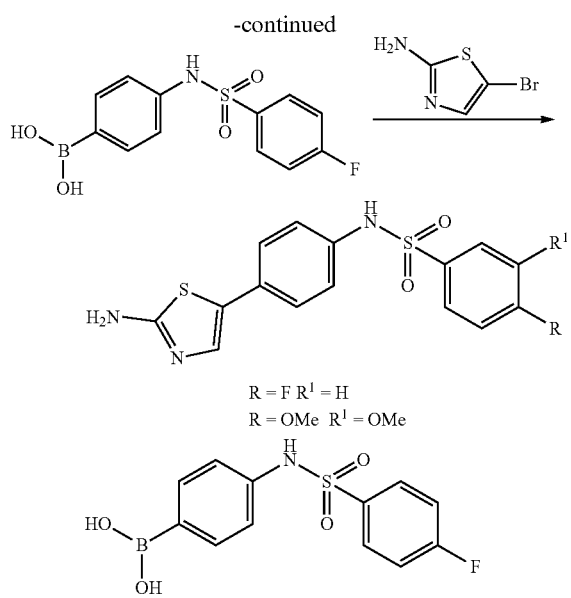

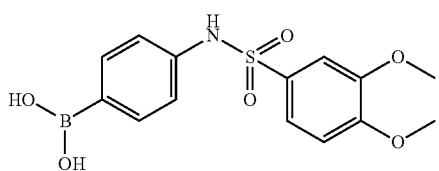 [SMILES: COc1ccc(S(=O)(=O)Nc2ccc(B(O)O)cc2)cc1OC]

[4-(4-fluorobenzenesulfonamido)phenyl]boronic acid 4-aminophenylboronic acid (1.5 g, 8.7 mmol), and 4-fluorophenylsulfonyl chloride (1.53 g, 7.9 mmol) were dissolved in pyridine (43 mL). The mixture was stirred at 5000 overnight, cooled to room temperature and solvent was removed in vacuo. Crude product was used in next step without any further purification (5.4 g, 200%). UPLC (254 nm): RT=2.88 min, 50% purity, [M-2H]=293.5.

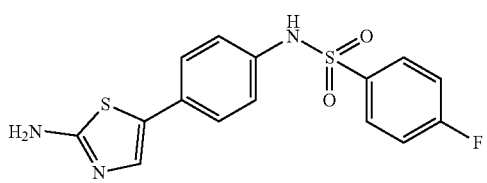 [SMILES: Nc1ncc(-c2ccc(NS(=O)(=O)c3ccc(F)cc3)cc2)s1]

[4-(3,4-dimethoxybenzenesulfonamdo)phenyl]boronic acid 4-aminophenylboronic acid (2.35 g, 11.6 mmol), and 3,4-dimethoxyphenylsulfonyl chloride (1.53 g, 7.9 mmol) were dissolved in pyridine (80 mL). The mixture was stirred at 50° C. overnight, cooled to room temperature and solvent was removed in vacuo. Crude product was used in next step without any further purification (8.1 g, 200%). UPLC (254 nm): RT=2.77 min, 50% purity, [M-2H]=335.6.

N-[4-(2-amino-1,3-thiazol-5-yl)phenyl]-4-fluorobenzene-1-sulfonamide (11). Solution of [4-(4-fluorobenzenesulfonamido)phenyl]boronic acid (2.75 g, 9.2 mmol), 2-amino-5-bromo-thiazole hydrobromide (2.00 g, 7.7 mmol) and potassium carbonate (3.21 g, 23.1 mmol) in 1,4-dioxane (40.0 mL) and water (4.0 mL) was degassed with argon flow over 20 min and [1,1'-bis(diphenylphosphino)ferrocene]dichloropalladium(II) complex with dichloromethane (0.84 g, 1.2 mmol) was added as one portion. Reaction mixture was stirred overnight at 130° C. After this time reaction was filtered thru celite, which was washed with DCM, water (40 mL) was added, layers were separated and water layer was extracted three with DCM (3×25 mL), organic layers were combined, dried over sodium sulfate, filtered and evaporated. Crude product was purified via column chromatography using Methanol in DCM (0-3%) as eluent, and fraction containing product was additional re-purified via preparative HPLC method to give the pure product as red solid (48 mg, 2%). LCMS-Method 1 (254 nm): RT=6.73 min, 99.6% purity, [M+H]=349.7. $^1$H NMR (300 MHz, DMSO-$d_6$) δ 10.36 (s, 1H), 7.84-7.76 (m, 2H), 7.45-7.36 (m, 2H), 7.28 (dd, J=6.6, 2.0 Hz, 3H), 7.14-6.97 (m, 4H).

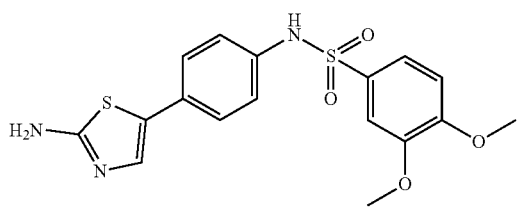 [SMILES: COc1ccc(S(=O)(=O)Nc2ccc(-c3cnc(N)s3)cc2)cc1OC]

N-[4-(2-amino-1,3-thiazol-5-yl)phenyl]-3,4-dimethoxybenzene-1-sulfonamide (12). Solution [4-(3,4-dimethoxybenzenesulfonamido)phenyl]boronic acid (1.64 g, 5.5 mmol), 2-amino-5-bromo-thiazole hydrobromide (1.20 g, 4.6 mmol) and potassium carbonate (3.21 g, 23.1 mmol) in 1,4-dioxane (40.0 mL) and water (4.0 mL) was degassed with argon flow over 20 min and [1,1'-bis(diphenylphosphino)ferrocene]dichloropalladium(II) complex with dichloromethane (0.51 g, 0.7 mmol) was added as one portion. Reaction mixture was stirred overnight at 130° C. After this time reaction was filtered thru celite, which was washed with DCM, water (40 mL) was added, layers were separated and water layer was extracted three with DCM (3×25 mL), organic layers were combined, dried over sodium sulfate, filtered and evaporated. Crude product was purified via column chromatography using Methanol in DCM (0-3%) as eluent, and fraction containing product was additional re-purified via preparative HPLC method to give the pure product as orange solid (45 mg, 3%). LCMS-Method 2 (200 nm): RT=2.99 min, 99.9% purity, [M+H]= 392.0. $^1$H NMR (300 MHz, DMSO-$d_6$) δ 8.16 (s, 1H), 7.34-7.22 (m, 5H), 7.13-6.95 (m, 5H), 3.79 (s, 3H), 3.76 (s, 3H).

Synthesis Method M

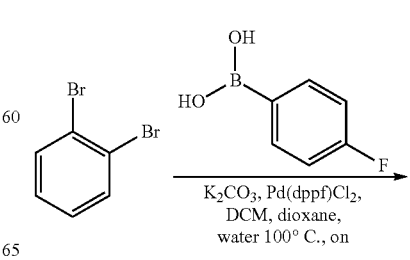

-continued

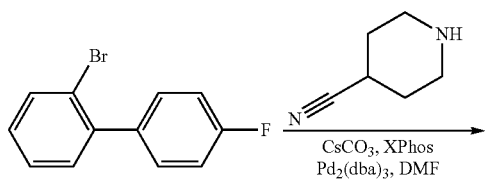

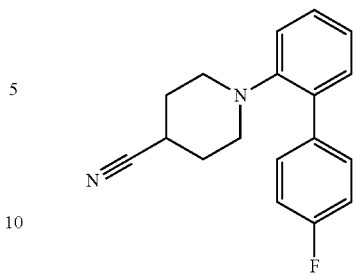

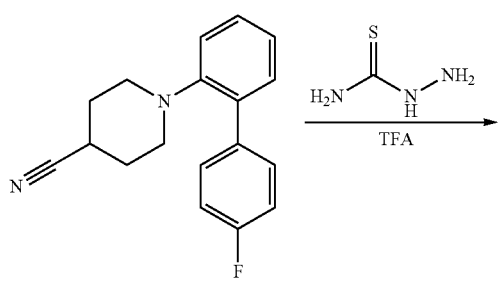

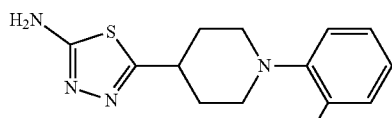

Cmp. L2

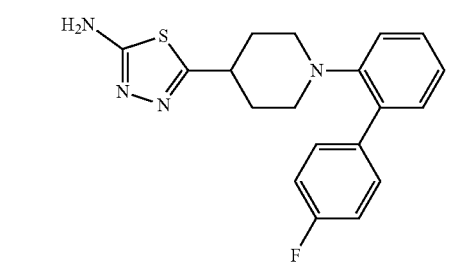 [SMILES: Nc1nnc(C2CCN(c3ccccc3-c3ccc(F)cc3)CC2)s1]

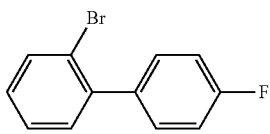

2-bromo-4'-fluoro-1,1'-biphenyl Solution of 1,2-dibromobenzene (8.26 g, 35.0 mmol), 4-flurophenylboronic acid (2.5 g, 17.9 mmol) and sodium carbonate (3.79 g, 35.0 mmol) in ethanol (35.0 mL), toluene (35.0 mL) and water (35.0 mL) was degassed with argon flow over 20 min and tetrakis (triphenylphosphine) palladium (0) (1.00 g, 0.9 mmol) was added as one portion. Reaction mixture was stirred overnight at 100° C. After this time reaction was filtered thru celite, layers were separated and water layer was extracted twice with ethyl acetate (2×15 mL), organic layers were combined, dried over sodium sulfate, filtered and evaporated. Crude product was purified via column chromatography using hexanes as eluent to give the title product (5.50 g, 122%). UPLC (254 nm): RT=4.33 min, 91% purity, [M+H]=not observed.

1-{4'-fluoro-[1,1'-biphenyl]-2-yl} piperidine-4-carbonitrile Solution of 2-bromo-4'-fluoro-1,1'-biphenyl (0.3 g, 1.2 mmol), piperidine-4-carbonitrile (0.2 g, 1.8 mmol), XantPhos (0.14 g, 0.24 mmol) and cesium carbonate (0.78 g, 2.4 mmol) in anhydrous 1,4-dioxane (3.0 mL), was degassed with argon flow over 20 min and tris (dibenzylideneacetone) dipalladium (0) (0.11 g, 0.12 mmol) was added as one portion. Reaction mixture was stirred overnight at 100° C. After this time reaction was filtered thru celite, washed with ethyl acetate and evaporated. Crude product was purified via column chromatography using ethyl acetate in hexanes (0-4%) as eluent to give the title product (0.18 g, 54%). UPLC (254 nm): RT=4.25 min, 90% purity, [M+H]=281.4.

5-(1-{4'-fluoro-[1,1'-biphenyl]-2-yl}piperidin-4-yl)-1,3,4-thiadiazol-2-amine (L2) Solution of 1-{4'-fluoro-[1,1'-biphenyl]-2-yl}piperidine-4-carbonitrile (0.18 g, 0.7 mmol) and thiosemicarbazide (0.09 g, 1.05 mmol) trifluoroacetic acid (1.5 mL) was stirred at 65° C. over 2 hours. After this time reaction was cooled to room temperature diluted with saturated sodium bicarbonate solution (15 mL) and extracted with DCM (3×15 mL), organic layers were combined, dried over sodium sulfate, filtered and evaporated. Crude product was triturated with ethyl acetate (1 mL) filtered off and dried under vacuum to give pure product (100 mg, 45%) LCMS (LCMS method: LCMS-002-20-80-95-12-05-25 (Gemini-BCM)-UV, 200 nm): RT=4.97 min, 96.7% purity, [M+H]= 355.2. $^1$H NMR (300 MHz, DMSO-$d_6$) δ 7.70-7.58 (m, 2H), 7.38-7.17 (m, 4H), 7.16-6.89 (m, 4H), 3.05 (d, J=11.8 Hz, 2H), 2.87 (ddd, J=11.5, 7.6, 3.9 Hz, 1H), 2.62 (t, J=11.3 Hz, 2H), 1.86 (d, J=12.7 Hz, 2H), 1.54 (qd, J=12.0, 3.8 Hz, 2H).

Synthesis Method N

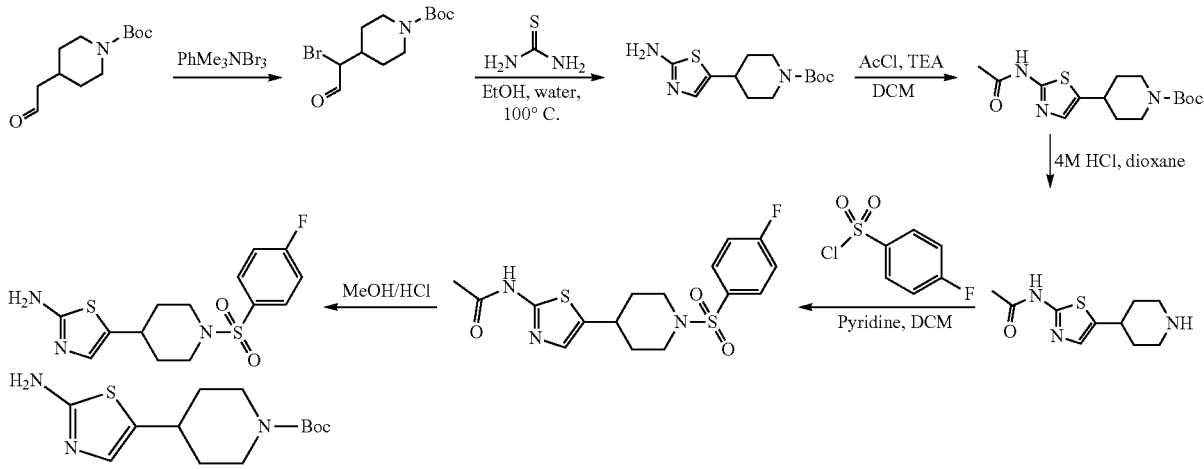

tert-Butyl-4-(2-amino-1,3-thiazol-5-yl)piperidine-1-carboxylate was synthesized in two steps according to the literature (overall yield: 60%).

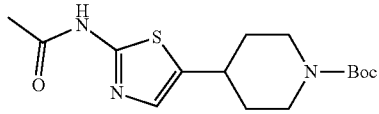 [SMILES: CC(=O)Nc1ncc(C2CCN(C(=O)OC(C)(C)C)CC2)s1]

tert-Butyl-4-(2-acetamido-1,3-thiazol-5-yl)piperidine-1-carboxylate. To the solution of tert-butyl-4-(2-amino-1,3-thiazol-5-yl)piperidine-1-carboxylate (3.75 g, 13.23 mmol) in anhydrous DCM (35 mL), under argon atmosphere, trietylamine (3.69 mL, 26.4 mmol) and acetylchloride (1.00 mL, 14.6 mmol) were added. Reaction mixture was stirred for 48 hours at ambient temperature. After that time water was added (50 mL) and the water layer was extracted five times with DCM (5×80 mL). Combined organic layers were dried over sodium sulfate, filtered and evaporated to provide the pure product (4.175 g, 97%). UPLC (254 nm): RT=4.27 min. [M+H]=326.25.

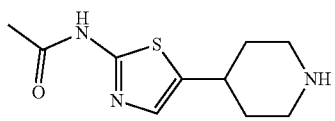

N-[5-(piperidin-4-yl)-1,3-thiazol-2-yl]acetamide. To the solution of tert-butyl 4-(2-acetamido-1,3-thiazol-5-yl)piperdino-1-carboxylate (4.175 g, 12.83 mmol) in THF (90.0 mL), 4M HCl in dioxane (10 mL) was added. Reaction mixture was stirred for 18 hours. After that time reaction mixture was filtered, the precipitation was washed with EA (2×40 mL) and dried under reduced pressure to give pure product (2.752 g, 82%). UPLC (254 nm): RT=2.1 min, [M+H]=226.25.

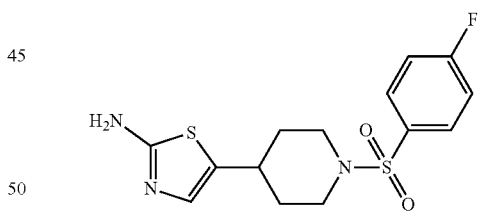

N-{5-[1-(4-fluorobenzenesulfonyl)piperidin-4-yl]-1,3-thiazol-2-yl}acetamide. To a solution of 3,4-dichlorobenzenosulfonyl chloride (182 mg, 0.94 mmol) in the mixture of solvents DCM (3.0 mL) and pyridine (3.0 mL) N-[5-(piperidin-4-yl)-1,3-thiazol-2-yl]acetamide (211 mg, 0.94 mmol) was added. The reaction mixture was stirred for 48 hours at ambient temperature. After that time solvents were evaporated and crude was taken to the next step.

5-[1-(4-fluorobenzenesulfonyl)piperidin-4-yl]-1,3-thiazol-2-amine (M1). N-{5-[1-(4-fluorobenzenesulfonyl)piperidin-4-yl]-1,3-thiazol-2-yl}acetamide (300 mg, 0.78 mmol) was dissolved in the solution of HCl (12 mL) and MeOH (12 mL). The reaction mixture was stirred for 18 hours at 80° C. After that time solution of saturated sodium biscarbonate was added and the water layer was extracted with DCM (3×10 mL). Combined organic layers were dried over sodium sulfate, filtered, evaporated and purified via column chromatography using 0-10% MeOH in DCM as eluent. Fractions containing the title compound were combined and concentrated. Product was re-purified via P-TLC using 4% MeOH in DCM as an eluent (16 mg, 6%). LCMS-Method 1 (220 nm): RT=6.37 min, 95.99% purity, [M+H]=342.07. $^{1}$H NMR (300 MHz, CD$_{3}$OD) δ 7.85-7.90

(m, 2H), 7.35-7.41 (m, 2H), 6.7 (s, 1H), 3.82 (d, J=12.0 Hz, 2H), 2.61-2.73 (m, 1H), 2.40-2.49 (m, 2H), 1.98-2.04 (m, 2H), 1.60-1.75 (m, 2H).

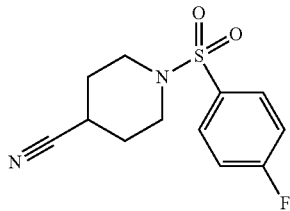 [SMILES: N#CC1CCN(S(=O)(=O)c2ccc(F)cc2)CC1]

1-(4-fluorobenzenesulfonyl)piperidine-4-carbonitrile. To a solution of piperidine-4-carbonitrile (500 mg, 4.54 mmol) in the mixture of solvents DCM (5.0 mL) and pyridine 4-fluorobenzenesulfonyl chloride (880 mg, 4.54 mmol) was added. The reaction mixture was stirred for 16 hours at ambient temperature. Reaction mixture was diluted with 1M HCl (50 ml) and DCM (50 ml) and layers were separated. Organic layer was washed twice with 1M HCl (2×50 ml) and concentrated to give desired product as beige solid. $^1$H NMR (400 MHz, Chloroform-d) δ 7.98-7.66 (m, 2H), 7.36-7.12 (m, 4H), 3.29-3.06 (m, 4H), 2.91-2.71 (m, 1H), 2.17-1.89 (m, 4H).

5-[1-(4-fluorobenzenesulfonyl)piperidin-4-yl]-1,3,4-thiadiazol-2-amine (M2). 1-(4-fluorobenzenesulfonyl)piperidine-4-carbonitrile (500 mg, 1.86 mmol) and thisemicarbazide (190 mg, 2.05 mmol) were dissolved in TFA (4.0 mL) and the reaction mixture was stirred for 2 hours at 60° C. After that time solvent was concentrated and residue was suspended in DCM:MeOH (4.0 ml, 95:5; vol:vol) solution and precipitate was filtered to afford desired compound as white solid (610 mg, 96.0%). LCMS-Method 2 (method: LCMS Method 2 (Gemini BCM)-UV, 200 nm): RT=4.29 min, 97.59% purity, [M+H]=343.13. $^1$H NMR (300 MHz, DMSO-$d_6$) δ 8.20-7.71 (m, 2H), 7.51 (t, J=8.8 Hz, 2H), 3.66 (dt, J=12.2, 3.7 Hz, 2H), 2.95 (ddd, J=11.3, 7.5, 3.8 Hz, 1H), 2.43 (dd. J=11.8, 2.6 Hz, 2H), 2.10-1.91 (m, 2H), 1.76-1.43 (m, 2H).

Synthesis Method O

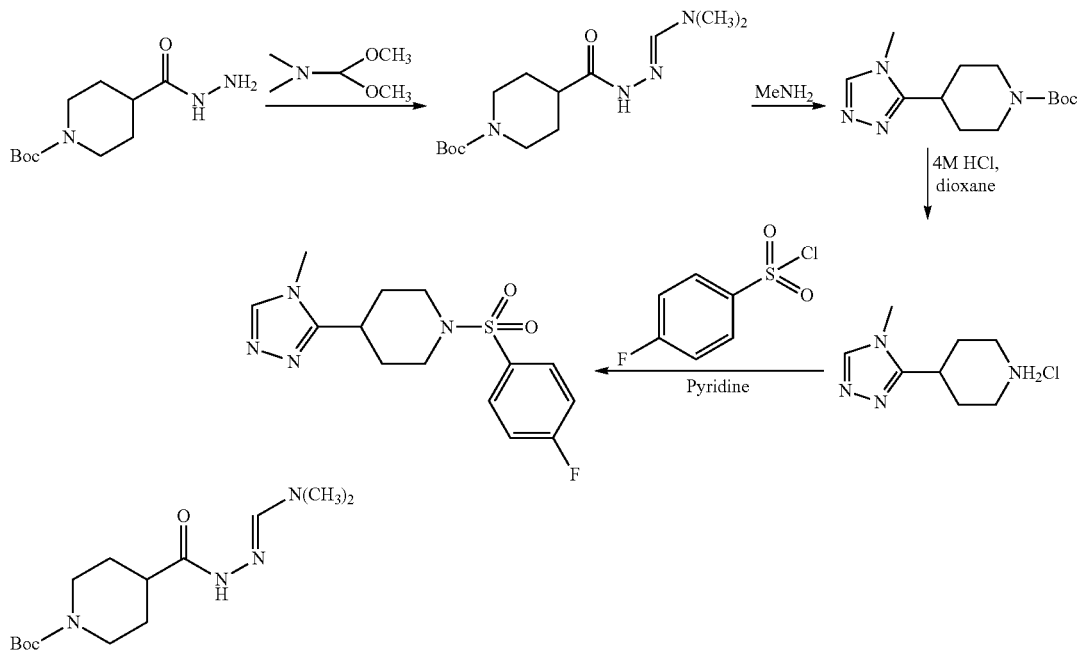

tert-butyl 4-(N'-[(1E)-(dimethylamino)methylidene]hydrazinecarbonyl)piperidine-1-carboxylate. To the solution tert-butyl 4-(hydrazinecarbonyl)piperdino-1-carboxylate (500 mg, 2.05 mmol) in DMF (5 mL) N,N-dimethylformamide dimethylacetal (245 mg, 2.05 mmol) was added. Reaction mixture was stirred for 18 hour at 100° C. After that time solvent was evaporated to obtain desired product (601 mg, 98%).

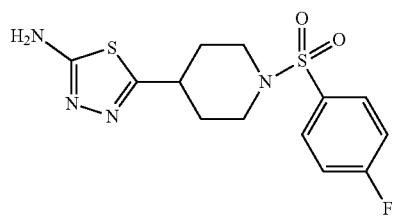 [SMILES: Nc1nnc(C2CCN(S(=O)(=O)c3ccc(F)cc3)CC2)s1]

tert-butyl 4-(4-methyl-4H-1,2,4-triazol-3-yl)piperidine-1-carboxylate. MeNH$_2$ 2M in THF (15 mL, 40.2 mmol) was added to the solution of tert-butyl 4-{N'-[(1E)-(dimethylamino)methylidene]hydrazinecarbonyl}piperidine-1-carboxylate (600 mg, 2.01 mmol) in anhydrous THF (6.0 mL)

under argon atmosphere. Reaction mixture was cooled to 0° C. and acetic acid (2 mL) was carefully added. Reaction mixture was stirred for 18 hour at 100° C. After that time reaction was cooled to room temperature and water (20 mL) was added and water layer was extracted three times with EA (3×50 mL). Combined organic layers were dried over sodium sulfate, filtered and evaporated to give crude compound (511 mg, 95%).

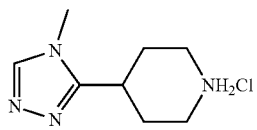

4-(4-methyl-4H-1,2,4-triazol-3-yl)piperidine. To the solution of tert-butyl 4-(4-methyl-4H-1,2,4-triazol-3-yl)piperidine-1-carboxylate (511 mg, 1.71 mmol) in THF (5.0 mL), 4M HCl in dioxane (6.0 mL) was added. Reaction mixture was stirred for 18 hours. After that time reaction mixture was filtered, the precipitate was washed with EA (2×40 mL) and dried under reduced pressure to give product (347 mg, 100%).

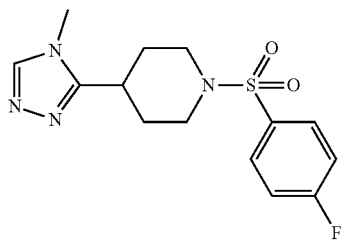 [SMILES: Cn1cnnc1C1CCN(S(=O)(=O)c2ccc(F)cc2)CC1]

1-(4-fluorobenzenesulfonyl)-4-(4-methyl-4H-1,2,4-triazol-3-yl)piperidine (N1). To a solution of 4-fluorobenzenosulfonyl chloride (117 mg, 0.60 mmol) in pyridine (1.0 mL) 4-(4-methyl-4H-1,2,4-triazol-3-yl)piperadine (100 mg, 0.60 mmol) was added. The reaction mixture was stirred for 18 hours at ambient temperature. After that time solvent was evaporated and 1 M HCl (5 mL) was added and the water layer was extracted with DCM (3×10 mL). Combined organic layers were dried over sodium sulfate, filtered and evaporated. Product was purified via P-TLC using 5% MeOH in DCM as an eluent (6 mg, 3%). LCMS-Method 2 (220 nm): RT=3.63 min, 96.34% purity, [M+H]=325.11 ¹H NMR (300 MHz, CDCl₃) δ 8.05 (s, 1H), 7.77-7.90 (m, 2H), 7.20-7.28 (m, 2H), 7.78-7.83 (m, 1H), 3.62 (s, 3H), 2.60-2.86 (m, 4H), 2.02-2.15 (m, 4H).

Synthesis Method P

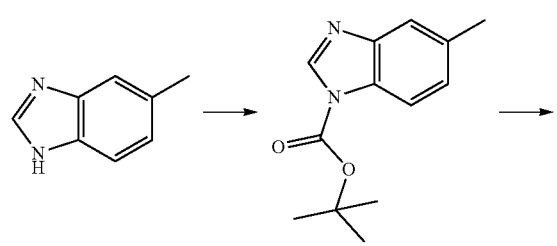

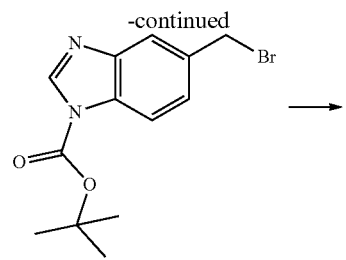

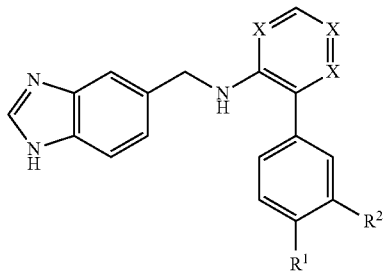

tert-butyl 5-methyl-1H-1,3-benzodiazole-1-carboxylate 5-methyl-1H-1,3-benzodiazole (0.5 g, 7.6 mmol), Boc anhydride (2.44 g, 11.4 mmol), DMAP (92 mg, 0.76 mmol) and triethylamine (2.11 mL, 15 mmol) were dissolved in acetonitrile (10 mL). The mixture was stirred at 80° C. overnight, cooled and solvent was removed in vacuo. Crude product was purified via column chromatography using DCM as eluent. Fractions containing the title compound were combined and concentrated (0.80 g, 46%). UPLC (254 nm): RT=3.75 min, 93.2% purity, [M+H]=233.2.

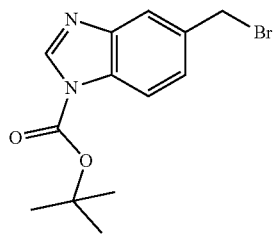 [SMILES: CC(C)(C)OC(=O)n1cnc2cc(CBr)ccc21]

tert-butyl 5-(bromomethyl)-1H-1,3-benzodiazole-1-carboxylate, tert-butyl 5-methyl-1H-1,3-benzodiazole-1-carboxylate (0.8 g, 3.44 mmol), N-bromosuccimide (0.64 g, 3.62 mmol), dibenzoyl peroxide (22 mg, 0.1 mmol) were suspended in tetrachloromethane (16 ml), Reaction mixture was stirred overnight at 90° C. After that time reaction mixture was cooled to 0° C., precipitate was filtered off and filtrate was concentrated in vacuo to give desired product as pale yellow oil. (0.95 g, 89%). UPLC (254 nm): RT=3.75 min, 80% purity, [M+H]=312.75.

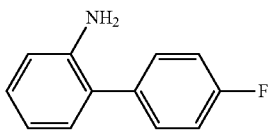 [SMILES: Nc1ccccc1-c1ccc(F)cc1]

4'-fluoro-[1,1'-biphenyl]-2-amine. Solution of 2-bromoaniline (1.5 g, 8.7 mmol), 4-flurophenylboronic acid (1.46 g, 10.5 mmol) and potassium carbonate (4.16 g, 30.1 mmol) in 1,4-dioxane (15.0 mL) and water (15.0 mL) was degassed with argon flow over 20 min and [1,1'-bis(diphenylphosphino)ferrocene]dichloropalladium(II) complex with dichloromethane (0.43 g, 0.5 mmol) was added as one portion. Reaction mixture was stirred overnight at 100° C. After this time reaction was filtered thru celite, layers were separated and water layer was extracted twice with ethyl acetate (2×15 mL), organic layers were combined, dried over sodium sulfate, filtered and evaporated. Crude product was purified via column chromatography using 10% ethyl acetate in hexanes as eluent to give the pure product (1.65 g, 100%). UPLC (254 nm): RT=3.31 min, 99% purity, [M+H]=187.9.

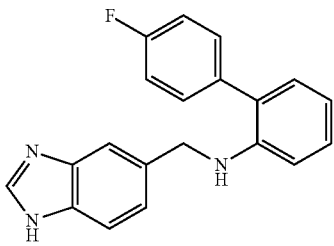 [SMILES: Fc1ccc(-c2ccccc2NCc2ccc3[nH]cnc3c2)cc1]

N-[(1H-1,3-benzodiazol-5-yl)methyl]-4'-fluoro-[1,1'-biphenyl]-2-amine (01). To the solution of 4'-fluoro-[1,1'-biphenyl]-2-amine (100 mg, 0.53 mmol) and tert-butyl 5-(bromomethyl)-1H-1,3-benzodiazole-1-carboxylate (244 mg, 0.59 mmol) in DMF (1.0 mL) sodium carbonate (170 mg, 1.6 mmol) was added. The reaction mixture was stirred overnight at 80° C. After that time reaction mixture was diluted with ethyl acetate (15.0 mL) and washed with semi-saturated brine (3×20 mL). Organic layer were dried over sodium sulfate, filtered, evaporated to provide the crude product, which was purified via column chromatography using MeOH in DCM 0-2% as an eluent to give desired product as off white solid (48 mg, 22%) LCMS-Method 2 (200 nm): RT=4.13 min, 97.2% purity. [M+H]=318.25. $^1$H NMR (300 MHz, DMSO-$d_6$) δ 8.15 (s, 1H), 7.62-7.43 (m, 3H), 7.32 (t, J=8.9 Hz, 2H), 7.18 (d, J=8.2 Hz, 1H), 7.05 (ddd, J=8.5, 7.4, 1.6 Hz, 1H), 6.97 (dd, J=7.5, 1.6 Hz, 1H), 6.70-6.44 (m, 2H), 5.32 (s, 1H), 4.40 (d, J=5.9 Hz, 2H).

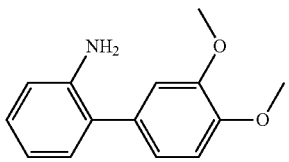 [SMILES: COc1ccc(-c2ccccc2N)cc1OC]

3',4'-dimethoxy-[1,1'-biphenyl]-2-amine. Solution of 2-bromoaniline (3.0 g, 17.4 mmol), 3,4-dimethoxyphenylboronic acid (3.81 g, 20.9 mmol) and potassium carbonate (8.32 g, 30.1 mmol) in 1,4-dioxane (30.0 mL) and water (30.0 mL) was degassed with argon flow over 20 min and [1,1'-bis(diphenylphosphino)ferrocene]dichloropalladium(II) complex with dichloromethane (0.85 g, 1.1 mmol) was added as one portion. Reaction mixture was stirred overnight at 100° C. After this time reaction was filtered thru celite, layers were separated and water layer was extracted twice with ethyl acetate (2×15 mL), organic layers were combined, dried over sodium sulfate, filtered and evaporated. Crude product was purified via column chromatography using ethyl acetate in hexanes 2-10% as eluent to give the pure product (3.2 g, 80%). UPLC (254 nm): RT=3.25 min, 90% purity, [M+H]=229.9.

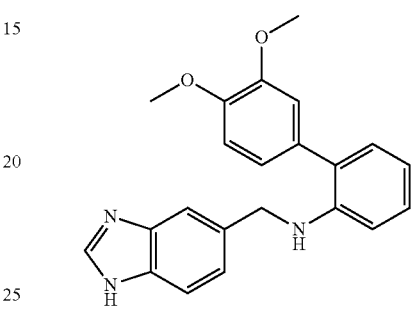

N-[(1H-1,3-benzodiazol-5-yl)methyl]-3',4'-dimethoxy-[1,1'-biphenyl]-2-amine(O2). To the solution of 3',4'-dimethoxy-[1,1'-biphenyl]-2-amine (200 mg, 0.87 mmol) and tert-butyl 5-(bromomethyl)-1H-1,3-benzodiazole-1-carboxylate (0.398 g, 0.96 mmol) in DMF (1.0 mL) sodium carbonate (277 mg, 2.62 mmol) was added. The reaction mixture was stirred overnight at 80° C. After that time reaction mixture was diluted with ethyl acetate (15.0 mL) and washed with semi-saturated brine (3×20 mL). Organic layer were dried over sodium sulfate, filtered, evaporated to provide the crude product, which was purified via column chromatography using MeOH in DCM 0-2% as an eluent to give desired product as off white solid (70 mg, 17%) LCMS-Method 2 (205 nm): RT=3.66 min. 96.5% purity, [M+H]=360.1. $^1$H NMR (300 MHz. DMSO-$d_6$) δ 8.16 (s, 1H), 7.52 (d, J=8.3 Hz, 2H), 7.20 (dd, J=8.3, 1.6 Hz, 1H), 7.12-6.87 (m, 5H), 6.61 (ddd, J=8.3, 5.9, 1.2 Hz, 2H), 5.26 (t, J=5.9 Hz, 1H), 4.40 (d, J=5.9 Hz, 2H).

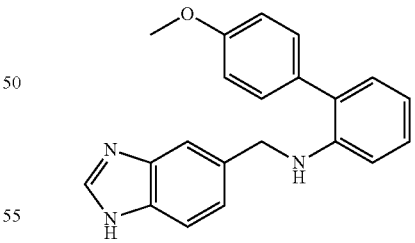

N-(1H-1,3-benzodiazol-5-ylmethyl)-2-(4-methoxyphenyl)aniline (O3). To the solution of 2-(4-methoxyphenyl) aniline (90 mg, 0.45 mmol) and tert-butyl 5-(bromomethyl)-1H-1,3-benzodiazole-1-carboxylate (156 mg, 0.50 mmol) in DMF (1.0 mL) sodium carbonate (144 mg, 1.36 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/

MeOH 100:0→98:2. Re-purification was performed via preparative TLC eluted with DCM/MeOH 95:5 to give desired product as off white solid (35 mg, 23%). LCMS-Method 2 (230 nm): RT=3.90 min, 96.6% purity, [M+H]=330.24. $^1$H NMR (300 MHz, Methanol-$d_4$) δ 8.13 (s, 1H), 7.56 (d, J=5.5 Hz, 2H), 7.36 (d, J=8.8 Hz, 2H), 7.25 (dd, J=8.4, 1.2 Hz, 1H), 7.15-6.93 (m, 4H), 6.75-6.63 (m, 2H), 4.45 (s, 2H), 3.84 (s, 3H).

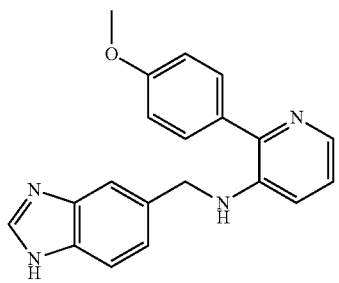 [SMILES: COc1ccc(-c2ncccc2NCc2ccc3[nH]cnc3c2)cc1]

N-(1H-1,3-benzodiazol-5-ylmethyl)-2-(4-methoxyphenyl)pyridin-3-amine (04). To the solution of 2-(4-methoxyphenyl)pyridin-3-amine (90 mg, 0.45 mmol) and tert-butyl 5-(bromomethyl)-1H-1,3-benzodiazole-1-carboxylate (155 mg, 0.50 mmol) in DMF (1.0 mL) sodium carbonate (143 mg, 1.36 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH/NH$_3$ 100:0:0→9:1:0.1. Re-purification was performed via preparative TLC eluted with DCM/MeOH/NH$_3$ 95:5:0.1 to give desired product as off white solid (10 mg, 7%). LCMS-Method 1 (205 nm): RT=4.66 min, 97.8% purity, [M+H]=331.27. $^1$H NMR (300 MHz. Methanol-$d_4$) δ 8.14 (s, 1H), 7.81 (d, J=5.7 Hz, 1H), 7.58 (t, J=3.9 Hz, 4H), 7.27 (d, J=9.6 Hz, 1H), 7.20-6.97 (m, 4H), 4.49 (s, 2H), 3.86 (s, 3H).

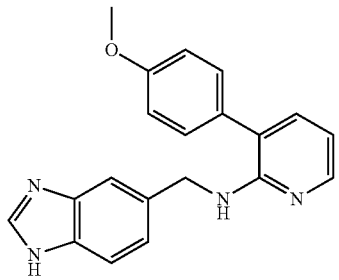

N-(1H-1,3-benzodiazol-5-ylmethyl)-3-(4-methoxyphenyl)pyridin-2-amine (05). To the solution of 3-(4-methoxyphenyl)pyridin-2-amine (100 mg, 0.50 mmol) and tert-butyl 5-(bromomethyl)-1H-1,3-benzodiazole-1-carboxylate (202 mg, 0.65 mmol) in DMF (1.0 mL) sodium carbonate (159 mg, 1.50 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH/NH$_3$ 95:5:0→9:1:0.1. Re-purification was performed via preparative TLC eluted with DCM/MeOH/NH$_3$ 95:5:0→9:1:0.1 to give desired product as white solid (4 mg, 2.5%). LCMS-Method 3 (200 nm): RT=2.66 min, 96.3% purity, [M+H]=331.11. $^1$H NMR (300 MHz, Methanol-$d_4$) δ 8.12 (s, 1H), 7.97 (dd, J=5.2, 1.8 Hz, 1H). 7.62-7.51 (m, 2H). 7.35 (t, J=8.7 Hz, 3H), 7.25 (d, J=9.7 Hz, 1H). 7.03 (d, J=8.8 Hz, 2H), 6.69 (dd, J=7.2, 5.2 Hz, 1H), 4.69 (s, 2H), 3.83 (s, 3H).

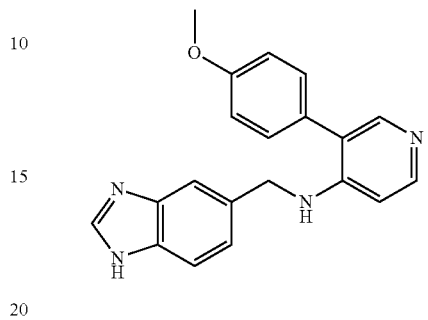

N-(1H-1,3-benzodiazol-5-ylmethyl)-3-(4-methoxyphenyl)pyridin-4-amine (06). To the solution of 3-(4-methoxyphenyl)pyridin-4-amine (100 mg, 0.50 mmol) and tert-butyl 5-(bromomethyl)-1H-1,3-benzodiazole-1-carboxylate (172 mg, 0.55 mmol) in DMF (1.0 mL) sodium carbonate (159 mg, 1.50 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH/NH$_3$ 95:5:0→9:1:0.1. Re-purification was performed via preparative TLC eluted with DCM/MeOH/NH$_3$ 95:5:0→9:1:0.1 to give desired product as white solid (12 mg, 7%). LCMS-Method 3 (245 nm): RT=2.36 min, 97.4% purity, [M+H]=331.25. $^1$H NMR (300 MHz, Methanol-$d_4$) δ 8.28 (s, 1H), 8.26-8.18 (m, 2H), 7.77-7.67 (m, 2H), 7.42-7.32 (m, 3H), 7.11 (d, J=6.7 Hz, 2H), 6.98 (d, J=7.1 Hz, 1H), 5.52 (s, 2H), 3.87 (s, 3H).

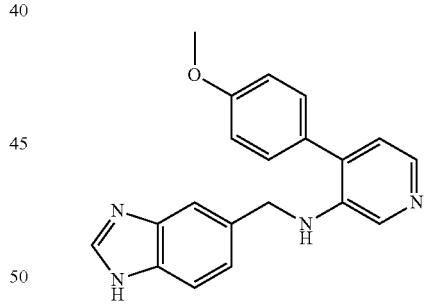

N-(1H-1,3-benzodiazol-5-ylmethyl)-4-(4-methoxyphenyl)pyridin-3-amine 07. To the solution of 4-(4-methoxyphenyl)pyridin-3-amine (100 mg, 0.50 mmol) and tert-butyl 5-(bromomethyl)-1H-1,3-benzodiazole-1-carboxylate (172 mg, 0.55 mmol) in DMF (1.0 mL) sodium carbonate (159 mg, 1.50 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH/NH$_3$ 95:5:0→9:1:0.1. Re-purification was performed via preparative HPLC to give desired product as white solid (5 mg, 4%). LCMS (LCMS-Method 3, 245 nm): RT=2.43 min, 73.7% purity, [M+H]=331.25. $^1$H NMR (300 MHz, Methanol-$d_4$) δ 8.36 (s, 1H), 8.30 (s, 1H), 8.23 (d, J=6.0 Hz, 1H), 7.91 (s, 1H), 7.73 (d, J=8.3 Hz, 1H), 7.67-7.51 (m, 4H), 7.44 (d, J=8.3 Hz, 1H), 7.12 (d, J=8.8 Hz, 2H), 6.92 (d, J=8.4 Hz, 1H), 5.77 (s, 2H), 3.88 (s, 3H).

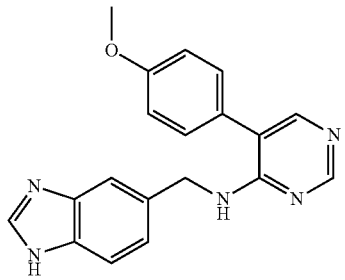

N-(1H-1,3-benzodiazol-5-ylmethyl)-5-(4-methoxyphenyl)pyrimidin-4-amine (08). To the solution of 5-(4-methoxyphenyl)pyrimidin-4-amine (50 mg, 0.25 mmol) and tert-butyl 5-(bromomethyl)-1H-1,3-benzodiazole-1-carboxylate (86 mg, 0.28 mmol) in DMF (0.5 mL) sodium carbonate (79 mg, 0.75 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via preparative HPLC to give desired product as yellowish solid (1.96 mg, 1.8%). LCMS-Method 12 (200 nm): RT=4.5 min, 100.0% purity, [M+H]=332.20. $^1$H NMR (300 MHz, Methanol-$d_4$) δ 8.86 (d, J=1.9 Hz, 1H), 8.30 (s, 1H), 8.22 (d, J=1.9 Hz, 1H), 7.80 (s. 1H), 7.72 (d, J=8.3 Hz, 1H), 7.44-7.35 (m, 3H), 7.14-7.06 (m, 2H), 5.51 (s, 2H), 3.87 (s, 3H).

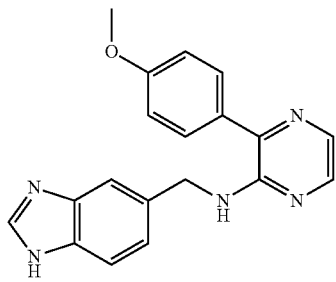 [SMILES: COc1ccc(-c2nccnc2NCc2ccc3[nH]cnc3c2)cc1]

N-(1H-1,3-benzodiazol-5-ylmethyl)-3-(4-methoxyphenyl)pyrazin-2-amine (09). To the solution of 3-(4-methoxyphenyl)pyrazin-2-amine (140 mg, 0.70 mmol) and tert-butyl 5-(bromomethyl)-1H-1,3-benzodiazole-1-carboxylate (240 mg, 0.77 mmol) in DMF (1.0 mL) sodium carbonate (221 mg, 2.09 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH/NH$_3$ 95:5:0→9:1:0.1. Re-purification was performed via preparative TLC eluted with DCM/MeOH/NH$_3$ 95:5:0→9:1:0.1 to give desired product as off white solid (5 mg, 2%). LCMS-Method 3 (270 nm): RT=3.04 min, 87.4% purity, [M+H]=332.24. $^1$H NMR (300 MHz, Methanol-$d_4$) δ 8.13 (s, 1H), 7.96 (d, J=2.9 Hz, 1H), 7.76 (d, J=2.9 Hz, 1H), 7.58 (dd, J=12.8, 8.6 Hz, 4H), 7.29 (dd, J=8.3, 1.4 Hz, 1H), 7.09 (d, J=8.8 Hz, 2H), 4.73 (s, 2H), 3.86 (s, 3H).

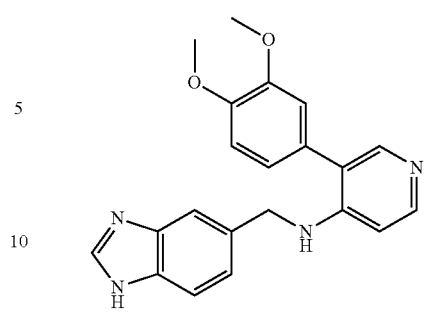

N-(1H-1,3-benzodiazol-5-ylmethyl)-3-(3,4-dimethoxyphenyl)pyridin-4-amine (010). To the solution of 3-(3,4-dimethoxyphenyl)pyridin-4-amine (100 mg, 0.43 mmol) and tert-butyl 5-(bromomethyl)-1H-1,3-benzodiazole-1-carboxylate (214 mg, 0.69 mmol) in DMF (1.0 mL) sodium carbonate (137 mg, 1.30 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH 95:5→9:1. Fractions containing product were collected and evaporated. Residue was suspended in MeOH and filtered to give desired product as white solid (11 mg, 7%). LCMS-Method 9 (200 nm): RT=2.8 min, 95.2% purity, [M+H]=361.16. $^1$H NMR (300 MHz, Methanol-$d_4$) δ 8.28 (d, J=2.2 Hz, 2H), 8.21 (dd, J=7.2, 1.9 Hz, 1H), 7.75 (s, 2H), 7.37 (dd, J=8.4, 1.5 Hz, 1H), 7.13 (d, J=8.2 Hz, 1H), 7.07-6.94 (m, 3H), 5.52 (s, 2H), 3.90 (s, 3H), 3.88 (s, 3H).

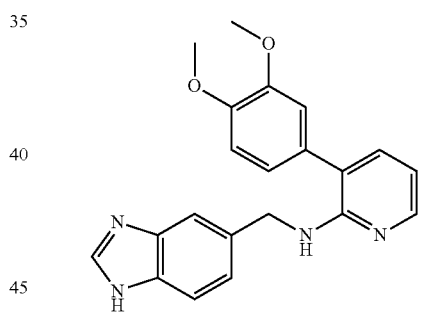

N-(1H-1,3-benzodiazol-5-ylmethyl)-3-(3,4-dimethoxyphenyl)pyridin-2-amine (011). To the solution of 3-(3,4-dimethoxyphenyl)pyridin-2-amine (100 mg, 0.43 mmol) and tert-butyl 5-(bromomethyl)-1H-1,3-benzodiazole-1-carboxylate (150 mg, 0.48 mmol) in DMF (1.0 mL) sodium carbonate (138 mg, 1.30 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH/NH$_3$ 95:5:0→9:1:0.1. Re-purification was performed via preparative TLC eluted with DCM/MeOH/NH$_3$ 95:5:0→9:1:0.1 to give desired product as off white solid (11 mg, 7%). LCMS-Method 1 (200 nm): RT=4.98 min, 93.2% purity, [M+H]=361.25. $^1$H NMR (300 MHz, Methanol-$d_4$) δ 8.13 (s, 1H), 7.98 (dd, J=5.2, 1.8 Hz, 1H), 7.55 (d, J=8.7 Hz, 2H), 7.37 (dd, J=7.2, 1.8 Hz, 1H), 7.27 (dd, J=8.3, 1.4 Hz, 1H), 7.09-6.91 (m, 3H), 6.69 (dd, J=7.2, 5.2 Hz, 1H), 4.70 (s, 2H), 3.85 (s, 3H), 3.79 (s, 3H).

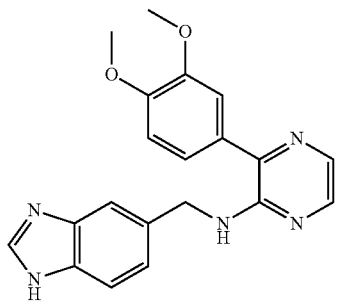 [SMILES: COc1ccc(-c2nccnc2NCc2ccc3[nH]cnc3c2)cc1OC]

N-(1H-1,3-benzodiazol-5-ylmethyl)-3-(3,4-dimethoxyphenyl)pyrazin-2-amine (012). To the solution of 3-(3,4-dimethoxyphenyl)pyrazin-2-amine (100 mg, 0.43 mmol) and tert-butyl 5-(bromomethyl)-1H-1,3-benzodiazole-1-carboxylate (175 mg, 0.56 mmol) in DMF (1.0 mL) sodium carbonate (137 mg, 1.30 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH/NH$_3$ 95:5:0→9:1:0.1. Re-purification was performed via preparative TLC eluted with DCM/MeOH/NH$_3$ 95:5:0→9:1:0.1 to give desired product as off white solid (8 mg, 5%). LCMS-Method 3 (200 nm): RT=2.97 min, 87.7% purity, [M+H]=362.21. $^1$H NMR (300 MHz, Methanol-d$_4$) δ 8.14 (s, 1H), 7.98 (d, J=2.8 Hz, 1H), 7.77 (d, J=2.8 Hz, 1H), 7.65-7.44 (m, 2H), 7.37-7.20 (m, 3H), 7.09 (d, J=8.2 Hz, 1H), 4.73 (s, 2H), 3.89 (s, 3H), 3.85 (s, 3H).

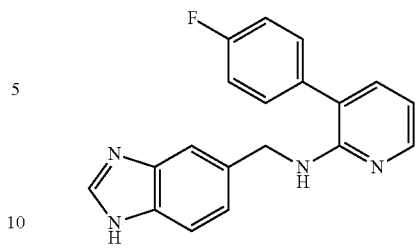

N-(1H-1,3-benzodiazol-5-ylmethyl)-3-(4-fluorophenyl)pyridin-2-amine (014). To the solution of 3-(4-fluorophenyl)pyridin-2-amine (70 mg, 0.37 mmol) and tert-butyl 5-(bromomethyl)-1H-1,3-benzodiazole-1-carboxylate (128 mg, 0.41 mmol) in DMF (0.7 mL) sodium carbonate (118 mg, 1.12 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via preparative HPLC. Re-purification was performed via preparative TLC eluted with DCM/MeOH/NH$_3$ 95:5:0.1 to give desired product as a white solid (7.7 mg, 4.95%). LCMS-Method 1 (200 nm): RT=5.04 min, 97.1% purity, [M+H]=319.23. $^1$H NMR (300 MHz, Methanol-d$_4$) δ 8.09 (s, 1H), 8.00 (dd, J=5.2, 1.8 Hz, 1H), 7.58-7.41 (m, 4H), 7.34 (dd. J=7.2, 1.8 Hz, 1H), 7.25-7.14 (m, 3H), 6.70 (dd, J=7.2, 5.2 Hz, 1H), 4.69 (s, 2H).

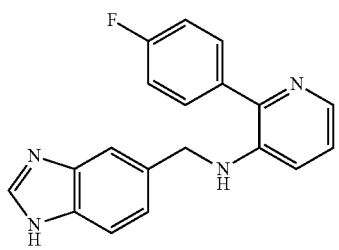 [SMILES: Fc1ccc(-c2ncccc2NCc2ccc3[nH]cnc3c2)cc1]

N-(1H-1,3-benzodiazol-5-ylmethyl)-2-(4-fluorophenyl)pyridin-3-amine (013). To the solution of 2-(4-fluorophenyl)pyridin-3-amine (110 mg, 0.58 mmol) and tert-butyl 5-(bromomethyl)-1H-1,3-benzodiazole-1-carboxylate (202 mg, 0.65 mmol) in DMF (1.0 mL) sodium carbonate (186 mg, 1.75 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH/NH$_3$ 95:5:0→9:1:0.1. Re-purification was performed via preparative TLC eluted with DCM/MeOH/NH$_3$ 95:5:0→9:1:0.1 to give desired product as off white solid (8 mg, 4%). LCMS-Method 1 (200 nm): RT=3.04 min, 96.1% purity, [M+H]=319.23. $^1$H NMR (300 MHz, $^1$H NMR (300 MHz,) δ 8.20 (s, 1H), 7.84 (d, J=4.5 Hz, 1H), 7.77-7.51 (m, 4H), 7.30 (t, J=8.6 Hz, 3H), 7.23-7.01 (m, 2H), 4.53 (s, 2H).

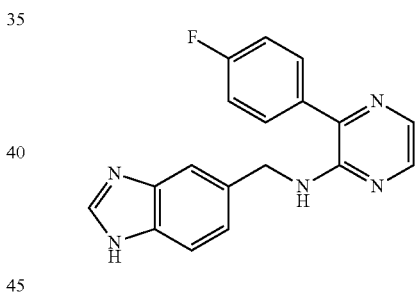

N-(1H-1,3-benzodiazol-5-ylmethyl)-3-(4-fluorophenyl)pyrazin-2-amine (015). To the solution of 3-(4-fluorophenyl)pyrazin-2-amine (100 mg, 0.53 mmol) and tert-butyl 5-(bromomethyl)-1H-1,3-benzodiazole-1-carboxylate (214 mg, 0.69 mmol) in DMF (1.0 mL) sodium carbonate (137 mg, 1.30 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH/NH$_3$ 95:5:0→9:1:0.1. Re-purification was performed via preparative TLC eluted with DCM/MeOH/NH$_3$ 95:5:0→9:1:0.1 to give desired product as off white solid (3 mg, 2%). LCMS-Method 1 (202 nm): RT=3.08 min, 95.4% purity, [M+H]=320.22. $^1$H NMR (300 MHz. Methanol-d$_4$) δ 8.13 (s, 1H). 8.00 (d, J=2.8 Hz, 1H), 7.79 (d, J=2.8 Hz, 1H), 7.70 (dd, J=8.8, 5.4 Hz, 2H), 7.62-7.51 (m, 2H), 7.33-7.23 (m, 3H). 4.73 (s, 2H).

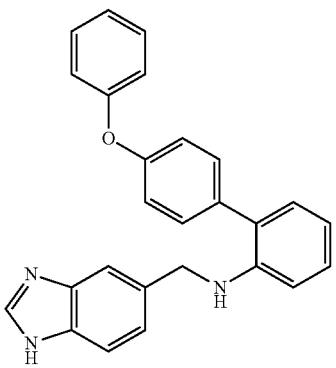 [SMILES: c1ccc(Oc2ccc(-c3ccccc3NCc3ccc4[nH]cnc4c3)cc2)cc1]

N-(1H-1,3-benzodiazol-5-ylmethyl)-2-(4-phenoxyphenyl)aniline (016). To the solution of 2-(4-phenoxyphenyl)aniline (100 mg, 0.38 mmol) and tert-butyl 5-(bromomethyl)-1H-1,3-benzodiazole-1-carboxylate (132 mg, 0.42 mmol) in DMF (1.0 mL) sodium carbonate (122 mg, 1.15 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH 1:0→96:4. Re-purification was performed via preparative TLC eluted with DCM/MeOH/NH$_3$ 95:5:0.1 to give desired product as a white solid (25 mg, 16.7%). LCMS-Method 2 (205 nm): RT=4.99 min, 99.6% purity, [M+H]=392.26. $^1$H NMR (300 MHz, Methanol-d$_4$) δ 8.13 (s, 1H), 7.57 (d, J=8.1 Hz, 2H), 7.47-7.33 (m, 4H), 7.27 (dd, J=8.5, 1.5 Hz, 1H), 7.17-7.02 (m, 7H), 6.71 (ddd, J=7.8, 6.2, 1.2 Hz, 2H), 4.48 (s, 2H).

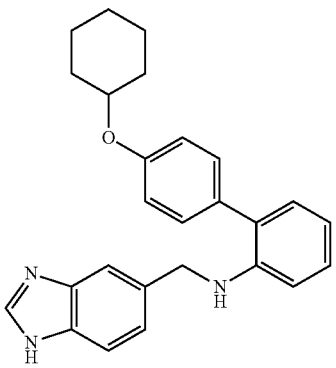 [SMILES: c1ccc(-c2ccc(OC3CCCCC3)cc2)c(NCc2ccc3[nH]cnc3c2)c1]

N-(1H-1,3-benzodiazol-5-ylmethyl)-2-[4-(cyclohexyloxy)phenyl]aniline (017). To the solution of 2-[4-(cyclohexyloxy)phenyl]aniline (100 mg, 0.37 mmol) and tert-butyl 5-(bromomethyl)-1H-1,3-benzodiazole-1-carboxylate (129 mg, 0.42 mmol) in DMF (1.0 mL) sodium carbonate (119 mg, 1.12 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via preparative TLC eluted with DCM/MeOH 95:5. Re-purification was performed via preparative TLC eluted with DCM/MeOH 95:5 to give desired product as a white solid (4.9 mg, 3.3%). LCMS-Method 2 (200 nm): RT=5.17 min, 100% purity, [M+H]=398.26. $^1$H NMR (300 MHz, Methanol-d$_4$) δ 8.12 (s, 1H), 7.55 (d, J=7.9 Hz, 2H), 7.37-7.21 (m, 3H), 7.11-6.96 (m, 4H), 6.68 (ddd, J=8.6, 5.5, 1.3 Hz, 2H), 4.44 (s, 2H), 4.34 (tt, J=8.4, 3.6 Hz, 1H), 2.06-1.75 (m, 4H), 1.66-1.28 (m, 6H).

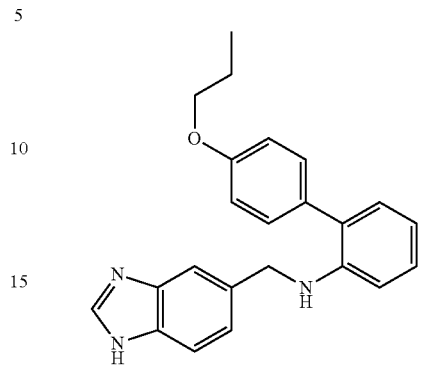

N-(1H-1,3-benzodiazol-5-ylmethyl)-2-(4-propoxyphenyl)aniline (018). To the solution of 2-(4-propoxyphenyl)aniline (100 mg, 0.44 mmol) and tert-butyl 5-(bromomethyl)-1H-1,3-benzodiazole-1-carboxylate (152 mg, 0.49 mmol) in DMF (1.0 mL) sodium carbonate (140 mg, 1.32 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH 1:0→98:2. Re-purification was performed via preparative TLC eluted with DCM/MeOH 95:5 to give desired product as a white solid (34.4 mg, 21.9%). LCMS-Method 2 (200 nm): RT=4.58 min, 100% purity, [M+H]=358.25. $^1$H NMR (300 MHz, Methanol-d$_4$) δ 8.09 (s, 1H), 7.53 (d, J=7.8 Hz, 2H), 7.36-7.25 (m, 2H), 7.20 (dd, J=8.4, 1.5 Hz, 1H), 7.10-6.89 (m, 4H), 6.66 (t, J=7.3 Hz, 2H), 4.37 (s, 2H), 3.90 (t, J=6.5 Hz, 2H), 1.77 (dtd, J=13.8, 7.4, 6.4 Hz, 2H), 1.02 (t, J=7.4 Hz, 3H).

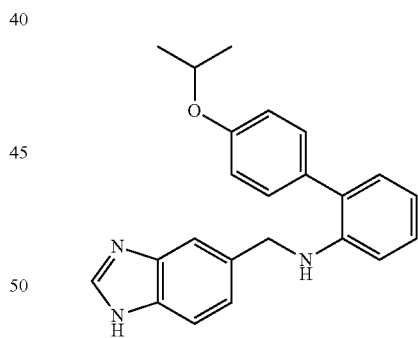

N-(1H-1,3-benzodiazol-5-ylmethyl)-2-[4-(propan-2-yloxy)phenyl]aniline (019). To the solution of 2-[4-(propan-2-yloxy)phenyl]aniline (100 mg, 0.44 mmol) and tert-butyl 5-(bromomethyl)-1H-1,3-benzodiazole-1-carboxylate (152 mg, 0.49 mmol) in DMF (1.0 mL) sodium carbonate (140 mg, 1.32 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH 1:0→99:1. Re-purification was performed via preparative TLC eluted with DCM/MeOH 95:5 to give desired product as a white solid (24.3 mg, 15.5%). LCMS-Method 4 (200 nm): RT=2.42 min, 97.3% purity, [M+H]=358.26. $^1$H NMR (300 MHz, Methanol-d$_4$) δ8.10 (s, 1H), 7.54 (d, J=7.9 Hz, 2H), 7.37-7.26 (m, 2H), 7.21 (dd, J=8.4, 1.5 Hz, 1H), 7.10-6.91 (m, 4H), 6.66 (t, J=7.3 Hz, 2H), 4.57 (hept, J=12.0, 6.0 Hz, 1H), 4.39 (s, 2H), 1.31 (d, J=6.0 Hz, 6H).

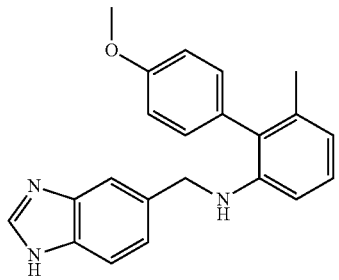 [SMILES: COc1ccc(-c2c(C)cccc2NCc2ccc3[nH]cnc3c2)cc1]

N-(1H-1,3-benzodiazol-5-ylmethyl)-2-(4-methoxyphenyl)-3-methylaniline (020). To the solution of 2-(4-methoxyphenyl)-3-methylaniline (100 mg, 0.47 mmol) and tert-butyl 5-(bromomethyl)-1H-1,3-benzodiazole-1-carboxylate (162 mg, 0.52 mmol) in DMF (1.0 mL) sodium carbonate (149 mg, 1.41 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH 1:0→97:3. Re-purification was performed via preparative TLC eluted with DCM/MeOH 9:1 to give desired product as a white solid (40.7 mg, 25.3%). LCMS (LCMS-Method 4, 205 nm): RT=2.14 min, 98.9% purity, [M+H]=344.27. $^1$H NMR (300 MHz, DMSO-d$_6$) δ 12.33 (d, J=11.8 Hz, 1H), 8.14 (s, 1H), 7.57-7.36 (m, 2H), 7.18-7.05 (m, 5H), 6.93 (t, J=7.8 Hz, 1H), 6.54-6.38 (m, 2H), 4.44 (d, J=17.8 Hz, 1H), 4.34 (d, J=5.1 Hz, 2H), 3.81 (s, 3H), 1.88 (s, 3H).

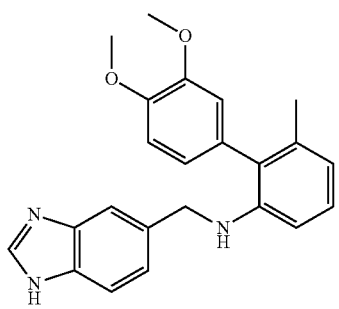 [SMILES: COc1ccc(-c2c(C)cccc2NCc2ccc3[nH]cnc3c2)cc1OC]

N-(1H-1,3-benzodiazol-5-ylmethyl)-2-(3,4-dimethoxyphenyl)-3-methylaniline (021). To the solution of 2-(3,4-dimethoxyphenyl)-3-methylaniline (100 mg, 0.41 mmol) and tert-butyl 5-(bromomethyl)-1H-1,3-benzodiazole-1-carboxylate (142 mg, 0.46 mmol) in DMF (1.0 mL) sodium carbonate (131 mg, 1.23 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH 1:0→97:3. Re-purification was performed via preparative TLC eluted with DCM/MeOH 95:5 to give desired product as a white solid (47.5 mg, 31%). LCMS (LCMS-Method 4, 205 nm):

RT=1.99 min, 97.3% purity, [M+H]=374.27. $^1$H NMR (300 MHz, DMSO-d$_6$) δ 12.33 (s, 1H), 8.14 (s, 1H), 7.52 (s, 1H), 7.41 (s, 1H), 7.10 (t, J=7.8 Hz, 2H), 6.93 (t, J=7.8 Hz, 1H), 6.79-6.71 (m, 2H), 6.47 (dd, J=15.8, 7.8 Hz, 1H), 4.55 (s, 1H), 4.34 (d, J=6.0 Hz, 2H), 3.79 (d, J=9.0 Hz, 6H), 1.92 (s, 3H).

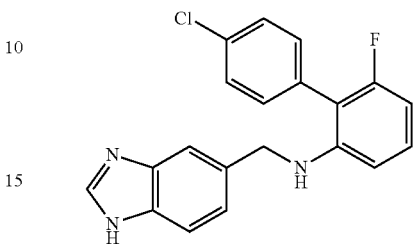

N-(1H-1,3-benzodiazol-5-ylmethyl)-2-(4-chlorophenyl)-3-fluoroaniline(O22). To the solution of 2-(4-chlorophenyl)-3-fluoroaniline (100 mg, 0.45 mmol) and tert-butyl 5-(bromomethyl)-1H-1,3-benzodiazole-1-carboxylate (156 mg, 0.50 mmol) in DMF (1.0 mL) sodium carbonate (143 mg, 1.35 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH 1:0→97:3. Re-purification was performed via preparative TLC eluted with DCM/MeOH 95:5 to give desired product as a white solid (40.6 mg, 25.6%). LCMS (LCMS-Method 4, 200 nm): RT=2.29 min, 94.2% purity, [M+H]=344.27. $^1$H NMR (300 MHz, DMSO-d$_6$) δ 12.33 (d, J=17.3 Hz, 1H), 8.15 (d, J=4.1 Hz, 1H), 7.58 (dd, J=8.8, 7.0 Hz, 3H), 7.50-7.36 (m, 3H), 7.20-7.10 (m, 1H). 7.05 (td, J=8.3, 6.8 Hz, 1H), 6.46-6.34 (m, 2H), 5.48 (dt, J=16.2, 6.0 Hz, 1H), 4.38 (t, J=6.0 Hz, 2H).

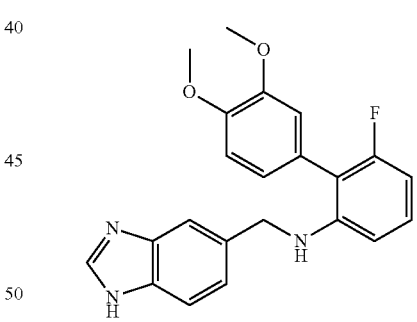

N-(1H-1,3-benzodiazol-5-ylmethyl)-2-(3,4-dimethoxyphenyl)-3-fluoroaniline (023). To the solution of 2-(3,4-dimethoxyphenyl)-3-fluoroaniline (100 mg, 0.40 mmol) and tert-butyl 5-(bromomethyl)-1H-1,3-benzodiazole-1-carboxylate (140 mg, 0.45 mmol) in DMF (1.0 mL) sodium carbonate (129 mg, 1.21 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH 1:0→97:3. Re-purification was performed via preparative TLC eluted with DCM/MeOH 9:1 to give desired product as a white solid (29.3 mg, 19.2%). LCMS (LCMS-Method 4, 200 nm): RT=1.92 min, 90.1% purity, [M+H]=378.23. $^1$H NMR (300

MHz, DMSO-d$_6$) δ 12.38 (s, 1H), 8.16 (s, 1H), 7.50 (s, 2H), 7.21-6.98 (m, 3H), 6.93-6.85 (m, 2H), 6.45-6.37 (m, 2H), 5.27 (s, 1H), 4.39 (d, J=6.0 Hz, 2H), 3.80 (d, J=7.1 Hz, 6H).

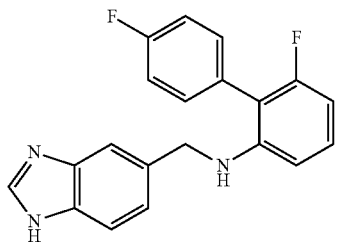

N-(1H-1,3-benzodiazol-5-ylmethyl)-3-fluoro-2-(4-fluorophenyl)aniline (O24). To the solution of 3-fluoro-2-(4-fluorophenyl)aniline (100 mg, 0.49 mmol) and tert-butyl 5-(bromomethyl)-1H-1,3-benzodiazole-1-carboxylate (168 mg, 0.54 mmol) in DMF (1.0 mL) sodium carbonate (155 mg, 1.46 mmol) was added. The reaction mixture was stirred overnight at 80° C. After that time reaction mixture was cooled down to RT and filtered through celite. Celite pad was washed with MeOH. Filtrate was evaporated to provide the crude product, which was purified via column chromatography using DCM/MeOH 1:0→97:3. Re-purification was performed via preparative TLC eluted with DCM/MeOH 9:1 to give desired product as a white solid (29.3 mg, 19.2%). LCMS (LCMS-Method 4, 205 nm): RT=2.12 min, 96.6% purity, [M+H]=336.23. $^1$H NMR (300 MHz, DMSO-d$_6$) δ 12.32 (s, 1H), 8.15 (s, 1H), 7.55 (s, 1H), 7.45-7.32 (m, 5H), 7.15 (s, 1H), 7.10-6.99 (m, 1H), 6.46-6.36 (m, 2H), 5.37 (s, 1H), 4.39 (d, J=6.0 Hz, 2H).

Synthesis Method Q

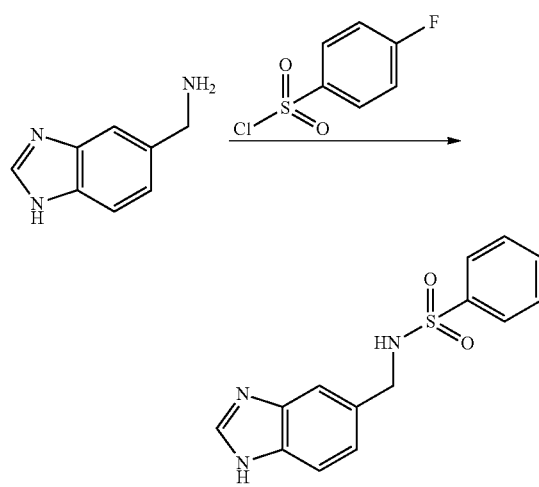

N-[(1H-1,3-benzodiazol-5-yl)methyl]-4-fluorobenzene-1-sulfonamide (P1) (1H-1,3-benzodiazol-5-yl)methanamine dihydrochloride (0.25 g, 1.15 mmol) was dissolved in pyridine (7 mL) and stirred at room temperature over 30 min. Then 4-fluorophenylsulfonyl chloride (0.21 g, 1.08 mmol), was added and reaction mixture was heated to 70° C. and stirred overnight. The mixture was quenched with 10 mL of 20% aqueous solution of sodium hydroxide and stirred at 70° C. for another night. Layers were separated and Pyridine was evaporated in vacuo. Crude product was purified via column chromatography using MeOH in DCM (0-3%) as eluent. Fractions containing the title compound were combined and concentrated (55 mg, 19%). LCMS-Method 1 (200 nm): RT=5.81 min, 93.2% purity, [M+ACN]=347.27. $^1$H NMR (300 MHz, DMSO-d$_6$) δ 8.17 (s, 1H), 8.04-7.66 (m, 2H), 7.56-7.31 (m, 4H), 7.05 (d, J=8.4 Hz, 1H), 4.10 (s, 2H).

Synthesis Method R

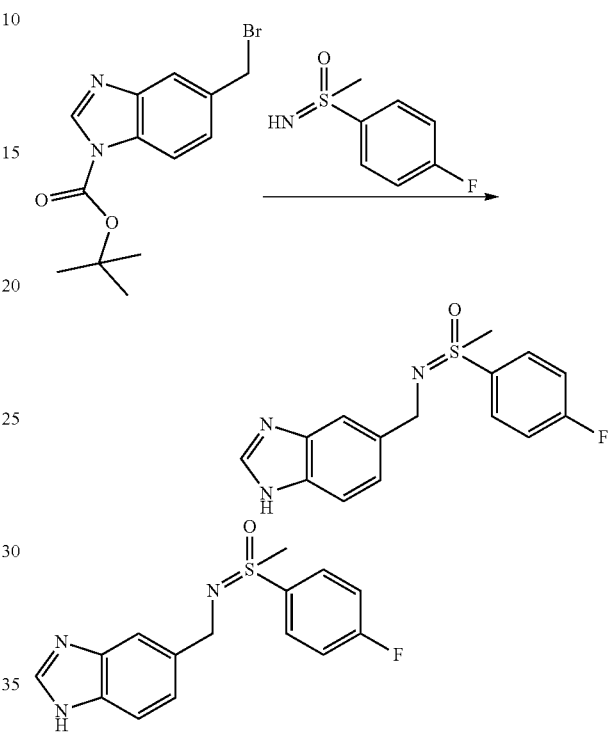

[(1H-1,3-benzodiazol-5-yl)methyl][(4-fluorophenyl) methyl)oxo-λ$^6$-sulfanylidene]amine (Q1) (4-fluorophenyl)(imino)methyl-λ$^6$-sulfanone (250 mg, 1.5 mmol) and potassium hydroxide (234 mg, 2.18 mmol) in DMSO (13.0 mL) were stirred at 50° C. over 1h. After this time reaction was cooled to room temperature and tert-butyl 5-(bromomethyl)-1H-1,3-benzodiazole-1-carboxylate (650 mg, 2.10 mmol) was added. Reaction was stirred overnight, and after this time water (50 mL) was added and extracted with DCM (5×30 mL). Combined organic layers were dried over sodium sulfate, filtered, evaporated to provide the solution of crude product in DMSO, which was purified preparative HPLC method to give title compound as colorless oil. (26 mg, 5%) LCMS-Method 1 (200 nm): RT=5.72 min, 96.3% purity, [M+H]=304.15. $^1$H NMR (300 MHz, DMSO-d$_6$) δ 8.14 (s, 1H). 8.03-7.91 (m, 2H). 7.54 (s, 1H), 7.51-7.42 (m, 3H), 7.12 (dd, J=8.3, 1.6 Hz, 1H), 4.15 (d, J=14.4 Hz, 1H), 3.98 (d, J=14.5 Hz, 1H), 3.25 (s, 3H).

Analytical Methods

NMR

The $^1$H NMR-Spectra (300 MHz) were recorded at a BRUKER FOURIER 300. The solvent was DMSO-De, unless otherwise specified. Chemical shifts are expressed as parts per million (ppm) downfiled from tetramethylsilan. Splitting patterns have been designated as follows: s (singulet), d (doublet), dd (doublet of doublet), t (triplet), m (multiplet) and br (broad signal).

HPLC-MS
LCMS-Method 1
Apparatus: Dionex UHPLC Ultimate 3000 with DAD detector/Thermo Scientific MSQ Plus
Column: Gemini-NX 3µ C18 (4.6×50 mm), 110A, column no. OOB-4453-EO, internal column no. 002
Reagents:—Formic acid ≥98%, Sigma-Aldrich
Acetonitrile for HPLC UV/gradient grade, Baker
µQ-water for LCMS
HPLC conditions:—Wavelength range: (190-340) nm±4 nm
Flow: 0.5 ml/min
Column temperature: 25° C.
Autosampler temperature: 20° C.
Injection volume: 2.0 µl
Analysis time: 14 min
Elution: gradient

| Time [min] | Mobile phase A [%] | Mobile phase B [%] | Flow [ml/min] |
|---|---|---|---|
| 0.0 | 95 | 5 | 0.5 |
| 2.0 | 95 | 5 | 0.5 |
| 9.5 | 20 | 80 | 0.5 |
| 10.5 | 20 | 80 | 0.5 |
| 12.0 | 95 | 5 | 0.5 |
| 14.0 | 95 | 5 | 0.5 |

Mobile phase A: 0.1% v/v water solution of formic acid
Mobile phase B: 0.1% v/v acetonitrile solution of formic acid
Solution for syringe washing: 20% MeOH
MS conditions:—Mass range: 100-1000 m/z
Ionization: alternate
Scan speed: 12 000 amu/sec LCMS-Method 2
Apparatus: Dionex UHPLC Ultimate 3000 with DAD detector/Thermo Scientific MSQ Plus
Column: Gemini-NX 3µ C18 (4.6×50 mm), 110A, column no. OOB-4453-EO, internal column no. 002
Reagents:—Formic acid ≥98%, Sigma-Aldrich
Acetonitrile for HPLC UV/gradient grade, Baker
µQ-water for LCMS
HPLC conditions:—Wavelength range: (190-340) nm±4 nm
Flow: 0.5 ml/min
Column temperature: 25° C.
Autosampler temperature: 20° C.
Injection volume: 2.0 µl
Analysis time: 12 min
Elution: gradient

| Time [min] | Mobile phase A [%] | Mobile phase B [%] | Flow [ml/min] |
|---|---|---|---|
| 0.0 | 80 | 20 | 0.5 |
| 6.7 | 20 | 80 | 0.5 |
| 7.5 | 20 | 80 | 0.5 |
| 7.8 | 5 | 95 | 0.5 |
| 9.5 | 5 | 95 | 0.5 |
| 10.0 | 80 | 20 | 0.5 |
| 12.0 | 80 | 20 | 0.5 |

Mobile phase A: 0.1% v/v water solution of formic acid
Mobile phase B: 0.1% v/v acetonitrile solution of formic acid
Solution for syringe washing: 20% MeOH
MS conditions:—Mass range: 100-1000 m/z
Ionization: alternate
Scan speed: 12 000 amu/sec LCMS-Method 3
Apparatus: Dionex UHPLC Ultimate 3000 with DAD detector/Thermo Scientific MSQ Plus
Column: Kinetex® 2.6 µm XB-C18 (4.6×50 mm), 110A, column no. OOB-4496-EO, internal column no. 019
Reagents:—Formic acid a 98%, Sigma-Aldrich
Acetonitrile for HPLC UV/gradient grade, Baker
µQ-water for LCMS
HPLC conditions:—Wavelength range: (190-340) nm±4 nm
Flow: 1.0 ml/min
Column temperature: 25° C.
Autosampler temperature: 20° C.
Injection volume: 2.0 µl
Analysis time: 7 min
Elution: gradient

| Time [min] | Mobile phase A [%] | Mobile phase B [%] | Flow [ml/min] |
|---|---|---|---|
| 0.0 | 95 | 5 | 1.0 |
| 1.0 | 95 | 5 | 1.0 |
| 4.75 | 20 | 80 | 1.0 |
| 5.25 | 20 | 80 | 1.0 |
| 6.0 | 95 | 5 | 1.0 |
| 7.0 | 95 | 5 | 1.0 |

Mobile phase A: 0.1% v/v water solution of formic acid
Mobile phase B: 0.1% v/v acetonitrile solution of formic acid
Solution for syringe washing: 20% MeOH
MS conditions:—Mass range: 100-1000 m/z
Ionization: alternate
Scan speed: 12 000 amu/sec LCMS-Method 4
Apparatus: Dionex UHPLC Ultimate 3000 with DAD detector/Thermo Scientific MSQ Plus
Column: Kinetex® 2.6 µm XB-C18 (4.6×50 mm), 110A, column no. OOB-4496-EO, internal column no. 019
Reagents:—Formic acid ≥98%, Sigma-Aldrich
Acetonitrile for HPLC UV/gradient grade, Baker
µQ-water for LCMS
HPLC conditions:—Wavelength range: (190-340) nm±4 nm
Flow: 1.0 ml/min
Column temperature: 25° C.
Autosampler temperature: 20° C.
Injection volume: 2.0 µl
Analysis time: 6 min
Elution: gradient

| Time [min] | Mobile phase A [%] | Mobile phase B [%] | Flow [ml/min] |
|---|---|---|---|
| 0.0 | 80 | 20 | 1.0 |
| 3.35 | 20 | 80 | 1.0 |
| 3.75 | 20 | 80 | 1.0 |
| 3.9 | 5 | 95 | 1.0 |
| 4.75 | 5 | 95 | 1.0 |
| 5.0 | 80 | 20 | 1.0 |
| 6.0 | 80 | 20 | 1.0 |

Mobile phase A: 0.1% v/v water solution of formic acid
Mobile phase B: 0.1% v/v acetonitrile solution of formic acid
Solution for syringe washing: 20% MeOH
MS conditions:—Mass range: 100-1000 m/z
Ionization: alternate
Scan speed: 12 000 amu/sec LCMS-Method 5

Apparatus: Dionex UHPLC Ultimate 3000 with DAD detector/Thermo Scientific MSQ Plus Column: Kinetex® 2.6 μm XB-C18 (4.6×50 mm), 110A, column no. OOB-4496-EO, internal column no. 019

Reagents:—Formic acid ≥98%, Sigma-Aldrich

Acetonitrile for HPLC UV/gradient grade. Baker

μQ-water for LCMS

HPLC conditions:—Wavelength range: (190-340) nm±4 nm

Flow: 1.0 ml/min
Column temperature: 25° C.
Autosampler temperature: 20° C.
Injection volume: 2.0 μl
Analysis time: 7 min
Elution: gradient

| Time [min] | Mobile phase A [%] | Mobile phase B [%] | Flow [ml/min] |
|---|---|---|---|
| 0.0 | 80 | 20 | 1.0 |
| 2.0 | 20 | 80 | 1.0 |
| 2.35 | 20 | 80 | 1.0 |
| 2.45 | 5 | 95 | 1.0 |
| 4.25 | 5 | 95 | 1.0 |
| 5.0 | 80 | 20 | 1.0 |
| 7.0 | 80 | 20 | 1.0 |

Mobile phase A: 0.1% v/v water solution of formic acid
Mobile phase B: 0.1% v/v acetonitrile solution of formic acid
Solution for syringe washing: 20% MeOH
MS conditions:—Mass range: 100-1000 m/z
Ionization: alternate
Scan speed: 12 000 amu/sec HPLC-Method 6

Apparatus: HPLC—MERCK CHROMASTER with gradient pump and DAD detector

Column: XBridge C18 3.5μ (4.6×150 mm), column no. 186003034, internal column no. 009

Reagents:
Methanol for HPLC Ultra Gradient HPLC Grade. Baker
Boric acid ≥99.5%, Sigma-Aldrich
Sodium hydroxide analytical grade, Eurochem BGD
purified water for HPLC HPLC Conditions:
Wavelength: 210.0 nm±4.0 nm
Flow: 0.5 mL/min
Column temperature: 25° C.
Autosampler temperature: 20° C.
Injection volume: 5 μL
Analysis time: 30 min
Elution: gradient

| Time [min] | Mobile phase A [%] | Mobile phase B [%] | Flow [mL/min] |
|---|---|---|---|
| 0.0 | 50 | 50 | 0.5 |
| 22.0 | 5 | 95 | 0.5 |
| 25.0 | 5 | 95 | 0.5 |
| 27.0 | 50 | 50 | 0.5 |
| 30.0 | 50 | 50 | 0.5 |

Mobile phase A:
Borate buffer c=5 mM, pH=9.6
Preparation: 0.618 g of boric acid placed in 2 L volumetric flask were dissolved in 1.5 L purified water. pH value was adjusted to 9.6 using 1M solution of NaOH (6 mL).
Finally, solution was diluted to the mark using purified water.

Mobile phase B:
1 L MeOH with the analogous amount of 1M NaOH as in phase A (3 mL).
Solution for syringe washing: acetonitrile LCMS-Method 7

Apparatus: Dionex UHPLC Ultimate 3000 with DAD detector/Thermo Scientific MSQ Plus Column: Gemini-NX 3μ C18 (4.6×50 mm), 110A, column no. OOB-4453-EO, internal column no. 002

Reagents:—Formic acid a 98%, Sigma-Aldrich

Acetonitrile for HPLC UV/gradient grade, Baker

μQ-water for LCMS

HPLC conditions:—Wavelength range: (190-340) nm±4 nm

Flow: 0.5 ml/min
Column temperature: 25° C.
Autosampler temperature: 20° C.
Injection volume: 2.0 μl
Analysis time: 12 min
Elution: gradient

| Time [min] | Mobile phase A [%] | Mobile phase B [%] | Flow [ml/min] |
|---|---|---|---|
| 0.0 | 60 | 40 | 0.5 |
| 6.7 | 20 | 80 | 0.5 |
| 7.5 | 20 | 80 | 0.5 |
| 7.8 | 5 | 95 | 0.5 |
| 9.5 | 5 | 95 | 0.5 |
| 10.0 | 60 | 40 | 0.5 |
| 12.0 | 60 | 40 | 0.5 |

Mobile phase A: 0.1% v/v water solution of formic acid
Mobile phase B: 0.1% v/v acetonitrile solution of formic acid
Solution for syringe washing: 20% MeOH
MS conditions:—Mass range: 100-1000 m/z
Ionization: alternate
Scan speed: 12 000 amu/sec LCMS-Method 8

Apparatus: Dionex UHPLC Ultimate 3000 with DAD detector/Thermo Scientific MSQ Plus Column: Gemini-NX 3μ C18 (4.6×50 mm), 110A, column no. OOB-4453-EO, internal column no. 002

Reagents:—Formic acid ≥98%, Sigma-Aldrich

Acetonitrile for HPLC UV/gradient grade, Baker

μQ-water for LCMS

HPLC conditions:—Wavelength range: (190-340) nm±4 nm

Flow: 0.5 ml/min
Column temperature: 25° C.
Autosampler temperature: 20° C.
Injection volume: 2.0 μl
Analysis time: 28 min
Elution: gradient

| Time [min] | Mobile phase A [%] | Mobile phase B [%] | Flow [ml/min] |
|---|---|---|---|
| 0.0 | 95 | 5 | 0.5 |
| 4.0 | 95 | 5 | 0.5 |
| 19.0 | 20 | 80 | 0.5 |
| 21.0 | 20 | 80 | 0.5 |
| 24.0 | 95 | 5 | 0.5 |
| 28.0 | 95 | 5 | 0.5 |

Mobile phase A: 0.1% v/v water solution of formic acid
Mobile phase B: 0.1% v/v acetonitrile solution of formic acid
Solution for syringe washing: 20% MeOH
MS conditions:—Mass range: 100-1000 m/z
Ionization: alternate
Scan speed: 12 000 amu/sec LCMS-Method 9

Apparatus: Dionex UHPLC Ultimate 3000 with DAD detector/Thermo Scientific MSQ Plus
Column: Kinetex XB-C18 2.6 μm (4.6×50 mm), 100A, column no. OOB-4496-EO, internal column no. 019
Reagents:—Formic acid ≥98%, Sigma-Aldrich
Acetonitrile for HPLC UV/gradient grade, Baker
μQ-water for LCMS
HPLC conditions:—Wavelength range: (190-340) nm±4 nm
Flow: 1.0 ml/min
Column temperature: 25° C.
Autosampler temperature: 20° C.
Injection volume: 2.0 μl
Analysis time: 7 min
Elution: gradient

| Time [min] | Mobile phase A [%] | Mobile phase B [%] | Flow [ml/min] |
|---|---|---|---|
| 0.0 | 100 | 0 | 1.0 |
| 1.0 | 95 | 5 | 1.0 |
| 4.0 | 80 | 20 | 1.0 |
| 4.75 | 20 | 80 | 1.0 |
| 5.25 | 20 | 80 | 1.0 |
| 6.0 | 95 | 5 | 1.0 |
| 7.0 | 100 | 0 | 1.0 |

Mobile phase A: 0.1% v/v water solution of formic acid
Mobile phase B: 0.1% v/v acetonitrile solution of formic acid
Solution for syringe washing: 20% MeOH
MS conditions:—Mass range: 100-1000 m/z
Ionization: alternate
Scan speed: 12 000 amu/sec LCMS-Method 10

Apparatus: Dionex UHPLC Ultimate 3000 with DAD detector/Thermo Scientific MSQ Plus
Column: Gemini-NX 3μ C18 (4.6×50 mm), 110A, column no. OOB-4453-EO, internal column no. 002
Reagents:—Formic acid a 98%, Sigma-Aldrich
Acetonitrile for HPLC UV/gradient grade, Baker
μQ-water for LCMS
HPLC conditions:—Wavelength range: (190-340) nm t 4 nm
Flow: 0.5 ml/min
Column temperature: 25° C.
Autosampler temperature: 20° C.
Injection volume: 2.0 μl
Analysis time: 12 min
Elution: gradient

| Time [min] | Mobile phase A [%] | Mobile phase B [%] | Flow [ml/min] |
|---|---|---|---|
| 0.0 | 70 | 30 | 0.5 |
| 6.7 | 20 | 80 | 0.5 |
| 7.5 | 20 | 80 | 0.5 |
| 7.8 | 5 | 95 | 0.5 |
| 9.5 | 5 | 95 | 0.5 |
| 10.0 | 70 | 30 | 0.5 |
| 12.0 | 70 | 30 | 0.5 |

Mobile phase A: 0.1% v/v water solution of formic acid
Mobile phase B: 0.1% v/v acetonitrile solution of formic acid
Solution for syringe washing: 20% MeOH
MS conditions:—Mass range: 100-1000 m/z
Ionization: alternate
Scan speed: 12 000 amu/sec LCMS-Method 11

Apparatus: Dionex UHPLC Ultimate 3000 with DAD detector/Thermo Scientific MSQ Plus
Column: Kinetex® 2.6 μm XB-C18 (4.6×50 mm), 110A, column no. OOB-4496-EO, internal column no. 019
Reagents:—Formic acid a 98%, Sigma-Aldrich
Acetonitrile for HPLC UV/gradient grade, Baker
μQ-water for LCMS
HPLC conditions:—Wavelength range: (190-340) nm t 4 nm
Flow: 1.0 ml/min
Column temperature: 25° C.
Autosampler temperature: 20° C.
Injection volume: 2.0 μl
Analysis time: 6 min
Elution: gradient

| Time [min] | Mobile phase A [%] | Mobile phase B [%] | Flow [ml/min] |
|---|---|---|---|
| 0.0 | 30 | 70 | 1.0 |
| 3.35 | 20 | 80 | 1.0 |
| 3.75 | 20 | 80 | 1.0 |
| 3.9 | 5 | 95 | 1.0 |
| 4.75 | 5 | 95 | 1.0 |
| 5.0 | 30 | 70 | 1.0 |
| 6.0 | 30 | 70 | 1.0 |

Mobile phase A: 0.1% v/v water solution of formic acid
Mobile phase B: 0.1% v/v acetonitrile solution of formic acid
Solution for syringe washing: 20% MeOH
MS conditions:—Mass range: 100-1000 m/z
Ionization: alternate
Scan speed: 12 000 amu/sec LCMS-Method 12

Apparatus: Dionex UHPLC Ultimate 3000 with DAD detector/Thermo Scientific MSQ Plus
Column: Gemini-NX 3μ C18 (4.6×50 mm), 110A, column no. OOB-4453-EO, internal column no. 002
Reagents:—Formic acid ≥98%, Sigma-Aldrich
Acetonitrile for HPLC UV/gradient grade, Baker
μQ-water for LCMS
HPLC conditions:—Wavelength range: (190-340) nm±4 nm
Flow: 0.5 ml/min
Column temperature: 25° C.
Autosampler temperature: 20° C.
Injection volume: 2.0 μl
Analysis time: 14 min
Elution: gradient

| Time [min] | Mobile phase A [%] | Mobile phase B [%] | Flow [ml/min] |
|---|---|---|---|
| 0.0 | 100 | 0 | 0.5 |
| 2.0 | 95 | 5 | 0.5 |
| 8.0 | 80 | 20 | 0.5 |
| 9.5 | 20 | 80 | 0.5 |
| 10.5 | 20 | 80 | 0.5 |
| 12.0 | 95 | 5 | 0.5 |
| 14.0 | 100 | 0 | 0.5 |

Mobile phase A: 0.1% v/v water solution of formic acid
Mobile phase B: 0.1% v/v acetonitrile solution of formic acid
Solution for syringe washing: 20% MeOH
MS conditions:—Mass range: 100-1000 m/z
Ionization: alternate
Scan speed: 12 000 amu/sec
UPLC-MS
Apparatus: Shimadzu LCMS-2020 Single Quadrupole Liquid Chromatograph Mass Spectrometer
Column: Acquity UPLC 1.8 µm C18 (2.1×50 mm), 100 Å, column no. 186003532, internal column no. Pur CC—MS001
Reagents:
Formic acid≥98%, Sigma-Aldrich,
Acetonitrile for HPLC UV/gradient grade, Baker,
purified water for HPLC.
UPLC Conditions:
Wavelength: 254 nm and 280 nm
Flow: 0.5 ml/min
Column temperature: 25° C.
Autosampler temperature: 20° C.
Injection volume: 3 µl
Analysis time: 6.0 min
Elution: gradient

| Time [min] | Mobile phase A [%] | Mobile phase B [%] | Flow [ml/min] |
|---|---|---|---|
| 0.01 | 95 | 5 | 0.5 |
| 4.00 | 5 | 95 | 0.5 |
| 5.00 | 5 | 95 | 0.5 |
| 5.20 | 95 | 5 | 0.5 |
| 6.00 | 95 | 5 | 0.5 |

Mobile phase A
0.1% v/v water solution of formic acid
Mobile phase B:
0.1% v/v acetonitrile solution of formic acid
Solution for syringe washing:
100% acetonitrile
MS Conditions:
Mass range: 50-1000 m/z
Ionization: alternate
Scan speed: 7500 u/sec
Activity Screening
Glutaminyl Cyclase, Assay Determination of IC50 Values and Calculation of KI Values
10 mM compound stock solutions were prepared in DMSO. For IC50 determination compound stocks were serially diluted (1:3) in DMSO.
All measurements were performed with an EnSpire Perkin Elmer multimode reader using glutaminyl-7-amino-4-methylcoumarin (H-Gln-AMC) as substrate and recombinant pyroglutamyl aminopeptidase (pGAP) as auxiliary enzyme. Reactions were carried out at ambient temperature in black 96-well half area microplates. Each sample consisted of 1 µl test compound solution or solvent (DMSO) and 49 µl QC appropriately diluted in assay buffer (50 mM Tris/HCl, pH 8.0 or 50 mM MES buffer, pH=6.0). After a 10 min preincubation at ambient temperature the enzyme reaction was started by adding 50 µl of Gln-AMC-substrate/pGAP mixture in assay buffer. Final substrate concentrations were 50 and 200 µM for measurement at pH 8.0 or 6.0, respectively. Release of flourogenic AMC were recorded at excitation/emission wavelengths of 380/460 nm. Initial velocity of the enzyme reaction was calculated by linear regression of the first 10 data points using the Enspire Manager software. Final evaluation and calculation of IC50s were performed using GraphPad Prism software. $IC_{50}$ values were calculated from normalized data (QC activity without inhibitor=100%) by nonlinear regression according to a 4-parameter logistic equation.
Ki-values were calculated according to the following formula: $Ki=IC50/(1+[S]/Km)$, where:
[S] reflects to the concentration of substrate in the assay (200 µM for pH 6.0, 50 µM for pH 8.0) and Km is the respective Michaelis-Menten constant (390 µM at pH 6.0, 62 µM at pH 8.0).
MALDI-TOF Mass Spectrometry
Matrix-assisted laser desorption/ionization mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals are recorded and filtered using LeCroy 9350M digital storage oscilloscope linked to a personal computer. Samples (5 µl) were mixed with equal volumes of the matrix solution. For matrix solution DHAP/DAHC was used, prepared by solving 30 mg 2',6'-dihydroxyacetophenone (Aldrich) and 44 mg diammonium hydrogen citrate (Fluka) in 1 ml acetonitrile/0.1% TFA in water (1/1, v/v). A small volume (≈1 µl) of the matrix-analyte-mixture was transferred to a probe tip and immediately evaporated in a vacuum chamber (Hewlett-Packard G2024A sample prep accessory) to ensure rapid and homogeneous sample crystallization.
For long-term testing of $Glu^1$-cyclization. Aβ-derived peptides were incubated in 100 µl 0.1 M sodium acetate buffer, pH 5.2 or 0.1 M Bis-Tris buffer, pH 6.5 at 30° C. Peptides were applied in 0.5 mM [Aβ(3-11)a] or 0.15 mM [Aβ(3-21)a] concentrations, and 0.2 U QC is added all 24 hours. In case of Aβ(3-21)a, the assays contained 1% DMSO. At different times, samples are removed from the assay tube, peptides extracted using ZipTips (Millipore) according to the manufacturer's recommendations, mixed with matrix solution (1:1 v/v) and subsequently the mass spectra recorded. Negative controls either contain no QC or heat deactivated enzyme. For the inhibitor studies the sample composition was the same as described above, with exception of the inhibitory compound added (5 mM or 2 mM of a test compound of the invention).
Compounds and combinations of the invention may have the advantage that they are, for example, more potent, more selective, have fewer side-effects, have better formulation and stability properties, have better pharmacokinetic properties, be more bioavailable, be able to cross blood brain barrier and are more effective in the brain of mammals, are more compatible or effective in combination with other drugs or be more readily synthesized than other compounds of the prior art.
Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.
All patents and patent applications mentioned throughout the specification of the present invention are herein incorporated in their entirety by reference.
The invention embraces all combinations of preferred and more preferred groups and embodiments of groups recited above.

The invention claimed is:

1. A compound of formula (XIIa):

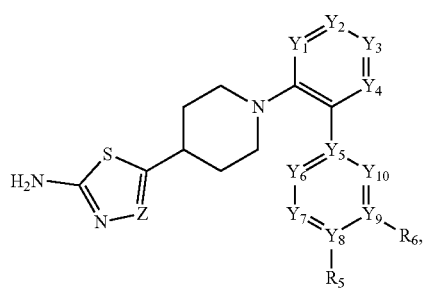

wherein
Z is selected from CH and N;
$Y_1$ to $Y_4$ and $Y_6$, $Y_7$ and $Y_{10}$ are CH;
$Y_5$ is C;
$Y_8$ and $Y_9$ are C;
$R_5$ is selected from halogen, alkyl and O-alkyl;
$R_6$ is selected from hydrogen, alkyl and O-alkyl.

2. A compound of formula (XIII):

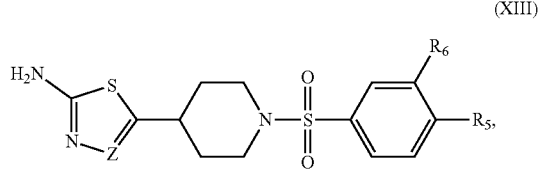

wherein
Z is selected from CH and N;
$R_5$ is selected from halogen, alkyl and O-alkyl; and
$R_6$ is selected from hydrogen, alkyl and O-alkyl.

3. The compound according to claim 2, which is a compound selected from:
5-[1-(4-fluorobenzenesulfonyl)piperidin-4-yl]-1,3-thiazol-2-amine;
5-[1-(4-fluorobenzenesulfonyl)piperidin-4-yl]-1,3,4-thiadiazol-2-amine;
or a pharmaceutically acceptable salt or solvate thereof, including all tautomers and stereoisomers.

4. A pharmaceutical composition comprising a compound according to claim 2 optionally in combination with one or more therapeutically acceptable diluents or carriers.

5. The pharmaceutical composition of claim 4, which comprises additionally at least one compound, selected from the group consisting of neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

6. The pharmaceutical composition of claim 4, which comprises additionally at least one compound, selected from the group consisting of PEP-inhibitors, LiCl, inhibitors of inhibitors of DP IV or DP IV-like enzymes, acetylcholinesterase (ACE) inhibitors, PIMT enhancers, inhibitors of beta secretases, inhibitors of gamma secretases, inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors, interferon-tau (trophoblastin) and SAIK-MS.

7. 5-{[2-({3',4'-dimethoxy-[1,1'-bipheny]-2-yl}amino)ethyl]sulfanyl}-1,3,4-thiadiazol-2-amine.

* * * * *

UNITED STATES PATENT AND TRADEMARK OFFICE
CERTIFICATE OF CORRECTION

| | | |
|---|---|---|
| PATENT NO. | : 12,384,772 B2 | Page 1 of 1 |
| APPLICATION NO. | : 17/737602 | |
| DATED | : August 12, 2025 | |
| INVENTOR(S) | : Ulrich Heiser et al. | |

It is certified that error appears in the above-identified patent and that said Letters Patent is hereby corrected as shown below:

In the Claims

In Column 201, Claim 1, Line 46, after "R5 is selected from halogen, alkyl and O-alkyl;" insert --and--

In Column 202, Claim 7, Line 60, delete "[1,1'-bipheny]" and insert --[1,1'-biphenyl]--

Signed and Sealed this
Thirtieth Day of September, 2025

John A. Squires
*Director of the United States Patent and Trademark Office*